US009206244B2

(12) United States Patent
Baumann et al.

(10) Patent No.: US 9,206,244 B2
(45) Date of Patent: Dec. 8, 2015

(54) IL4/IL13 BINDING REPEAT PROTEINS AND USES

(71) Applicant: Janssen Biotech, Inc., Horsham, PA (US)

(72) Inventors: Michael Baumann, Zurich (CH); Gaby Tresch, Pfaffikon (CH); Steven Jacobs, Spring House, PA (US); Karyn O'Neil, Spring House, PA (US)

(73) Assignee: Janssen Biotech, Inc., Horsham, PA (US)

( * ) Notice: Subject to any disclaimer, the term of this patent is extended or adjusted under 35 U.S.C. 154(b) by 0 days.

(21) Appl. No.: 14/225,821

(22) Filed: Mar. 26, 2014

(65) Prior Publication Data

US 2014/0206599 A1 Jul. 24, 2014

Related U.S. Application Data

(62) Division of application No. 13/458,578, filed on Apr. 27, 2012, now Pat. No. 8,722,618.

(60) Provisional application No. 61/480,999, filed on Apr. 29, 2011, provisional application No. 61/481,008, filed on Apr. 29, 2011, provisional application No. 61/481,021, filed on Apr. 29, 2011.

(51) Int. Cl.
| | |
|---|---|
| *C07K 14/705* | (2006.01) |
| *C07K 14/47* | (2006.01) |
| *A61K 38/00* | (2006.01) |

(52) U.S. Cl.
CPC ............... *C07K 14/705* (2013.01); *C07K 14/47* (2013.01); *A61K 38/00* (2013.01); *C07K 2319/70* (2013.01)

(58) Field of Classification Search
None
See application file for complete search history.

(56) References Cited

U.S. PATENT DOCUMENTS

| 7,417,130 B2 | 8/2008 | Stumpp et al. |
| 7,875,465 B2 | 1/2011 | Shiotsuka et al. |
| 2009/0082274 A1 | 3/2009 | Stumpp et al. |
| 2011/0262964 A1 | 10/2011 | Bedouelle et al. |

FOREIGN PATENT DOCUMENTS

| WO | WO 90/02809 A1 | 3/1990 |
| WO | WO 93/08278 A1 | 4/1993 |
| WO | WO 93/10214 A1 | 5/1993 |
| WO | WO 98/34120 A1 | 6/1998 |
| WO | WO 08/48008 A1 | 10/1998 |
| WO | WO 98/48008 A1 | 10/1998 |
| WO | WO 00/32823 A1 | 6/2000 |
| WO | WO 02/20565 A2 | 3/2002 |
| WO | WO 2007/006665 A1 | 1/2007 |
| WO | WO 2009/138413 A1 | 11/2009 |
| WO | WO 2010/060748 A1 | 6/2010 |

OTHER PUBLICATIONS

Arima, et al., "Upregulation of IL-13 concentration in vivo by the IL13 variant associated with bronchial asthma," Journal of Allergy and Clinical Immunology, 109(6): 980-987 (2002).
Binz, et al., "Engineering novel binding proteins from nonimmunoglobulin domains," Nature Biotechnology, 23(10): 1257-1268 (2005).
Binz, et al., "Designing Repeat Proteins: Well-expressed, Soluble and Stable Proteins from Combinatorial Libraries of Consensus Ankyrin Repeat Proteins," Journal of Molecular Biology, 332: 489-503 (2003).
Binz, et al., "High-affinity binders selected from designed ankyrin repeat protein libraries," Nature Biotechnology, 22(5): 575-582 (2003).
Blease, et al., "Therapeutic Effect of IL-13 Immunoneutralization During chronic Experimental Fungal Asthma," The Journal of Immunology, 166: 5219-5224 (2001).
Borish, et al., "Efficacy of soluble IL-4 receptor for the treatment of adults with asthma," Journal of Allergy and Clinical Immunology, 107(6): 963-970 (2001).
Breekveldt-Postma, et al., "Extent of uncontrolled disease and associated medical costs in severe asthma- a PHARMO study," Current Medical Research and Opinions, 24(4): 976-983 (2009).
Brightling, et al., "Interleukin-13: prospects for new treatments," Clinical & Experimental Allergy, 40: 42-49 (2009).
Di Lorenzo, et al., "Serum Levels of Soluble CD23 in Patients with Asthma or Rhinitis Monosensitive to *Parietaria*. Its Relation to Total Serum IgE Levels and Eosinophil Cationic Protein during and out of the Pollen Season," Allergy and Asthma Procedures, 20: 119-125 (1999).
Forcer, et al., "A novel strategy to design binding molecules harnessing the modular nature of repeat proteins," FEBS Letters, 539: 2-6 (2003).
Gebauer, et al., "Engineered protein scaffolds as next-generation antibody therapeutics," Current Opinion in Chemical Biology, 13: 245-255 (2009).
Geiger, et al., "Deamidation, Isomerization, and Racemization at Asparaginyl and Aspartyl Residues in Peptides," The Journal of Biological Chemistry, 262(2): 785-794 (1987).
Grünig, et al., "Requirement for IL-13 Independently of IL-4 in Experimental Asthma," Science, 282: 226-2263 (1998).

(Continued)

*Primary Examiner* — Amber D Steele
*Assistant Examiner* — Schuyler Milton
(74) *Attorney, Agent, or Firm* — Eric Dichter

(57) ABSTRACT

IL4/IL13-binding proteins comprise binding domains, which inhibit IL4/IL13 binding to IL4Ralpha and common gamma chain complexes (Type 1) and inhibit IL4 binding to IL4Ralpha and IL13Ralpha1 complexes (Type 2), and IL13 binding to IL13Ralpha1 and/or IL13Ralpha2, are useful in the treatment of cancer, inflammatory, and other pathological conditions, such as allergic or fibrotic conditions, especially pulmonary conditions.

8 Claims, 13 Drawing Sheets

(56) References Cited

OTHER PUBLICATIONS

Hanes, et al., "In vitro selection and evolution of functional proteins by using ribosome display," Proceedings of the National Academy of Science USA, 94: 4937-4942 (1997).

Heaton, et al., "An immunoepidemiological approach to asthma: identification of in-vitro T-cell response patterns associated with different wheezing phenotypes in children," Lancet, 365: 142-149 (365).

Heinzmann, et al., "Genetic variants of IL-13 signalling and human asthma and atopy," Human Molecular Genetics, 9(4): 549-599 (2000).

Hijnen, et al., "Serum thymus and activation-regulated chemokine (TARC) and cutaneous T cell-attracting chemokine (CTACK) levels in allergic diseases: TARC and CTACK are disease-specific markers for atopic dermatitis," Journal of Allergy & Clinical Immunology, 113(2): 334-340 (2004).

Hirel, et al., "Extent of N-terminal methionine excision from *Escherichia coli* proteins is governed by the side-chain length of the penultimate amino acid," Proceedings of the National Academy of Science USA, 86: 8247-8251 (1989).

Idzerda, et al., "Human Interkeukin 4 Receptor Confers Biological Responsiveness and Defines a Novel Receptor Superfamily," Journal of Experimental Medicine, 171: 861-873 (1990).

Imai, et al., "Selective recruitment of CCR4-bearing $T_h2$ cells toward antigen-presenting cells by the CC chemokines thymus and activation-regulated chemokine and macrophage-derived chemokine," International Immunology, 11(1): 81-88 (1999).

Kasaian, et al., "Interkeukin-13 Neutralization by Two Distinct Receptor Blocking Mechanisms Reduces Immunoglogulin E Responses and Lung Inflammation in Cynomolgus Monkeys," The Journal of Pharmacology and Experimental Therapeutics, 325: 882-892 (2008).

Kasaian, et al., "IL-13 as a therapeutic target for respiratory disease," Biochemical Pharmacology, 76: 147-155 (2008).

Krause, et al., "Blockade of interleukin-13-mediated cell activation by a novel inhibitory antibody to human IL-13 receptor α1," Molecular Immunology, 43: 1799-1807 (2006).

LaPorte, et al., "Molecular and Structural Basis of Cytokine Receptor Pleiotropy in the Internleukin-4/13 System," Cell, 132: 259-272 (2008).

Leung, et al., "Association between TARC C-431T and atopy and asthma in children," Journal of Allergy and Clinical immunology, 114(10):199-202 (2004).

McKinley, et al., "$T_H17$ Cells Mediate Steroid-Resistant Airway Inflammation and Airway Hyperresponsibeness in Mice," The Journal of Immunology, 181: 4089-4097 (2008).

Nelms, et al., THE IL-4 RECEPTOR: Sigaling Mechanisms and Biologic Functions, Annual Review of Immunology, 17: 701-738 (1999).

Pantoliano, et al., "High-Density Miniaturized Thermal Shift Assays as a General Strategy for Drug Discovery," Journal of Biomolecular Screening, 6: 429-440 (2001).

A.H. Partridge, "Non-adherence to endocrine therapy for breast cancer," Annals of Oncology, 17: 183-184 (2008).

Pene, et al., "IgE production by normal human lymphocytes in induced by interleukin 4 and suppressed by interferons γ and α and prostaglandin $E_2$," Proceedings of the National Academy of Science USA, 85: 6880-6994 (1988).

Perkins, et al., "IL-4 induces IL-13-independent allergic airway inflammation," Journal of Allergy and Clinical Immunology, 118: 410-419 (2006).

Sanchez-Guerrero, et al., "Soluble CD23 (sCD23) serum levels and lymphocyte subpopulations in peripheral blood in rhinitis and extrinsic and intrinisic asthma," Allergy, 49: 587-592 (1994).

Sanford, et al., "Polymorphisms in the IL4, IL4RA, and FCERIB genes and asthma severity," Journal of Allergy and Clinical Immunology, 106: 135-140 (2000>.

Arne Skerra, "Engineered protein scaffolds for molecular recognition," Journal of Molecular Recognition, 13: 167-187 (2000).

Steiner, et al., "Efficient Selection of DARPins with Sub-nanomolar Affinities using SRP Phage Display," Journal of Molecular Biology, 382: 1211-1227 (2008).

Stumpp, et al., "DARPins: A new generation of protein therapeutics," Drug Discovery Today, 13 (15/16): 695-701 (2008).

Therien, et al., "Adenovirus IL-13-Induced Airway Disease in Mice," American Journal of Respiratory, Cellular and Molecular Biology, 39: 26-35 (2008).

Thom, et al., "Probing a protein-protein interaction by in vitro evolution," Proceedings of the National Academy of Science, 103(20): 7619-7624 (2006).

Tomkinson, et al., "A Murine IL-4 Receptor Antagonist That Inhibits IL-4- and IL-13-Induced Responses Prevents Antigen-Induced Airway Eosinophilia and Airway Hyperresponsiveness," The Journal of Immunology, 166: 5792-5800 (2001).

Vladich, et al., "IL-13 R130Q, a common variant associated with allergy and asthma, enhances effector mechanisms essential for human allergic inflammation," The Journal of Clinical Investigation, 115(3): 747-754 (2005).

Wenzel, et al., "IL4Rα Mutations Are Associated with Asthma Exacerbations and Mast Cell/IgE Expression," American Journal of Respiratory and Critical Care Medicine, 175: 570-576 (2007).

Marsha Wills-Karp, "Interleukin-13 in asthma pathogenesis," Immunological Reviews, 202: 175-190 (2004).

Wraight, et al., "Adherence to asthma self-management plans with inhaled corticosteroid and oral prednisone: a descriptive analysis," Respirology, 7: 133-139 (2002).

Thomas A. Wynn, "Fibrotic Disease and the $T_H1/T_H2$ Paradigm," Nature Reviews, 4: 583-594 (2004).

Yang, et al., "Anti-IL-13 monoclonal antibody inhibits airway hyperresponsiveness, inflammation and airway remodeling," Cytokine, 28: 224-232 (2004).

Yang, et al., "Therapeutic Dosing with Anti-Interkeukin-13 Monoclonal Antibody Inhibits Asthma Progression in Mice," The Journal of Pharmacology and Experimental Therapeutics, 313(1): 8-15 (2005).

Zhand, et al., "Ribosome display: selecting and evolving proteins in vitro that specifically bind to a target," Nature Methods, 4(3): 269-279 (2007).

Zhand, et al., "Selection and Characterization of Her2 Binding-designed Ankyrin Repeat Proteins," The Journal of Biological Chemistry, 281 (46): 35167-35175 (2006).

Zhu, et al., "Pulmonary expression of interleukin-13 causes inflammation, mucus hypersecretion, subepithelial fibrosis, physiologic abnormalities, and eotaxin production," Journal of Clinical Investigation, 103: 779-788 (1999).

Zhu, et al., "CD4 Cells: Fates, functions, and faults," Blood, 112: 1557-1569 (2008).

UniProt Accession No. P05112 (origination date Aug. 13, 1987).
UniProt Accession No. P24394 (origination date Mar. 1, 1992).
UniProt Accession No. P31785 (origination date Jul. 1, 1993).
UniProt Accession No. P78552 (origination date Nov. 1, 1997).
UniProt Accession No. Q14627 (origination date Nov. 1, 1997).

Kramer, et al., "Structural Determinants for Improved Stability of Designed Ankyrin Repeat Proteins with a Redesigned C-Capping Module," Journal of Molecular Biology, 404: 381-391 (2010).

Stumpp, et al. DARPins: A new generation of protein therapeutics, Drug Discovery Today, 13: 695-701 (2008).

Kuttner, et al., "Linker peptide and affinity tag for detection and purification of single-chain FV fragments," BioTechniques, 36: 864-870 (2004).

PCT International Search Report dated Jan. 28, 2013.

```
          10        20        30        40        50        60
       .  |   .    |    .    |    .    |    .    |    .    |
MRGSHHHHHHGSDLDKKLLEAARAGQDDEVRILMANGADVNARDSYGSTPLHLAAREGHL 70        80        90       100       110       120
       .  |   .    |    .    |    .    |    .    |    .    |
EIVEVLLKYGADVNAADFIGDTPLHLAAYRGHLEIVEVLLKYGADVNASDITGETPLHLA 130       140       150       160
       .  |   .    |    .    |    .    |    .
AQIGHLEIVEVLLKHGADVNAQDKFGKTPADIAADNGHEDIAEVLQKLN

13           DLDKKLLEAARAGQDDEVRILMANG 37
38    ADVNARDSYGSTPLHLAAREGHLEIVEVLLKYG 70
71    ADVNAADFIGDTPLHLAAYRGHLEIVEVLLKYG 103
104   ADVNASDITGITPLHLAAQIGHLEIVEVLLKHG 136
137   ADVNAQDKFGKTPADIAADNGHEDIAEVLQKLN
```

FIG. 12

```
              10         20         30         40         50         60
       .      |    .     |    .     |    .     |    .     |    .     |
human  PGPVPPSTALRELIEELVNITQNQKAPLCNGSMVWSINLTAGMYCAALESLINVSGCSAI
       # # cyno   PGPVPPSTALKELIEELVNITQNQKAPLCNGSMVWSINLTAGVYCAALESLINVSGCSAI 70         80         90        100        110
       .      |    .     |    .     |    .     |    .     |
human  EKTQRMLSGFCPHKVSAGQFSSLHVRDTKIEVAQFVKDLLLHLKKLFREGRFN
                  #               #              #       #
cyno   EKTQRMLNGFCPHKVSAGQFSSLRVRDTKIEVAQFVKDLLVHLKKLFREGQFN
```

IL4/IL13 BINDING REPEAT PROTEINS AND USES

CROSS-REFERENCE TO RELATED APPLICATIONS

This application is a divisional of U.S. application Ser. No. 13/458,578, filed 27 Apr. 2012, currently allowed, which claims the benefit of U.S. Provisional Application Ser. No. 61/480,999, filed 29 Apr. 2011, U.S. Provisional Application Ser. No. 61/481,008, filed 29 Apr. 2011, and U.S. Provisional Application Ser. No. 61/481,021 filed 29 Apr. 2011, the entire contents of which are incorporated herein by reference in their entireties.

FIELD OF THE INVENTION

The present invention relates to recombinant binding proteins comprising a binding domain which is a repeat protein comprising designed modular repeat units and selected for the ability to inhibit the binding of IL4 and IL13 to their cognate receptors thereby representing useful and stable therapeutic proteins. More particularly, the present invention is directed to bi-specific IL4/IL13 binding proteins comprising ankyrin repeat modules.

BACKGROUND OF THE INVENTION

Interleukin 4 (human IL4, UniProt PO5112) is a 129 amino acid cytokine derived from T cells and mast cells with multiple biological effects on many cell types including B-cells, T-cells and nonlymphoid cells including monocytes, endothelial cells and fibroblasts. IL4 is a pleiotropic cytokine and has been implicated in many of the cellular responses associated with asthma including IgE production, inflammation, airway hypersensitivity, and goblet cell hyperplasia (Perkins, et al., J Allergy Clin Immunol 118: 410-9, 2006; Pene, et al., Proc Natl Acad Sci USA 85: 6880-4, 1988). Its production by both T-cells and mast cells is regulated by a variety of mediators and cytokines that sustain Th2-mediated responses. IL4 signaling is mediated via two receptor complexes, the Type I receptor complex and the Type II receptor complex. Signaling through the type II receptor complex, composed of one IL-4Rα and one IL13Rα1 chain, is largely responsible for the shared biological effects of IL4 and IL13 and both IL4 and IL13 may contact the components of the complex. The type I receptor complex, comprised of the IL-4Rα and common γ-chain is, exclusively responsive to IL4 and mediates IL4 responses in T-cells which do not express IL13αR1 (Idzerda, et al., J Exp Med 171: 861-73, 1990; Nelms, et al., Annu Rev Immunol 17: 701-38, 1999).

Neutralizing the effects of IL4 using antibodies or as demonstrated by the responses of IL4 deficient mice, inhibits allergen-specific IgE and reduces eosinophilia (Zhu and Paul, Blood 112: 1557-69, 2008), as well as airway hyperresponsiveness (AHR) (Heaton, et al., Lancet 365: 142-9, 2005) in murine models of TH2 inflammation. Similarly, soluble IL4 receptor has been used to inhibit IL4 signaling and has been shown to reduce allergen-induced AHR as well as VCAM-1 expression, mucus production and eosinophil recruitment to the lungs of mice (McKinley, et al., J Immunol 181: 4089-97, 2008). In human cells, IL4 has been shown to drive the differentiation of naïve T helper (Th0) lymphocytes into TH2 lymphocytes (Breekveldt-Postma, et al., Curr Med Res Opin 24: 975-83, 2008; Wraight, et al., Respirology 7: 133-9, 2002). TH2 cells have been shown to secrete IL-4, IL-5, IL-9 and IL13 but do not produce IFNγ, contributing to an imbalance of pro-inflammatory TH2 cytokines (Partridge, Ann Oncol 17: 183-4, 2006). Neutralization of IL4 with antibodies that inhibit receptor binding blocks T-cell differentiation ((Idzerda, et al., J Exp Med 171: 861-73, 1990; Nelms, Keegan et al., Annu Rev Immunol 17: 701-38, 1999)). Polymorphisms in the genes encoding IL4, IL4Ra, and IL13 have been associated with asthma, in fact, both IL4 and IL4Ra polymorphisms are associated with severe asthma and exacerbations of asthma (Sandford, et al., J Allergy Clin Immunol 106: 135-40, 2000; Wenzel, et al., Am J Respir Crit Care Med 175: 570-6, 2007). Based on the perceived central role of IL4 in asthma, biotherapeutics that inhibit the activity of IL4 were expected to be valuable tools for the treatment of asthma and other Th2-associated pathologies. However the results of clinical studies using a soluble IL4 receptor were disappointing and showed minimal differences in the incidence of asthma exacerbations between placebo and treatment groups (Borish, et al., J. Allergy Clin. Immunology 107: 963-70, 2001).

Like IL4, Interleukin 13 (IL13) is cytokine identified from activated human T lymphocytes. Over the last 10 years, a variety a reports have demonstrated a role for IL13 in many of the cellular responses associated with asthma including IgE production, inflammation, airway hypersensitivity, mucus production and lung fibrosis (Kasaian and Miller, Biochem Pharmacol 76: 147-55, 2008). Its production is regulated by a variety of mediators and cytokines that interact in a positive feedback loop to sustain Th2-mediated immune responses. IL13 signaling is predominantly mediated via the Type 2 receptor, IL13α1 and IL-4Rα complex. The Type 2 complex, when present, is also activated by IL4 binding (Wills-Karp, Immunological Reviews 202: 175-90, 2004; LaPorte, et al., Cell 132: 259-72, 2008). IL13Ralpha2, is a receptor capable of high affinity binding of IL13 and may play a more functional role either by attenuation of the actions of IL13 and IL4 or via induction of TGF-beta and development of lung fibrosis.

A variety of in vivo data supports a role for IL13 in the pathogenesis of asthma. In cynomolgus monkey models of allergic respiratory disease, antibodies that block the action of IL13 have been shown to reduce lung inflammation (Kasaian, et al., J Pharmacol Exp Ther 325: 882-92, 2008). In humans, increased IL13 levels can be measured in the bronchial tissue, nasal lavage fluid, and induced sputum from asthmatic patients. Genetic polymorphisms that are associated with asthma have been identified at the IL13 locus (Heinzmann, et al., Hum Mol Genet 9: 549-59, 2000). In addition, IL13 appears to play an important role in other atopic diseases including dermal fibrosis and atopic dermatitis. Antibodies or other protein molecules that inhibit the activity of IL13 may be valuable therapeutics for the treatment of asthma and other atopic diseases (Brightling, et al., Clin Exp Allergy 40: 42-9).

Taken together, the in vivo and in vitro data for IL13 and IL4 suggest that therapeutics that can inhibit the actions of both cytokines may be efficacious agents for the treatment of asthma.

The technical problem underlying the present invention is to identify novel IL-4 and IL-13 antagonists (e.g., neutralizing binders) which can be used alone or in combination for an improved treatment of inflammatory disorders, cancer, atopic diseases and other pathological conditions associated with allergic or atopic responses, e.g., asthma, eosinophilia, and fibrotic conditions and where pulmonary functions are affected, to provide for local delivery of an IL4, IL-13, or an IL4 and IL13, neutralizing molecule.

SUMMARY OF THE INVENTION

The present invention relates to binding protein constructs comprising IL4/IL13-binding ankyrin repeat (AR) proteins capable of binding IL4 and IL13 and that inhibit bioactivity of IL4 and IL13. An IL4 and IL13 inhibiting construct as exemplified herein is comprised of an IL4-binding AR repeat domain linked to an IL13-binding AR repeat domain. Such bispecific AR proteins have application as biotherapeutics for a variety of Th2 mediated diseases, including asthma and other atopic diseases associated with the presence or bioactivity of IL4 and IL13.

The present invention also relates to binding protein constructs comprising IL4 or IL13-binding ankyrin repeat (AR) proteins capable of binding IL4 or IL13 and that inhibit bioactivity of IL4 or IL13. An IL4 or IL13 inhibiting construct as exemplified herein is comprised of an IL4-binding AR repeat domain or an IL13-binding AR repeat domain. Such bispecific AR proteins have application as biotherapeutics for a variety of Th2 mediated diseases, including asthma and other atopic diseases associated with the presence or bioactivity of IL4 or IL13.

The invention further relates to nucleic acid molecules encoding the recombinant binding proteins of the present invention, and to a pharmaceutical composition comprising one or more of the binding proteins or nucleic acid molecules.

The invention further relates to a method of treatment of inflammatory diseases, cancer, atopic diseases and other pathological conditions, especially pulmonary conditions, such as asthma and those conditions leading to pulmonary fibrosis, using the binding proteins of the invention. In a particular embodiment, the binding proteins capable of IL4-binding or IL13-binding, alone or in combination may be used in methods of prophylactic or therapeutic treatment to prevent, ameliorate, reduce or eliminate the symptoms or pathophysiology of IL4 and/or IL13 mediated disease. A particular method of treatment is by local delivery of an IL4-binding protein and/or IL-13-binding protein of the invention. In one embodiment of the method of treatment, the IL4-binding protein and/or IL-13-binding protein is administered as an aerosolized formulation. In one method of local delivery, the aerosolized formulation comprising an IL4-binding protein and/or IL-13-binding protein is administered to pulmonary compartment of the subject in need of treatment. The method of treatment is provided to a subject, as prophylactic or therapeutic treatment comprising the IL4-binding protein and/or IL-13-binding protein where the subject is diagnosed or suspected of having a condition, such as asthma, an inflammatory disorder, cancer, atopic disease, or other pathological conditions associated with allergic or atopic responses, e.g., eosinophilia, and fibrotic conditions and, especially, where pulmonary functions are affected.

BRIEF DESCRIPTION OF THE FIGURES

FIG. 2A is a graph representing the neutralization of IL13 and IL4 dependent activities before and after 30 minutes of nebulization. Concentration of aerosolized AR protein or AR protein retained in the cup were assessed by A280 and the activity was measured using an IL13 STAT6 activation assay; pre-nebulized AR protein (shown in squares); aerosolized AR protein (shown in triangles); and retained AR protein (shown in diamonds).

FIG. 2B is a graph representing the neutralization of IL13 and IL4 dependent activities before and after 30 minutes of nebulization. Concentration of aerosolized AR protein or AR protein retained in the cup were assessed by A280 and the activity was measured using an IL4 dependent HT2 proliferation assay; pre-nebulized AR protein (shown in squares); aerosolized AR protein (shown in triangles); and retained AR protein (shown in diamonds).

FIG. 11 shows the amino acid sequence of IL13 Binding Protein 6G9 (SEQ ID NO:162) and alignment of ankyrin repeats. Residues involved in binding IL13 are underlined. E114 (italics) may also be involved. Secondary structure elements are indicated by letters "t" (β-turn) and "h" (helix).

FIG. 12 shows a sequence alignment of human and cyno IL13. The 6G9 epitope residues are underlined.

DETAILED DESCRIPTION OF THE INVENTION

Abbreviations

Figure 1A:
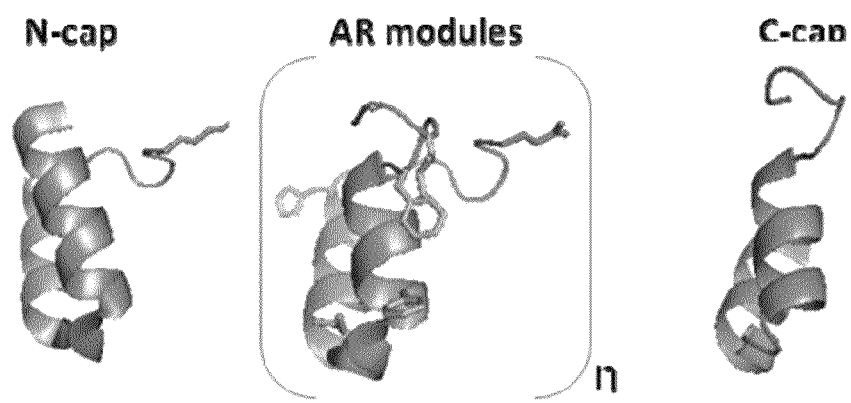
FIG. 1A is a schematic ribbon diagram of a binding protein showing N- and C-Caps and a binding domain comprising multiple ARs

CCL17=chemokine (CC-motif) ligand 17; ECD=extracellular domain; IL=interleukin; TARC=Thymus and Activation-Regulated Chemokine, PBS=phosphate buffered saline; AR=ankyrin repeat; MEM=Minimum Essential Media, NEAA=Non-Essential Amino Acids, SPR=surface plasmon resonance.

Definitions

The term "protein" refers to a polypeptide, wherein at least part of the polypeptide has, or is able to; acquire a defined three-dimensional arrangement by forming secondary, tertiary, or quaternary structures within and/or between its polypeptide chain(s). If a protein comprises two or more polypeptides, the individual polypeptide chains may be linked non-covalently or covalently, e.g. by a disulfide bond between two polypeptides. A part of a protein, which individually has, or is able to acquire a defined three-dimensional arrangement by forming secondary or tertiary structures, is termed "protein domain." Such protein domains are well known to the practitioner skilled in the art.

In the context of the present invention, the term "polypeptide" relates to a molecule consisting of multiple, i.e., two or more, amino acids linked via peptide bonds. Preferably, a polypeptide consists of more than eight amino acids linked via peptide bonds.

The term "binding protein" refers to a protein comprising one or more binding domains. In various embodiments of the invention, the binding protein comprises two, three, or four binding domains. Furthermore, any such binding protein may comprise additional protein domains that are not binding domains, multimerization moieties, polypeptide tags, polypeptide linkers and/or a single Cys residue. Examples of multimerization moieties are immunoglobulin heavy chain constant regions which pair to provide functional immunoglobulin Fc domains, and leucine zippers or polypeptides comprising a free thiol which forms an intermolecular disulfide bond between two such polypeptides. Free thiol, residing on e.g. a Cys residue, may be used for conjugating other moieties to the polypeptide, for example, by using the maleimide chemistry well known to the person skilled in the art. Preferably, said binding protein is a recombinant binding protein. Also preferably, the binding domains of the binding protein of the invention possess different target specificities. Non-proteinaceous atoms, such as metals; actives, and non-proteinaceous material may be attached or associated with the binding protein of the invention in a useful composition.

The term "binding domain" as used herein, means a protein domain exhibiting the same or substantially the same "fold" (three-dimensional arrangement) as a protein scaffold and having a specified property, such as binding a target molecule. A protein scaffold will have exposed surface areas in which amino acid insertions, substitutions or deletions are highly tolerable which may be modified to provide a binding domain with a selected, specified or determined property. Other specified properties of a binding domain may include: binding to a target, blocking of target binding or target activity, activation of a target-mediated reaction, enzymatic activity, and related further properties. Depending on the type of desired property, one of ordinary skill will be able to identify and perform the necessary steps for screening and/or selection of a binding domain with the desired property. Such a binding domain may be obtained by rational, or most commonly, combinatorial protein engineering techniques, skills which are known in the art (Skerra, A., J. Mol. Recog. 13, 167-187, 2000; Binz, H. K., Amstutz, P. and Plückthun, A., Nat. Biotechnol. 23, 1257-1268, 2005). For example, a binding domain having a selected property can be obtained by a method comprising the steps of (a) providing a diverse collection of protein domains exhibiting the same fold as a protein scaffold as defined further below; and (b) screening said diverse collection and/or selecting from said diverse collection to obtain at least one protein domain having said property. The diverse collection of protein domains may be provided by several methods in accordance with the screening and/or selection system being used, and may comprise the use of methods well known to the person skilled in the art, such as phage display or ribosome display libraries.

As described herein, the binding domain is a "repeat domain" or a "designed repeat domain." Such a repeat domain may comprise one, two, three or more internal repeat modules that will participate in binding to a target or other specified property. Preferably, such a repeat domain further comprises an N-terminal capping module, two to four internal repeat modules, and a C-terminal capping module. Preferably, said binding domain is an ankyrin repeat domain or designed ankyrin repeat domain where the repeat modules sequences are from naturally proteins (repeat units) or are derived from consensus sequences of the natural repeat units (repeat modules). Thus, a repeat domain can be naturally occurring or can be formed, such as those obtained as the result of the inventive procedure explained in patent publication WO 02/20565.

A binding protein according to the invention may be a "repeat protein" or "designed repeat protein" which refers to a protein comprising two or more consecutive repeat units or modules (FIGS. 1A and 1B) which are structural units, each having the same fold, and which stack tightly to create a structure having a joint hydrophobic core. The stacked arrangements of the repeat units of a repeat protein, which independently lack the ability to form a stable protein domain or have specific functional activity, assemble within a tandem array of between 2 and 25 or more repeating units (modules) and form a repeat domain having a superhelical structure capable of protein-protein interactions. The term "folding topology" or "fold" refers to the tertiary structure of the repeat units within the repeat protein. Repeat modules or repeat units are of relatively short sequence motifs, typically from 20 to 40 amino acid residues in length. In most cases, repeat units will exhibit a high degree of sequence identity (same amino acid residues at corresponding positions) or sequence similarity (amino acid residues being different, but having similar physicochemical properties), and some of the amino acid residues might be key residues being strongly conserved in the different repeat units found in naturally occurring proteins. However, a high degree of sequence variability by amino acid insertions and/or deletions, and/or substitutions between the different repeat units will be possible as long as the common folding topology is maintained.

The term "repeat unit" refers to amino acid sequences comprising repeat sequence motifs of one or more naturally occurring repeat proteins, wherein said "repeat units" are found in multiple copies, and which exhibit a defined folding topology common to all said motifs determining the fold of the protein. Such repeat units comprise framework residues and interaction residues. Examples of such repeat units are armadillo repeat units, leucine-rich repeat units, ankyrin repeat units, tetratricopeptide repeat units, HEAT repeat units, and leucine-rich variant repeat units. Naturally occurring proteins containing two or more such repeat units are referred to as "naturally occurring repeat proteins." The amino acid sequences of the individual repeat units of a repeat protein may have a significant number of mutations, substitutions, additions and/or deletions when compared to each other, while still substantially retaining the general pattern, or motif, of the repeat units.

The term "repeat modules" refers to the repeated amino acid sequences of designed repeat proteins or domains. Each repeat module comprised in a repeat domain is derived from one or more repeat units of one family of naturally occurring repeat proteins where the members of said group comprise similar repeat units. Such "repeat modules" may comprise positions with amino acid residues present in all copies of the repeat module ("fixed positions") and positions with differing or "randomised" amino acid residues ("randomised positions"). Examples of such repeat modules are armadillo repeat modules, leucine-rich repeat modules, ankyrin repeat modules, tetratricopeptide repeat modules, HEAT repeat modules, and leucine-rich variant repeat modules. The amino acid sequences of the individual repeat units/repeat modules of a repeat protein may have a significant number of mutations, substitutions, additions and/or deletions when compared to each other, while still substantially retaining the general pattern, or motif, of the repeat units/repeat modules.

The term "set of repeat modules" refers to the total number of repeat modules present in a repeat domain. Such "set of repeat modules" present in a repeat domain comprises two or more consecutive repeat modules, and may comprise just one type of repeat module in two or more copies, or two or more different types of modules, each present in one or more copies. In the set of repeat modules, the order of the modules determines the composition of the repeat domain and, where a repeat domain has been selected for a specific activity, the repeat domain biological function, such as a binding domain. The repeat units/modules in a repeat domain will herein be numbered consecutively from the N-terminus of the polypeptide to the C-terminus of the polypeptide.

The term "repeat sequence motif" refers to an amino acid sequence, which is deduced from one or more repeat units or repeat modules. Such repeat sequence motifs comprise framework residue positions and target interaction residue positions. Said framework residue positions correspond to the positions of framework residues of the repeat units (or modules). Likewise, said target interaction residue positions correspond to the positions of target interaction residues of the repeat units (or modules). The target interaction residues will generally be positioned along one face of the repeat domain. An example of such a repeat sequence motif is an ankyrin repeat sequence motif, such as shown in SEQ ID NO: 1.

The term "framework residues" relates to amino acid residues of the repeat units, or the corresponding amino acid residues of the repeat modules, which contribute to the folding topology, i.e., which contribute to the fold of said repeat unit (or module) or which contribute to the interaction with a neighboring unit (or module). Such contribution might be the interaction with other residues in the repeat unit (module), or the influence on the polypeptide backbone conformation as found in α-helices or β-sheets, or amino acid stretches forming linear polypeptides or loops.

The term "target interaction residues" refers to amino acid residues of the repeat units, or the corresponding amino acid residues of the repeat modules, which may contribute to the interaction of the repeat unit (or module) with a target substance. Such contribution might be the direct interaction with the target substances, or the influence on other directly interacting residues, e.g., by stabilizing the conformation of the polypeptide of a repeat unit (or module) to allow or enhance the interaction of directly interacting residues with said target. Such framework and target interaction residues may be identified by analysis of the structural data obtained by physicochemical methods, such as X-ray crystallography, NMR and/or CD spectroscopy, or by comparison with known and related structural information well known to practitioners in structural biology and/or bioinformatics.

Preferably, the repeat units/modules used for the deduction of a repeat sequence motif are homologous repeat units, wherein the repeat units comprise the same structural motif and wherein more than 70% of the framework residues of said repeat units are identical to each other. Preferably, more than 80% of the framework residues of said repeat units are identical. Most preferably, more than 90% of the framework residues of said repeat units are identical. Computer programs to determine the percentage of identity between polypeptides, such as Fasta, Blast or Gap, are known to the person skilled in the art. More preferably, the repeat units used for the deduction of a repeat sequence motif are homologous repeat units obtained from repeat domains selected on a target, for example, as described in Example 1, and having the same target-specificity.

Repeat sequence motifs comprise fixed positions and randomized positions. The term "randomized position" refers to an amino acid position in a repeat sequence motif, wherein two or more amino acids are allowed at said amino acid position, for example, wherein any of the usual twenty naturally occurring amino acids are allowed, or wherein most of the twenty naturally occurring amino acids are allowed, such as amino acids other than cysteine, or amino acids other than glycine, cysteine and proline. These amino acids may be in modified form as known in the art. Most often, such randomized positions correspond to the positions of target interaction residues. However, some positions of framework residues may also be randomized.

The term "capping module," "capping unit" or "N-Cap" (for an N-terminal capping module) or "C-Cap" (for a C-terminal capping module) refers to a polypeptide fused to the N- or C-terminal repeat module of a repeat domain, wherein said capping module forms tight tertiary interactions with the adjacent repeat unit thereby providing a cap that shields the hydrophobic core of said repeat module at the side not in contact with the consecutive repeat module from the solvent. Said N- and/or C-terminal capping module may be, or may be derived from, a capping unit or other domain found in a naturally occurring repeat protein adjacent to a repeat unit. The N- or C-Cap forms tight tertiary interactions with the adjacent repeat unit. Such capping units may have sequence similarities to the repeat sequence motif. Capping modules and capping repeats are described in WO 02/020565 and exemplified herein.

The term "target" refers to a molecule, polypeptide or protein, carbohydrate, complexes of two or more molecules, which may exist in isolated form or reside in a biological form, such as on or in a cell or a tissue sample and may exist in multiple forms, such as naturally occurring or non-naturally occurring chemical modifications, for example, modified by phosphorylation, acetylation, or methylation, or exhibiting damage or cross-linked residues such as may occur upon reaction with ionizing radiation or reactive oxygen species caused be natural or non-natural processes. In the particular application of the present invention, the target is a soluble protein which is a cytokine.

By IL4, IL-4, or hIL4, is meant a small cytokine, human Interleukin 4 (UniProt P05112, SEQ ID NO: 4) or a species homolog thereof. Where specifically stated, the species homolog sequence is specified, e.g. cynomolgous monkey IL4, cyno IL4, or cIL4 (SEQ ID NO: 5). The protein is also known as B-cell stimulatory factor 1, B-cell growth factor, BCGF1, BCGF-1, BSF1, BSF-1, and Lymphocyte stimulatory factor 1, among other names. The human mature protein is expressed as a 153 amino acid polypeptide (UniProt P05112) with a 24 amino acid signal peptide, a single N-linked glycosylation site, and is cleaved to produce a 129 amino acid mature protein (SEQ ID NO: 1) with three interchain disulfide bonds. Two types of IL4 receptor exist: Type 1 and Type 2. Type 1 is a heterodimer consisting of the IL4 R-alpha (IL4 RA, CD124, UniProt P24394 and where SEQ ID NO: 6 represents the ECD thereof) and the common receptor subunit gamma, CD132 (IL2RG, UniProt P31785, SEQ ID NO: 7). The Type 2 receptor is a heterodimer consisting of IL4 R-alpha and IL13R-alpha1 (IL13RA1, CD213a1, UniProt P78552, SEQ ID NO: 8). IL13 (SEQ ID NO: 101) but not IL4 binds the Type 2 receptor by binding the IL13RA protein. In addition, IL13 binds IL13RA2 (SEQ ID NO: 102).

A "consensus amino acid residue" is the amino acid found most frequently at a certain position in a sequence identified by structural and/or sequence aligning of multiple repeat units. If two or more, e.g., three, four or five, amino acid residues are found with a similar probability in said two or more repeat units, the consensus amino acid may be one of the most frequently found amino acids or a combination of said two or more amino acid residues.

As used herein, the term "affinity" of binding between two molecules refers to a biophysical measurement of strength of interaction. The term "$K_{dis}$" or "$K_D$" or "$K_d$" as used herein, is intended to refer to the dissociation rate of a particular composition-target interaction. The "$K_D$," is the ratio of the rate of dissociation ($k_2$), also called the "off-rate ($k_{off}$)" or "$k_d$," to the rate of association ($k_1$) or "on-rate ($k_{on}$)" or "$k_a$." Thus, $K_D$ equals $k_2/k_1$ or $k_{off}/k_{on}$ or $k_d/k_a$ and is expressed as a molar concentration (M). It follows that the smaller $K_D$, the stronger the binding. Thus, a $K_D$ of $10^{-6}$M (or 1 µM) indicates weak binding compared to $10^{-9}$M (or 1 nM). The $K_D$ can be determined by surface plasmon resonance or the Kinexa method, as practiced by those of skill in the art. The measured affinity of a particular protein-protein interaction can vary if measured under different conditions (e.g., salt concentration, pH). Thus, measurements of affinity (e.g., $K_D$, $k_{on}$, $k_{off}$) are preferably made with standardized solutions of protein, and a standardized buffer.

The repeat proteins of the invention, selected for their biological activity resulting from interactions with other proteins or peptides, can be further modified to enhance or impart additional biophysical or biological properties to the molecules such as a polypeptide tag, a radioisotope, a chelator, and a multimerizing domain, which may be of a proteinaceous or a nonproteinaceous nature. For example, the ability to persist in the body can be enhanced by the addition of certain physiologically compatible polymers or the fusion of an immunoglobulin constant domain sequence to the protein. Examples of non-proteinaceous polymer molecules are hydroxyethyl starch (HES), polyethylene glycol (PEG), polypropylene glycol, or polyoxyalkylene. Modifications that enhance the ability of the protein to persist in the body through a decrease in clearance or increase in re-uptake are referred to as "half-life extending" modifications.

The term "polypeptide tag" refers to an amino acid sequence attached to a polypeptide/protein, wherein said amino acid sequence is useful for the purification, detection, or targeting of said polypeptide/protein, or wherein said amino acid sequence improves the physicochemical behavior of the polypeptide/protein, or wherein said amino acid sequence possesses an effector function. The individual polypeptide tags, moieties and/or domains of a binding protein may be connected to each other directly or via polypeptide linkers. These polypeptide tags are all well known in the art and are fully available to the person skilled in the art. Examples of polypeptide tags are small polypeptide sequences, for example, His, myc, FLAG, or Strep-tags or moieties, such as enzymes (for example enzymes like alkaline phosphatase), which allow the detection of said polypeptide/protein, or moieties which can be used for targeting (such as immunoglobulins or fragments thereof) and/or as effector molecules.

Examples of multimerization moieties are immunoglobulin heavy chain constant regions which pair to provide functional immunoglobulin Fc domains, and leucine zippers or polypeptides comprising a free thiol which forms an intermolecular disulfide bond between two such polypeptides.

The term "polypeptide linker" refers to an amino acid sequence, which is able to link, for example, two protein domains, a polypeptide tag and a protein domain, a protein domain and a non-polypeptide moiety, such as polyethylene glycol or two sequence tags. Such additional domains, tags, non-polypeptide moieties and linkers are known to the person skilled in the relevant art. A polypeptide linker or any intervening sequence between the repeat modules may be any sequence which does not interfere with the topology or the fold of the module or the ability of the modules to stack. Particular examples of such linkers are flexible glycine-serine-linkers of variable lengths; preferably, said linkers have a length between 2 and 16 amino acids, and Proline-Threonine linkers.

Overview

Figure 1B:
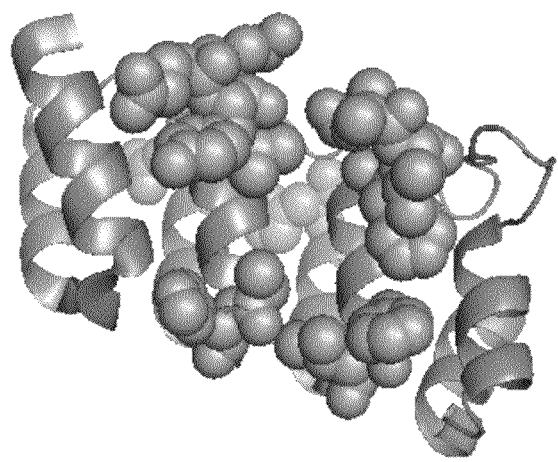
FIG. 1B is a schematic ribbon diagram of a binding protein showing a complete ankyrin repeat domain comprising an N-Cap, two ankyrin repeat modules and a C-Cap.
Figure 3:
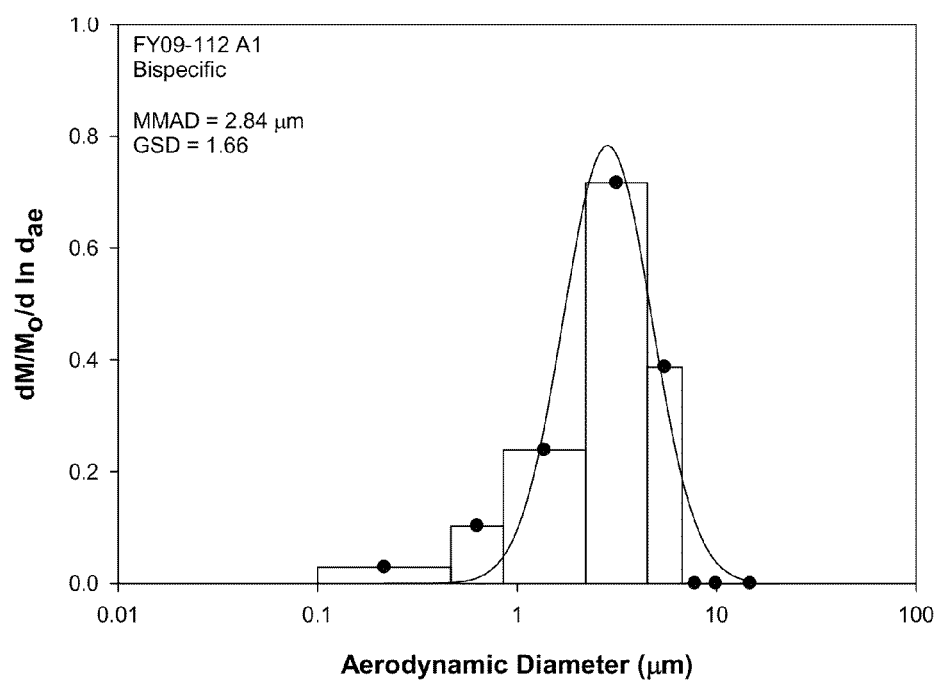
FIG. 3 shows the particle size distribution for AR protein 11G11-21H2 as evaluated by cascade impaction using a solution of AR protein 11G11-21H2 prepared at 20 mg/ml in PBS. The MMAD is 2.84 μm and the GSD is 1.66 μm.
Figure 4:
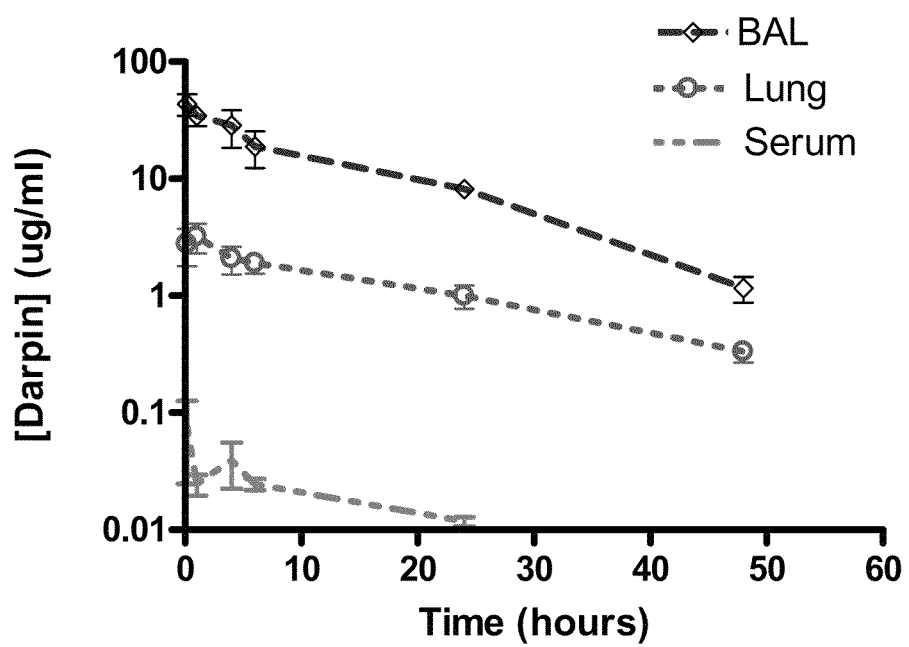
FIG. 4 shows a plot of data for 11G11-21H2 serum, lung tissue or bronchial lavage fluid (BAL) concentrations over time after dosing via intratracheal instillation groups of mice (n=5) and sacrificed at various timepoints.
Figure 5:
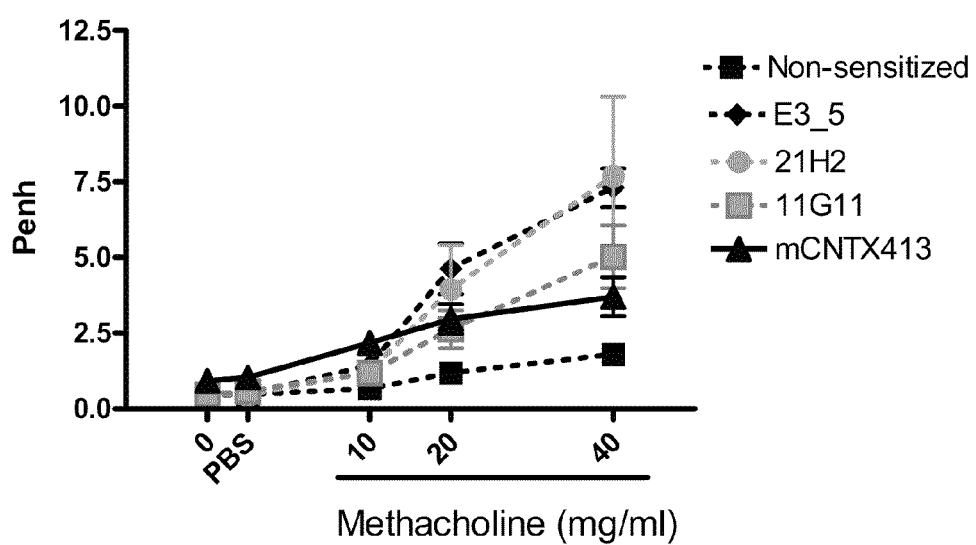
FIG. 5 shows the effect of repeat protein 11G11 or repeat protein 11G11-21H2 dosed via intratracheal instillation on OVA-induced airway hyperresponsiveness to methacholine in the acute OVA sensitization and challenge model. Non-sensitized, vehicle challenged (NSV) animals (shown in solid squares); Control AR protein (shown in solid diamonds); 11G11 20 mg/kg (shown in squares); 21H2 20 mg/kg (shown in solid circles); 11G11-21H2 AR protein, 40 mg/kg (shown in solid triangles).
Figure 6:
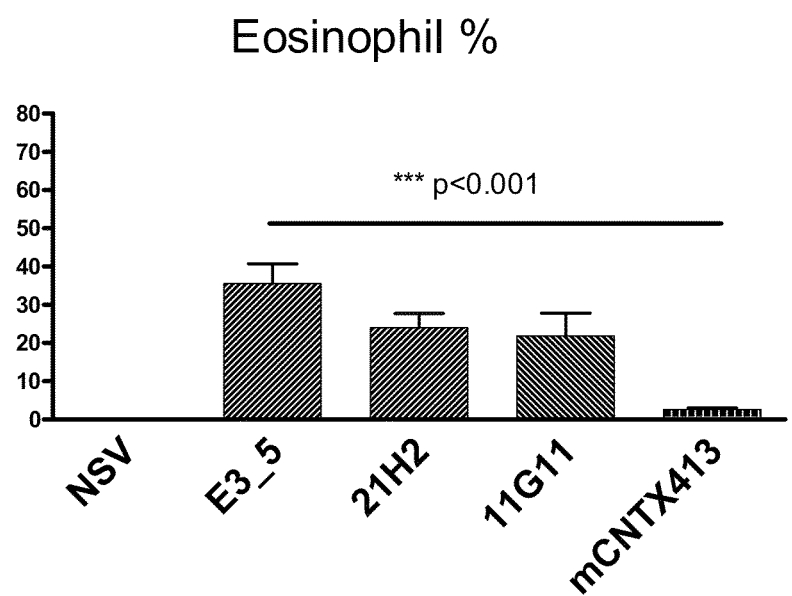
FIG. 6 is a bar graph showing the effect of various AR constructs on ovalbumin induced eosinophil recruitment to the lungs of Balb/C mice in the acute OVA sensitization and challenge model. The effect of 11G11-21H2 protein (labeled mCNTX413) is significantly different from the either monospecific AR protein 21H2 or 11G11 alone.
Figure 7:
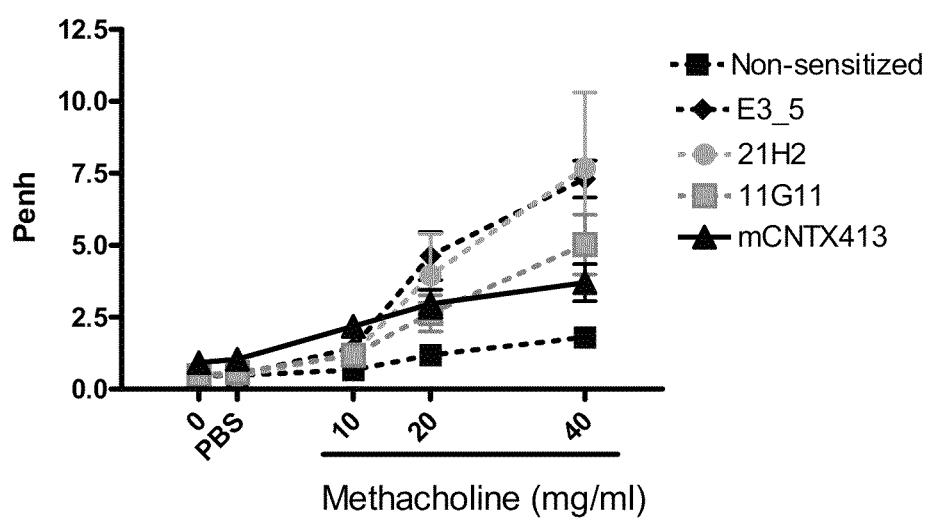
FIG. 7 shows the effect of various AR constructs (with 11G11-21H2 labeled mCNTX413) on OVA induced eosinophil recruitment to the lungs.

New IL4 and IL13 binding proteins were identified using libraries of repeat proteins comprising a consensus 33 amino acid ankyrin repeat module containing diversified potential interaction residues (any amino acid except cysteine, glycine or proline). As described herein, the amino acids at randomized positions in stacked repeat modules form an interaction surface that can bind with high affinity to a variety of targets (FIGS. 1A and 1B). Binders have been selected from libraries of potential binding domains encompassing two to four AR modules having diversified amino acids at specific residue position and, which repeat domain is flanked by an N-terminal and C-terminal module. A preferred binding domain of the invention is a repeat domain or a designed repeat domain, preferably as described in WO 02/20565; Binz, H. K. et al., 2004, loc. cit.).

In a specific embodiment, the invention relates to a recombinant IL4 binding protein comprising a binding domain with specificity for IL4 selected from a library of repeat proteins comprising one or more repeat modules with the AR sequence motif (SEQ ID NO: 1)
$X_1DX_3X_4GX_6TPLHLAAX_{14}X_{15}GHLEIVEVLLKX_{27}GADVNA$, wherein $X_1$, $X_3$, $X_4$, $X_6$, $X_{14}$, and $X_{15}$ represent, independently of each other, an amino acid residue selected from the group consisting of A, D, E, F, H, I, K, L, M, N, Q, R, S, T, V, W and Y. $X_{27}$ represents A, H, N, or Y;

an N-terminal capping module of the amino acid sequence:

(SEQ ID NO: 2)
DLGKKLLEAARAGQDDEVRILMANGADVNA;

and
a C-terminal capping module has an amino acid sequence:

(SEQ ID NO: 3)
QDKFGKTAFDISIDNGNEDLAEILQKLN.

The term "AR" means an ankyrin repeat module and "AR1" means the first tandem AR of an ankyrin repeat domain, the term "AR2" means the second AR of an ankyrin repeat domain, the term "AR3" means the third AR of an ankyrin repeat domain, and the term "AR4" means the fourth AR of an ankyrin repeat domain. When arranged in tandem, the AR1 module is N-terminus of the AR2 module; the AR2 module is N-terminus of the AR3 module and, as applicable, the AR3 module is N-terminus of the AR4 module such that an AR arrangement is AR1-AR2-AR3-AR4. ARs do not include N-Cap or C-Cap sequences and, preferably, each AR has an N-Cap and C-Cap module. It will be appreciated that SEQ ID NO:2 is an example of an N-Cap sequence and SEQ ID NO:3 is an example of an C-Cap sequence and that these sequences may be modified as needed.

In specific embodiment, the invention relates to a recombinant IL13 binding protein comprising a binding domain with specificity for IL13 selected from a library of repeat proteins comprising one or more repeat modules with the AR sequence motif (SEQ ID NO: 1)
$X_1DX_2X_3GX_4TPLHLAAX_5X_6GHLEIVEVLLKX_7GADVNA$, wherein $X_1$, $X_2$, $X_3$, $X_4$, $X_5$, and $X_6$ represent, independently of each other, an amino acid residue selected from the group consisting of A, D, E, F, H, I, K, L, M, N, Q, R, S, T, V, W and Y. $X_7$ represents A, H, N, and Y;

an N-terminal capping module of the amino acid sequence (wherein bracketed sequences mean alternate amino acids for that position):

(SEQ ID NO: 174)
DL[D,G]KKLLEAARAGQDDEVRILMANGADVNA;

and
a C-terminal capping module has an amino acid sequence:

(SEQ ID NO: 175)
QDKFGKT[A,P][A,F]DI[A,S][A,I]DNG[H,N]ED[I,L]

AE[I,V]LQK[A,L][A,N].

In addition to substitutions of the residues at the positions diversified in the creation of libraries based on the formula N-Cap-[AR]$_n$-C-Cap; generic binding protein mutations are encompassed by the identified binding protein structures. Generic mutations can be applied to any binding protein of the invention, in that these mutations occur within positions of the sequence that are common to all binding proteins of the above referenced library of binding domains. Common generic changes to specified residues of a binding domain of the invention are as summarized below.

| Module | Position | Final Amino Acid Residue |
| --- | --- | --- |
| N-Cap | 1 | G, A |
| N-Cap | 3 | D |
| AR | 27 | H, Y, A |
| C-Cap | 27 | A |
| C-Cap | 28 | A |

Position 1 of the N-Cap is mutated from Asp to Gly or Ala to aid in the processing of the N-terminal methionine residue for expression in *E. coli* (Hirel et. al. PNAS 86:8247-8251 1989). Position 3 of the N-Cap is mutated from Gly to Asp, as this mutation has been found to stabilize the repeat protein consensus sequence as described in WO2010/060748. As the AR sequence motif (SEQ ID NO: 1) position 28 of the framework is Gly, there is the possibility of isolating AR proteins consisting of the sequence $Asn_{27}$-$Gly_{28}$. The Asn-Gly dipeptide is prone to deamidation reactions (Geiger and Clarke J. Biol. Chem. 252:785-794, 1987) and therefore position 27 of isolated Asn-Gly sequences can be mutated to His, Tyr or Ala to avoid potential deamidation. In some cases, the residue at position 27 is changed to Ala to reduce the potential immunogenicity of the region of the protein. Finally, target binding AR proteins selected by ribosome display end with the amino acid sequence Leu-Asn in the C-cap. This sequence is appended onto the AR proteins in order to accommodate a restriction site for sub-cloning into expression vectors for screening. The preferred amino acid sequence of these positions is Ala-Ala.

The invention relates to a binding protein comprising a binding domain, wherein said binding domain inhibits IL13 binding to IL13Ralpha1 or IL13Ralpha2 or IL4 binding to IL4RA and wherein said binding protein and/or binding domain has a midpoint denaturation temperature (Tm) above 40° C. upon thermal unfolding and forms less than 5% (w/w) insoluble aggregates at concentrations up to 10 g/L when incubated at 37° C. for 1 day in phosphate buffered saline (PBS). In a specific embodiment, the IL13 binding protein is comprised of two or three repeat modules represented by SEQ ID NO: 1 proceeded by an N-terminal capping module such as SEQ ID NO: 2 or 174, and followed by a C-terminal capping module such as SEQ ID NO: 3 or 175.

The invention relates to a binding protein comprising a binding domain, wherein said binding domain inhibits IL4 binding to IL4RA. Preferably, the $K_D$ for the interaction of the binding domain to IL4 is below $10^{-7}$M, below $10^{-8}$ M, below $10^{-9}$M, or, in certain embodiments below $10^{-10}$ M. Methods to determine dissociation constants of protein-protein interactions, such as surface plasmon resonance (SPR) based technologies, are well known to the person skilled in the art.

The invention relates also to a binding protein comprising a binding domain, wherein said binding domain inhibits IL13 binding to IL13Ralpha1 and/or IL13Ralpha2. Preferably, the $K_D$ for the interaction of the binding domain to IL13 is below $10^{-7}$M, below $10^{-8}$M, below $10^{-9}$M, or, in certain embodiments below $10^{-10}$ M. Methods to determine dissociation constants of protein-protein interactions, such as surface plasmon resonance (SPR) based technologies, are well known to the person skilled in the art.

Preferably, the binding protein and/or binding domain has a midpoint denaturation temperature (Tm) above 45° C., more preferably above 50° C., more preferably above 55° C., and most preferably above 60° C. upon thermal unfolding. A binding protein or a binding domain of the invention possesses a defined secondary and tertiary structure under physiological conditions. Thermal unfolding of such a polypeptide results in a loss of its tertiary and secondary structure, which can be followed, for example, by circular dichroism (CD) measurements. The midpoint denaturation temperature of a binding protein or binding domain upon thermal unfolding corresponds to the temperature at the midpoint of the cooperative transition in physiological buffer upon heat denaturation of said protein or domain by slowly increasing the temperature from 10° C. to about 100° C. The determination of a midpoint denaturation temperature upon thermal unfolding is well known to the person skilled in the art. This midpoint denaturation temperature of a binding protein or binding domain upon thermal unfolding is indicative of the thermal stability of said polypeptide.

Also preferred is a binding protein and/or binding domain forming less than 5% (w/w) insoluble aggregates at concentrations up to 20 g/l, preferably up 40 g/L, more preferably up to 60 g/L, even more preferably up to 80 g/L, and most preferably up to 100 g/L when incubated for over 5 days, preferably over 10 days, more preferably over 20 days, more preferably over 40 days, and most preferably over 100 days at 37° C. in aqueous solution. The formation of insoluble aggregates can be detected by the appearance of visual precipitations, gel filtration or dynamic light scattering, which strongly increases upon formation of insoluble aggregates. Insoluble aggregates can be removed from a protein sample by centrifugation at 10,000×g for 10 minutes. Preferably, a binding protein and/or binding domain forms less than 2%, 1%, 0.5%, 0.2%, 0.1%, or 0.05% (w/w) insoluble aggregates under the mentioned incubation conditions at 37° C. in PBS. Percentages of insoluble aggregates can be determined by separation of the insoluble aggregates from soluble protein, followed by determination of the protein amounts in the soluble and insoluble fraction by standard quantification methods.

Bioactivity

An $EC_{50}$ value is the concentration of a substance, such as a binding protein or binding domain, which is required to produce for 50% of the complete or predetermined maximum effect under a specific set of conditions. When the effect is blocking or inhibiting an activity, the value is termed an inhibitory concentration producing 50% reduction in the effect ($IC_{50}$). An $IC_{50}$ value may be applied to inhibition in vitro of an experimental determined parameter, such as the release of a detectable amount of a pathologic marker, or biomarker, from a cell, tissue, organ or in the body of a subject or animal. Such measurements may be direct measures of the activity of the protein composition or may be surrogates or downstream markers of the biological activity to be modified.

IL4 shares several biological activities with IL13. For example, either IL4 or IL13 can cause IgE isotype switching in B cells (Tomkinson et al. 2001 J. Immunol. 166:5792-5800). Additionally, increased levels of cell surface CD23 and serum CD23 (sCD23) have been reported in asthmatic patients (Sanchez-Guerrero et al. (1994) Allergy 49:587-92; DiLorenzo et al. (1999) Allergy Asthma Proc. 20.119-25). In addition, either IL4 or IL13 can upregulate the expression of MHC class II and the low-affinity IgE receptor (CD23) on B cells and monocytes, which results in enhanced antigen presentation and regulated macrophage function (Tomkinson et al., supra). Importantly, either IL4 or IL13 can increase the expression of VCAM-1 on endothelial cells, which facilitates preferential recruitment of eosinophils (and T cells) to the airway tissues (Tomkinson et al., supra). Either IL4 or IL13 can also increase airway mucus secretion, which can exacerbate airway responsiveness (Tomkinson et al., supra). By acting to block signaling pathways which are different from those of IL13, IL4 inhibitors/antagonists can be used to inhibit differentiation of naïve T-cells to Th2 cells.

The present invention further relates to methods for using a binding protein which has both IL4 and IL13 neutralizing activity as described to inhibit an IL4 and IL13 mediated biological activity including but not limited to: IgE production; CD23 upregulation on B cells or monocytes; upregulation of VCAM-1 on endothelial cells, eosinophil recruitment, TGFbeta induction, increased mucus secretion; fibrosis caused by fibroblast proliferation, collagen synthesis, and extracellular-matrix remodeling (Wynn T A et al. Nat Rev Immunol. 2004; 4: 583-94) or by stimulation of TGFbeta; and stimulation of 15-lipoxygenase activity with release of leukotrienes (e.g., LTA4, LTB4, LTC4, LTD4, LTE4, and/or LTF4). Therefore, any of IgE production, LTA4 and LTB4 release from blood monocytes, eosinophil recruitment, TGF-beta release, enhanced collagen synthesis, and extracellular-matrix remodeling may be used as measurement of the bioactivity of the effects of the IL4 or IL13 binding protein described herein.

IL13 bioassays also include the proliferation of cancerous or precancerous cell types such as TF-1 erythroleukemic cells. IL13 neutralization can be measured specifically as the ability of the IL13 binding protein to reduce IL13 binding to IL13R-alpha1 or IL13R-alpha2.

An IL13 binding composition of the invention can inhibit IL13 binding in a way that the apparent dissociation constant ($K_d$) between IL13 and IL13Ralpha2 or IL13Ralpha2 or an IL4 binding composition of the invention can inhibit IL4 binding in a way that the apparent dissociation constant ($K_d$) between IL4 and IL4RA is increased more than $10^2$-fold, preferably more than $10^3$-fold, more preferably more than $10^4$-fold, more preferably more than $10^5$-fold, and most preferably more than $10^6$-fold. Preferred for IL13-binding is a binding protein and/or binding domain that inhibits IL13 or the human IL13 R130Q protein variant (IL13 R130Q—Vladich et al. "IL13 R130Q, a common variant associated with allergy and asthma, enhances effector mechanisms essential for human allergic inflammation" J Clin Invest. 2005; 115(3):747-754) binding to IL13Ralpha2 under specified in vitro conditions with an $IC_{50}$ value below 100 nM, preferably below 10 nM, and more preferably below 1.0 nM.

IL4 neutralization can be measured specifically as the ability of the IL4 binding protein to reduce IL4 binding to IL4 RA. The IL4 binding proteins of the invention are characterized by the ability to inhibit IL4 dependent phosphorylation of STAT6 in a cell expressing a Type 2 IL4 receptor complex, such as a recombinant HEK cell line expressing a STAT6-bla reporter. The IL4 binding proteins are further characterized as having the additional property of being able to block or reduce signaling in a cell having the Type 1 IL4 receptor complex, such as demonstrated by inhibiting naive T-cell differentiation to the Th2 phenotype. The IL4 binding protein may block or reduce stimulation of IL-4 dependent TARO production from cells, such as A549 cells in the presence of 67 pM IL4. The IL4 binding protein of the invention binds to human and to *Macaque* spp. monkey IL4 homolog protein.

When an IL4 binding protein of the invention is coupled to an IL13 binding protein, the composition can inhibit IL13 binding in a way that the apparent dissociation constant ($K_d$) between IL13 and IL13Ralpha1 or IL13Ralpha2 is increased more than $10^2$-fold, preferably more than $10^3$-fold, more preferably more than $10^4$-fold, more preferably more than $10^5$-fold, and most preferably more than $10^6$-fold. Preferred is a binding protein and/or binding domain that inhibits IL13 or the human IL13 R130Q protein variant (IL13 R130Q, Vladich et al. *J Clin Invest.* 2005; 115(3):747-754) binding to IL13Ralpha2 under specified in vitro conditions with an $IC_{50}$ value below 100 nM, preferably below 10 nM, and more preferably below 1.0 nM.

One embodiment of the invention is a binding protein comprising a repeat module capable of blocking human IL4 or IL4 and IL13 activation of STAT6 phosphorylation in HEK-Blue STAT-6 cells which display the IL13Ralpha1 and IL4 RA proteins and, which when activated by IL4 or IL13, induces secretion of a reporter protein which is an active enzyme alkaline phosphatase capable of transforming substrate to a chromophor. The binding protein of the invention inhibits IL4 or IL4 and IL13 activation of STAT6 with an $IC_{50}$ of 1 nM or less, and preferably, 100 pM or less, and more preferably 10 pM or less in an in vitro assay. In addition, the binding protein of the invention inhibits cyno IL4 or IL13 from binding to the same cells with an $IC_{50}$ which is 5 nM or less, and preferably 1 nM or less and, in addition, where the ratio between the $IC_{50}$ for human IL4 or IL13 and the cynomolgous homologue IL4 or IL13 $IC_{50}$ inhibition of STAT6 in engineered HEK-blue cells is 10 or less in an in vitro assay. Representative assays are described herein an known to those in the art.

Whereas, thymus and activation-regulation chemokine (TARO) is upregulated by IL13 (Imai et al. (1999) Int. Immunol. 11:81-88), induces the migration of TH2 cells (Hijnen et al. (2004) J. All. Clin. Immun. 113(2):334-40) and is upregulated in the airways of asthmatic patients (Leung et al. (2004) J. All. Clin. Immun. 114(1): 199-202); an embodiment of the binding protein and/or binding domain of the invention will inhibit TARO production by A549 cells with an $IC_{50}$ value below 500 pM, preferably below 100 pM, and more preferably below 50 pM in the presence of 67 pM IL4.

Compositions

The IL4-binding AR compositions of the invention conform to the formula of a binding protein (N-Cap-[AR]$_n$-C-Cap (I)) having two or three repeat modules which have affinity for binding to IL13 measured as a $K_D$ of $10^{-6}$ M or less, a $K_D$ of $10^{-7}$ M or less, a $K_D$ of $10^{-8}$ M or less, or a $K_D$ of $10^{-9}$ M or less, which binding protein molecules are comprised of a repeat module of SEQ ID NO: 1. In one embodiment of the IL4-binding protein, the AR domain comprises a repeat module with the sequence selected from any of SEQ ID NOS: 31-81.

In a particular embodiment of the invention, the IL4-binding protein, the AR1 sequence is selected from the group consisting of SEQ ID NOS: 31-46; followed by a second designed ankyrin repeat domain (AR2) selected from the group consisting of SEQ ID NOS: 47-61; and, optionally, where the second designed ankyrin repeat unit is followed by a third designed ankyrin repeat (AR3) unit selected from the group consisting of SEQ ID NOS: 62-78; and, optionally, the AR3 repeat unit is followed by an AR4 unit selected from the group consisting of SEQ ID NO: 79-81.

In a particular embodiment, the IL4 binding protein comprises an ankyrin repeat module with the ankyrin repeat sequence of SEQ ID NO: 53, wherein said repeat module is preceded by a repeat module with the ankyrin repeat sequence motif of SEQ ID NO: 36 and/or followed by a repeat module with the ankyrin repeat sequence motif of SEQ ID NO: 68.

In a particular embodiment, the IL4 binding protein comprises an ankyrin repeat module with the ankyrin repeat sequence of SEQ ID NO: 56, wherein said repeat module is preceded by a repeat module with the ankyrin repeat sequence motif of SEQ ID NO: 39 and/or followed by a repeat module with the ankyrin repeat sequence motif of SEQ ID NO: 71.

In a particular embodiment, the IL4 binding protein comprises an AR unit with the sequence of SEQ ID NO: 59, wherein said repeat module is preceded by a repeat module with the AR sequence motif of SEQ ID NO: 43 and/or followed by a repeat module with the AR sequence motif of SEQ ID NO: 74.

In further embodiments exemplified herein, the AR units tandem arrangement is as specified in Table 3 by the designated SEQ ID NO: corresponding to the AR sequence motif at the specified position in the binding protein.

In one embodiment, the invention is an IL4 binding protein, wherein one AR unit selected from SEQ ID NOS: 31-81 is preceded by an N-Cap comprising SEQ ID NO: 2 and variants thereof. The variants comprise SEQ ID NO: 1 and molecules having 75% or greater identity to any of the molecules of SEQ ID NOS: 31-81 that bind to IL4 protein. In another embodiment, the invention is an IL4 binding protein, wherein one AR unit selected from SEQ ID NOS: 31-81 is followed by a C-cap comprising SEQ ID NO: 3 and variants thereof.

The IL4 binding protein having a binding domain with binding specificity for IL4 comprising the AR unit sequence selected from SEQ ID NOS: 31-81, may have its sequence modified for the purpose of: improving expression in a host cell, reducing the potential for one or more residues to undergo oxidation, reducing the potential for residues to undergo chemical deamidation, reducing the potential for a host to which the binding protein is administered to mount an immunological response, and/or where one or more residues is added or modified for the purpose of joining the IL13 binding protein with another protein or moiety. The binding protein will retain the binding specificity, affinity, and biophysical characteristics of solubility in aqueous solutions and lack of tendency to self-aggregate, and have a melting temperature greater than 45° C.

The invention more specifically encompasses an IL4 binding protein derived from a consensus sequence (motif) or observed frequency of identity of a particular amino acid at a diversified position obtained from a multi-sequence alignment of repeat units. For example, the IL4 binding protein may comprise ankyrin repeat modules AR1, AR2, and AR3 arranged in tandem having sequence motif of SEQ ID NO: 1, and wherein the AR1 module has an amino acid according to the formula (wherein bracketed sequences mean alternate amino acids for that position):

$X_1$D-[DW]-G$X_4$TPLHLAA-[TD]-GHLEIVEVLLK$X_7$GADVNA, wherein $X_1$ is selected from T, V, I, L, S, A, E, F, H, K, and Y; $X_4$ is selected from D, F, L, I, N, E, S, Y, and T; and $X_7$ is selected from H, N, and Y (SEQ ID NO: 82);

the AR2 module having an amino acid sequence represented by the formula:

$X_1$D-$X_2X_3$-G$X_4$TPLHLAA-[$X_5X_6$]-GHLEIVEVLLK$X_7$GADVNA, wherein $X_1$ is selected from S, I, D, Q, A, E, H, K, L, M, N, and V; $X_2X_3$ is selected from AM, RM, AI, AS, NF, NI, NL, MN, WN, SQ, DD, DT, ET, and LF; $X_4$ is selected from D, M, L, F, I, N, W, and Y; $X_5X_6$ is selected from VY, VE, FF, FV, AD, AT, DF, FD, VD, LY, YY, and WT and $X_7$ is selected from H, N, and Y (SEQ ID NO: 83); and the AR3 module having an amino acid sequence represented by the formula:

$X_1$D-$X_2X_3$-G F-TPLHLAA-$X_5X_6$-GHLEIVEVLLK$X_7$GADVNA, wherein $X_1$ is selected from M, K, V, E, N, Q, T, S and Y; $X_2X_3$ is selected from FS, QT, LA, HH, SH, IL, IS, NL, MI, SN, RT, and LH; $X_5X_6$ is selected from FY, FS, NF, VD, EF, FA, FF, FW, SY, YN, and YY; and $X_7$ is selected from H, N, and Y (SEQ ID NO: 84).

In another embodiment, IL4 binding protein may comprise ankyrin repeat modules AR1, AR2, and AR3 arranged in tandem having sequence motif of SEQ ID NO: 1, and wherein the AR1 module has an amino acid according to the formula:

TD-[DW]-G$X_4$TPLHLAA-[TD]-GHLEIVEVLLK$X_7$GADVNA, wherein $X_4$ is selected from D, F, L, I, N, E, Y, and T and $X_7$ is selected from H, N, and Y (AR1-F, SEQ ID NO:85);

the AR2 module has an amino acid sequence represented by the formula:

$X_1$D-[AM]-G$X_4$TPLHLAA-[VY]-GHLEIVEVLLK$X_7$GADVNA, wherein $X_1$ is selected from S, I, D, Q, A, E, H, K, N, and V; $X_4$ is selected from D, M, L, F, I, and Y; and $X_7$ is selected from H, N, and Y (AR2-F, SEQ ID NO: 86); and the AR3 module has an amino acid sequence represented by the formula:

$X_1$D-[$X_2X_3$]-G-F-TPLHLAA-[FY]-GHLEIVEVLLK$X_7$GADVNA, wherein $X_1$ is selected from M, K, V, E, N, T, S, and Y; $X_2X_3$ is selected from FS, QT, LA, HH, SH, IL, IS, NL, MI, SN, RT, LH, and VH; and $X_7$ is selected from H, N, and Y (AR3-F, SEQ ID NO: 87).

Based on optimized, active IL4 binding protein sequences, an IL4 binding protein of the invention may comprise ankyrin repeat modules AR1, AR2, and AR3 arranged in tandem having sequence motif of SEQ ID NO: 1, and wherein the AR1 module has an amino acid according to the formula:

[A,L,T]-DD-[S,W]-G-[D,I,Y]-TPLHLAA-[E,T]-DGHLEIVEVLLK-[A,H]-GADVNA (AR1-O) (SEQ ID NO: 88), followed by an AR2 module according to the formula:

[A,N,Q]-D-[NL,RL,AI]-GDTPLHLAA-[WT,FV,LY]-GHLEIVEVLLK-[A,Y]-GADVNA (AR2-O) (SEQ ID NO: 89), followed by an AR3 module according to the formula:

[T,V,Y]-D-[1S, LA, LH]-G-[F,I,V]-TPLHLAAF-[W,Y]-GHLEIVEVLLK-[A,H]-GADVNA (AR3-O) (SEQ ID NO: 90); where the bracketed entries represent the alternative amino acid residue or pair of residues.

In a preferred embodiment, the binding domains of the IL4 binding proteins include an N-capping module and a C-capping module as described and exemplified herein.

The IL13-binding AR compositions of the invention conform to the formula of a binding protein (N-Cap-[AR]$_n$-C-Cap (I)) having two or three repeat modules which have affinity for binding to IL13 measured as a $K_D$ of $10^{-6}$ M or less, a $K_D$ of $10^{-7}$ M or less, a $K_D$ of $10^{-8}$ M or less, or a $K_D$ of $10^{-9}$ M or less, which binding protein molecules are comprised of a repeat module of SEQ ID NO: 1. In one embodiment of the IL4-binding protein, the AR domain comprises a repeat module with the sequence selected from any of SEQ ID NOS: 108-155.

In a particular embodiment of the invention, the IL13-binding protein, the AR1 repeat sequence is selected from the group consisting of SEQ ID NOS: 108-125; followed by a second designed ankyrin repeat domain (AR2) selected from the group consisting of SEQ ID NOS: 109-143; and, optionally, where the second designed ankyrin repeat unit is, optionally, followed by a third designed ankyrin repeat domain (AR3) selected from the group consisting of SEQ ID NOS: 144-155.

The invention more specifically encompasses an IL13 binding protein derived from a consensus sequence (motif) or observed frequency of identity of a particular amino acid at a diversified position obtained from a multi-sequence alignment of repeat units. For example, the IL13 binding protein may comprise ankyrin repeat modules AR1, AR2, and AR3 arranged in tandem having sequence motif of SEQ ID NO: 1, and wherein the AR1 module has an amino acid sequence according to the formula:

$X_1DX_2$-$X_3$-GSTPLHLAA-RH-GHLEIVEVLLK$X_7$GADVNA, wherein $X_1$ is chosen from T, A, F, E, I, K, M, S, R, V, W; $X_2$ is selected from D, E, H, I, K, M, S, T, and V; $X_3$ is F or Y; and $X_7$ may be H, N, or Y (Formula AR1-C, SEQ ID NO: 156).

the AR2 module has an amino acid sequence according to the formula;

$X_1$DFIGDTPLHLAAY-$X_4$-GHLEIVEVLLK$X_7$GADVNA, wherein $X_1$ is chosen from N, T, A, D, K, E, H, M, and F; $X_4$ may be H or R; and $X_7$ may be H, N, or Y (Formula AR2-C, SEQ ID NO: 158); and the AR3 module has an amino acid sequence according to the formula:

$X_1$D-$X_2$TGETPLHLAA-$X_5X_6$-GHLEIVEVLLK$X_7$GADVNA, wherein $X_1$ is chosen from D, S, T, K, E, and M; $X_2$ is chosen from A, I, T, and V or is absent; $X_5X_6$ are a pair of residues chosen from SM, HL, YH; and $X_7$ may be H, N, or Y (Formula AR3-C, SEQ ID NO: 160);

wherein the residues appearing in brackets are used in the alternative.

In one embodiment of the IL13-binding protein, the AR domain comprises a repeat module with the sequence selected from any of SEQ ID NOS: 108-155. In another embodiment, a binding protein with an AR domain, N-Cap and C-cap modules, may be constructed using the formulas provided herein for the tandem repeat modules such as N-Cap-[AR1-C:AR2-C:AR3-C]-C-cap where the repeat modules are specified by SEQ ID NO: 156, 158 and 160; or N-Cap-[AR1-F:AR2-F:AR3-F]-C-cap where the repeat modules are specified by SEQ ID NO: 157, 159, and 161; or N-Cap-[AR1-O:AR2-O:AR3-O]-C-cap where the repeat modules are specified by SEQ ID NO: 168, 169, and 170; and the N-cap and C-cap are specified by SEQ ID NO: 2 or 171 and SEQ ID NO: 3 and 172, respectively, or modification as described herein or as required for further chemical linkage, biological processing, and the like.

The IL13 binding protein comprising at least one repeat domain with binding specificity for IL13 comprising the repeat unit sequence selected from SEQ ID NOS: 108-155, may have its sequence modified for the purpose of: improving expression in a host cell, reducing the potential for one or more residues to undergo oxidation, reducing the potential for residues to undergo chemical deamidation, reducing the potential for a host to which the binding protein is administered to mount an immunological response, and/or where one or more residues is added or modified for the purpose of joining the IL13 binding protein with another protein or moiety. The binding protein will retain the binding specificity, affinity, and biophysical characteristics of solubility in aqueous solutions and lack of tendency to self-aggregate, and have a melting temperature greater than 45° C.

In one embodiment, the invention is an IL13 binding protein, wherein one ankyrin repeat module selected from SEQ ID NOS: 108-155 is preceded by an N-Cap comprising SEQ ID NO: 2 and variants thereof. The variants comprise SEQ ID NO:1 and molecules having 75% or greater identity to any of the molecules of SEQ ID NOS: 162-167 that bind to IL13 protein and/or IL13 R130Q. In another embodiment, the invention is an IL13 binding protein, wherein one ankyrin repeat domain selected from SEQ ID NOS: 162-167 is followed by a C-cap comprising SEQ ID NO: 3 and variants thereof. In further embodiments exemplified herein, the AR units tandem arrangement is as specified in Table 4 by the designated SEQ ID NO: corresponding to the AR sequence motif at the specified position in the binding protein.

In one embodiment, the invention is an IL13 binding protein, wherein one AR unit selected from SEQ ID NOS: 108-155 is preceded by an N-Cap comprising SEQ ID NO: 2 and variants thereof. The variants comprise SEQ ID NO: 1 and molecules having 75% or greater identity to any of the molecules of SEQ ID NOS: 108-155 that bind to IL13 protein. In another embodiment, the invention is an IL13 binding protein, wherein one AR unit selected from SEQ ID NOS: 108-155 is followed by a C-cap comprising SEQ ID NO: 3 and variants thereof.

A binding protein that competes with IL13Ralpha2 for binding to IL13 with a selected repeat domain can be identified by methods well known to the person skilled in the art, such as a competition Enzyme-Linked ImmunoSorbent Assay (ELISA). Further, a modified binding protein having one or more modified repeat unit sequences may be tested for activity using a competition binding to IL13 with a binding protein known to compete with IL13Ralpha2 for binding to IL13.

Functional Properties

An IL4 binding protein that competes with IL4RA for binding to IL4 or an IL13 binding protein that competes with IL13Ralpha1 and IL13Ralpha2 for binding to IL13 with a selected repeat domain can be identified by methods well known to the person skilled in the art, such as a competition Enzyme-Linked ImmunoSorbent Assay (ELISA). Further, where a modified IL4 or IL13 neutralizing binding protein having one or more modified repeat unit sequences is desired to be produced, the activity of the modified binding protein may be tested for activity using a competition binding to of the modified binding protein with the unmodified protein. A modified IL4 binding protein may be tested in competition with a known IL4 binding protein for binding to IL4 and a modified IL13 binding protein may be tested in competition with an IL13 binding protein known to compete with IL13Ralpha1 and IL13Ralpha2 for binding to IL13.

In one embodiment of a modified binding protein, one or more of the amino acid residues of the repeat modules of said repeat domain are exchanged by an amino acid residue found at the corresponding position on alignment of a repeat unit. In one aspect, up to 30% of the amino acid residues are exchanged, more frequently, up to 20%, and even more frequently, up to 10% of the amino acid residues are exchanged. Most preferably, the source of the exchanged residue is a repeat unit which is a naturally occurring repeat unit. In still another particular embodiment, the amino acid residues are exchanged with amino acids which are not found in the corresponding positions of repeat units.

In further embodiments, any of the IL4 and/or IL13 binding proteins or domains described herein may be covalently bound to one or more additional moieties, including, for example, a moiety that improves persistence in the circulation or decreases elimination from the body (i.e., improves pharmacokinetics), a labeling moiety (e.g., a fluorescent label, such as fluorescein, or a radioactive tracer), a moiety that facilitates protein purification (e.g., a small peptide tag, such as a His- or strep-tag), a moiety that provides effector functions for improved therapeutic efficacy (e.g., the Fc part of an antibody to provide antibody-dependent cell-mediated cytotoxicity), a toxic protein moiety, such as *Pseudomonas aeruginosa* exotoxin A (ETA) or a small molecular toxic agent such as a maytansinoid, calicheamicin, or platinum containing DNA alkylating agents. Improved pharmacokinetics may be assessed according to the perceived therapeutic need. Often it is desirable to increase bioavailability and/or increase the time between doses, possibly by increasing the time that a protein remains available in the serum after dosing. In some instances, it is desirable to improve the continuity of the serum concentration of the protein over time (e.g., decrease the difference in serum concentration of the protein shortly after administration and shortly before the next administration). Moieties that slow clearance of a protein from the blood include hydroxyethyl starch (HES), polyethylene glycol (PEG), sugars (e.g., sialic acid), well-tolerated protein moieties (e.g., Fc fragment or serum albumin), and binding domains or peptides with specificity and affinity for abundant serum proteins, such as those capable of binding to serum albumin.

Nucleic Acids and Uses

In a further embodiment, the invention relates to nucleic acid molecules encoding the particular IL4 and/or IL13 binding proteins and, further, a vector comprising the nucleic acid molecule. In general, a bacterial expression vector will contain (1) regulatory elements, usually in the form of viral promoter or enhancer sequences and characterized by a broad host and tissue range; (2) a sequence, facilitating the insertion of a DNA fragment within the vector; and (3) the sequences encoding the final protein. The vector will likely also contain (4) a selectable marker gene(s) (e.g., the beta-lactamase gene), often conferring resistance to an antibiotic (such as ampicillin), allowing selection of initial positive transformants; and (5) sequences facilitating the replication of the vector in bacterial and mammalian host cells, or sequences promoting stable insertion into the genome of the host. A plasmid origin of replication are included for propagation of the expression construct in bacteria such as *E. coli* and for transient expression in Cos cells, the SV40 origin of replication is included in the expression plasmid. In addition, a suitable mammalian cell line may be used having the properties addressed above.

Therefore, the invention contemplates host cells used in the recombinant expression of the IL4 and IL13 binding protein repeat domains and proteins and more complex constructs comprising the IL4 and IL13 binding repeat proteins, which host cells will comprise the nucleic acids encoding such proteins. The IL4 and IL13 binding proteins may be purified from cultures in which such host cells are maintained as batch or continuous cultures by methods known in the art. The isolated proteins may be expressed with appended moieties, such as tags, that facilitate purification and which can be subsequently removed prior to final formulation and packaging of the protein for its intended use.

Formulations and Uses of IL4 and IL13 Binding Repeat Proteins

A pharmaceutical composition of the invention comprises one or more of the above mentioned binding proteins, in particular, binding proteins comprising repeat domains, or nucleic acid molecules encoding the particular binding proteins and, optionally, a pharmaceutically acceptable carrier and/or diluent. Pharmaceutically acceptable carriers and/or diluents are known to the person skilled in the art and are explained in more detail below. Even further, the invention comprises a diagnostic composition comprising one or more of the above mentioned binding proteins, in particular, binding proteins comprising repeat domains. Where delivery of a nucleic acid encoding the IL4 and IL13 binding protein is performed, the pharmaceutical preparation of the therapy vector can include the vector in an acceptable diluent, or can comprise a slow release matrix in which the vector is imbedded. Alternatively, where the complete vector can be produced intact from recombinant cells, e.g., retroviral vectors, the pharmaceutical preparation can include one or more cells which produce the nucleic acid delivery system.

A pharmaceutical composition of the invention is a stable formulation comprising the IL4 and IL13 binding protein, which may be an aqueous phosphate buffered saline or mixed salt solution or, alternatively, preserved solutions and formulations, multi-use preserved formulations suitable for pharmaceutical or veterinary use in a pharmaceutically acceptable formulation. Suitable vehicles and their formulation, inclusive of other proteins, e.g., human serum albumin, are described, for example, in e.g. Remington: The Science and Practice of Pharmacy, 21$^{st}$ Edition, Troy, D. B. ed., Lipincott Williams and Wilkins, Philadelphia, Pa. 2006, Part 5, Pharmaceutical Manufacturing pp 691-1092, See especially pp. 958-989. The formulations to be used for in vivo administration may be aseptic or sterile. This is readily accomplished by filtration through sterile filtration membranes but other methods may be applied, such as heat, gas or chemical sterilization, or by the use of ionizing radiation to some or all of the components of the formulation.

The pharmaceutical composition may be administered by any suitable method within the knowledge of the skilled practitioner, wherein the administration may be performed by another or self-administered. The route of administration may be selected from a variety of delivery methods including but not limited to: intravenous (I.V.); intramusclular (I.M.); subcutaneous (S.C.); transdermal; pulmonary; transmucosal (oral, intranasal, intravaginal, rectal); using a formulation in a tablet, capsule, solution, powder, gel, particle; and contained in a syringe, an implanted device, osmotic pump, cartridge, micropump; or other means appreciated by the skilled artisan, as well-known in the art.

For example, site specific administration may be to body compartment or cavity such as intrarticular, intrabronchial, intraabdominal, intracapsular, intracartilaginous, intracavitary, intracelial, intracelebellar, intracereboventricular, intracolic, intracervical, intragastric, intrahepatic, intracardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravascular, intravesical, intralesional, vaginal, rectal, buccal, sublingual, intranasal, or transdermal means.

The IL4 and IL13 binding protein can be administered directly to the respiratory tract by a nebulizer, such as jet nebulizer or an ultrasonic nebulizer. Typically, in a jet nebulizer, a compressed air source is used to create a high-velocity air jet through an orifice. As the gas expands beyond the nozzle, a low-pressure region is created, which draws a solution of protein through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer. In an ultrasonic nebulizer, high-frequency electrical energy is used to create vibrational, mechanical energy, typically employing a piezoelectric transducer. This energy is transmitted to the formulation of protein either directly or through a coupling fluid, creating an aerosol including the protein. Advantageously, particles of protein delivered by a nebulizer have a particle size less than about 10 μm, preferably in the range of about 1 μm to about 5 μm, and most preferably about 2 μm to about 3 μm.

Indications

The invention further provides novel methods of treatment of IL4 and IL13 mediated diseases and conditions, in particular, respiratory conditions, such as asthma and pulmonary fibrosis, cardiovascular conditions, cancer, dermatological, and fibrotic conditions. The present invention provides high affinity IL4/IL13 bispecific binding proteins, and nucleic acids encoding them, capable of blocking the biological activity of IL4, in vitro, in vivo, or in situ including, but not limited to, inhibiting wild-type or natural variants of human IL4 binding to IL-4RA or fragments thereof, inhibiting IL4 RA complexes on cells from signaling in the presence of IL4, and preventing or suppressing IL4-dependent differentiation of naïve T-cells to Th2 cells.

Binding proteins capable of binding and neutralizing IL13 have one or more properties selected from: inhibiting binding of IL13 to human IL13 receptor alpha 1 (IL13Ralpha1) (UniProt. P78552) or fragments thereof, inhibiting human IL13 or natural variants of human IL13 binding to the human IL13 receptor alpha 2 (IL13Ralpha2) (UniProt. Q14627) or fragments thereof, preventing or suppressing human IL13-dependent proliferation of human tumor cells, inhibiting human IL13-dependent IgE production, reducing eosinophilic infiltration of tissues, and which protein has a specific binding site on human IL13.

In one aspect, a method of treating a human patient afflicted with a disease or disorder selected from the group consisting of a form of asthma which can be named allergic asthma, severe asthma, difficult asthma, brittle asthma, nocturnal asthma, premenstrual asthma, steroid resistant asthma, steroid dependent asthma, aspirin induced asthma, adult-onset asthma, pediatric asthma, or exercise induced asthma; atopic disease such as atopic dermatitis; allergic rhinitis; Crohn's disease; COPD; fibrotic diseases or disorders such as idiopathic pulmonary fibrosis, progressive systemic sclerosis, hepatic fibrosis, radiation-induced fibrosis, chemotherapy-induced fibrosis; hepatic granulomas; schistosomiasis, leishmaniasis, diseases of cell cycle regulation such as Hodgkins disease; B cell chronic lymphocytic leukaemia; which method comprises administering a therapeutically effective amount of an IL4/IL13 binding protein.

Examples of IL4/IL13-associated disorders or conditions include, but are not limited to, disorders chosen from one or more of: IgE-related disorders, including but not limited to, atopic disorders, e.g., resulting from an increased sensitivity to IL4/IL13 (e.g., atopic dermatitis, urticaria, eczema, and allergic conditions such as allergic rhinitis and allergic enterogastritis); respiratory disorders, e.g., asthma (e.g., allergic and nonallergic asthma (e.g., asthma due to infection with, e.g., respiratory syncytial virus (RSV), e.g., in younger children)), chronic obstructive pulmonary disease (COPD), and other conditions involving airway inflammation, eosinophilia, fibrosis and excess mucus production, e.g., cystic fibrosis and pulmonary fibrosis, systemic sclerosis (SSc), and idiopathic pulmonary fibrosis (IPF) and sarcoidosis, desquamative interstitial pneumonia, acute interstitial pneumonia, respiratory bronchiolitis-associated interstitial lung disease, idiopathic bronchiolitis obliterans with organizing pneumonia; lymphocytic interstitial pneumonitis; Langerhans' cell granulomatosis; idiopathic pulmonary hemosiderosis; acute bronchitis; pulmonary alveolar proteinosis; bronchiectasis; atelectasis; cystic fibrosis; inflammatory and/or autoimmune disorders or conditions, gastrointestinal disorders or conditions (e.g., inflammatory bowel diseases (IBD) and eosinophilic esophagitis (EE), and eosinophilic-mediated gastrointestinal disease, ulcerative colitis and/or Crohn's disease), liver disorders or conditions (e.g., cirrhosis, hepatocellular carcinoma), and scleroderma; tumors or cancers (e.g., soft tissue or solid tumors), such as leukemia, glioblastoma, and lymphoma, e.g., Hodgkin's lymphoma; viral infections (e.g., from HTLV-I); fibrosis of other organs, e.g., fibrosis of the liver (e.g., fibrosis caused by a hepatitis B and/or C virus); and suppression of expression of protective type 1 immune responses, (e.g., during vaccination).

The method of treating a subject includes administering a high affinity IL4 and IL13 bispecific binding protein to the subject, in an amount effective to reduce one or more symptoms of the disorder or condition (e.g., in an amount effective to reduce one or more of: a respiratory symptom (e.g., bronchoconstriction), IgE levels, release or levels of histamine or leukotriene, or eotaxin levels in the subject). In the case of prophylactic use (e.g., to prevent, reduce or delay onset or recurrence of one or more symptoms of the disorder or condition), the subject may or may not have one or more symptoms of the disorder or condition.

In one embodiment, the high affinity IL4 and IL13 bispecific binding protein inhibits or reduces one or more symptoms associated with an early phase of the IL4 or IL13 associated disorder, e.g., an "early asthmatic response" or "EAR." For example, the IL4 and IL13 bispecific binding protein reduces one or more symptoms associated with an EAR, at about 0.25 to 3 hours after an insult (e.g., allergen exposure) until about 3 hours after insult (e.g., allergen exposure). The IL4 and IL13 bispecific binding protein can decrease or prevent one or more symptoms of the EAR as compared to the level or degree of the symptom in the subject in the absence of the IL4 and IL13 bispecific binding protein. Alternatively, the IL4 and IL13 bispecific binding protein can prevent as large of an increase in the symptom, e.g., as compared to the level or degree of the symptom in the subject in the absence of the IL4 and IL13 bispecific binding protein) including, but not limited to, one or more of: a release of at least one allergic mediator such as a leukotriene and/or histamine, e.g., from airway mast or basophil cells; an increase in the levels of at least one allergic mediator, such as a leukotriene and/or histamine; bronchoconstriction; and/or airway edema.

In other embodiments, the IL4 and IL13 bispecific binding protein inhibits or reduces one or more symptoms associated with a late phase of an IL4 or IL13 associated disorder, e.g., a "late asthmatic response" or "LAR." For example, the IL13 binding protein reduces one or more symptoms associated with an LAR, e.g., at about 3 hours and up to about 24 hours after an insult (e.g., allergen exposure). For example, the IL4 and IL13 bispecific binding protein can decrease or prevent one or more symptoms of the LAR (e.g., as compared to the level or degree of the symptom in the subject in the absence of the binding protein), e.g., one or more of: airway reactivity and/or an influx and/or activation of inflammatory cells, such as lymphocytes, eosinophils and/or macrophages, e.g., in the airways and/or bronchial mucosa. Alternatively, the IL4 and IL13 bispecific binding protein can prevent as large of an increase in the symptom, e.g., as compared to the level or degree of the symptom in the subject in the absence of the IL4 and IL13 bispecific binding protein.

The IL4 and IL13 bispecific binding protein can be administered prior to the onset or recurrence of one or more symptoms associated with the IL4/IL13-disorder or condition, but before a full manifestation of the symptoms associated with the disorder or condition. In certain embodiments, the IL4 and IL13 bispecific binding protein is administered to the subject prior to exposure to an agent that triggers or exacerbates an IL4/IL13-associated disorder or condition, e.g., an allergen, a pollutant, a toxic agent, an infection and/or stress. In some embodiments, the IL4 and IL13 bispecific binding protein is administered prior to, during, or shortly after exposure to the agent that triggers and/or exacerbates the IL13-associated disorder or condition. For example, the IL4 and IL13 bispecific binding protein can be administered 1, 5, 10, 25, or 24 hours; 2, 3, 4, 5, 10, 15, 20, or 30 days; or 4, 5, 6, 7 or 8 weeks, or more before or after exposure to the triggering or exacerbating agent. Typically, the IL4 and IL13 bispecific binding protein can be administered anywhere between 24 hours and 2 days before or after exposure to the triggering or exacerbating agent.

In another embodiment of the invention, an IL4 and IL13 bispecific binding protein inhibiting the activity of human IL4 or IL13 or naturally occurring variant, as described above, can be used in combination with a second binding protein or with an active that is a small molecule which can act additively or synergistically with the IL4 and IL13 bispecific binding protein or can act through a complementary mechanism to ameliorate one or more disease symptoms or sequelae. For example, an IL4 binding protein that is an IL4 antagonist could be administered with an IL13 binding protein. Since many disease pathologies are multi-factorial, efficacy may be improved by combining agents that inhibit multiple targets on one pathway or multiple targets on different pathways. One advantage of the IL4 and IL13 bispecific binding proteins of the invention is the ability to genetically link them together so that one binding protein inhibits one target and a second binding protein inhibits a different target or multiple targets. Alternatively, a specific cysteine residue could be introduced into a unique position on the binding protein that does not interfere with binding and used to directly couple a small molecule therapeutic. Coadministration of an IL4 and IL13 bispecific binding protein with a second therapeutic agent is also possible.

Examples of preferred additional therapeutic agents that can be coadministered and/or coformulated with an IL4 and IL13 bispecific binding protein include: inhaled steroids; beta-agonists, e.g., short-acting or long-acting beta-agonists; antagonists of leukotrienes or leukotriene receptors; combination drugs such as ADVAIR®; IgE inhibitors, e.g., anti-IgE antibodies (e.g., XOLAIR®); phosphodiesterase inhibitors (e.g., PDE4 inhibitors); xanthines; anticholinergic drugs; mast cell-stabilizing agents such as cromolyn; IL4 inhibitors (e.g., an IL4 inhibitor antibody, IL4 receptor fusion or an IL4 mutein); IL-5 inhibitors; eotaxin/CCR3 inhibitors; and antihistamines. Such combinations can be used to treat asthma and other respiratory disorders. Additional examples of therapeutic agents that can be co-administered and/or co-formulated with an IL4 and IL13 bispecific binding protein include one or more of: TNF antagonists (e.g., a soluble fragment of a TNF receptor, e.g., p55 or p75 human TNF receptor or derivatives thereof, e.g., 75 kd TNFR-IgG (75 kD TNF receptor-IgG fusion protein, ENBREL®)); TNF enzyme antagonists, e.g., TNFalpha converting enzyme (TACE) inhibitors; muscarinic receptor antagonists; TGFbeta antagonists; interferon gamma; perfenidone; chemotherapeutic agents, e.g., methotrexate, leflunomide, or a sirolimus (rapamycin) or an analog thereof, e.g., CCI-779; COX2 and cPLA2 inhibitors; NSAIDs; immunomodulators; and NFkB inhibitors, among others.

Method of Producing the IL4 and IL13 Binding Protein

The IL4 and IL13 bispecific binding protein according to the invention may be obtained and/or further evolved by several methods, such as ribosomal display (WO 98/48008), display on the surface of bacteriophages (WO 90/02809, WO 07/006,665) (a different signal sequence that allows export of folded proteins may be required; Steiner, D. et al. JMB 2008 382(5) 1211-1227) or bacterial cells (WO 93/10214), display on plasmids (WO 93/08278) or by using covalent RNA-repeat protein hybrid constructs (WO 00/32823), or intracellular expression and selection or screening such as by protein complementation assay (WO 98/341120). Such methods are known to the person skilled in the art.

A library of ankyrin repeat proteins used for the selection, screening, and characterization of a binding protein according to the invention may be obtained according to protocols known to the person skilled in the art (WO 02/020565, Binz, H. K. et al., JMB, 332, 489-503, 2003, and Binz et al., 2004, loc. cit). The use of such a library for the selection of human IL4 and IL13 specific binding proteins is given in Example 1. In analogy, the ankyrin repeat sequence motifs as presented above can used to build libraries of ankyrin repeat proteins that may be used for the selection or screening of human IL4 and/or IL13 binding proteins. Furthermore, repeat domains of the present invention may be modularly assembled from repeat modules according the current inventions and appropriate capping modules (Forrer, P., et al., FEBS letters 539, 2-6, 2003) using standard recombinant DNA technologies (e.g. WO 02/020565, Binz et al., 2003, loc. cit. and Binz et al., 2004, loc. cit).

As the nucleic acids encoding the desired IL4 and/or IL13 binding repeat modules are identified from, for example, the libraries described herein comprising designed repeat modules coded in tandem repeats to form binding domains; they are isolated and used to form expression vectors for use as therapeutics or for construction of host cells for the purpose of preparing and purifying the IL4 and IL13 bispecific binding domains. The host cells may be bacterial, insect, plant, or mammalian and or may be selected from COS-1, COS-7, HEK293, BHK21, CHO, BSC-1, Hep G2, 653, SP2/0, 293, HeLa, myeloma, lymphoma, yeast, insect or plant cells; or may be any derivative, subline, immortalized or transformed cell related to the aforementioned cell types or cell lines.

The invention is not restricted to the particular embodiments described in the Examples. Other sources may be used and processed following the general outline described below.

EXAMPLES

All of the starting materials and reagents disclosed below are known to those skilled in the art, and are available commercially or can be prepared using well-known techniques.
Materials Chemicals were purchased from Fluka (Switzerland). Oligonucleotides were from Microsynth (Switzerland). Unless stated otherwise, DNA polymerases, restriction enzymes and buffers were from New England Biolabs (USA) or Fermentas (Lithuania). The cloning and protein production strain was *Escherichia coli* XL1-blue (Stratagene, USA). The PBS used contained 137 mM NaCl, 10 mM phosphate, and 2.7 mM KCl at pH 7.4

Designed Ankyrin Repeat Protein Libraries

The N2C and N3C designed ankyrin repeat protein libraries are described (WO 02/20565; Binz et al. 2003, loc. cit.; Binz et al. 2004, Nat Biotechnol 22: 575-82, 2004; Binz, et al., J Mol Biol 332: 489-503, 2003). The digit in N2C (e.g., 2 ankyrin repeat modules) and N3C (e.g., 3 ankyrin repeat modules) describes the number of randomized ankyrin repeat modules present between the N-terminal and C-terminal capping modules. The nomenclature used to define the positions inside the repeat units and modules is based on Binz et al. 2004, loc. cit. with the modification that borders of the repeat modules and repeat units are shifted by one amino acid position. For example, position 1 of a repeat module of Binz et al. 2004 (loc. cit.) corresponds to position 2 of a repeat module of the current disclosure (SEQ ID NO: 1) and consequently position 33 of a repeat module or of the N-cap module of Binz et al. 2004, loc. cit. corresponds to position 1 of a following repeat module as presently described. All the DNA sequences were confirmed by sequencing.

Example 1

Selection of Binding Proteins Comprising a Repeat Domain With Binding Specificity for IL4 and IL13

The selection of IL4- and IL13-binding specific ankyrin repeat proteins was performed by ribosome display (Hanes and Plückthun, loc. cit.) using a recombinant human IL4 target protein (UniProt Accession No: P05112, SEQ ID NO: 4) and IL13 protein.

Selection and Screening of Human IL4 Binding Proteins:

In total, nine ribosome display selection rounds on biotinylated human IL4 (Peprotech #200-04, mature protein produced in *E. coli*) were performed with the N2C and N3C AR protein libraries. The first four rounds were standard ribosome display selection rounds according to previously published protocols, using decreasing target concentration and increasing washing stringency to increase selection pressure from round 1 to round 4 (Binz, Amstutz, Kohl, Stumpp, Briand, Forrer, Grutter and Pluckthun, Nat Biotechnol 22: 575-82, 2004; Zahnd, et al., Nat Methods 4: 269-79, 2007). The pools after these four initial rounds were screened for binders to human IL4 by crude extract ELISA and a crude extract cellular HEK/STAT6 functional assay. The selected binders were of nanomolar affinity ($K_D$), as revealed by SPR measurements of single clones (data not shown).

To specifically enrich higher affinity AR proteins, two off-rate selection rounds with increased selection stringency, each followed by one or two standard selection rounds, were performed after the first four rounds (Zahnd, et al., J Biol Chem 281: 35167-75, 2006).

Following this sixth round of ribosome display, single clones obtained from these rounds were screened by crude extract cellular HEK/STAT6 functional assay, to identify the most potent candidates. The pool of selected AR proteins was subcloned into a T5 promoter based vector for expression. Following expression, crude lysates from 200 individual AR proteins were assessed for binding to recombinant IL4 by ELISA and inhibition of IL4 dependent STAT6 phosphorylation in HEK-STAT6 cells. Lysates were prepared by transforming plasmids encoding specific AR proteins into *E. coli* XL-1 blue cells. A 1.2 ml starter culture in Luria Bertani medium (LB) containing 50 ug/ml ampicillin and 1% glucose was inoculated with a single colony. The starter cultures were incubated overnight at 37° C., shaking at 220 rpm. On the next day, a part of the overnight culture was used as inoculum of 0.9 ml LB. Protein expression was induced using 500 uM isopropyl β-D-1-thiogalactopyranoside (IPTG). Cultures were incubated 4 hours at 37° C., shaking at 220 rpm. Cell pellets were harvested by centrifugation and lysed with 50 μl B-Per solution (Pierce). These lysates were diluted with PBS before using them in subsequent screening assays.

In order to assess the binding to IL4, each crude extract of the lysates containing a binding protein was added to Maxisorp ELISA plate pre-coated with neutravidin and biotinylated IL4 and incubated for 1 hour. After extensive washing, bound AR proteins were detected using an anti-RGS-His6-HRP conjugate (34450, Qiagen).

In parallel, the same 200 single clone *E. coli* lysates were subjected to a cellular inhibition assay. The activity of each crude extract sample was assayed for their ability to inhibit IL4 dependent activation of STAT6 using HEK-Blue STAT-6 cells (Invivogen™ SanDiego, Calif.). Stimulation of HEK-Blue STAT-6 cells was carried out as follows: on Day 1, cells were plated in 96-well cell culture plates at a density of 2.5×10$^5$/ml in 100 μl of cell culture media (DMEM with 4.5 g/L Glucose (11995, Gibco/Invitrogen, Carlsbad, Calif.), 10% Heat Inactivated FBS (10082, Gibco/Invitrogen, Carlsbad, Calif.), 10 μg/mL Blasticidin S, a peptidyl nucleoside antibiotic active (Invivogen), and 100 pg/mL Zeocin™, a copper-chelated glycopeptide antibiotic produced by *Streptomyces* CL990 (Invivogen) for 8 hours. On the same day, 100 μl of cell culture media containing the diluted AR protein crude extracts premixed with 50 pg/ml (3.3 pM) human IL4 (Peprotech) were added. The plates were incubated overnight at 37° C. and 5% CO$_2$. To measure secreted embryonic Alkaline™ phosphatase, 30 μl of each cell supernatant was mixed with 80 μl of Quanti-Blue™ (Invivogen) in a clear 96-well plate. The plate was incubated for 1 hour at 37° C. and absorbance at 620 nm was read using a plate reader.

As the initial screen of 200 clones produced only a few AR proteins that bound with high affinity to IL4 and effectively inhibited signaling, single clone crude extracts of 5100 more AR proteins obtained following additional rounds of ribosome display with off-rate selection (rounds 7, 8, and 9) were tested for their ability to inhibit IL4 dependent STAT6 phosphorylation as described above. The activity of these clones were compared in this assay to a benchmark AR protein, clone C06_28E5, found in the first round screen to bind to IL4 with an apparent affinity of 50 pM as revealed by SPR and inhibit STAT6 production with an 1050 of 3 pM in the presence of 3 pM IL4. Thus, comparing subsequently selected clones to the test values of the benchmark allowed for expedient selection of additional high potency candidates.

Based on the results of the STAT6 phosphorylation screen, 22 AR proteins (SEQ ID NO: 9-30) that showed inhibition of IL4 with better or equal activity compared to that of the benchmark were selected for further characterization.

The selection of IL13-binding specific ankyrin repeat proteins was performed by ribosome display (Hanes and Plückthun, loc. cit.) using a human IL13 variant (R130Q) target protein. The IL13 R130Q variant (R110Q of SEQ ID NO: 1) is a variant of human IL13 that has been linked to atopic patients (Arima et al. J. Aller. Clin. Immunol. 109:980-987, 2002).

Selection and Screening of Human IL13 Binding Proteins:

In total, 6 ribosome display selection rounds on human IL13 R130Q (Peprotech) were performed in solution with both the N2C and N3C AR libraries. The first four rounds of selection employed standard ribosome display selection, using decreasing target concentration and increasing washing stringency to increase selection pressure from round 1 to round 4 (Binz et al. Nature Biotech 22:575-582, 2004). After four rounds of panning, the pools were screened for binders to human IL13 in the crude extract using an ELISA format. The selected binders were of nanomolar affinity, as revealed by BIAcore measurements of single clones (data not shown).

Following the fourth round of ribosome display selection, the pool of selected binding proteins were cloned into a T5 promoter based expression vector. Following expression, 200 individual binding proteins were assessed for binding as crude extracts to human L-13 R130Q captured on neutravidin plates. Of these, 32 binding proteins with the highest binding signal by ELISA were expressed and purified by immobilized metal ion affinity chromatography (IMAC) and screened for their ability to inhibit IL13R13Q dependent binding to human IL13Rα2-Fc fusion using an ELISA format: binding protein candidates (10 nM or 100 nM final concentration) were preincubated with 10 nM biotinylated human IL13 R130Q for 30 minutes, the binding protein-IL13 mixture was added to a Maxisorp ELISA plate pre-coated with IL13Rα2-Fc (R&D Systems) and incubated for 15 minutes to capture free biotinylated IL13 and detected using streptavidin-horse radish peroxidase. The relative amount of inhibition produced by the binding protein was assessed by comparing the signal measured for 10 nM biotinylated IL13 with no binding protein added. Based on the results of this screening assay at 10 nM binding protein, which was equimolar to the IL13R130Q, IL13 binding protein 2F1 was chosen as a benchmark for all further screenings.

To identify higher affinity human IL13 binders, the output from the fourth round of standard ribosome display screening (above) was subjected to an off-rate selection round with increased selection stringency. A final standard selection round was performed to amplify and recover the off-rate selected binding proteins. Again, crude extracts were screened for binding to IL13 as described above and the signal relative to 2F1 binding protein was assessed. To enable differentiation between high and low affinity binding proteins, the dilution of the crude extracts of 1:10 was chosen because it allowed clear differentiation of binding proteins with stronger binding to IL13 than the benchmark binding protein 2F1. About 700 binding protein clones were assayed in this manner.

In parallel, crude extracts screened for binding were evaluated for their ability to inhibit IL13 dependent activation of STAT6 using HEK-Blue STAT-6 cells (InVivogen, SanDiego, Calif.). To enable differentiation between high and low affinity binding proteins, an optimal dilution of the crude extract (1:5200) was selected. In the HEK-Blue STAT-6 cells, IL13 activates the IL13Rα1: IL4R complex (Type 2 receptor) to induce secretion of an embryonic alkaline phosphatase (SEAP) reporter gene via the STAT-6 signaling pathway. Stimulation of HEK-Blue STAT-6 cells using crude protein extracts was carried out as follows: on Day 1, cells were plated in 96-well cell culture plates at a density of $2.5 \times 10^5$/ml in 100 uL of cell culture media (DMEM with 4.5 g/L Glucose (11995, Gibco/Invitrogen, Carlsbad, Calif.) with 10% Heat Inactivated FBS (10082, Gibco/Invitrogen, Carlsbad, Calif.), 10 μg/mL Blasticidin (Invivogen), and 100 μg/mL Zeocin (Invivogen)) for 24 hours. On Day 2, 100 μL of cell culture media containing the appropriate concentration of AR protein premixed with 1 ng/mL (80 pM) human IL13 (Peprotech) was added to the cells. The plates were incubated for 24 hours at 37° C. and 5% $CO_2$. To measure secreted embryonic alkaline phosphatase, 40 μL of each cell supernatant was mixed with 160 μL of Quanti-Blue (Invivogen) in a clear 96-well plate. The plate was incubated for 2 hours at 37° C. and absorbance at 650 nm was read using a plate reader.

Figures 2A, 2B:
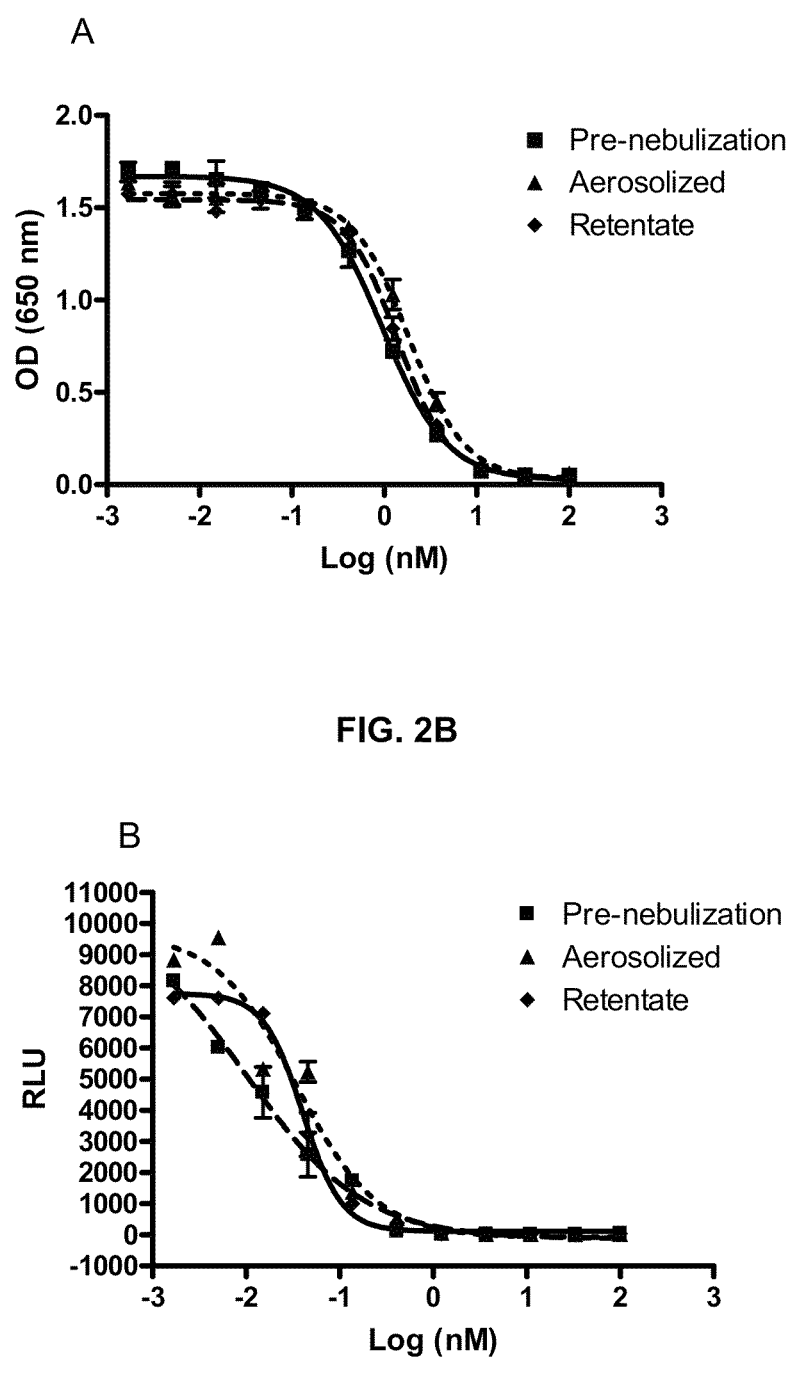

By evaluating 700 tested crude extracts, 94 binding proteins were identified as showing higher binding and inhibition activity than the benchmark binding protein 2F1. HEK/STAT6 and ELISA screening data were plotted against each other to identify binding proteins that performed better than the benchmark binding protein 2F1 in both screening and activity assays (FIGS. 2A and 2B). In this plot, a lower HEK/STAT6 signal indicates higher inhibition of IL13 dependent signaling through IL13Ralpha1 and increasing ELISA signal indicates increasing affinity for IL13. The benchmark binding protein 2F1 is indicated with a filled triangle at the intersection of the crosshairs. All binding proteins lying in the lower right quadrant (94) indicated by grey shading were identified for further characterization.

Example 2

Characterization of IL4 and IL13 Binding Proteins

The 22 AR proteins selected for further characterization were expressed using a T5-promoter based system in the cytoplasm of *E. coli* and purified via immobilized metal ion affinity chromatography (IMAC). Briefly, AR proteins were transformed in *E. coli* XL-1 blue cells and used to inoculate a 5 ml starter culture in Luria Bertani medium (LB) containing 50 μg/ml ampicillin and 1% glucose. The starter cultures were incubated overnight at 37° C., shaking at 220 rpm. On the next day, the overnight culture was used as inoculum of 50 ml LB. At a cell density of $OD_{600}$=0.7, protein expression was induced using 500 μM isopropyl β-D-1-thiogalactopyranoside (IPTG). Cultures were incubated 4 hours at 37° C., shaking at 220 rpm. Cell pellets were harvested by centrifugation. Cells were ruptured by the addition of 1 mg/ml lysozyme, 50 KU/ml DNAse I and sonification for 30 minutes on ice. The insoluble fraction was removed by centrifugation. The clarified supernatant was filtered using 0.22 µM filters. These supernatants were loaded on columns packed with 250 µl Ni-NTA superflow resin (Qiagen). Purification was carried out following the instructions of the manufacturer. 20 ml Tris buffered saline (TBS) containing 20 mM imidazole and 10% glycerol was used as wash buffer, and 600 µl TBS containing 250 mM imidazole was used to elute AR proteins from the column.

SEC of Selected Human IL4 Binding AR Proteins

The 22 purified AR protein samples were analyzed for aggregation by size exclusion chromatography (SEC) using a Superdex 75 5/150 column (GE healthcare) and a PBS pH 7.4 mobile phase. 10 uL of each sample was injected per run with a flow rate of 0.3 mL/min. The column was calibrated using conalbumin, ovalbumin, carbonic anhydrase, ribonuclease A, and aprotinin protein standards. Elution of the AR proteins from the column was monitored by absorbance at 214 nm. The elution profiles of the samples were evaluated to identify AR protein candidates that eluted predominantly as monomers as evidenced by a single peak eluting at the appropriate volume for a 15 kDa protein (for N2C library) (18 kDA protein for N3C library) determined using MW standards. The results of biophysical properties of characterized IL4-binding AR proteins are summarized in Table 1.

Affinity Determination of Purified Hit AR Proteins

Purified binders selected as "hits" were ranked by their affinity on a ProteOn XPR-36 instrument (Bio-Rad). ProteOn is an optical biosensor instrument that measures protein-protein interactions in real time, based on Surface Plasmon Resonance technology similar to Biacore (GE). A rapid experimental protocol was performed as follows: On a GLC sensor chip (Bio-Rad), Neutravidin (Thermo Scientific) was covalently immobilized to a density of >5000 RU using amine coupling chemistry as described by the manufacturer. On one flow cell, biotinylated IL4 (Peprotech) was immobilized to a level of 250 RU, while another flow cell was used as reference, with neutravidin immobilized only. From each of the purified AR proteins, three different concentrations (25, 12.5, 6.25 nM) were analyzed, and kinetic parameters were calculated by fitting using a Langmuir 1:1 model. The $k_a$, $k_d$, and $K_D$ obtained for each AR protein from these measurements are presented in Table 1, where E is base 10. The retrieved values were used to rank the AR proteins by their affinity.

TABLE 1

| AR protein | SEC | ka (M-1S-1) | kd (S-1) | $K_D$ (pM) | SEQ ID NO: |
|---|---|---|---|---|---|
| C06_6E9 | broad monomer | 9.56E+05 | 7.16E-05 | 74.9 | 27 |
| C06_28E5 | monomer | 9.22E+05 | 4.61E-05 | 50 | 16 |
| C06_19C3 | monomer | 9.62E+05 | 9.73E-05 | 101 | 11 |
| C06_17A11 | monomer | 1.03E+06 | 1.40E-04 | 136 | 10 |
| C06_20B8 | monomer | 2.02E+06 | 1.63E-04 | 80.9 | 13 |
| C06_13A10 | monomer | 2.52E+06 | 1.49E-04 | 59.2 | 9 |
| C06_19F8 | monomer | 3.66E+04 | 5.18E-05 | 1410 | 12 |
| C06_26H2 | dimer shoulder | 3.47E+06 | 2.47E-04 | 71.2 | 14 |
| C06_28D4 | multiple peaks | 1.62E+06 | 1.38E-04 | 85.6 | 15 |
| C06_42A11 | monomer | 7.27E+05 | 5.43E-06 | 7.5 | 17 |
| C06_42C7 | monomer | 1.83E+06 | 1.79E-04 | 97.8 | 18 |
| C06_43G2 | monomer | 1.40E+06 | 5.98E-05 | 42.7 | 19 |
| C06_44C12 | monomer | 8.64E+05 | 3.77E-05 | 43.6 | 20 |
| C06_44F6 | monomer | 2.07E+06 | 2.00E-04 | 96.7 | 21 |
| C06_48F3 | monomer | 8.72E+05 | 1.51E-04 | 174 | 22 |
| C06_50E5 | monomer | 7.25E+05 | 1.26E-04 | 174 | 23 |
| C06_53E9 | monomer | 8.62E+05 | 2.81E-04 | 326 | 24 |

TABLE 1-continued

| AR protein | SEC | ka (M-1S-1) | kd (S-1) | $K_D$ (pM) | SEQ ID NO: |
|---|---|---|---|---|---|
| C06_53G6 | monomer | 6.96E+05 | 5.11E-05 | 73.4 | 25 |
| C06_54C2 | monomer | 4.03E+05 | 1.61E-04 | 400 | 26 |
| C06_14A4 | broad monomer | 3.18E+05 | 2.73E-05 | 85.8 | 30 |
| C06_24H1 | broad peak | n.a. | n.a. | n.a. | 28 |
| C06_4A7 | monomer | n.a. | n.a. | n.a. | 29 |

AR Protein Composition

The compositions of the 22 AR proteins represented as expressed proteins are given in SEQ ID NO: 9-30. It was found that the 22 AR proteins represented 51 unique AR modules as given by SEQ ID NO: 31-81. In some instances, mutations in the N-cap module occurred including (based on SEQ ID NO: 2) D1N, K5E, R11S, A12V, R19H, V28A, and A30V alone or in combination. One AR protein, C06_26H2 was found to have G16R in the C-cap (SEQ ID NO: 3).

The specific sequences of the AR units are shown in the sequence tables for each of the modules and all 22 IL4 binding proteins.

The compositions of each of the AR protein binding domains are listed below in Table 2 as the corresponding SEQ ID NO: according to the formula AR1-AR2-AR3 or AR1-AR2-AR3-AR4.

TABLE 2

| AR Protein | AR1 SEQ ID NO: | AR2 SEQ ID NO: | AR3 SEQ ID NO: | AR4 SEQ ID NO: |
|---|---|---|---|---|
| C06_13A10 | 31 | 47 | 62 | |
| C06_17A11 | 32 | 48 | 63 | |
| C06_19C3 | 33 | 49 | 63 | |
| C06_19F8 | 33 | 50 | 64 | |
| C06_20B8 | 34 | 51 | 65 | |
| C06_26H2 | 35 | 52 | 66 | 81 |
| C06_28D4 | 34 | 53 | 67 | |
| C06_28E5 | 36 | 53 | 68 | |
| C06_42A11 | 37 | 54 | 69 | |
| C06_42C7 | 34 | 51 | 64 | |
| C06_43G2 | 38 | 55 | 70 | 80 |
| C06_44C12 | 39 | 56 | 71 | |
| C06_44F6 | 39 | 57 | 72 | |
| C06_48F3 | 40 | 58 | 71 | |
| C06_50E5 | 33 | 49 | 63 | |
| C06_53E9 | 42 | 58 | 73 | |
| C06_53G6 | 43 | 59 | 74 | |
| C06_54C2 | 33 | 49 | 75 | |
| C06_6E9 | 44 | 60 | 76 | 79 |
| C06_24H1 | 45 | 56 | 77 | |
| C06_4A7 | 46 | 61 | 78 | |
| C06_14A4 | 37 | 54 | 78 | |

In comparing the 22 AR1 modules represented by 15 unique sequences (SEQ ID NO: 31-46), there was a preference for T at $X_1$, for D at $X_2$ of the AR sequence motif, for W at $X_3$, and D at $X_6$. The usage of pairs of amino acids at adjacent variable positions ($X_2X_3$ and $X_5X_6$) was also tabulated as shown below (Table 3). DW was the most frequently occurring doublet for $X_2X_3$ and TD was the most frequently occurring doublet for $X_5X_6$. Thus, the AR1 module can be represented by the amino acid sequence
$X_1$D-[DW]-G$X_4$TPLHLAA-[TD]-GHLEIVEVLLK$X_7$GADVNA, wherein $X_1$ and $X_4$, are chosen from residues as shown in Table 4 and $X_7$ may be H, N, or Y (C-AR1, SEQ ID NO: 82). Alternatively, the AR1 motif may be chosen from an amino acid sequence represented by the formula:

TD-[DW]-GX$_4$TPLHLAA-[TD]-GHLEIVEVLLKX$_7$GADVNA, wherein X$_4$ is chosen from the residues listed in Table 4 and X$_7$ may be H, N, or Y (F-AR1, SEQ ID NO: 85).

TABLE 3

| IL4 Binding AR1 | Variants and Frequency |
| --- | --- |
| X$_1$ | T x7, V x3, I x2, L x2, S x2, A, E, F, H, K, Y |
| X$_2$X$_3$ | DW x6, DS x4, HD x3, AW x2, EW, SD, SS, VT, NS, KD, RI |
| X$_4$ | D x7, F x4, L x4, Y x2, I, N, E, S, T |
| X$_5$X$_6$ | TD x5, ED x3, AD x3, DD, MD, ID, EI, IE, VY x2, LL x2, W IL4-Dependent TARC Production TARC is a key regulator of Th2-mediated inflammation in allergic asthma. Stimulation of A549 cells by IL4 in vitro leads to the production of TARC. This assay complements the HEK-STAT6 assay described above as it demonstrates the ability of an inhibitor to block IL4 signaling in primary cells. Each AR protein was assayed for inhibition of IL4 dependent TARC production in A549 cells as follows: on Day 1 cells were plated overnight in 96-well culture plates at a density of $2.5 \times 10^5$/ml in 100 μl of cell culture media (alphaMEM with GlutaMax, +10% heat-inactivated FBS, 1× Sodium Pyruvate, and 1×MEM NEAA (Gibco). This media also serves as the assay media. On Day 2 cells were washed once with 200 μl of culture media and stimulated with 200 μl of culture media containing 200 ng/ml (11 nM) recombinant human TNF-alpha and 67 pM recombinant IL4 premixed with appropriate concentration of AR protein. The plates were incubated for 24 hours at 37° C. and 5% $CO_2$. Supernatants were harvested and stored at −80° C. for further analysis. CCL17/TARC Duo Set ELISA kit (RandDSystems) was used to quantify the amount of TARC in the samples using the manufacturer's protocol and a 1:5 dilution of the samples. Data were plotted as a function of AR protein concentration and fit to a sigmoidal dose response using the PRIZM software (GraphPad PRISM) to determine $IC_{50}$ values (Table 6).

STAT6 Signaling in RA-1 Cells

Each AR protein was assayed for inhibition of IL4 induced STAT6 signaling in STAT6-bla RA-1 cells. The CellSensor® STAT6-bla RA-1 Cell Line contains a beta-lactamase reporter gene under control of the STAT6 response element stably integrated into Ramos-1 (RA-1) cells. In contrast to the HEK-Blue STAT6 cells described above which signal through Type II complexes, RA-1 cells signal through Type I complexes and can be used to confirm the inhibition of IL4 stimulation through Type I complexes.

The assays were performed as recommended by the manufacturer, Invitrogen (Cat. No. K1243). On Day 1, RA-1 cells were plated in black 96-half area well cell culture plates (with clear bottom) at a density of 937,500 cells/ml in 32 μl of Assay Buffer. For cell-free control wells, 32 μl of assay buffer was added. A CD40 solution was prepared (50 μl of stock at 100 μg/ml to 950 assay buffer) and 4 μl was added to each well (final concentration was 556 ng/mL) to ensure that cells respond to IL4. The cells were spun at 14×g for 30 sec and placed in 37° C., 5% $CO_2$ for 16 hours. On Day 2, 4 μl of assay buffer was added to the cells containing a 10× concentration for the range of hIL4 to obtain the $EC_{50}$. For inhibition studies, a 10× inhibition solution containing the AR protein was premixed with a 10×hIL4 at the $EC_{50}$ and then added to the cells. The concentration of hIL4 was 20.8 pM. The plates were spun at 14×g for 30 sec and placed in 37° C., 5% $CO_2$ for 5 hours. Thereafter, 8 μl of the Live BLAzer-FRET B/G ($CCF_4$-AM) solution was added to each well (composed of 6 μl of solution A, 60 μl of Solution B, and 934 μl of solution C) and spun at 14×g for 30 sec. The plates were protected from light and incubated at room temperature for 2.5 hours. Plates were measured on the Envision Machine with bottom read capabilities using an excitation filter at 409/20 nm and two emission filters: one at 460/40 nm and one at 530/30 nm. A dual mirror was also used. To analyze the fluorescence reading, the background was subtracted (values from the cell-free wells) from both 460 nm and 530 nm and a 460/530 ratio was determined. The ratio was then plotted against concentration in the GraphPad PRIZM software to obtain an $IC_{50}$ value.

TABLE 6

Characterized Bioactivity for the IL4-binding AR proteins

| AR protein | IL4RA Binding Inhibition $IC_{50}$ (pM) | HEK Stat6 Inhibition $IC_{50}$ (pM) | A549 TARC Inhibition $IC_{50}$ (pM) | Type 1 Complex inhibition $IC_{50}$ (pM) |
|---|---|---|---|---|
| C06_6E9 (SEQ ID NO: 27) | 7.6 ± 0.8 | 0.6 ± 0.2 | 130.9 ± 7.4 | 0.4 ± 0.1 |
| C06_28E5 (SEQ ID NO: 16) | 10.2 ± 1.8 | 1.4 ± 0.6 | 174.4 ± 6.0 | 1.5 ± 1.0 |
| C06_19C3 (SEQ ID NO: 11) | 6.3 ± 0.3 | 1.5 ± 0.3 | Nd | nd |
| C06_17A11 (SEQ ID NO: 10) | 74.4 ± 17.6 | 3.0 ± 1.3 | Nd | nd |
| C06_20B8 (SEQ ID NO: 13) | 20.5 ± 6.3 | 4.0 ± 0.5 | 288.5 ± 37.4 | 3.8 ± 1.6 |
| C06_13A10 (SEQ ID NO: 9) | 30.6 ± 18.9 | 5.4 ± 1.3 | 621.1 ± 79.3 | 6.6 ± 5.9 |
| C06_19F8 (SEQ ID NO: 12) | 17.6 ± 3.4 | 15.2 ± 3.8 | Nd | nd |
| C06_26H2 (SEQ ID NO: 14) | 31.4 ± 0.0 | 3.3 ± 1.4 | Nd | nd |
| C06_28D4 (SEQ ID NO: 15) | 35.3 ± 0.0 | 3.2 ± 2.6 | Nd | nd |
| C06_42A11 (SEQ ID NO: 17) | 65.6 ± 0.0 | 19.3 ± 7.2 | 324.7 ± 34.6 | 3.2 ± 3.0 |
| C06_42C7 (SEQ ID NO: 18) | 45.9 ± 0.0 | 6.8 ± 5.3 | Nd | nd |
| C06_43G2 (SEQ ID NO: 19) | 23.5 ± 0.0 | 1.6 ± 1.4 | 261.9 ± 18.2 | 0.8 ± 0.5 |
| C06_44C12 (SEQ ID NO: 20) | 20.3 ± 0.0 | 1.1 ± 1.2 | 231.1 ± 9.3 | 1.7 ± 1.4 |
| C06_44F6 (SEQ ID NO: 21) | 15.8 ± 0.0 | 6.4 ± 6.6 | 142.1 ± 5.4 | 24.9 ± 16.5 |
| C06_48F3 (SEQ ID NO: 22) | 19.7 ± 0.0 | 4.7 ± 4.9 | Nd | nd |
| C06_50E5 (SEQ ID NO: 23) | 14.8 ± 0.0 | 3.5 ± 1.0 | Nd | nd |
| C06_53E9 (SEQ ID NO: 24) | 17.8 ± 0.0 | 14.3 ± 7.1 | Nd | nd |
| C06_53G6 (SEQ ID NO: 25) | 16.1 ± 0.0 | 2.1 ± 2.1 | 135.1 ± 9.3 | 0.9 ± 0.6 |
| C06_54C2 (SEQ ID NO: 26) | 16.8 ± 0.0 | 3.2 ± 0.7 | Nd | nd |
| C06_24H1 (SEQ ID NO: 28) | 71.7 ± 0.0 | 241.3 ± 58.8 | Nd | nd |
| C06_4A7 (SEQ ID NO: 29) | 44.3 ± 0.0 | 443.6 ± 181.4 | Nd | nd |

The composite of biophysical and biochemical data described in Example 2 (Table 1) were used to select 9 AR protein molecules, C06_13A10, C06_20B8, C06_28E5, C06_42A11, C06_44C12, C06_44F6, C06_53G6, C06_43G2, and C06_6E9 for optimization. These AR proteins were chosen because each was found to be monomeric by SEC, able to bind to recombinant IL4 with a $K_D$<9.7E-11, inhibit IL4-dependent signaling in HEK-STAT6 cells with a potency >67 pM, and inhibit the binding of recombinant IL4 to the IL4 receptor with an $IC_{50}$<66 pM. The ten lead AR proteins were subjected to further cell based assays to confirm the inhibition of IL4-dependent signaling in additional cell based assays.

The AR proteins C06_44C12, C06_53G6, and C06_28E5 were selected for optimization.

Expression and Purification of Binding Protein Candidates

The 94 binding protein candidates selected for further characterization were expressed using a T5-promotor based system which allows for *E. coli* cytoplasmic expression and purified via immobilized metal ion affinity chromatography (IMAC). Briefly, *E. coli* XL-1 Blue cells were transformed with binding protein expression plasmids and used to inoculate a 5 ml starter culture in Luria Bertani medium (LB)

containing 50 μg/mL ampicillin and 1% glucose. The starter cultures were incubated overnight at 37° C., shaking at 220 rpm. Overnight cultures were used to inoculate 50 mL LB containing 50 μg/ml ampicillin. At a cell density of $OD_{600}$=0.7, protein expression was induced using 500 μM isopropyl β-D-1-thiogalactopyranoside (IPTG). Cultures were incubated 4 hours at 37° C., shaking at 220 rpm. Cell pellets were harvested by centrifugation. Cells were ruptured by the addition of 1 mg/mL lysozyme and sonification for 30 minutes on ice. The insoluble fraction was removed by centrifugation. The clarified supernatant was filtered using 0.22 μM filters. These supernatants were loaded on columns packed with 250 μL Ni-NTA superfow resin (QIAgen). Purification was carried out following the instructions of the manufacturer. 20 mL Tris buffered saline (TBS) containing 20 mM imidazole and 10% glycerol was used as wash buffer, and 600 μL TBS containing 250 mM imidazole and 10% glycerol was used to elute the binding proteins.

SEC of Selected Human IL13 Binding Proteins

The 94 binding protein samples were analyzed for aggregation by size exclusion chromatography (SEC) using a TOSOH G2000SWXL column and a PBS pH 7.4 mobile phase. 20 μL of each sample was injected per run with a flow rate of 0.2 mL/min. The column was calibrated using conalbumin, ovalbumin, carbonic anhydrase, ribonuclease A, and aprotinin protein standards. Elution of the binding proteins from the column was monitored by absorbance at 214 nm. The elution profiles of the samples were evaluated to identify binding protein candidates that eluted predominantly as monomers.

Thermal Stability of IL13 Binding Proteins:

The melting temperatures of the selected IL13-binding protein samples were measured using Thermofluor technology (Pantoliano et. al. J Biomol Screening: 6:429-440, 2001). Thermofluor is a high throughput kinetic measurement of protein unfolding as a function of heat. As samples are heated, ANS in the sample buffer binds to hydrophobic regions generally buried in the folded molecule inducing an increase in dye fluorescence. After purification (above), each sample was exchanged into PBS buffer pH 7.4 using PD Multi-trap G25 resin (GE Healthcare) and the concentration estimated using the absorbance at 280 nm. Sample concentrations ranged from 1-50 μM. Binding protein unfolding was monitored between 37-95° C. with fluorescence measured every 0.5° C. in continuous ramp mode. Melting temperatures measured ranged from 54° C. to >95° C. for these samples. No melt was detected for several samples, indicating either that the stability is greater than 95° C. or that the protein concentration was too low to accurately measure the fluorescence (data not shown).

Neutralization of IL13 Dependent STAT6 Phosphorylation

The activity of each purified binding protein was assayed for their ability to inhibit IL13 dependent activation of STAT6 using HEK-Blue STAT-6 cells as described above. Full inhibition curves were assessed for each candidate and absorbance data were plotted as a function of binding protein concentration to a sigmoidal dose response using the PRIZM software (GraphPad PRIZM) to determine $IC_{50}$ values (data not shown).

Single Point Affinity Screening

The affinity of all purified binding proteins was assessed by ProteOn (BioRad) using a rapid affinity screening protocol as follows. On a GLC sensor chip (Biorad), neutravidin was covalently immobilized to a density of >5000 RU using amine coupling chemistry as described by the manufacturer. On one flow cell, biotinylated IL13 R130Q (Peprotech) was immobilized to a level of 250 RU; a second flowcell was used as reference with only neutravidin immobilized. From each of the purified binding proteins, a concentration of 50 nM was analyzed, and kinetic parameters were estimated by fitting using a Langmuir 1:1 model. The retrieved values were used to rank the binding proteins in terms of apparent affinity. These binding proteins had an on-rate ($k_a$) of between 1.7 and $9.6 \times 10^5$ $1/M^{-s}$ and an off-rate ($k_d$) ranging from $1.3 \times 10^{-5}$ to $1.1 \times 10^{-4}$ 1/s providing a $K_D$ of $2.1 \times 10^{-11}$ to $1.7 \times 10^{-8}$ M.

Based on the initial screens, 16 lead molecules were chosen for further characterization. A panel of 16 lead binding proteins which exhibited largely monomeric elution from an SEC, had an affinity ($K_D$)<1.5 nM, inhibited IL13 dependent STAT6 phosphorylation with an $IC_{50}$ better than 100 pM and had a Tm of greater than 50° C. by Thermofluor analysis was selected for larger scale expression, purification and characterization as described below.

Expression

E coli XL-1 Blue cells were transformed with binding protein expression plasmids. A single colony was picked and grown at 37° C. in 500 mL TB media containing carbenicillin. When the culture density reached an $A_{600}$ of between 0.7 and 1.0 unit, expression was induced with 0.4 mM IPTG and incubated for an additional 4 h at 37° C. Bacterial pellets were recovered by centrifugation and stored frozen until use. Frozen bacterial pellets were thawed and lysed in 50 mM sodium phosphate pH 7.5, 500 mM sodium chloride, 20 mM imidazole and containing an EDTA-free protease inhibitor cocktail. Resuspended pellets were sonicated and bacterial debris was collected by centrifugation in a JA-17 rotor at 17,000×g for 30 min. Soluble lysates were filtered and 2 mL of Ni-NTA resin (Qiagen) was added to each lysate followed by slow stirring for at least 1 h at 4° C. to capture the His-tagged binding proteins. The resin-containing lysate was poured into a column and washed with 8 column volumes of 50 mM sodium phosphate pH 7.5, 500 mM sodium chloride and 20 mM imidazole. The His-tagged protein was eluted from the resin with 8 column volumes of 50 mM sodium phosphate pH 7.5, 500 mM sodium chloride containing 500 mM imidazole. Further purification was achieved by size exclusion chromatography using a Superdex 200 26/60 column equilibrated in PBS pH 7.0.

Thermal Stability of Binding Protein Leads

The thermal stabilities of the 16 binding protein candidates were measured by differential scanning calorimetry (DSC). For Tm measurements, DSC is a more precise analytical method than the Thermoflour analysis used for high throughput screening. Each sample was dialyzed extensively against PBS pH 7.4 and diluted to a concentration of 1 mg/mL. Melting temperatures were measured for these samples using a model VP DSC instrument equipped with an autosampler (Microcal). Samples were heated from 10° C. to 95° C. at a rate of 1° C. per minute. A buffer only scan collected between each sample scan was subtracted from the sample scan to allow calculation a baseline for integration. Data were fit to a two state unfolding model and results are presented in Table 7. The binding proteins analyzed expressed a wide range of melting temperatures from 48° C. to 85° C.

Binding Affinity for Human IL13

Recombinant human IL13 (Peprotech) was minimally biotinylated on ice using sulfo-NHS-LCLC-Biotin and desalted into the experimental running buffer containing 10 mM HEPES, 150 mM NaCl, pH 7.4, 0.01% Tween-20, and 0.1 mg/mL BSA. Biotinylated IL13 was captured at three different surface densities (from about 150, 50, and 25 RU) onto three different BIAcore SA (streptavidin) sensor chips. Each binding protein sample was tested at 40 nM as the highest concentration in a 3-fold dilution series over the three different density IL13 surfaces. The dissociation phase for the highest concentration of the binding protein sample was monitored for one hour. The response data from each of the different density surfaces was globally fitted in order to extract estimates of the kinetic and affinity constants which are provided in Table 7 below.

TABLE 7

Biophysical Characterization of binding proteins

| Binding protein | SEC Pattern | Tm (DSC) | $k_a$ (M-1s-1) X 10^-6 | $k_d$ (s-1) X 10^5 | $K_D$ (pM) |
|---|---|---|---|---|---|
| 7H3 | monomer, small shoulder | 53.15 | 4.26 | 56.0 | 131.4 |
| 7G11 | monomer | 50.87 | 1.62 | 5.30 | 32.8 |
| 7D2 | monomer | 82.62 | 3.06 | 29.2 | 95.5 |
| 5H7 | monomer, broad | 61.3 | 3.40 | 89.4e | 263 |
| 5D12 | monomer | 73.53 | 1.099 | 18.44 | 167.8 |
| 5D3 | monomer | 61.89 | 0.877 | 14.36 | 164 |
| 5D2 | monomer, shoulder | 55.26 | 1.506 | 21.79 | 144.7 |
| 5B9 | monomer + aggregates | 77.11 | 1.060 | 17.87 | 168.6 |
| 6D4 | monomer + aggregates | 76.39 | 1.171 | 9.08e | 77.6 |
| 6G9 | monomer | 85.22 | 0.995 | 5.741 | 57.7 |
| 6G11 | Dimer | 61.35 | 0.754 | 8.00 | 106 |
| 9E11 | monomer/dimer | n.d. | 0.640 | 1.3 | 21 |
| 10A6 | aggregate | 48.36 | 2.76 | 20.1 | 72.9 |
| 7C6 | aggregate | 81.54 | 4.82 | 22.4 | 46.4 |
| 7D7 | multiple peaks | 64.59 | 0.3.1 | 6.25 | 204 |
| 9F8 | monomer, broad | n.d. | 0.93 | 9.9 | 110 |

Neutralization of IL13 Dependent Activities

The activity of each binding protein sample was assayed for inhibition of IL13 dependent STAT6 phosphorylation as described above using 80 pM IL13. Data are shown in Table 7. Likewise, each binding protein sample was assayed for the ability to inhibit STAT6 phosphorylation stimulated by IL13 from cynomologous monkey in order to verify cross reactivity with this species for future toxicology and pharmacokinetic studies. Recombinant cyno IL13 was expressed and purified from *E. coli* as a SUMO-tag fusion protein. The SUMO-tag was subsequently enzymatically cleaved from IL13 in preparation for inhibition assays. Neutralization of cyno IL13 was assayed as follows: on Day 1, cells were plated in 96-well cell culture plates at a density of $2.5 \times 10^5$ per ml in 100 uL of cell culture media (DMEM with 4.5 g/L Glucose (11995, Gibco/Invitrogen, Carlsbad, Calif.) with 10% Heat Inactivated FBS (10082, Gibco/Invitrogen, Carlsbad, Calif.), 10 μg/mL Blasticidin (Invivogen), and 100 μg/mL Zeocin (Invivogen)) for 24 hours. On Day 2, 100 μL of cell culture media containing the appropriate concentration of AR protein premixed with 1 ng/mL (80 pM) recombinant cyno IL13 was added to the cells. The plates were incubated for 24 hours at 37° C. and 5% $CO_2$. To measure secreted embryonic alkaline phosphatase, 40 μL of each cell supernatant was mixed with 160 μL of Quanti-Blue (Invivogen) in a clear 96-well plate. The plate was incubated for 2 hours at 37° C. and absorbance at 650 nm was read using a plate reader. Results of cyno IL13 inhibition are presented in Table 8 below.

IL13 Dependent TARC Production

TARC(CCL17) release from A549 cells (a human lung carcinoma-derived cell line) can be stimulated by IL13.

Each binding protein was assayed for inhibition of IL13 dependent TARC production in A549 cells as follows: on Day 1 cells were plated overnight in 96-well culture plates at a density of $1.0 \times 10^6$/ml in 200 μL of cell culture media (alpha-MEM with GlutaMax, +10% heat-inactivated FBS, 1× Sodium Pyruvate, and 1×MEM NEAA (Gibco)). This media also serves as the assay media. On Day 2 cells were washed once with 200 μL of culture media and stimulated with 200 μL of culture media containing 200 ng/mL (11 nM) recombinant human TNF-alpha and 1 ng/mL (80 pM) recombinant IL13 premixed with appropriate concentration of binding protein. The plates were incubated for 24 hours at 37° C. and 5% $CO_2$. Supernatants were harvested and stored at −80° C. for further analysis. A kit was used to measure human CCL17/TARC Duo Set ELISA (R&D Systems) in the samples according to the manufacturer's protocol and where the samples were used at a 1:5 dilution. Data were plotted as a function of binding protein concentration and fit to a sigmoidal dose response using the PRIZM software (GraphPad PRIZM) to determine $IC_{50}$ values (Table 8 below).

IL13:IL13Rα2 Binding

Binding protein inhibition of IL13 binding to Rα2 was assessed using IL13Rα2-Fc (R&D Systems) conjugated to carboxylated Luminex microspheres according to the manufacturer's protocol. For biotinylation of IL13, recombinant human IL13 R130Q (Peprotech) was biotinylated at a 4:1 ratio using EZ-Link NHS-LC-Biotin (Pierce, #21336) for 2 hours at RT. The protein was dialyzed in PBS overnight to remove excess biotinylation reagent. For neutralization experiments, 5000 IL13 Rα2-Fc conjugated beads in 50 μl were added to each well of a 96-well filter plate (Millipore). 50 μl of biotinylated human IL13 at 1 ng/ml (80 pM) was mixed with an appropriate dilution of binding protein in Luminex Assay Buffer (PBS, 1% BSA, pH 7.4). The plate was incubated for 1 hour at RT in the dark on a plate shaker, set to shake vigorously to avoid bead aggregation. The plate was washed 3 times with 150 μl of wash buffer (PBS, 1% BSA, pH 7.4., 0.05% Tween-20) using a vacuum manifold followed by the addition of 50 μl of Streptavidin PE at 25 μg/ml and incubated at RT for 20 minutes. The plates were washed again and 100 μl of sheath fluid was added and the plate was placed on the shaker for 1 minute. Plates were read using a Luminex® 100 system; data were plotted as a function of binding protein concentration. $IC_{50}$ values were determined by fitting the data to the equation for sigmoidal dose response using PRIZM software (GraphPAD PRIZM). The inhibition constants for the lead binding proteins are listed in Table below.

TABLE 8

Neutralization of IL13 Dependent Activity

| Binding protein | STAT6 Phospho IC50 (pM) | TARC expression IC50 (PM) | IL13: IL13Ra2 binding IC50 (pM) | Cyno IL13 STAT6 IC50 (pM) |
|---|---|---|---|---|
| 7H3 | 25.3 | 69.6 | 66.9 | 387.8 |
| 7G11 | 2.5 | 19.6 | 3.4 | 98.0 |
| 7D2 | 4.8 | 14.6 | 8.3 | 307.0 |
| 5H7 | 42.9 | 132.3 | 157.9 | 526.9 |
| 5D12 | 5.4 | 34.1 | 10.2 | 159.1 |
| 5D3 | 16.9 | 88.3 | 37.5 | 3022.1 |
| 5D2 | 20.3 | 71.4 | 32.2 | 223.6 |
| 5B9 | 16.5 | 372.3 | 13.4 | 653.5 |
| 6D4 | 4.2 | 83.3 | 4.8 | 51.3 |
| 6G9 | 17.4 | 64.0 | 31.0 | 96.4 |
| 6G11 | 19.8 | 281.8 | 10.1 | 1207.8 |
| 9E11 | 0.9 | 109.1 | 5.8 | 33.4 |
| 10A6 | 8.0 | 123.3 | 7.5 | 1929.9 |
| 7C6 | 2.7 | 158.7 | 10.6 | 48.0 |
| 7D7 | 10.5 | 353.6 | 58.0 | 161.5 |
| 9F8 | 55 | n.d. | n.d. | n.d. |

AR Protein Compositions

The sequences of the ankyrin repeat domains of the 2F1 and 16 lead anti human IL13 binding proteins where each binding protein follows the format of (N-Cap)-(AR)n-(C-Cap) where n=2 or 3 were analyzed.

It was found that the 2F1 and the additional 16 binding proteins represented 46 distinct AR modules as listed in the sequence tables below where a dot indicates that the amino acid present at its position for a certain AR corresponds to the corresponding amino acid of the AR repeat motif (SEQ ID NO: 1). In a few cases, where framework mutations were observed in the selected binding protein sequence they are noted. In a few cases, deletions arose during the ribosome display selection process; these deletions are noted with a dash (-). Binding protein 10A6 contains only 2 ARs. In all cases, the C-Cap sequence starts immediately after residue 33 of the last AR.

The composition of each of the binding domain tandem AR units (AR1-AR2-AR3) of each binding protein are listed below (Table 9 below)

TABLE 9

Binding Protein Composition

| IL13 Binding Protein | AR1 SEQ ID NO: | AR2 SEQ ID NO: | AR3 SEQ ID NO: |
|---|---|---|---|
| 6G9 | 109 | 127 | 144 |
| 7G11 | 110 | 128 | 145 |
| 9F8 | 111 | 129 | 145 |
| 10A6 | 112 | 130 | Absent |
| 5B9 | 113 | 131 | 146 |
| 7D2 | 114 | 132 | 147 |
| 6G11 | 115 | 133 | 148 |
| 7D7 | 116 | 134 | 149 |
| 5D12 | 117 | 135 | 150 |
| 5D2 | 118 | 136 | 145 |
| 7H3 | 119 | 137 | 145 |
| 5D3 | 120 | 138 | 145 |
| 5H7 | 121 | 139 | 151 |
| 9E11 | 122 | 140 | 152 |
| 6D4 | 123 | 141 | 153 |
| 7C6 | 124 | 142 | 154 |
| 2F1 | 125 | 143 | 155 |

In comparing the AR1 modules which represented by 17 unique sequences (SEQ ID NO: 9-25) (Table 10 below), there was a preference for Y or F at position 4 ($X_3$) of the motif, S at position 6 ($X_4$), R at position 14 ($X_5$), H at position 15 ($X_6$), and at position 27 ($X_7$) H or Y.

Thus, the IL13 binding AR1 module can be represented by the formula
$X_1DX_2$-[F,Y]-GSTPLHLAA-RH-GHLEIVEVLLK$X_7$GADVNA, wherein $X_1$ is chosen from residues as shown below and $X_7$ may be H, N, or Y (AR1-C, SEQ ID NO: 156). Alternatively, the AR1 motif may be chosen from an amino acid sequence represented by the formula:
TDYGSTPLHLAARHGHLEIVEVLLK$X_7$GADVNA, wherein $X_7$ may be H, N, or Y (AR1-F, SEQ ID NO: 157).

TABLE 10

| IL13 Binding AR1 | Variants and Frequency (17) |
|---|---|
| $X_1$ | T x4, A x2, F x2, E, I, K, M, S x2, R, V, W |
| $X_2X_3$ | $X_2X_3$ = DY x2, SY x2, DF x2, EF, IF, LF, IL, IY, MY x2, HF, VF, KY, TY |

TABLE 10-continued

| IL13 Binding AR1 | Variants and Frequency (17) |
|---|---|
| | $X_2$ = D, E, H, I, K, M, S, T, V |
| | $X_3$ = Y x9, F x7, L |
| $X_4$ | S x14, D, I, T |
| $X_5X_6$ | $X_5X_6$ = RH x8, RE x3, RS x3, RQ, RT, HH |
| | $X_5$ = R x16, always basic side chain |
| | $X_6$ = H x9, E x3, S x3, Q, T |
| $X_7$ | H, Y, N |

In comparing the 17 AR2 modules which represented by 17 unique sequences (SEQ ID NO: 127-143) (Table 11 below), there was no dominant residue (more than 50% frequency) at $X_1$, however, at the randomized positions $X_3$, $X_4$, $X_5$ and $X_6$ of the AR sequence motif there was a most frequently used amino acid. The usage of pairs of amino acids at adjacent variable positions ($X_2X_3$ and $X_5X_6$) was also tabulated as shown below. FI was the most frequently occurring doublet for $X_2X_3$. Thus, the IL13-binding AR2 module can be represented by the formula (wherein the bracketed residues are alternate amino acids for that position):

$X_1$DFIG DTPLHLAAY-$X_6$-GHLEIVEVLLK$X_7$GADVNA, wherein $X_1$ is chosen from N, T, A, D, K, E, H, M, and F; $X_6$ may be H or R; and $X_7$ may be H, N, or Y (AR2-C, SEQ ID NO: 158). Alternatively, the AR2 sequence may be chosen from an amino acid sequence represented by the formula
[A, D, N, T, K]-DFIG DTPLHLAAY-[H,R]-GHLEIVEVLLK-[H,N,Y]-GADVNA (AR2, SEQ ID NO: 159).

TABLE 11

| IL13 Binding AR2 | Variants and Frequency (17) |
|---|---|
| $X_1$ | N x4, T x3, A x2, D x2, K x2, E, H, M, F |
| $X_2X_3$ | $X_2X_3$ = FI x9, MI x4, FA, FL x2, II |
| | $X_2$ = F x12, M x4, I |
| | $X_3$ = I x14, L x2, A |
| $X_4$ | D x15, Y, N |
| $X_5X_6$ | $X_5X_6$ = YH x6, YR x6, FK, FR, VY, WH, YN |
| | $X_5$ = Y x13, F 2x, V, W, Y (always hydrophobic side chain) |
| | $X_6$ = H x7, R x7, K, N, Y |
| $X_7$ | H, Y, N |

In comparing the 16 AR3 modules which represented by 12 unique sequences (SEQ ID NO: 144-155), there was no dominant residue (more than 50% frequency) at any of $X_1$, $X_2$, $X_5$, or $X_6$ of the AR sequence motif, however, $X_3$ was most frequently T, and $X_4$ was most frequently E. The usage of pairs of amino acids at adjacent variable positions ($X_2X_3$ and $X_5X_6$) was also tabulated as shown below. IT was the most frequently occurring doublet for $X_2X_3$. SM was the most frequently occurring doublet for $X_5X_6$. Thus, the IL13-binding AR3 module can be represented by the amino acid sequence
$X_1$D-$X_2$ TG-E-TPLHLAA-[$X_5X_6$]-GHLEIVEVLLK$X_7$GADVNA, wherein $X_1$ and $X_2$, are chosen from the residues in Table 12 below, and $X_5X_6$ are selected from the pair SM, HL, and YH; and
$X_7$ may be H, N, or Y (AR3-C, SEQ ID NO: 160). Alternatively, the AR3 motif may be chosen from an amino acid sequence represented by the formula
$X_1$D-IT-G-E-TPLHLAA-SM-GHLEIVEVLLK$X_7$GADVNA, wherein $X_1$ is chosen from the residues listed in Table 12 below and $X_7$ may be H, N, or Y (AR3-F, SEQ ID NO: 161).

TABLE 12

| IL13 Binding AR3 | Variants and Frequency (16) |
|---|---|
| $X_1$ | D x5, S x5, T x2, K x2, E, M |
| $X_2X_3$ | $X_2X_3$ = IT x7, -H x5, -N, AW, TS, VT |
| | $X_2$ = I x7, -x6, A, T, V |
| | $X_3$ = T x8, H x5, N, S, T, W |
| $X_4$ | E x10, D x5, T |
| $X_5X_6$ | $X_5X_6$ = SM x5, HL x2, YH x2, HN, QI, YT, TA, DS, ER, ES |
| | $X_5$ = S x5, H x3, Y x3, D, E x2, Q, T |
| | $X_6$ = M x5, L x2, H x2, S x2, A, I, N, R, T |
| $X_7$ | N, H, Y |

Example 3

Optimization of Lead Molecules

To optimize selected IL4-binding AR proteins for large scale manufacturing, formulation, and stability, it was necessary to mutate several residues that were found in the variable residues, $X_1$-$X_6$ of SEQ ID NO: 1. For example, oxidation of purified recombinant proteins can lead to product heterogeneity and loss of activity. In order to reduce the risk of these modifications, Met residues found in the variable sequences were mutated to amino acids of similar chemical makeup or to those found in other sequence related IL4 binding AR proteins. In addition, several mutations were made to eliminate potential sites of immunogenicity as assessed by the presence of potential T-cell epitopes. Finally, random amino acid changes to the ankyrin repeat framework occasionally arose during the PCR steps used for ribosome display selection. Such residues were reverted to the consensus designed ankyrin repeat sequence.

AR protein C06__44C12 was engineered by mutating AR2 position 4 ($X_3$) from Met to Leu in order to avoid potential oxidation in the IL4 binding site. Position 27 ($X_7$) of AR2 and AR3 were mutated from Tyr to Ala in order to eliminate potential T-cell epitopes based on an analysis of neighboring upstream and downstream residues, and remove potential sites of deamidation. Similar mutations were made to C06__28E5, changing position 27 of AR1 and AR2 from Tyr to Ala. For C06__53G6, position 1 of the N-cap was changed from Asn to Asp to restore the ankyrin consensus sequence and position 27 of AR1 was mutated from Tyr to Ala as described above.

After optimization, the AR modules based on the motif formula (SEQ ID NO: 1) for these three proteins were:

TABLE 13

| Motif Designation | Position Number | AR1 | AR2 | AR3 |
|---|---|---|---|---|
| $X_1$ | 1 | A, L, T | A, N, Q | T, V, Y |
| $X_2X_3$ | 3-4 | DS, DW | NL, RL, AI | IS, LA, LH |
| $X_4$ | 6 | D, I, Y | D | F, I, V |
| $X_5X_6$ | 14-15 | ED, TD | WT, FV, LY | FY, FW |
| $X_7$ | 27 | A, H | A, Y | A, H |

The mutations described here were made in a singular or combinatorial manner, in order determine the effect each mutation had on activity. Engineered AR proteins of the sequences designated, were assayed for binding to recombinant IL4, inhibition of IL4 dependent signaling, solubility by SEC, and determination of the melting temperature by DSC (Table 14).

TABLE 14

| Activity of Optimized anti IL4 AR proteins | | | | | | |
|---|---|---|---|---|---|---|
| AR protein | SEQ ID | ka (×10^−6) | $k_d$ (×10^6) | $K_D$ (pM) | $IC_{50}$ STAT6 (pM) | $T_m$ (° C.) |
| C06__44C12v2 | 91 | 5.14 | 8.24 | 1.6 | 6.9 | 68.2 |
| C06__28E5v1 | 92 | 0.657 | 5.50 | 8.38 | 3.1 | 72.4 |
| C06__53G6 | 93 | 3.37 | 6.07 | 1.8 | 1.4 | 73.7 |

Positional tandem AR units for optimized IL4 binding proteins are represented by the AR formulas:

```
                                    (AR1-O, SEQ ID NO: 88)
[A,L,T]-DD-[S,W]-G-[D,I,Y]-TPLHLAA-[E,T]-DG

HLEIVEVLLK-[A,H]-GADVNA, (AR2-O, SEQ ID NO: 89)
[A,N,Q]-D-[NL,RL,AI]-GDTPLHLAA-[WT,FV,LY]-

GHLEIVEVLLK-[A,Y]-GADVNA,
and (AR3-O, SEQ ID NO: 90)
[T,V,Y]-D-[IS,LA,LH]G-[F,I,V]-TPLHLAAF-

[W,Y]-GHLEIVEVLLK-[A,H]-GADVNA;
``` where the bracketed entries represent the alternative amino acid residue or pair of residues in the three optimized binding proteins which exhibit the desired biologic activities. Therefore, IL4 binding proteins may be constructed from these AR motifs by tandem positioning in the order specified.

IL13 Binding Proteins

Three IL13-binding candidate binding proteins; 7G11, 6G9 and 9F8, were selected for protein optimization for potential large scale manufacturing, formulation, and stability. Each candidate was modified by multiple rounds of site directed mutagenesis.

Mutations were designed that have been found to generally increase the stability of binding proteins, decrease potential immunogenicity, remove the N-terminal HIS tag, enhance the processing of the N-terminal methionine, or remove potential sites of oxidation or deamidation in the putative antigen binding site. The mutations introduced into all final molecules included: N-Cap, position 3 (G to D) to improve the biophysical behavior was introduced to all lead molecule candidates and the terminal residues of the C-cap changed to a di-alanine. In addition, candidates 6G9 and 9F8 were found to contain the 27Asn-Gly28 dipeptide in the modules and therefore, residue 27 was substituted.

Besides the mutations described above which can be applied generically to all binding proteins, a number of mutations specific to the activity of binding proteins 6G9, 7G11, and 9F8 were introduced. Oxidation of purified recombinant proteins can lead to product heterogeneity and loss of activity. In order to reduce the risk of these modifications, Met and Cys residues found in the ankyrin repeat modules of 6G9, 9F8 and 7G11 were mutated to amino acids of similar chemical makeup or to those found in other IL13 binding proteins. Additionally, a number of mutations in the ankyrin repeats of these binding proteins were made to eliminate potential sites of immunogenicity suggested by screening in T-cell activation assays. Finally, for proteins expressed in *E. coli*, processing of the N-terminal methionine residue can be affected by the amino acid immediately following the N-terminal methionine Hirel et. al. PNAS 86:8247-8251 1989. Total processing of this methionine residue is desirable to increase the homogeneity of the purified product. In the N-Cap, position 1 was changed from aspartic acid to glycine or alanine in order to determine if the N-terminal methionine residue could be efficiently processed when expressed without the HIS tag. A summary of the binding protein specific mutations in specific repeat module positions examined for 6G9, 9F8 and 7G11 is shown in Table 15.

The generic and specific mutations described above were made in singular, or in a combinatorial manner, in order determine the results of each change on activity. Engineered binding proteins were assayed for binding to recombinant IL13, inhibition of IL13 dependent signaling, and determination of the melting temperature by DSC. All of the candidates remained monomeric as determined by SEC. In most cases, the activity and affinity of the mutant were not significantly different from the parent molecule. The properties of each of the three parent and the final optimized lead candidates are shown in Table 15.

TABLE 15

| Binding protein | Module | Position | Replacement Residues | Purpose |
|---|---|---|---|---|
| 6G9 | AR2 | 1 | A | Reduce immune response potential |
| | AR2 | 3 | F, I, A, L | Reduce oxidation |
| | AR3 | 27 | H | Reduce immune response potential |
| 7G11 | AR2 | 27 | Y | Reduce oxidation |
| | AR2 | 29 | A | Reduce immune response potential |
| | AR3 | 14 | T, L, I, V | Reduce oxidation |
| 9F8 | AR2 | 1 | F | Reduce oxidation |
| | AR3 | 13 | Q | Reduce immune response potential |
| | AR3 | 14 | I | Reduce oxidation |

Affinity Analysis of Lead Candidates

Complete kinetic data describing binding of various engineered binding protein molecules to human IL13 was measured using a method similar to that described above for the single point affinity analysis. Briefly, streptavidin (Pierce) was immobilized to similar levels (~1800 RUs) on all six channels of a ProteOn GLC chip via amine coupling (pH 5.0). Biotinylated hIL13 was captured at different surface densities (600~100 RUs) on different channels. Protein binding was tested starting at 40 nM diluted in a 3-fold concentration series over the different density IL13 surfaces; a buffer sample was injected to monitor the baseline stability. Dissociation phases for all concentrations of each binding protein sample were monitored for one hour at a flow rate of 100 μl/min. Response data for all concentration series from the different density surfaces were globally fit to a 1:1 simple langmuir binding model to extract values of the kinetic ($k_{on}$, $k_{off}$) and affinity ($K_D$) constants provided in Table 16.

Purification of Untagged Binding Proteins

Binding proteins without a HIS tag were subcloned into a pET27 vector modified to include a ligase independent cloning site by standard PCR methods and expressed in BL21-GOLD(DE3) *E. coli* strain (Stratagene). Expression was performed in terrific broth after inducing expression by the addition of 1 mM IPTG at 30° C. Cells were harvested 5 hours after induction by centrifugation and frozen at −20° C. Frozen cell pellets were resuspended in lysis buffer composed of 20 mM histidine pH 6.4 at a concentration of 0.1 g of pellet per mL of buffer. Cell lysis was accomplished by sonication and the lysate cleared by centrifugation at >15,000×g followed by filtration through a 0.45 um filter. Cleared lysates were loaded onto a 5 mL HiTrap Q FF column (GE Healthcare) in lysis buffer. A linear gradient from lysis buffer to buffer B, 20 mM Histidine pH 6.4 with 600 mM NaCl, over 20 column volumes eluted the binding proteins from the Q column. Fractions were analyzed by SDS-PAGE and those containing binding protein were pooled and heated to 70° C. for 20 minutes and then placed on ice for 30 minutes. Precipitated, contaminating proteins were removed by centrifugation. The supernatant of the precipitation step containing the binding protein was then concentrated by ultrafiltration and purified on a Superdex 75 16/60 column (GE Healthcare) with PBS as the mobile phase. The heat step after the initial ion exchange chromatography step was omitted for binding proteins with lower melting temperatures, such as 9F8r3. The biophysical properties and bioactivity measurements for each construct is summarized in Table 16.

TABLE 16

| Binding protein | SEQ ID NO: | Mutations compared to Parent (Generic) | Mutations compared to parent (Specific) | $K_D$ (M) | $T_m$ (° C.) | HEK STAT6 $IC_{50}$ (pM) |
|---|---|---|---|---|---|---|
| 6G9 | 162 | | | 2.49E−11 | 86.8 | 17.4 |
| 6G9r13 | 163 | Ncap D1A<br>Ncap G3D<br>AR2 N27Y<br>Ccap L27A<br>Ccap N28A | AR2 K1A<br>AR2 M3F | 2.51E−11 | 82.7 | 5.6 |
| 7G11 | 166 | | | 1.68E−11 | 50.9 | 2.5 |
| 7G11r7 | 167 | NcapDIG<br>NcapG3D<br>AR3 N26H<br>Ccap L27A<br>Ccap N28A | AR2 C27Y<br>AR3 M14T | 2.42E−11 | 53.5 | 85 |
| 9F8 | 164 | | | 1.64E−12 | — | N.D. |
| 9F8r3 | 165 | Ncap DIG<br>Ncap G3D<br>AR3 N26H<br>Ccap L27A<br>Ccap N28A | AR2 M1F<br>AR3 S13Q<br>AR3 M14I | 6.56E−11 | 49.6 | 201.9 |

Positional tandem AR units for optimized IL13 binding proteins are represented by the AR formulas:

```
                                  (AR1-O,SEQ ID NO: 168)
[R,S,T]-D-[S,W]-[Y,F]-[D,G]-STPLHLAAR-[E,H]-

GHLEIVEVLLKYGADVNA;

(AR2-O,SEQ ID NO: 169)
[A,F]-DFIGDTPLHLAAYRGHLEIVEVLLKYGADVNA,
and (AR3-O,SEQ ID NO: 170)
[S,D]-[HT]-G-[S,D]-TPLHLAA-[QI,ST]-GHLEIVEVLLK

HGADVNA;
``` wherein the bracketed entries represent the alternative amino acid residue or pair of residues in the three optimized binding proteins which exhibit the desired biologic activities. Therefore, IL13 binding proteins may be constructed from these AR motifs by tandem positioning in the order specified. The IL13 binding protein according to the formula N-Cap-$[AR]_n$-C-Cap additionally comprises an N-Cap selected from SEQ ID NO: 2 or a variant thereof, such as those exemplified by the formula of SEQ ID NO: 171, and a C-Cap such as SEQ ID NO: 3 or 172 or variants thereof.

Example 4

Bivalent AR Protein Constructs

The three IL4-binding AR protein molecules described in Example 3 were combined with a previously discovered anti-IL13 AR protein designated 6G9_V1 (SEQ ID NO: 94) in order to produce a bispecific molecule that could block signaling of both human IL13 and IL4.

Nucleic acid sequences for each AR protein synthesized to include a sequence encoding for a (GGGGS)$_4$ linker between the 2 AR proteins. Alternative GS linkers with the formula (GGGGS)$_n$ may be used to join AR proteins. The length of the linker can be varied to control binding domain availability, steric and other properties of the molecule A total of 6 bispecific AR proteins were synthesized representing the 6G9 linked either at N-terminal to the IL4 binding protein or C-terminal to the IL4 binding protein (SEQ ID NO: 95-100) to examine the effects of the orientation of the AR proteins relative to one another on activity. Each coding nucleic acid sequence was cloned into the expression vector and purified by IMAC chromatography as described above for monospecific AR proteins.

The bispecific AR proteins were evaluated for binding to hIL13 and IL4 as well as the ability to inhibit IL13 and IL4 dependent signaling.

In the HEK-Blue STAT-6 cells, IL13 activates the IL13RA1: IL4R complex (Type 2 receptor) to induce secretion of an embryonic alkaline phosphatase (SEAP) reporter gene via the STAT-6 signaling pathway. An assay for IL13 dependent activation of STAT6 using HEK-Blue STAT-6 cells is commercially available (InVivogen, SanDiego, Calif.). To enable differentiation between high and low affinity binding proteins, an optimal dilution of the crude extract (1:5200) was selected. Stimulation of HEK-Blue STAT-6 cells using crude protein extracts was carried out as follows: on Day 1, cells were plated in 96-well cell culture plates at a density of 2.5×10$^5$/ml in 100 uL of cell culture media (DMEM with 4.5 g/L Glucose (11995, Gibco/Invitrogen, Carlsbad, Calif.) with 10% Heat Inactivated FBS (10082, Gibco/Invitrogen, Carlsbad, Calif.), 10 microgm/mL Blasticidin (Invivogen), and 100 microgm per mL Zeocin (Invivogen)) for 24 hours. On Day 2, 100 microL of cell culture media containing the appropriate concentration of AR protein premixed with 1 ng/mL (80 pM) human IL13 (Peprotech) or cyno IL13 was added to the cells. The plates were incubated for 24 hours at 37° C. and 5% CO$_2$. To measure secreted embryonic alkaline phosphatase, 40 microL of each cell supernatant was mixed with 160 microL of Quanti-Blue (Invivogen) in a clear 96-well plate. The plate was incubated for 2 hours at 37° C. and absorbance at 650 nm was read using a plate reader.

All of the bispecific AR proteins retained their ability to bind with high affinity to hIL13 and IL4 (Table 17) irrespective of the orientation of the construct as well as the ability to inhibit IL13 and IL4 dependent signaling (Tables 18 and 19).

TABLE 17

Biophysical properties of bispecific AR proteins

| Bispecific AR protein | SEQ ID No. | IL13 Ra2 Binding IC$_{50}$ (pM) | Affinity to IL13 (pM) | IL-4RA Binding IC$_{50}$ (pM) | Affinity to IL4 (pM) | Tm (° C.) |
|---|---|---|---|---|---|---|
| C01_6G9_V1_C06_28E5_V1 | 95 | 32 ± 19 | 16.6 | 24 ± 9 | 3.1 | 72.4/83.6 |
| C06_28E5_V1_C01_6G9_V1 | 96 | 36 ± 19 | 10.6 | 25 ± 10 | 21.7 | 76.8/80.8 |
| C01_6G9_V1_C06_44C12_V2 | 97 | 23 ± 15 | 9.1 | 25 ± 11 | 2.0 | 70.3/83.3 |
| C06_44C12_V2_C01_6G9_V1 | 98 | 28 ± 14 | 11.6 | 17 ± 5 | 1.7 | 72.6/82.6 |
| C01_6G9_V1_C06_53G6_V1 | 99 | 99 ± 15 | 9.3 | 15 ± 7 | 3.1 | 76.0/79.8 |
| C06_53G6_V1_C01_6G9_V1 | 100 | 199 ± 27 | 38.4 | 34 ± 28 | 10.9 | 76.8/80.0 |

TABLE 18

Neutralization of IL13 dependent activity by bispecific AR proteins

| | SEQ ID No: | IL13 Ra2 Binding IC$_{50}$ (pM) | HEK Stat6 human IL13 IC$_{50}$ (pM) | A549/TARC IL13 IC$_{50}$ (pM) |
|---|---|---|---|---|
| C01_6G9_V1_C06_28E5_V1 | 95 | 32 ± 19 | 19 ± 9 | 92 ± 103 |
| C06_28E5_V1_C01_6G9_V1 | 96 | 36 ± 19 | 19 ± 5 | 84 ± 80 |
| C01_6G9_V1_C06_44C12_V2 | 97 | 23 ± 15 | 15 ± 9 | 128 ± 155 |
| C06_44C12_V2_C01_6G9_V1 | 98 | 28 ± 14 | 14 ± 7 | 63 ± 76 |
| C01_6G9_V1_C06_53G6_V1 | 99 | 99 ± 15 | 15 ± 8 | 75 ± 83 |
| C06_53G6_V1_C01_6G9_V1 | 100 | 199 ± 27 | 27 ± 13 | 131 ± 70 |

TABLE 19

Neutralization of IL4 dependent activity by bispecific AR proteins

| Construct Composition | SEQ ID No: | IL4R Binding IC$_{50}$ (pM) | HEK Stat6 hIL4 IC$_{50}$ (pM) | A549/TARC IL4 IC$_{50}$ (pM) | Ramos Assay IC$_{50}$ (pM) |
|---|---|---|---|---|---|
| C01_6G9_V1_C06_28E5_V1 | 95 | 24 ± 9 | 2.0 ± 0.6 | 33 ± 14 | 6.9 ± 2.8 |
| C06_28E5_V1_C01_6G9_V1 | 96 | 25 ± 10 | 1.1 ± 0.4 | 39 ± 13 | 5.4 ± 2.5 |
| C01_6G9_V1_C06_44C12_V2 | 97 | 25 ± 11 | 7.2 ± 2.8 | 55 ± 3 | 8.6 ± 5.3 |
| C06_44C12_V2_C01_6G9_V1 | 98 | 17 ± 5 | 0.7 ± 0.3 | 16 ± 9 | 5.8 ± 6.1 |
| C01_6G9_V1_C06_53G6_V1 | 99 | 15 ± 7 | 0.5 ± 0.2 | 24 ± 10 | 4.8 ± 5.6 |
| C06_53G6_V1_C01_6G9_V1 | 100 | 34 ± 28 | 3.9 ± 1.7 | 50 ± 7 | 8.0 ± 9.4 |

Example 5

Optimization of Bispecific AR Proteins

In addition to substitutions of the residues at the positions diversified in the creation of libraries based on the formula N-cap-[AR]n-C-cap as well as those mutations described above, generic AR protein mutations may be incorporated. These mutations can be applied to any AR protein molecule, in that these mutations occur within positions of the sequence that are common to all AR proteins as summarized in Table 20 below.

TABLE 20

Protein Mutations

| Module | Position | Possible Residues | Rationale |
|---|---|---|---|
| N-Cap | 1 | G, A | Process N-terminal methionine |
| N-Cap | 3 | D | Stabilize AR proteins |
| AR | 27 | Y, H | Reduce deamidation |
| C-Cap | 27 | A | Remove restriction site/restore AR module |
| C-Cap | 28 | A | Remover restriction site/restore AR module |

For proteins expressed in *E. coli*, processing of the N-terminal methionine residue can be affected by the amino acid immediately following the N-terminal methionine (Hirel, et al., Proc Natl Acad Sci USA 86: 8247-51, 1989). Total processing of this methionine residue is desirable to increase the homogeneity of the purified product. In the N-Cap, position 1 was changed from aspartic acid to glycine or alanine in order to determine if the N-terminal methionine residue could be efficiently processed when expressed without the HIS tag. Position 3 of the N-cap is mutated from Gly to Asp, as this mutation has been found to stabilize the AR protein consensus sequence as described in WO2 01/0060748. Position 27 of the AR modules is restricted in diversity to Asn, Tyr, or His in the AR protein library design (Binz et al. Nature Biotech 22:575-582, 2004). As position 28 of the framework is Gly, there is the possibility of isolating AR proteins consisting of the sequence 27Asn-Gly28. The Asn-Gly di-peptide is prone to deamidation reactions (Geiger and Clarke, J Biol Chem 262: 785-94, 1987). As such, position 27 of isolated Asn-Gly sequences can generally be mutated to either Tyr or His. In addition, IL4-binding AR proteins selected by ribosome display end with the amino acid sequence Leu-Asn in the C-cap. This sequence is appended onto the AR proteins in order to accommodate a restriction site for sub-cloning into expression vectors for screening. The preferred amino acid sequence of these positions is Ala-Ala. The C-cap has been further mutated for stability and optimized expression characteristics (SEQ ID NO: 103).

An examplary, optimized bispecific IL4/IL13 binding protein is that given in SEQ ID NO: 104.

Example 6

Generation of Surrogate Anti-Murine IL4 AR Proteins

As human and murine IL4 share only 41% sequence identity, it is unlikely that AR proteins selected against human IL4 cross react with mouse IL4. Thus, to enable studies in mouse models where murine IL4 has been demonstrated to play a role in asthma pathologies, it was necessary to select a AR protein that specifically binds to murine IL4 with subnanomolar affinity. Five rounds of ribosome display selection were completed with the N2C and N3C AR protein libraries (Binz, et al., Nat Biotechnol 22: 575-82, 2004) using biotinylated murine IL4 (Peprotech) followed by capture on neutravidin beads. To identify high affinity binders, an off rate selection strategy was performed as follows: biotinylated mIL4 (5 nM) was bound to ribosome displayed AR proteins for either 2 or 6 hours followed by incubation with 2.1 mM unbiotinylated IL4 as a competitor for 4 or 16 hours. AR proteins with a slow off-rate remaining attached to the biotinylated mIL4 were captured on neutravidin particles. An additional round of ribosome display selection was performed under standard conditions to enrich for the high affinity binders. Selected AR proteins were screened using purified AR protein for inhibition of mIL4 dependent HT2 proliferation. HT2 cells, T-lymphocytes isolated from murine spleens (ATCC, CRL-1841™) were cultured using the manufacturer's recommendations (RPMI 1640, 2 mM L-glutamine, 1.5 g/L sodium bicarbonate, 4.5 g/L glucose, 10 mM HEPES, 1.0 mM sodium pyruvate, 0.05 mM 2-mercaptoethanol, 100-200 IU/ml IL-2, and 10% FBS). For the proliferation assay, the cells were removed from the flask and washed 4 times in assay buffer consisting of culture media without IL-2 and plated in 96-well opaque-bottom plates at a density of $5.0 \times 10^4$ cells/ml in 50 µl. Cells were treated with 74 pM IL4 and appropriate concentrations of AR protein and incubated at 37° C., 5% CO2 for 48 hours. Cell Titer Glo (Promega G7571) was added to the assay plate (100 µL), covered and placed on a shaker for 40 minutes at room temperature. Luminescence was measured from a top read using the SpectraMax M5 plate reader (Molecular Devices, Sunnyvale, Calif.). Based on affinity for mIL4, neutralization of mIL4 binding to IL4R, neutralization of mIL4 dependent HT2 proliferation, thermal stability and monodispersity by size exclusion chromatography, AR protein C06__21H2 (SEQ ID NO: 105) was chosen as the surrogate mIL4 binding AR protein for in vivo work.

Bispecific Activity

In order to test the effects of simultaneous inhibition of both IL4 and IL13 inhibition in murine models of asthma, a bispecific AR protein linking C06__21H2 and C02__11G11 (SEQ ID NO: 106), a potent murine IL13 inhibitor was engineered to link the N-terminus of C06__21H2 to the C-terminus of C02__11G11 via a $(GGGGS)_4$ polypeptide linker. An N-terminal histidine tag was appended to the N-terminus in order to aide purification, as described above.

Example 7

Nebulization of 11G11-21H2

In order to evaluate the potential to deliver a AR protein via nebulization using a rodent inhalation system, nebulization stability studies were performed with the surrogate bispecific AR protein (11G11-21H2). Aerosols were generated with a Pari LC Plus jet nebulizer connected to compressed air with an inlet pressure of 20 psi. This resulted in an output flow of ~5 L/min. Solution formulations of 11G1-21H2 were prepared at 20 mg/mL in PBS. Aerosols were directed through approximately 24 in. of a 1.58-cm (diameter) delivery line. The delivery line was fitted with forced air dilution flow of approximately 10 L/min. Aerosols transited into a flow-past 24-port nose-only rodent exposure chamber. The chamber exhaust flow rate was adjusted to a volumetric flow rate of approximately 20 L/min, resulting in the chamber being slightly negative to ambient conditions. Aerosols were collected on 47-mm Zefluor filters at a nominal volumetric flow rate of 1.0 L/min. Samples recovered from filters were analyzed by SEC and absorbance at 280 nm to assess potential aggregates and AR protein concentration.

Particle size distribution was measured by a Mercer-style, seven-stage cascade impactor (IN-TOX Products, Inc., Albuquerque, N. Mex.). Impactor samples were collected for between 1 and 2 min, as aerosol concentration required, at a nominal flow rate of 2 L/min. Impactor data were analyzed to determine the mass median aerodynamic diameter (MMAD) and geometric standard deviation (GSD). In order to extract the samples from the filters they were rolled and placed in glass vials. Four milliliters of PBS was added to each vial. The vials were sealed and placed on a rotator for 45 minutes at 40 rpm. Samples were transferred into HPLC vials for analysis. The samples were then analyzed by size exclusion chromatography (SEC). The analysis showed that nebulized AR protein 11G11-21H2, collected as condensed aerosol at 30 minutes and 1 hour, the main peaks eluted at 6.09 minute. In the sample of 11G11-21H2 remaining in the sample cup post nebulization; the main peak eluted at 5.9 minutes. The sample increase in sample concentration with longer nebulization times was evidenced by an increase in peak intensity.

The samples were also tested for activity in the IL13 and IL4 dependent Stat6 and IL4 dependent HT2 proliferation assay respectively as previously described. Prior to testing, the concentration of aerosolized AR protein or AR protein retained in the cup were assessed by A280 and the activity was measured using the IL13 STAT6 activation assay (FIG. 2A) or the IL4 dependent HT2 proliferation assay (FIG. 2B); pre-nebulized AR protein, squares; aerosolized AR protein, triangles; retained AR protein, diamonds. These experiments showed that the bispecific AR protein construct, 11G11-21H2, was monodisperse by SEC and retains both activities. Cascade impaction data shown in FIG. 3 indicated that the nebulized AR protein 11G11-21H2 has an MMAD of 2.84 μm with a GSD of 1.66 appropriate for rodent exposures.

Example 8

Pharmacokinetic Profile of 11G11-21H2

The pharmacokinetic profile of 11G11-21H2 was determined for protein delivered via intratracheal instillation at 4 mg/kg, in healthy or mice sensitized and challenged with ovalbumin to mimic the asthmatic lung. Animals were anesthetized with 3-5% isoflurane until they failed to respond to toe pinch and did not respond to having the catheter inserted into the trachea. A 20 gauge catheter or smaller was inserted into the trachea and the compound instilled into the lungs in a smooth motion. The volume of solution inserted during a single instillation was approximately 50 μL Data were collected at multiple times points with n=5 mice/time point. The concentration of the 11G11-21H2 construct was determined from bronchoaveolar lavage (BAL), lung homogenate and serum samples by ELISA using AR protein specific antibodies (FIG. 4). There was no significant difference in PK profiles obtained in normal vs diseased mice and the predicted terminal half life in the mouse BAL and lungs is ~6-8 hrs. The overall systemic exposure, as assessed by serum concentration, was significantly lower than the exposure achieved in the lung. At $t_{max}$, BAL levels were on average greater than 40 μg/ml while serum levels were less than 100 ng/mL (approximately 400-fold lower relative to BAL concentration). AR protein concentration assessed by ELISA in BAL samples, lung homogenates or serum. Serum concentrations beyond 24 hours were below the level of detection for the assay.

For comparison, due to their small size, AR proteins that are dosed systemically by intravenous injection clear from circulation with a half-life of less than 30 minutes (data not shown).

Example 9

In Vivo Data for 11G11-21H2

In order to evaluate the ability of 11G11-21H2 to inhibit both IL4 and IL13 dependent outcomes in vivo, the murine acute OVA sensitization and challenge model was used. Briefly, 8-10 wk old female BALB/c mice were immunized with an intraperitoneal injection of a mixture of ovalbumin (OVA, 10 microgram) and aluminum hydroxide (Alum, 2 mg) in sterile water on day 0 and 7. Mice were then challenged intranasally with ovalbumin for 2 days starting on day 14 and sacrificed for analysis on day 16. For the non-sensitized group, mice were immunized with sterile water only and treated with PBS by inhalation (vehicle control). For all other groups, mice were sensitized with OVA and treated with 11G11 (anti-IL13 AR protein), 21H2 (anti-IL4 AR protein), 1G11-21H2 (anti-IL4; anti-IL13 bispecific AR protein) or E3__5 (a non-binding control AR protein) at 20 mg/kg (mono-specifics) or 40 mg/kg (bispecific). 11G11-21H2 or E3__5 was delivered via intratracheal instillation 1× per day beginning the day before OVA challenge and up to the day before sacrifice (day 13-16). Forty eight hours following the last OVA challenge, mice were anesthetized and their pulmonary function (response to methacholine challenge) tested by whole body plethysmography (Buxco) and then immediately sacrificed. BAL (1 mL PBS) was performed post mortem to collect cells and fluid from all animals, cell number and differentials were calculated and BAL supernatant was frozen at −80° C.

As shown in FIG. 5, both 11G11 and 11G11-21H2 inhibited OVA induced airway hyperresponsiveness in response to methacholine. In addition blockade of both IL4 and IL13 using mCNTX413 11G11-21H2 inhibited OVA induced eosinophil recruitment to the lungs, a hallmark of allergen associated inflammatory diseases, of mice as shown in FIG. 6. In this model, eosinophil recruitment is largely TH2 cytokine (i.e. IL4, IL13) dependent. Data is shown as eosinophil percentages of the total cellular infiltrate.

Example 10

Crystal Structure of IL13 Binding Protein and Cyno IL-13

The crystal structure of the complex between IL13 binding protein 6G9 (SEQ ID NOS: 162 formed from ARs in SEQ ID NOS: 109, 127 and 144) and found in bi-specific IL4/IL13 binding protein (SEQ ID NOS: 41, 104 and 177) and cyno IL13 was determined at 1.6 Å resolution. The conformational epitope has been identified, as well as the binding protein residues involved in target recognition.

The following abbreviations are used: HEPES: N-(2-hydroxyethyl)-piperazine-N'-2-ethanesulfonic acid; MES: 2-(N-morpholino)ethanesulfonic acid; PBS: phosphate buffered saline; PEG: polyethylene glycol; RMSD: root-mean-square deviation; SEC: size exclusion chromatography; binding protein 6G9 was developed to bind IL13 with high affinity and block signaling through its receptor IL13Rα1/IL4Rα.

6G9 binds human IL13 with a $K_D$ in the picomolar range and exhibits cross-reactivity towards cyno IL13. For insight into the mechanism of action, binding protein 6G9 was crystallized in complex with cyno IL13. The structure was determined at 1.6 Å resolution.

Proteins

Cyno IL13 with the N-terminal SUMO tag was expressed in *E. coli* and purified by HisTrap, SUMO tag cleavage, and SEC in a final PBS buffer, pH 7.2; Lot No. 081126-CP00721y.

Complex Preparation

Binding protein 6G9 was further purified on a MonoQ HR 5/5 column (GE Healthcare) equilibrated with 20 mM MES, pH 6.5 (buffer A). Elution was performed with an 11-29% gradient of 20 mM MES, pH 6.5, 1 M NaCl (buffer B) in 40 column volumes. The main peak fractions were concentrated and used for complex formation.

Binding protein:IL13 complex was prepared by mixing 6G9 with excess IL13 at a molar ratio of 1:1.1 and incubated for 2 hours at 4° C. SEC on a Superdex 200 column separated the unbound species. The complex was concentrated using an Amicon-Ultra 5 kDa device to 13.75 mg/mL in 20 mM HEPES pH 7.5, 100 mM NaCl.

Crystallization

Crystallization of the complex was carried out by the vapor-diffusion method at 20° C. using an Oryx4 robot (Douglas Instruments). The experiments were composed of equal volumes of protein and reservoir solution in a sitting drop format in 96-well Corning 3550 plates. The initial screening was performed with the PEGs suite (Qiagen) and in-house screens IH1 and IH2, and protein complex solution at 13.75 mg/mL. Plate-shaped stacked crystals appeared from IH2 conditions A1-A4 with 0.1 M Na acetate buffer, pH 4.5, 18-25% PEG 3350, and either 0.2 M lithium sulfate or 0.2 M ammonium sulfate. These crystals were used to prepare seeds for microseed matrix screening in a stabilizing solution of 0.1 M Na acetate buffer, pH 4.5, 25% PEG 3350, and 0.2 M lithium sulfate. Seeding was performed using 0.2 µL protein, 0.05 µL seeds, and 0.15 µL reservoir. Diluted protein complex (4.8 mg/mL) and 50-fold diluted seeds were used for optimization of conditions. X-ray quality crystals were obtained from 0.1 M Na acetate, pH 4.5, 11% PEG 3350, 0.2 M Li$_2$SO$_4$. The crystal data are given in Table 21.

X-Ray Data Collection and Structure Determination

For X-ray data collection, one crystal was soaked for a few seconds in a cryo-protectant solution containing 0.1 M Na acetate, pH 4.5, 20% PEG 3350, 0.2 M LiCl, 20% glycerol and was frozen in liquid nitrogen. Diffraction data were collected at the Swiss Light Source synchrotron over a 180° crystal rotation with 0.25-sec exposures per 0.25°-image and were processed with the program XDS. X-ray data statistics are given in Table 21.

TABLE 21

Crystal data, X-ray data, and refinement statistics.

| Crystal data | | |
| --- | --- | --- |
| Space group | C2221 | |
| Unit cell axes (Å) | 52.41, 78.49, 119.44 | |
| Molecules/asym. unit | 1 complex | |
| Vm (Å3/Da) | 2.0 | |
| Solvent content (%) | 39 | |
| X-ray data | | |
| Resolution (Å) | 30-1.6 | (1.64-1.60) |
| No. measured reflections | 210,223 | (14,049) |
| No. unique reflections | 32,998 | (2,329) |
| Completeness (%) | 99.6 | (96.4) |
| Redundancy | 6.4 | (6.0) |

TABLE 21-continued

Crystal data, X-ray data, and refinement statistics.

| | | |
| --- | --- | --- |
| Rmerge (I) | 0.065 | (0.542) |
| <I/σ> | 17.1 | (3.7) |
| B-factor (Wilson) (A2) | 25.7 | |
| Refinement | | |
| Resolution (Å) | 15-1.6 | |
| No. refls used in refinement | 31,810 | |
| Completeness (%) | 96.4 | |
| No. all atoms | 2,129 | |
| No water molecules | 218 | |
| R-factor (%) | 0.169 | |
| R-free (%) | 0.196 | |
| RMSD bond lengths (Å) | 0.008 | |
| RMSD bond angles (°) | 1.1 | |
| RMSD B-factor main-chain (Å2) | 2.5 | |
| Mean B-factor (Å2) | 23.2 | |

The structure was solved by molecular replacement. The crystal structures of binding protein 6G9 (DAR6G9XP01) and human IL-13 (I130062G02) were used as search models. All crystallographic calculations were performed with the CCP4 suite of programs. Model adjustments were carried out using the program COOT. The refinement statistics are given in Table 21.

Binding Protein/IL13 Interface

Figure 8:
FIG. 8 is a ribbon presentation of the complex between Binding protein 6G9 (top) and IL13 (below). Arrows indicate "opening" of the IL13 binding protein upon IL13 binding.

The crystal structure of the complex is shown in FIG. 8. Binding protein 6G9 binds helices A and D of IL13 so that helix D fits in the major groove of the binding protein molecule. The ridge formed by four β-turns of the ankyrin repeats fits into the space between helices A and D. Target recognition involves all 4 β-turns and 4 out of 5 helices forming the groove. The interface is extensive and covers nearly 1,000 Å2 on each molecule.

Comparison of the binding protein structures in complex with IL13 and alone indicates that the binding protein molecule is relatively rigid. Upon binding the target (IL13), binding protein opens by ~3.5° as shown in FIG. 8.

Figure 9:
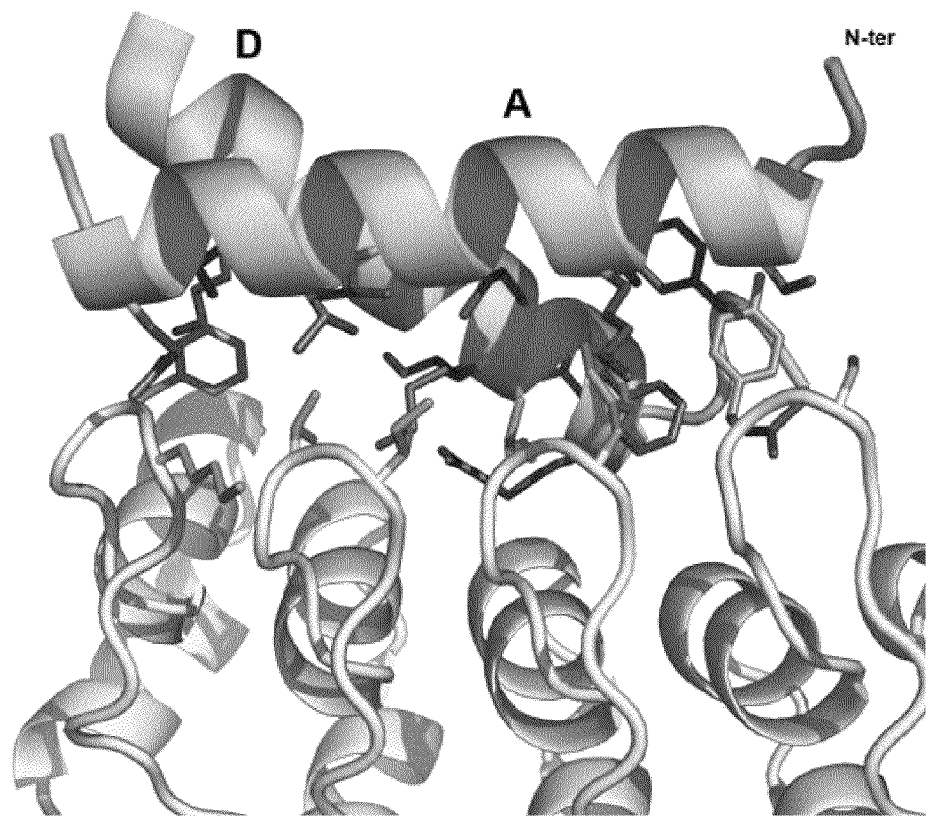
FIG. 9 shows interactions at the IL13 binding protein loops. It shows a back view with respect to FIG. 8.

Intermolecular interactions at the ridge are mostly hydrophobic (FIG. 9). They involve binding protein residues Ser45-Tyr46 (β-turn 1), Phe78-Ile79 (β-turn 2), Ile111-Val112 (β-turn 3), Lys144-Phe145 (β-turn 4).

Figure 10:
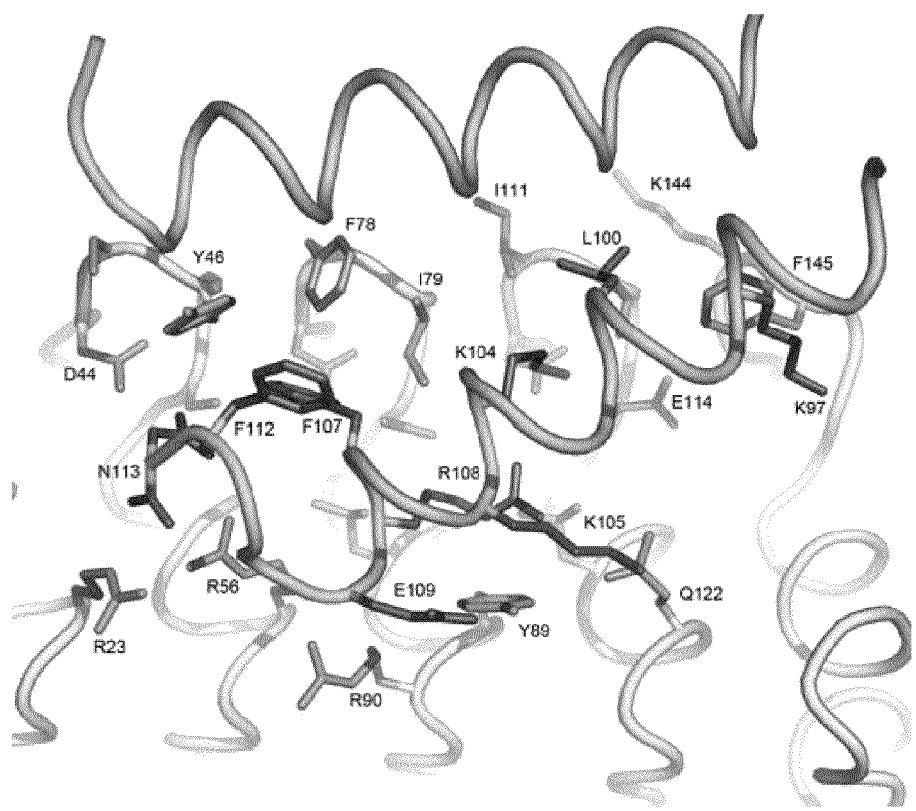
FIG. 10 shows interactions at the IL13 binding protein groove. It shows a top view with respect to FIG. 8.

Interactions at the groove of binding protein involve both hydrophobic and charged residues (FIG. 10). In total 20 binding protein residues are involved in binding IL13, based on the 4-Å cut-off distance (FIG. 11). The binding protein epitope on IL13 includes 17 residues, 10 from helix D and 7 from helix A (FIG. 12). The sequences shown in FIG. 12 have a 1 residue difference from SEQ ID NO:101 as a result of a leader sequence Pro residue at the start of the sequence (not in SEQ ID NO:101).

Three residues at the end of helix D seem to contribute a good portion of the binding energy: F107, R108 and N113 (each are 1 amino acid different in position than in SEQ ID NO: 101 for which it is F106, R107 and N112). The latter provides the C-terminal carboxyl group, which forms 3 salt bridges, to R23 (two) and R56 (FIG. 10). The side chain of N113 makes 3 H-bonds (to D44, S46, R56) and a van-der-Waals contact to Y46. Obviously, this binding protein must be very sensitive to the presence of N113 as the C-terminal residue of IL13. One residue shorter or longer will most likely limit binding.

The neutralization effect of 6G9 is due to blocking the IL13 interaction with the receptor chain IL13Rα1. 6G9 does not interfere with IL4Rα as can be judged from the crystal structure of IL13:IL13Rα1:IL4Rα complex.

Electrostatic Interactions

Although charged residues play a significant role in the interactions, their distribution is quite unexpected. The binding surface of IL13 formed by helices A and D is positively charged due to a number of basic residues. The groove of binding protein, however, also bears a positive charge in the left (N-terminal) half, i.e. exactly where it binds IL13. Somehow, the positive charge of the central cluster (R23, R56, R90) is balanced by the IL13 C-terminal charge and the dipole of helix D. The acidic patch in the groove that includes D77, D81, D110, E114, D143, D151 and D155, does not contribute much to the interactions.

Cross Reactivity

Human and cyno IL13 differ in only 6 positions (FIG. 12). One of them, position 11, happens to be in the 6G9 epitope. However, this residue (Arg in human, Lys in cyno) contacts the binding protein through the aliphatic part of the side chain. Therefore, no difference in binding is expected between human and cyno IL13.

Also, the R/Q substitution in position 111 should not affect binding. Curiously, residue 111 is the only residue in the C-terminal portion of helix D that is not involved in the interactions (FIG. 12). Gln in this position is observed in cyno IL13 and in the natural variant of human IL13 (in the old literature, it is referred as Q130). In conclusion, binding protein 6G9 should bind cyno IL13 and both variants of human IL13 equally well.

IL13 Structure

Figure 13:
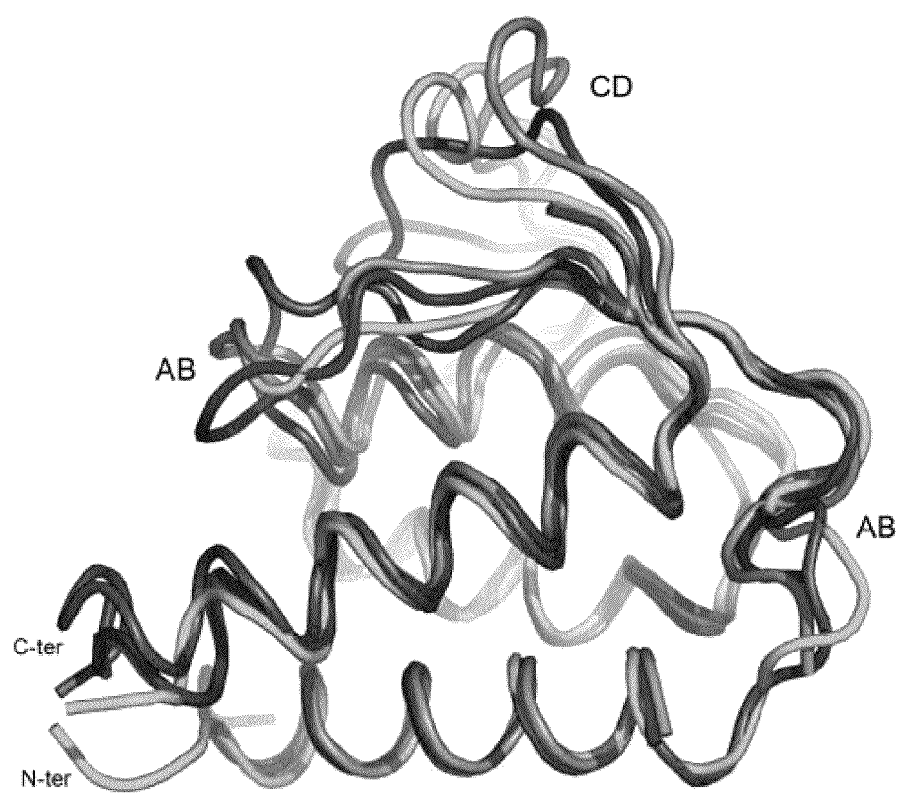
FIG. 13 shows a superposition of IL-13 structures from complexes with binding protein 6G9 and 3 different IL13 antibodies.

The IL13 structure is available for comparisons from the antibody complexes determined previously. All these antibodies bind IL13 at the surface formed by helices A and D. Superposition of the structures show that the arrangement of helices in the 4-helical bundle is essentially the same in all structures (FIG. 13). Some differences at the N- and C-termini may be due to interactions with the corresponding receptor molecules. Note that there is no difference between two of the IL13 antibodies, which share the same CDRs. Helix D in the binding protein complex is straight, whereas it is noticeably bent in the antibody complexes. The angular deviation is about 15°, which translates into a 3.3 Å shift at residue 110.

In contrast to the helical core, loops AB and CD connecting the helices exhibit substantial variability. In the present structure, loop CD is completely disordered. Given their flexibility, the observed conformations of the loops are most likely affected by crystal packing since the loops are not involved in contacts with antibodies.

The crystal structure of the IL13:Binding protein 6G9 complex has revealed that this binding protein recognizes helices A and D of IL13. The epitope is virtually the same as that of one of the IL13 antibodies. The C-terminal carboxyl group of N113 is a key element of the epitope. Target recognition involves all 4 β-turns and 4 out of 5 helices forming the groove. R23 from the N-terminal cap is an essential recognition residue. Binding protein-IL13 interactions at the ridge formed by β-turns are predominantly hydrophobic. Interactions at the groove are both hydrophobic and electrostatic. Upon binding IL13, the binding protein molecule opens by ~3.5°.

Sequence alignment indicates that the binding protein epitope identified here for cyno IL13 is preserved in wt human IL13 and R111Q (aka R130Q) human variant. Therefore, binding protein 6G9 is expected to be cross-reactive towards these species. The neutralization effect of binding protein 6G9 is due to blocking the IL13 interaction with the receptor chain IL13Rα1. 6G9 does not interfere with IL4Rα. The acetate ion bound to R108 of IL13 is located at the binding protein-IL13 interface. This suggests that not only acetate but possibly other anions, e.g. phosphate, may have a negative impact on binding by the binding protein.

Sequence Tables

| SEQ ID NO: | Name | Sequence | Features |
|---|---|---|---|
| 1 | AR Consensus | $X_1DX_3X_4GX_6TPLH$ $LAAX_{14}X_{15}GHLEI$ $VEVLLKX_{27}GAD$ VNA | $X_1$, $X_3$, $X_4$, $X_6$, $X_{14}$, and $X_{15}$ = A, D, E, F, H, I, K, L, M, N, Q, R, S, T, V, W or Y<br>$X_{27}$ = H, N, or Y |
| 2 | N-Cap | DLGKKLLEAA RAGQDDEVRI LMANGADVNA | |
| 3 | C-Cap, library | QDKFGKTAFD ISIDNGNEDL AEILQKLN | |
| 4 | IL4,Human, P05112, mature chain | HKCDITLQE IIKTLNSLTE QKTLCTELTV TDIFAASKNT TEKETFCRAA TVLRQFYSHH EKDTRCLGAT AQQFHRHKQL IRFLKRLDRN LWGLAGLNSC PVKEANQSTL ENFLERLKTI MREKYSKCSS | |
| 5 | IL4, cynomolgous (UniProt P79339,25-153) | HKCDITLQEIIKTLNSLTEQKTLCTKLTITDILAA SKNTTEKETFCRAATVLRQFYSHHEKDTRCLGATA QQFHRHKQLIRFLKRLDRNLWGLAGLNSCPVKEAN QSTLENFLERLKTIMREKYSKCSS | |
| 6 | IL4RA ECD (P24394,24-232) receptor for IL4 | GN MKVLQEPTCVSDYMSISTCEWKMNGPTNCSTELRL LYQLVFLLSEAHTCIPENNGGAGCV CHLLMDDVVSADNYTLDLWAGQQLLWKGSFKPSEH VKPRAPGNLTVHTNVSDTLLLTWSN PYPPDNYLYNHLTYAVNIWSENDPADFRIYNVTYL | |

| SEQ ID NO: | Name | Sequence | Features |
|---|---|---|---|
| | | EPSLRIAASTLKSGISYRARVRAWA QCYNTTWSEWSPSTKWHNSYREPFEQH | |
| 7 | IL2RG,CD132, cytokine receptor common subunit gamma (P31785,23-262) receptor for IL4 & IL13 | LNTTILTPNGNEDTTADFFLTTMPTDSLSVSTLPL PEVQCFVFNVEYMNCTWNSSSEPQP TNLTLHYWYKNSDNDKVQKCSHYLFSEEITSGCQL QKKEIHLYQTFVVQLQDPREPRRQA TQMLKLQNLVIPWAPENLTLHKLSESQLELNWNNR FLNHCLEHLVQYRTDWDHSWTEQSV DYRHKFSLPSVDGQKRYTFRVRSRFNPLCGSAQHW SEWSHPIHWGSNTSKENPFLFALEA | |
| 8 | IL13Ralpha1, CD213a1; P78552,A27-T343 | GGGGAAPTETQPPVTNLSVSVENLCTVIWTWNPPE GASSNCSLWYFSHFGDKQDKKIAPE TRRSIEVPLNERICLQVGSQCSTNESEKPSILVEK CISPPEGDPESAVTELQCIWHNLSY MKCSWLPGRNTSPDTNYTLYYWHRSLEKIHQCENI FREGQYFGCSFDLTKVKDSSFEQHS VQIMVKDNAGKIKPSFNIVPLTSRVKPDPPHIKNL SFHNDDLYVQWENPQNFISRCLFYE VEVNNSQTETHNVFYVQEAKCENPEFERNVENTSC FMVPGVLPDTLNTVRIRVKTNKLCY EDDKLWSNWSQEMSIGKKRNST | |
| 9 | C06 13A10 | DLGKKLLEAARAGQDDEVRILMANGADVNVSDRIG NTPLHLAAVYVHLEIVEVLLKNGADVNALDDDGLT PLHLAAADGHLEIVEVLLKHGADVNATDSHVWTPL HLAAFFGHLEIVEVLLKYGADVNAQDKFGKTAFDI SIDNGNEDLAEILQKLN | |
| 10 | C06 17A11 | DLGKKLLEAARAGQDDEVRILMANGADVNAIDEWG DTPLHLAAIEGHLEIVEVLLKYGADVNASDAMGMT PLHLAAVYGYLEIVEVLLKNGADVNAMDFSGFTPL HLAAFSGHLEIVEVLLKYGADVNAQDKFGKTAFDI SIDNGNEDLAEILQKLN | |
| 11 | C06 19C3 | DLGKKLLEAARAGQDDEVRILMANGADVNATDDWG DTLLHLAATDGHLEIVEVLLKNGADVNAIDAMGMT PLHLAAVYGYLEIVEVLLKNGADVNAMDFSGFTPL HLAAFSGHLEIVEVLLKYGADVNAQDKFGKTAFDI SIDNGNEDLAEILQKLN | |
| 12 | C06 19F8 | DLGKKLLEAARAGQDDEVRILMANGADVNATDDWG DTLLHLAATDGHLEIVEVLLKNGADVNASDSQGLT PLHLAAYYGHLEIVEVLLKYGADVNANDHHGITPL HLAAFAGHLEIVEVLLKYGADVNAQDKFGKTAFDI SIDNGNEDLAEILQKLN | |
| 13 | C06 20B8 | DLGKKLLEAASAGQDDEVHILMANGADVNAVDHDG FTPLHLAAADGHLEIVEVLLKHGADVNADDNFGWT PLHLAAFFGHLEIVEVLLKHGADVNAKDQTGLTPL HLAAVDGHLEIVEVLLKHGADVNAQDKFGKTAFDI SIDNGNEDLAEILQKLN | |
| 14 | C06 26H2 | DLGKKLLEAARAGQDDEVRILMANGADVNAYDSSG DTPLHVAAIDGHLEIVEVLLKHGADVNASDASGDT PLHLAADFGHLKIVEVLLKHGADVNAEDMIGITPL HLAAYNGHLEIVEVLLKNGADVNASDVHGFTPLHL AAFIGHLGIVEVLLKYDADVNAQDKFGKTAFDISI DNRNEDLAEILQKLN | |
| 15 | C06 28D4 | DLGKELLEAASAGQDDEVHILMANGADVNAVDHDG FTPLHLAAADGHLEIVEVLLKHGADVNADDNFGWT PLHLAAFFGHLEIVEVLLKHGADVNAKDQTGLTPL HLAAVDGHLEIVEVLLKNGADVNAQDKFGKTAFDI SIDNGNEDLAEILQKLN | |
| 16 | C06 28E5 | DLGKKLLEAARAGQDDEVRILMANGADVNAADDSG ITPLHLAAEDGHLEIVEVLLKYGADVNAQDNLGDT PLHLAAWTGHLEIVEVLLKNGADVNAYDISIGITPL HLAAFYGHLEIVEVLLKHGADVNAQDKFGKTAFDI SIDNGNEDLAEILQKLN | |

| SEQ ID NO: | Name | Sequence | Features |
|---|---|---|---|
| 17 | C06 42A11 | DLGKKLLEAASVGQDDEVHILMANGADVNATDAWG LTPLHLAALLGHLEIVEVLLKHGADVNAHDETGFT PLHLAAVEGHLEIVEVLLKYGADVNASDILGRTPL HLAANFGHLEIVEVLLKHGADVNAQDKFGKTAFDI SIDNGNEDLAEILQKLN | |
| 18 | C06 42C7 | DLGKKLLEAASAGQDDEVRILMANGADVNAVDHDG FTPLHLAAADGHLEIVEVLLKHGADVNADDNFGWT PLHLAAFFGHLEIVEVLLKHGADVNAKDQTGLTPL HLAAVDGHLEIVEVLLKHGADVNAQDKFGKTAFDI SIDNGNEDLAEILQKLN | |
| 19 | C06 43G2 | DLGKKLLEAARAGQDDEVRILMANGADVNAKDVTG ETPLHLASWEGHLEIVEVLLKHGADVNAQDLFGIT PLHLAAATDGHLEIVEVLLKNGADVNATDSNGFTP LHLAASYGHLEIVDVLLKNGADVNAHDFDGFTPLH LAASWGHLEIVEVLLKYGADVNAQDKFGKTAFDIS IDNGNEDLAEILQKLN | |
| 20 | C06_44C12 | DLGKKLLEAASAGQDDEVHILMANGADVNALDDSG YTPLHLAAEDGHLEIVEVLLKHGADVNAADRMGDT PLHLAAFVGHLEIVEVLLKYGADVNAVDLAGVTPL HVAAFYGHLEIVEVLLKYGADVNAQDKFGKTAFDI SIDNGNEDLAEILQKLN | |
| 21 | C06 44F6 | DLGKELLEAARAGQDDEVHILMANGADVNALDDSG YTPLHLAAEDGHLEIVEVLLKHGADVNAMDNIGNT SLHLAAFDGHLEIVEVLLKYGADVNAVDLAGVTPL HVAAFYGHLEIVEVLLKHGADVNAQDKFGKTAFDI SIDNGNEDLAEILQKLN | |
| 22 | C06 48F3 | DLGKKLLEAARAGQDDEVRILMANGADVNAFDDSG LTPLHLAADDGHLEIVEVLLKHGADVNAADRMGDT PLHLAAFVGHLEIVEVLLKYGADVNAVDLAGVTPL HVAAFYGHLEIVEVLLKYGADVNAQDKFGKTAFDI SIDNGNEDLAEILQKLN | |
| 23 | C06 50E5 | DLGKKLLEAARAGQDDEVRILMANGADANATDDWG DTLLHLAATDGHLEIVEVLLKNGADVNAIDAMGMT PLHLAAVYGYLEIVEVLLKNGADVNAMDFSGFTPL HLAAFSGHLEIVEVLLKYGADVNAQDKFGKTAFDI SIDNGNEDLAEILQKLN | |
| 24 | C06 53E9 | DLGKELLEAASAGQDDEVHILMANGADVNASDKDG STPLHLAAVYGHLEIVEVLLKYGADVNAEDMNGYT PLHLAAADGHLEIVEVLLKYGADVDAKDRTGWTPL HLAGEFGHLEIVEVLLKYGADVNAQDKFGKTAFDI SIDNGNEDLAEILQKLN | |
| 25 | C06 53G6 | NLGKKLLEAARAGQDDEVRILMANGADVNATDDWG DTLLHLAATDGHLEIVEVLLKYGADVNANDAIGDT PLHLAALYGHLEIVEVLLKYGADVNATDLHGFTPL HLAAFWGHLEIVEVLLKHGADVNAQDKFGKTAFDI SIDNGNEDLAEILQKLN | |
| 26 | C06 54C2 | DLGKKLLEAARAGQDDEVRILMANGADVNATDDWG DTLLHLAATDGHLEIVEVLLKNGADVNAIDAMGMT PLHLAAVYGYLEIVEVLLKNGADVNAMDFSGFTPL HLTAFSGHLEIVEVLLKYGADVNAQDKFGKTAFDI SIDNGNEDLAEILQKLN | |
| 27 | C06 6E9 | DLGKKLLEAARAGQDDEVRILMANGADVNAIDSDG TTPLHLAAMDGHLEIVEVLLKYGADVNAVDWNGDT PLHLAAVDGHLEIVEVLLKYGADVNAQDNLGDTPL HLAAYYGHLEIVEVLLKHGADVNASDFHGITPLHL AAFSGHLEIVEVLLKYGADVNAQDKFGKTAFDISI DNGNEDLAEILQKLN | |
| 28 | C06_24H1 | DLGKKLLEAARAGQDDEVRILMANGADVNAHDNSG FTPLHLAAEIGHLEIVEVLLKYGADVNAADRMGDT PLHLAAFVGHLEIVEVLLKYGADVNAVDLAGVTPL HVAAFYGHLEIVEVLLKNGADVNAQDKFGKTAFDI SIDNGNEDLAEILQKLN | |

| SEQ ID NO: | Name | Sequence | Features |
|---|---|---|---|
| 29 | C06 4A7 | DLGKKLLEAARAGQDDEVRILMANGADVNAEDDWG LTPLHLAAMLGHLEIVEVLLKYGADVNAKDDTGFT PLHLAAVEGHLEIVEVLLKYGADVNASDILGRTPL HLAANFGHLEIVEVLLKYGADVNAQDKFGKTAFDI SIDNGNEDLAEILQKLN | |
| 30 | C06 14A4 | DLGKKLLEAARAGQDDEVRILMANGADVNATDAWG LTPLHLAALLGHLEIVEVLLKHGADVNAHDETGFT PLHLAAVEGHLEIVEVLLKYGADVNASDILGRTPL HLAANFGHLEIVEVLLKYGADVNAQDKFGKTAFDI SIDNGNEDLAEILQKLN | |
| 31 | AR1 C06 13A10 | SDRIGNTPLH LAAVYHLEI VEVLLKNGAD VNA | |
| 32 | AR1 C06 17A11 | IDEWGDTPLH LAAIEGHLEI VEVLLKYGAD VNA | |
| 33 | AR1 C06 19C3 & AR1 C06_19F8 | TDDWGDTLLH LAATDGHLEI VEVLLKNGAD VNA | |
| 34 | AR1 C06 20B8, AR1 C06_28D4, & AR1 C06 42C7 | VDHDGFTPLH LAAADGHLEI VEVLLKHGAD VNA | |
| 35 | AR1 C06 26H2 | YDSSGDTPLH VAAIDGHLEI VEVLLKHGAD VNA | |
| 36 | AR1 C06 28E5 | ADDSGITPLH LAAEDGHLEI VEVLLKYGAD VNA | |
| 37 | AR1 C06_42A11, AR1 C06 14A4, & AR1 C06 14A4 | TDAWGLTPLH LAALLGHLEI VEVLLKHGAD VNA | |
| 38 | AR1 C06 43G2 | KDVTGETPLH LASWEGHLEI VEVLLKHGAD VNA | |
| 39 | AR1 C06 44C12 & AR1 C06 44F6 | LDDSGYTPLH LAAEDGHLEI VEVLLKHGAD VNA | |
| 40 | AR1C06 48F3 | FDDSGLTPLH LAADDGHLEI VEVLLKHGAD VNA | |
| 33 | AR1 C06 50E5 & AR1 C06 54C2 | TDDWGDTLLH LAATDGHLEI VEVLLKNGAD VNA | |
| 42 | AR1C06 53E9 | SDKDGSTPLH LAAVYGHLEI VEVLLKYGAD VNA | |
| 43 | AR1C06 53G6 | TDDWGDTLLH LAATDGHLEI VEVLLKYGAD VNA | |
| 44 | AR1C06 6E9 | IDSDGTTPLH LAAMDGHLEI VEVLLKYGAD VNA | |
| 45 | AR1C06 24H1 | HDNSGFTPLH LAAEIGHLEI VEVLLKYGAD VNA | |
| 46 | AR1C06_4A7 | EDDWGLTPLH LAAMLGHLEI VEVLLKYGAD VNA | |
| 47 | AR2C06 13A10 | LDDDGLTPLH LAAADGHLEI VEVLLKHGAD VNA | |
| 48 | AR2C06 17A11 | SDAMGMTPLH LAAVYGYLEI VEVLLKNGAD VNA | |

| SEQ ID NO: | Name | Sequence | Features |
|---|---|---|---|
| 49 | AR2 C06 19C3, AR2 C06_50E5, & AR2 C06 54C2 | IDAMGMTPLH LAAVYGYLEI VEVLLKNGAD VNA | |
| 50 | AR2C06 19F8 | SDSQGLTPLH LAAYYGHLEI VEVLLKYGAD VNA | |
| 51 | AR2 C06 20B8, AR2 C06_28D4, & AR2 C06 42C7 | DDNFGWTPLH LAAFFGHLEI VEVLLKHGAD VNA | |
| 52 | AR2C06_26H2 | SDASGDTPLH LAADFGHLKI VEVLLKHGAD VNA | |
| 53 | AR2 C06 28E5 | QDNLGDTPLH LAAWTGHLEI VEVLLKNGAD VNA | |
| 54 | AR2 C06 42A11 & AR2 C06_14A4 | HDETGFTPLH LAAVEGHLEI VEVLLKYGAD VNA | |
| 55 | AR2 C06 43G2 | QDLFGITPLH LAAATDGHLEI VEVLLKNGAD VNA | |
| 56 | AR2 C06_44C12, AR2 C06 48F3, & AR2 C06_24H1 | ADRMGDTPLH LAAFVGHLEI VEVLLKYGAD VNA | |
| 57 | AR2 C06 44F6 | MDNIGNTSLH LAAFDGHLEI VEVLLKYGAD VNA | |
| 58 | AR2 C06 53E9 | EDMNGYTPLH LAAADGHLEI VEVLLKYGAD VDA | |
| 59 | AR2 C06 53G6 | NDAIGDTPLH LAALYGHLEI VEVLLKYGAD VNA | |
| 60 | AR2 C06 6E9 | VDWNGDTPLH LAAVDGHLEI VEVLLKYGAD VNA | |
| 61 | AR2 C06 4A7 | KDDTGFTPLH LAAVEGHLEI VEVLLKYGAD VNA | |
| 62 | AR3 C06 13A10 | TDSHVWTPLH LAAFFGHLEI VEVLLKYGAD VNA | |
| 63 | AR3 C06_17A11, AR3 C06_19C3, & AR3 C06_50E5 | MDFSGFTPLH LAAFSGHLEI VEVLLKYGAD VNA | |
| 64 | AR3 C06 19F8 | NDHHGITPLH LAAFAGHLEI VEVLLKYGAD VNA | |
| 65 | AR3 C06 20B8 | KDQTGLTPLH LAAVDGHLEI VEVLLKHGAD VNA | |
| 66 | AR3 C06 26H2 | EDMIGITPLH LAAYNGHLEI VEVLLKNGAD VNA | |
| 67 | AR3 C06 28D4 & AR3 C06_42C7 | KDQTGLTPLH LAAVDGHLEI VEVLLKNGAD VNA | |
| 68 | AR3 C06 28E5 | YDISGITPLH LAAFYGHLEI VEVLLKHGAD VNA | |
| 69 | AR3 C06 42A11 | SDILGRTPLH LAANFGHLEI VEVLLKHGAD VNA | |

-continued

| SEQ ID NO: | Name | Sequence | Features |
|---|---|---|---|
| 70 | AR3 C06 43G2 | TDSNGFTPLH LAASYGHLEI VDVLLKNGAD VNA | |
| 71 | AR3 C06 44C12 & AR3 C06_48F3 | VDLAGVTPLH VAAFYGHLEI VEVLLKYGAD VNA | |
| 72 | AR3 C06 44F6 | VDLAGVTPLH VAAFYGHLEI VEVLLKHGAD VNA | |
| 73 | AR3 C06 53E9 | KDRTGWTPLH LAGEFGHLEI VEVLLKYGAD VNA | |
| 74 | AR3 C06_53G6 | TDLHGFTPLH LAAFWGHLEI VEVLLKHGAD VNA | |
| 75 | AR3 C06 54C2 | MDFSGFTPLH LTAFSGHLEI VEVLLKYGAD VNA | |
| 76 | AR3 C06 6E9 | QDNLGDTPLH LAAYYGHLEI VEVLLKHGAD VNA | |
| 77 | AR3 C06 24H1 | VDLAGVTPLH VAAFYGHLEI VEVLLKNGAD VNA | |
| 78 | AR3 C06 4A7 & AR3 C06_14A4 | SDILGRTPLH LAANFGHLEI VEVLLKYGAD VNA | |
| 79 | AR4 C06 6E9 | SDFHGITPLH LAAFSGHLEI VEVLLKYGAD VNA | |
| 80 | AR4 C06 26H2 | SDVHGFTPLH LAAFIGHLGI VEVLLKYDAD VNA | |
| 81 | AR4 C06 43G2 | HDFDGFTPLH LAASWGHLEI VEVLLKYGAD VNA | |
| 82 | AR1-C | $X_1$DDWG$_6$TPLHLAATDGHLEIVEVLLK$X_{27}$GADVNA | $X_1$ is selected from T, V, I, S, A, V, and H $X_6$ is selected from D, F, L, I, N, E, Y, and T $X_{27}$ is selected from H, N, and Y |
| 83 | AR2-C | $X_1$D$X_3$$X_4$G$X_6$TPLHLAA$X_{14}$$X_{15}$GHLEIVEVLLK$X_{27}$GAD VNA | $X_1$ is selected from S, I, D, Q, A, E, H, K, N, and V $X_3$ is selected from A, D, E, L, M, N, S, and W $X_4$ is selected from D, F, I, L, M, N, Q, S, and T $X_6$ is selected from D, M, L, F, I, and Y; $X_{14}$ is selected from A, D, F, L, V, and Y $X_{15}$ is selected from D, E, F, T, V, W, and Y $X_{27}$ is selected from H, N, and Y |
| 84 | AR3-C | $X_1$D$X_3$$X_4$GFTPLHLAA$X_{14}$$X_{15}$GHLEIVEVLLK$X_{27}$GAD VNA | $X_1$ is selected from M, K, V, |

-continued

| SEQ ID NO: | Name | Sequence | Features |
|---|---|---|---|
| | | | E, N, T, S and Y<br>$X_3$ is selected from F, H, I, L, M, N, Q, R, and S<br>$X_4$ is selected from A, H, I, L, N, S, and T<br>$X_{14}$ is selected from E, F, N, 5, V and Y<br>$X_{15}$ is selected from A, D, F, I, N, 5, and Y<br>$X_{27}$ is selected from H, N, and Y |
| 85 | AR1-F | TDDWGX$_6$TPLHLAATDGHLEIVEVLLKX$_{27}$GADVNA | $X_6$ is selected from D, F, L, I, N, E Y, and T<br>$X_{27}$ is selected from H, N, and Y |
| 86 | AR2-F | X$_1$DAMGX$_6$TPLHLAAVYGHLEIVEVLLKX$_{27}$GADVNA | $X_1$ is selected from A, D, E, H, I, K, N, Q, and V<br>$X_6$ is selected from D, F, I, L, M and, Y<br>$X_{27}$ is selected from H, N, and Y |
| 87 | AR3-F | X$_1$DX$_3$X$_4$GFTPLHLAAFYGHLEIVEVLLKX$_{27}$GADVNA | $X_1$ is selected from E, K, M, N, T, 5, V and Y<br>$X_3$ is selected from F, H, I, L, M, N, Q, S, and VR,<br>$X_4$ is selected from A, H, I, L, N, S, and T<br>$X_{27}$ is selected from H, N, and Y |
| 88 | AR1-O | X$_1$DDX$_4$GX$_6$TPLHLAAX$_{14}$DGHLEIVEVLLKX$_{27}$GADVNA | $X_1$ is selected from A, L, and T<br>$X_4$ is selected from S and W<br>$X_6$ is selected from D, I, and Y<br>$X_{14}$ is selected from E and T<br>$X_{27}$ is selected from A and H |
| 89 | AR2-O | X$_1$DX$_3$X$_4$GDTPLHLAAX$_{14}$X$_{15}$GHLEIVEVLLKX$_{27}$GADVNA | $X_1$ is selected from A, N, and Q<br>$X_3$ is selected from A, N, and R<br>$X_4$ is selected from I and L<br>$X_{14}$ is selected |

| SEQ ID NO: | Name | Sequence | Features |
|---|---|---|---|
| | | | from F, L and W<br>X$_{15}$ is selected from T, V, and Y<br>X$_{27}$ is selected from A and Y |
| 90 NA | AR3-O | X$_1$DX$_3$X$_4$GX$_6$TPLHLAAFX$_{15}$GHLEIVEVLLKX$_{27}$GADV | X$_1$ is selected from T, V, and Y<br>X$_3$ is selected from I and L<br>X$_4$ is selected from A, H, and S<br>X$_6$ is selected from F, I, and V<br>X$_{15}$ is selected from W and Y<br>X$_{27}$ is selected from A and H |
| 91 | C06_44C12v2 | DLGKKLLEAASAGQDDEVHILMANGADVNALDDS<br>GYTPLHLAAEDGHLEIVEVLLKHGADVNAADRLG<br>DTPLHLAAFVGHLEIVEVLLKAGADVNAVDLAGV<br>TPLHVAAFYGHLEIVEVLLKAGADVNAQDKFGKT<br>AFDISIDNGNEDLAEILQKLN | |
| 92 | C06_28E5v1 | DLGKKLLEAARAGQDDEVRILMANGADVNAADDS<br>GITPLHLAAEDGHLEIVEVLLKAGADVNAQDNLG<br>DTPLHLAAWTGHLEIVEVLLKAGADVNAYDISGI<br>TPLHLAAFYGHLEIVEVLLKHGADVNAQDKFGKT<br>AFDISIDNGNEDLAEILQKLN | |
| 93 | C06_53G6v1 | DLGKKLLEAARAGQDDEVRILMANGADVNATDDW<br>GDTLLHLAATDGHLEIVEVLLKAGADVNANDAIG<br>DTPLHLAALYGHLEIVEVLLKYGADVNATDLHGF<br>TPLHLAAFWGHLEIVEVLLKHGADVNAQDKFGKT<br>AFDISIDNGNEDLAEILQKLN | |
| 94 | C01_6G9_V1 | DLDKKLLEAARAGQDDEVRILMANGADVNARDSY<br>GSTPLHLAAREGHLEIVEVLLKYGADVNAADFIG<br>DTPLHLAAYRGHLEIVEVLLKYGADVNASDITGE<br>TPLHLAAQIGHLEIVEVLLKHGADVNAQDKFGKT<br>AFDISIDNGNEDLAEILQKLN | |
| 95 | C01_6G9_V1_C06_28E5V1 | DLDKKLLEAARAGQDDEVRILMANGADVNARDSY<br>GSTPLHLAAREGHLEIVEVLLKYGADVNAADFIG<br>DTPLHLAAYRGHLEIVEVLLKYGADVNASDITGE<br>TPLHLAAQIGHLEIVEVLLKHGADVNAQDKFGKT<br>AFDISIDNGNEDLAEILQKLGGGGSGGGGSGGGG<br>SGGGGSRSDLGKKLLEAARAGQDDEVRILMANGA<br>DVNAADDSGITPLHLAAEDGHLEIVEVLLKAGAD<br>VNAQDNLGDTPLHLAAWTGHLEIVEVLLKAGADV<br>NAYDISGITPLHLAAFYGHLEIVEVLLKHGADVN<br>AQDKFGKTAFDISIDNGNEDLAEILQKLN | |
| 96 | C06_28E5_V1C01_6G9_V1 | DLGKKLLEAARAGQDDEVRILMANGADVNAADDS<br>GITPLHLAAEDGHLEIVEVLLKAGADVNAQDNLG<br>DTPLHLAAWTGHLEIVEVLLKAGADVNAYDISGI<br>TPLHLAAFYGHLEIVEVLLKHGADVNAQDKFGKT<br>AFDISIDNGNEDLAEILQKLNGGGGSGGGGSGGG<br>GSGGGGSDLDKKLLEAARAGQDDEVRILMANGAD<br>VNARDSYGSTPLHLAAREGHLEIVEVLLKYGADV<br>NAADFIGDTPLHLAAYRGHLEIVEVLLKYGADVN<br>ASDITGETPLHLAAQIGHLEIVEVLLKHGADVNA<br>QDKFGKTAFDISIDNGNEDLAEILQKLN | |
| 97 | C01_6G9_V1_C06_44C12_V2 | DLDKKLLEAARAGQDDEVRILMANGADVNARDSY<br>GSTPLHLAAREGHLEIVEVLLKYGADVNAADFIG<br>DTPLHLAAYRGHLEIVEVLLKYGADVNASDITGE<br>TPLHLAAQIGHLEIVEVLLKHGADVNAQDKFGKT<br>AFDISIDNGNEDLAEILQKLNGGGGSGGGGSGGGG | |

| SEQ ID NO: | Name | Sequence | Features |
|---|---|---|---|
| | | GSGGGGSDLGKKLLEAASAGQDDEVHILMANGAD VNALDDSGYTPLHLAAEDGHLEIVEVLLKHGADV NAADRLGDTPLHLAAFVGHLEIVEVLLKAGADVN AVDLAGVTPLHVAAFYGHLEIVEVLLKAGADVNA QDKFGKTAFDISIDNGNEDLAEILQKLN | |
| 98 | Co6_44C12_V2_ C01_6G9_V1 | DLGKKLLEAASAGQDDEVHILMANGADVNALDDS GYTPLHLAAEDGHLEIVEVLLKHGADVNAADRLG DTPLHLAAFVGHLEIVEVLLKAGADVNAVDLAGV TPLHVAAFYGHLEIVEVLLKAGADVNAQDKFGKT AFDISIDNGNEDLAEILQKLNGGGGSGGGGSGGG GSGGGGSDLDKKLLEAARAGQDDEVRILMANGAD VNARDSYGSTPLHLAAREGHLEIVEVLLKYGADV NAADFIGDTPLHLAAYRGHLEIVEVLLKYGADVN ASDITGETPLHLAAQIGHLEIVEVLLKHGADVNA QDKFGKTAFDISIDNGNEDLAEILQKLN | |
| 99 | C01_6G9_V1_ C06_53G6_V1 | DLDKKLLEAARAGQDDEVRILMANGADVNARDSY GSTPLHLAAREGHLEIVEVLLKYGADVNAADFIG DTPLHLAAYRGHLEIVEVLLKYGADVNASDITGE TPLHLAAQIGHLEIVEVLLKHGADVNAQDKFGKT AFDISIDNGNEDLAEILQKLNGGGGSGGGGSGGG GSGGGGSDLGKKLLEAARAGQDDEVRILMANGAD VNATDDWGDTLLHLAATDGHLEIVEVLLKAGADV NANDAIGDTPLHLAALYGHLEIVEVLLKYGADVN ATDLHGFTPLHLAAFWGHLEIVEVLLKHGADVNA QDKFGKTAFDISIDNGNEDLAEILQKLN | |
| 100 | C06_53G6_V1_ C01_6G9_V1 | DLGKKLLEAARAGQDDEVRILMANGADVNATDDW GDTLLHLAATDGHLEIVEVLLKAGADVNANDAIG DTPLHLAALYGHLEIVEVLLKYGADVNATDLHGF TPLHLAAFWGHLEIVEVLLKHGADVNAQDKFGKT AFDISIDNGNEDLAEILQKLNGGGGSGGGGSGGG GSGGGGSDLDKKLLEAARAGQDDEVRILMANGAD VNARDSYGSTPLHLAAREGHLEIVEVLLKYGADV NAADFIGDTPLHLAAYRGHLEIVEVLLKYGADVN ASDITGETPLHLAAQIGHLEIVEVLLKHGADVNA QDKFGKTAFDISIDNGNEDLAEILQKLN | |
| 101 | Human IL13 and variant, where X is R or Q | GPVPPSTALRELIEELVNITQNQKAPLCNGSMVW SINLTAGMYCAALESLINVSGCSAIEKTQRMLSG FCPHKVSAGQFSSLHVRDTKIEVAQFVKDLLLHL KKLFREGXFN | |
| 102 | Interleukin- 13 receptor subunit alpha 2, *Homo sapiens* (>Q14627,27-380) | DTEIKVNPPQDFEIVDPGYLGYLYLQWQPPLSD HFKECTVEYELKYRNIGSETWKTIIT KNLHYKDGFDLNKGIEAKIHTLLPWQCTNGSEVQ SSWAETTYWISPQGIPETKVQDMDCV YYNWQYLLCSWKPGIGVLLDTNYNLFYWYEGLDH ALQCVDYIKADGQNIGCRFPYLEASD YKDFYICVNGSSENKPIRSSYFTFQLQNIVKPLP PVYLTFTRESSCEIKLKWSIPLGPIP ARCFDYEIEIREDDTTLVTATVENETYTLKTTNE TRQLCFVVRSKVNIYCSDDGIWSEWS DKQCWEGEDLSKKTLLRFWLPFGFILILVIFVTG LLLRKPNTYPKMIPEFFCDT | |
| 103 | Modified C-cap | QDKFGKTPADIAADNGHEDIAEVLQKAA | |
| 104 | Human bispecific (Re-engineered 44C12-linker- 6G9 w modified C-cap) | DLGKKLLEAARAGQDDEVRILMANGADVNALDDS GYTPLHLAAEDGHLEIVEVLLKHGADVNAADRLG DTPLHLAAFVGHLEIVEVLLKAGADVNAVDLAGV TPLHVAAFYGHLEIVEVLLKAGADVNAQDKFGKT PADIAADNGHEDIAEVLQKAAGGGGSGGGGSGGG GSGGGGSGSDLDKKLLEAARAGQDDEVRILMANG ADVNARDSYGSTPLHLAAREGHLEIVEVLLKYGA DVNAADFIGDTPLHLAAYRGHLEIVEVLLKYGAD VNASDITGETPLHLAAQIGHLEIVEVLLKHGADV NAQDKFGKTPADIAADNGHEDIAEVLQKAA | |

| SEQ ID NO: | Name | Sequence | Features |
|---|---|---|---|
| 177 | Human bispecific (Re-engineered 44C12-linker-6G9 w modified C-cap) | GSDLGKKLLEAARAGQDDEVRILMANGADVNALD DSGYTPLHLAAEDGHLEIVEVLLKHGADVNAADR LGDTPLHLAAFVGHLEIVEVLLKAGADVNAVDLA GVTPLHVAAFYGHLEIVEVLLKAGADVNAQDKFG KTPADIAADNGHEDIAEVLQKAAGGGGSGGGGSG GGGSGGGGSGSDLDKKLLEAARAGQDDEVRILMA NGADVNARDSYGSTPLHLAAREGHLEIVEVLLKY GADVNAADFIGDTPLHLAAYRGHLEIVEVLLKYG ADVNASDITGETPLHLAAQIGHLEIVEVLLKHGA DVNAQDKFGKTPADIAADNGHEDIAEVLQKAA | |
| 41 | Human bispecific (44C12-linker-6G9) | DLGKKLLEAASAGQDDEVRILMANGADVNALDDS GYTPLHLAAEDGHLEIVEVLLKHGADVNAADRLG DTPLHLAAFVGHLEIVEVLLKAGADVNAVDLAGV TPLHVAAFYGHLEIVEVLLKAGADVNAQDKFGKT AFDISIDNGNEDLAEILQKAAGGGGSGGGGSGGG GSGGGGSGSDLDKKLLEAARAGQDDEVRILMANG ADVNARDSYGSTPLHLAAREGHLEIVEVLLKYGA DVNAADFIGDTPLHLAAYRGHLEIVEVLLKYGAD VNASDITGETPLHLAAQIGHLEIVEVLLKHGADV NAQDKFGKTAFDISIDNGNEDLAEILQKAA | |
| 178 | Human bispecific (44C12-linker-6G9) | GSDLGKKLLEAASAGQDDEVRILMANGADVNALD DSGYTPLHLAAEDGHLEIVEVLLKHGADVNAADR LGDTPLHLAAFVGHLEIVEVLLKAGADVNAVDLA GVTPLHVAAFYGHLEIVEVLLKAGADVNAQDKFG KTAFDISIDNGNEDLAEILQKAAGGGGSGGGGSG GGGSGGGGSGSDLDKKLLEAARAGQDDEVRILMA NGADVNARDSYGSTPLHLAAREGHLEIVEVLLKY GADVNAADFIGDTPLHLAAYRGHLEIVEVLLKYG ADVNASDITGETPLHLAAQIGHLEIVEVLLKHGA DVNAQDKFGKTAFDISIDNGNEDLAEILQKAA | |
| 105 | C06_21H2 mu IL4 binding protein surrogate | DLGEKLLEAARAGQDDEVRILMANGADVNAYDDD GMTPLHLAAKSGHLEIVEVLLKHGADVNAMDITG SAPLHLAADLGHLEIVEVLLKHGADVNAIDYLGA TPLHLAATYGHPEIVEVLLKYGADVNAQDKFGKT AFDISIDNGNEDLAEILQKLN | |
| 106 | 21H2 mu IL13 binding protein surrogate | DLGEKLLEAARAGQDDEVRILMANGADVNAYDDD GMTPLHLAAKSGHLEIVEVLLKHGADVNAMDITG SAPLHLAADLGHLEIVEVLLKHGADVNAIDYLGA TPLHLAATYGHPEIVEVLLKYGADVNAQDKFGKT AFDISIDNGNEDLAEILQKLN | |
| 107 | 11G11-21H2 Bispecific surrogate | MRGSHHHHHHGSDLGKKLMEAARAGQDDEVRILM ANGADVNAKDLFGITPLHLAAVYGHLEIVEVLLK HGADVNATDNWGSTPLHLAAQFGHLEIVEVLLKY GADVNAQDKFGKTAFDISIDNGNEDLAEILQKLG GGGSGGGGSGGGGSGGGGSRSDLGEKLLEAARAG QDDEVRILMANGADVNAYDDDGMTPLHLAAKSGH LEIVEVLLKHGADVNAMDITGSAPLHLAADLGHL EIVEVLLKHGADVNAIDYLGATPLHLAATYGHPE IVEVLLKYGADVNAQDKFGKTAFDISIDNGNEDL AEILQKLN | |

Note:
SEQ ID NOS: 41, 104, 177, and 178 optionally have a Met residue at the N-terminus IL13 Binding Protein AR Sequences

| SEQ ID NO: | Name | Sequence | Clones |
|---|---|---|---|
| 108 | AR | XDXXGXTPLH LAAXXGHLEI VEVLLKXGAD VNA | |
| 109 | AR1 | R•SY•S•••• •••RE••••• ••••••Y••• ••• RDSYGSTPLH LAAREGHLEI VEVLLKYGAD VNA | 6G9 |
| 110 | AR1 | T•EFDS•••• •••RH••••• ••••••Y••• ••• TDEFDSTPLH LAARHGHLEI VEVLLKYGAD VNA | 7G11 |
| 111 | AR1 | S•IF•S•••• •••RH••••• ••••••Y••• ••• SDIFGSTPLH LAARHGHLEI VEVLLKYGAD VNA | 9F8 |
| 112 | AR1 | I•HFDS•••• •••RH••••• ••••••N••• ••• IDHFDSTPLH LAARHGHLEI VEVLLKNGAD VNA | 10A6 |

-continued

| # | AR | Sequence | Clone |
|---|---|---|---|
| 113 | AR1 | T•VF•S•••• •••RH•••• ••••••H••• ••• <br> TDVFGSTPLH LAARHGHLEI VEVLLKHGAD VNA | 5B9 |
| 114 | AR1 | F•DF•S•••• •••RS•••• ••••••H••• ••• <br> FDDFGSTPLH LAARSGHLEI VEVLLKHGAD VNA | 7D2 |
| 115 | AR1 | E•IL•I•••• •••HH•••• ••••••H••• ••• <br> EDILGITPLH LAAHHGHLEI VEVLLKHGAD VNA | 6G11 |
| 116 | AR1 | T•TY•S•••• •••RHC•Q•• ••••••H••• ••• <br> TDTYGSTPLH LAARHCHQEI VEVLLKHGAD VNA | 7D7 |
| 117 | AR1 | V•DY•S•••• •••RQ•••• ••••••N••• ••• <br> VDDYGSTPLH LAARQGHLEI VEVLLKNGAD VNA | 5D12 |
| 118 | AR1 | K•LF•S•••• •••RH•••• ••••••N••• ••• <br> KDLFGSTPLH LAARHGHLEI VEVLLKNGAD VNA | 5D2 |
| 119 | AR1 | T•MY•S•••• •••RH•••• ••••••Y••• ••• <br> TDMYGSTPLH LAARHGHLEI VEVLLKYGAD VNA | 7H3 |
| 120 | AR1 | W•SY•S•••• •••RE•••• ••••••Y••• ••• <br> WDSYGSTPLH LAAREGHLEI VEVLLKYGAD VNA | 5D3 |
| 121 | AR1 | A•MY•T•Q•• •••RT•••• ••••••Y••• ••• <br> ADMYGTTPQH LAARTGHLEI VEVLLKYGAD VNA | 5H7 |
| 122 | AR1 | S•IY•S•••• •••RH•••• ••••••N••• ••• <br> SDIYGSTPLH LAARHGHLEI VEVLLKNGAD VNA | 9E11 |
| 123 | AR1 | A•DY•S•••• •••RS•••• ••••••H••• ••• <br> ADDYGSTPLH LAARSGHLEI VEVLLKHGAD VNA | 6D4 |
| 124 | AR1 | M•KY•S•••• •••RS•••• ••••••H••• ••• <br> MDKYGSTPLH LAARSGHLEI VEVLLKHGAD VNA | 7C6 |
| 125 | AR1 | F•DF•D•••• •••RE•••• ••••••K••• ••• <br> FDDFGDTPLH LAAREGHLEI VEVLLKKGAD VNA | 2F1 |
| 126 | | XDXXGXTPLH LAAXXGHLEI VEVLLKXGAX VNA | |
| 127 | AR2 | K•MI•D•••• •••YR•••• ••••••N••• ••• <br> KDMIGDTPLH LAAYRGHLEI VEVLLKNGAD VNA | 6G9 |
| 128 | AR2 | A•FI•D•••• •••YR•••• ••••••C•V• ••• <br> ADFIGDTPLH LAAYRGHLEI VEVLLKCGVD VNA | 7G11 |
| 129 | AR2 | M•FI•D•••• •••YR•••• ••••••Y•V• ••• <br> MDFIGDTPLH LAAYRGHLEI VEVLLKYGVD VNA | 9F8 |
| 130 | AR2 | D•FL•D•••• •••YH••D• ••••••H••• ••• <br> DDFLGDTPLH LAAYHGHLDI VEVLLKHGAD VNA | 10A6 |
| 131 | AR2 | T•FI•D•••• •••YH•••• ••••••H••• ••• <br> TDFIGDTPLH LAAYHGHLEI VEVLLKHGAD VNA | 5B9 |
| 132 | AR2 | H•MI•D•••• •••YH•••• ••••••Y••• ••• <br> HDMIGDTPLH LAYHEGHLEI VEVLLKYGAD VNA | 7D2 |
| 133 | AR2 | N•FA•Y•••• •••VY•••• ••••••Y••• ••• <br> NDFAGYTPLH LAAVYGHLEI VEVLLKYGAD VNA | 6G11 |
| 134 | AR2 | N•FI•D•••• •••WH•••• ••••••N••• ••• <br> NDFIGDTPLH LAAWHGHLEI VEVLLKNGAD VNA | 7D7 |
| 135 | AR2 | D•FI•D•••• •••FK•••• ••••••N••• ••• <br> DDFIGDTPLH LAAFKGHLEI VEVLLKNGAD VNA | 5D12 |
| 136 | AR2 | E•FI•D•••• •••YR•••• ••••••Y•V• ••• <br> EDFIGDTPLH LAAYRGHLEI VEVLLKYGVD VNA | 5D2 |
| 137 | AR2 | F•FI•D•••• •••YR•••• ••••••Y•V• ••• <br> FDFIGDTPLH LAAYRGHLEI VEVLLKYGVD VNA | 7H3 |
| 138 | AR2 | K•MI•D•••• •••YR•••• ••••••Y•V• ••• <br> KDMIGDTPLH LAAYRGHLEI VEVLLKYGVD VNA | 5D3 |
| 139 | AR2 | A•FL•D•••• •••YH•••• ••••••H••• ••• <br> ADFLGDTPLH LAAYHGHLEI VEVLLKHGAD VNA | 5H7 |
| 140 | AR2 | N•MI•D•••• •••YH•••• ••••••H••• ••• <br> NDMIGDTPLH LAAYHGHLEI VEVLLKHGAD VNA | 9E11 |
| 141 | AR2 | N•FI•D•••• •••YN•••• ••••••N••• ••• <br> NDFIGDTPLH LAAYNGHLEI VEVLLKNGAD VNA | 6D4 |
| 142 | AR2 | T•FI•D•••• •••YH•••• ••••••H••• ••• <br> TDFIGDTPLH LAAYHGHLEI VEVLLKHGAD VNA | 7C6 |
| 143 | AR2 | T•II•N•••• •••FR•••• ••••••H••• ••• <br> TDIIGNTPLH LAAFRGHLEI VEVLLKHGAD VNA | 2F1 |
| 144 | AR3 | S•IT•E•••• •••QI•••• ••••••Y••• ••• <br> SDITGETPLH LAAQIGHLEI VEVLLKYGAD VNA | 6G9 |
| 145 | AR3 | D•H-•D•••• •••SM•••• ••••••N••• ••• <br> DDHYGDTPLH LAASMGHLEI VEVLLKNGAD VNA | 7G11,9F8, 7H3,5D3,5D2 |
| 146 | AR3 | K--N•E•••• •••YH••PD• ••••••H••• ••• <br> K--NGETPLH LAAYHGHPDI VEVLLKHGAD VNA | 5B9 |
| 147 | AR3 | K•TS•T•••• •••DS•••• ••••••H••• ••• <br> KDTSGTTPLH LAADSGHLEI VEVLLKHGAD VNA | 7D2 |
| 148 | AR3 | T•AW•E•••• •••YT•••• ••••••HD•• ••• <br> TDAWGETPLH LAAYTGHLEI VEVLLKHDAD VNA | 6G11 |
| 149 | AR3 | M•VT•E•••• •••YH••D• ••••••N••• ••• <br> MDVTGETPLH LAAYHGHLDI VEVLLKNGAD VNA | 7D7 |
| 150 | AR3 | S•IT•E•••• •••TA•••• ••••••H••• ••• <br> SDITGETPLH LAATAGHLEI VEVLLKHGAD VNA | 5D12 |
| 151 | AR3 | S•IT•E•••• •••HL•••• ••••••Y••• ••• <br> SDITGETPLH LAAHLGHLEI VEVLLKYGAD VNA | 5H7 |
| 152 | AR3 | S•IT•E•••• •••HN•••• ••••••Y••• ••• <br> SDITGETPLH LAAHNGHLEI VEVLLKYGAD VNA | 9E11 |

| | | -continued | |
|---|---|---|---|
| 153 | AR3 | T•IT•E•••• •••ER•••• ••••••N••• ••T<br>TDITGETPLH LAAERGHLEI VEVLLKNGAD VNT | 6D4 |
| 154 | AR3 | E•IT•E•••• •••ES•••• ••••••H••• •••<br>EDITGETPLH LAAESGHLEI VEVLLKHGAD VNA | 7C6 |
| 155 | AR3 | S•IT•E•••• •••HL•••• ••••••Y••• •••<br>SDITGETPLH LAAHLGHLEI VEVLLKYGAD VNA | 2F1 |

| SEQ ID NO | NAME | Sequence | Features |
|---|---|---|---|
| 156 | AR1-C | $X_1DX_3X_4GSTPLHLAARHGHLEIVEVLLKX_{27}GADVNA$ | $X_1$ is selected from T, A, F, E, I, K, M, S, R, V, and W<br>$X_3$ is selected from D, E, H, I, K, M, S, T, and V<br>$X_4$ is F or Y<br>$X_{27}$ is H, N, or Y |
| 157 | AR1-F | $TDYGSTPLHLAARHGHLEIVEVLLKX_{27}GADVNA$ | $X_{27}$ H, N, or Y |
| 158 | AR2-C | $X_1DFIGDTPLHLAAYX_{15}GHLEIVEVLLKX_{27}GADVNA$ | $X_1$ is selected from N, T, A, D, K, E, H, M, and F<br>$X_{15}$ is selected from H and R<br>$X_{27}$ is selected from H, N, and Y |
| 159 | AR2-F | $X_1DFIGDTPLHLAAYX_{15}GHLEIVEVLLKX_{27}GADVNA$ | $X_1$ is selected from A, D, N, T, and K<br>$X_{15}$ is selected from H and R<br>$X_{27}$ is selected from H, N, and Y |
| 160 | AR3-C | $X_1DX_3TGETPLHLAAX_{14}X_{15}GHLEIVEVLLKX_{27}GADVNA$ | $X_1$ is selected from D, E, K, M, S, and T<br>$X_3$ is selected from I, A, T and V or is absent (SEQ ID NO: 179)<br>$X_{14}$ is selected from D, E, H, Q, S, T, and Y<br>$X_{15}$ is selected from M, L, H, S, A, I, N, R, and T<br>$X_{27}$ is selected from H, N, and Y |
| 161 | AR3-F | $X_1DITGETPLHLAASMGHLEIVEVLLKX_{27}GADVNA$ | $X_1$ is selected |

| | | | |
|---|---|---|---|
| | | | from D and S |
| | | | X₂₇ is selected from H, N, and Y |
| 162 | 6G9 | DLGKKLLEAARAGQDDEVRILMANGADVNA RDSYGSTPLHLAAREGHLEIVEVLLKYGADVNA KDMIGDTPLHLAAYRGHLEIVEVLLKNGADVNA SDITGETPLHLAAQIGHLEIVEVLLKYGADVNA QDKFGKTAFDISIDNGNEDLAEILQKLN | |
| 163 | 6G9r13 | ALDKKLLEAARAGQDDEVRILMANGADVNA RDSYGSTPLHLAAREGHLEIVEVLLKYGADVNA ADFIGDTPLHLAAYRGHLEIVEVLLKYGADVNA SDITGETPLHLAAQIGHLEIVEVLLKHGADVNA QDKFGKTAFDISIDNGNEDLAEILQKAA | |
| 164 | 9F8 | DLGKKLLEAARAGQDDEVRILMANGADVNA SDIFGSTPLHLAARHGHLEIVEVLLKYGADVNA MDFIGDTPLHLAAYRGHLEIVEVLLKYGVDVNA DDHGDTPLHLAASMGHLEIVEVLLKNGADVNA QDKFGKTAFDISIDNGNEDLAEILQKLN | |
| 165 | 9F8r3 | GLDKKLLEAARAGQDDEVRILMANGADVNA SDIFGSTPLHLAARHGHLEIVEVLLKYGADVNA FDFIGDTPLHLAAYRGHLEIVEVLLKYGVDVNA DDHGDTPLHLAAQIGHLEIVEVLLKHGADVNA QDKFGKTAFDISIDNGNEDLAEILQKAA | |
| 166 | 7G11 | DLGKKLLEAARAGQDDEVRILMANGADVNA TDEFDSTPLHLAARHGHLEIVEVLLKYGADVNA ADFIGDTPLHLAAYRGHLEIVEVLLKCGVDVNA DDHGDTPLHLAASMGHLEIVEVLLKNGADVNA QDKFGKTAFDISIDNGNEDLAEILQKLN | |
| 167 | 7G11r7 | GLDKKLLEAARAGQDDEVRILMANGADVNA TDEFDSTPLHLAARHGHLEIVEVLLKYGADVNA ADFIGDTPLHLAAYRGHLEIVEVLLKYGVDVNA DDHGDTPLHLAASTGHLEIVEVLLKHGADVNA QDKFGKTAFDISIDNGNEDLAEILQKAA | |
| 168 | AR1-0 | $X_1DX_3X_4X_5STPLHLAARX_{15}GHLEIVEVLLKYGADVNA$ | $X_1$ is R, S, or T; $X_3$ is S or W; $X_4$ is F or Y; $X_5$ is D or G; and $X_{15}$ is E or H |
| 169 | AR2-0 | $X_1DFIGDTPLHLAAYRGHLEIVEVLLKYGADVNA$ | $X_1$ is A or F; |
| 170 | AR3-0 | $X_1DX_3X_4GX_6TPLHLAAX_{14}X_{15}GHLEIVEVLLKHGADVNA$ | $X_1$ is D or S; $X_3$ is H or S; $X_4$ is G or T; $X_6$ is D or S; $X_{14}$ is Q or S; $X_{15}$ is I or T |
| 171 | N-cap Variants | $X_1LX_3KKLLEAA$ RAGQDDEVRI LMANGADVNA | $X_1$ is A, D, or G; $X_3$ is D or G; |
| 172 | C-cap variant | QDKFGKTPAD IAADNGHEDI AEVLQKAA | |
| 173 | 11G11 | GSDLGKKLMEAARAGQDDEVRILMANGADVNAKDLFGI TPLHLAAVYGHLEIVEVLLKHGADVNATDNWGSTPLHL AAQFGHLEIVEVLLKYGADVNAQDKFGKTAFDISIDNG NEDLAEILQKLN | |
| 174 | N-cap | $X_1KKLLEAARAGQDDEVRILMANGADVNA$ | $X_1$ is D or G; |
| 175 | C-cap | $QDKFGKTX_8X_9DIX_{12}X_{13}DNGX_{17}EDX_{20}AEX_{23}LQKX_{27}X_{28}$ | $X_8$ is A or P; $X_9$ is A or F; $X_{12}$ is A or S; $X_{13}$ is A or I; $X_{17}$ is H or N; $X_{20}$ is I or L; $X_{23}$ is I or V; $X_{27}$ is A or L; $X_{28}$ is A or N |
| 176 | Coding sequence for human bi-specific (re-engineered 44C12-linker-6G9 with | atgggatccgacctgggtaagaaaactgctggaagctgc tcgtgctggtcaggacgacgaagttcgtatcctgatgg ctaacggtgctgacgttaacgctctggatgatagcggt tatacaccgctgcatctggcagcggaagatggtcatct ggaaattgttgaagttctgctgaaacacggtgccgatg tgaatgccgcagatcgtctgggtgatactccgctgcat ctggctgccttttgttggccatctggaaatcgtagaggt gctgctgaaagcaggcgcagatgtaaacgcagttgatc tggcaggcgttaccccctctgcacgttgcagcatttat | |

-continued

| | |
|---|---|
| modified C-cap) | ggacacttagaaattgtggaggtactgctgaaggcagg<br>tgcagacgttaacgcacaggataaatttggtaaaaccc<br>cggcggatattgcggcggataatggccatgaggatatt<br>gcagaagtgctgcaaaaggcggcgggcggcggtggctc<br>tggcggtggtggctctggcggtggcggttctggcggtg<br>gtggctctggatccgacctggataagaaactgctggaa<br>gcagcacgtgcaggtcaggatgatgaagttcgtattct<br>gatggcaaatggcgccgatgttaatgcacgtgatagct<br>atggtagcacaccgctgcatctggctgcacgtgagggt<br>catctggaaattgtggaagtgctgctgaaatacggtgc<br>cgatgtgaatgccgcagattttattggtgatacccgt<br>tacatctggctgcgtatcgtggccatttagaaatcgtg<br>gaggttctgttaaaatacggcgcagacgttaatgcaag<br>cgatattaccggtgaaacccctctgcatttagcagcgc<br>agattggccacctggaaatcgtcgaagttttactgaaa<br>catggcgcagatgttaacgcacaggataaatttggtaa<br>aaccccggcggatattgcggcggataatggccatgagg<br>atattgcagaagtgctgcagaaggcggcg |

The invention claimed is:

1. An isolated nucleic acid molecule comprising a nucleotide sequence encoding a binding protein comprising (i) an IL4-binding ankyrin repeat domain having the amino acid sequence of SEQ ID NO: 91 and an IL13-binding ankyrin repeat domain having the amino acid sequence of SEQ ID NO: 94 or (ii) an amino acid sequence selected from the group consisting of SEQ ID NOS: 41, 104, 177, and 178.

2. An isolated nucleic acid vector comprising the nucleotide acid molecule according to claim 1.

3. An isolated host cell comprising the isolated nucleic acid molecule according to claim 1, wherein the host cell is prokaryotic or eukaryotic.

4. The host cell according to claim 3, wherein said host cell is at least one selected from *E. Coli*, yeast, baculovirus, COS-1, COS-7, HEK293, BHK21, CHO, BSC-1, Hep G2, 653, SP2/0, 293, HeLa, P3X63Ag8.653, and SP2/0-Ag14, myeloma, and lymphoma cells.

5. An isolated nucleic acid molecule comprising a nucleotide sequence of SEQ ID NO: 176.

6. An isolated nucleic acid vector comprising the nucleotide acid molecule according to claim 5.

7. An isolated host cell comprising the isolated nucleic acid molecule according to claim 5, wherein the host cell is prokaryotic or eukaryotic.

8. The host cell according to claim 7, wherein said host cell is at least one selected from *E. Coli*, yeast, baculovirus, COS-1, COS-7, HEK293, BHK21, CHO, BSC-1, Hep G2, 653, SP2/0, 293, HeLa, P3X63Ag8.653, and SP2/0-Ag14, myeloma, and lymphoma cells.

* * * * *

SEQUENCE LISTING

<160> NUMBER OF SEQ ID NOS: 185

<210> SEQ ID NO 1
<211> LENGTH: 33
<212> TYPE: PRT
<213> ORGANISM: Artificial Sequence
<220> FEATURE:
<223> OTHER INFORMATION: Synthetic conseneus ankyrin repeat sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid

<400> SEQUENCE: 1

Xaa Asp Xaa Xaa Gly Xaa Thr Pro Leu His Leu Ala Ala Xaa Xaa Gly
1               5                   10                  15

His Leu Glu Ile Val Glu Val Leu Leu Lys Xaa Gly Ala Asp Val Asn
            20                  25                  30

Ala

<210> SEQ ID NO 2
<211> LENGTH: 30
<212> TYPE: PRT
<213> ORGANISM: Artificial Sequence
<220> FEATURE:
<223> OTHER INFORMATION: Synthetic ankyrin repeat cap

<400> SEQUENCE: 2

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala
            20                  25                  30

```
<210> SEQ ID NO 3
<211> LENGTH: 28
<212> TYPE: PRT
<213> ORGANISM: Artificial Sequence
<220> FEATURE:
<223> OTHER INFORMATION: Synthetic ankyrin repeat cap

<400> SEQUENCE: 3

Gln Asp Lys Phe Gly Lys Thr Ala Phe Asp Ile Ser Ile Asp Asn Gly
1               5                   10                  15

Asn Glu Asp Leu Ala Glu Ile Leu Gln Lys Leu Asn
            20                  25

<210> SEQ ID NO 4
<211> LENGTH: 129
<212> TYPE: PRT
<213> ORGANISM: Homo sapiens

<400> SEQUENCE: 4

His Lys Cys Asp Ile Thr Leu Gln Glu Ile Ile Lys Thr Leu Asn Ser
1               5                   10                  15

Leu Thr Glu Gln Lys Thr Leu Cys Thr Glu Leu Thr Val Thr Asp Ile
            20                  25                  30

Phe Ala Ala Ser Lys Asn Thr Thr Glu Lys Glu Thr Phe Cys Arg Ala
        35                  40                  45

Ala Thr Val Leu Arg Gln Phe Tyr Ser His His Glu Lys Asp Thr Arg
    50                  55                  60

Cys Leu Gly Ala Thr Ala Gln Gln Phe His Arg His Lys Gln Leu Ile
65                  70                  75                  80

Arg Phe Leu Lys Arg Leu Asp Arg Asn Leu Trp Gly Leu Ala Gly Leu
                85                  90                  95

Asn Ser Cys Pro Val Lys Glu Ala Asn Gln Ser Thr Leu Glu Asn Phe
            100                 105                 110

Leu Glu Arg Leu Lys Thr Ile Met Arg Glu Lys Tyr Ser Lys Cys Ser
        115                 120                 125

Ser

<210> SEQ ID NO 5
<211> LENGTH: 129
<212> TYPE: PRT
<213> ORGANISM: Cynomolgus

<400> SEQUENCE: 5

His Lys Cys Asp Ile Thr Leu Gln Glu Ile Ile Lys Thr Leu Asn Ser
1               5                   10                  15

Leu Thr Glu Gln Lys Thr Leu Cys Thr Lys Leu Thr Ile Thr Asp Ile
            20                  25                  30

Leu Ala Ala Ser Lys Asn Thr Thr Glu Lys Glu Thr Phe Cys Arg Ala
        35                  40                  45

Ala Thr Val Leu Arg Gln Phe Tyr Ser His His Glu Lys Asp Thr Arg
    50                  55                  60

Cys Leu Gly Ala Thr Ala Gln Gln Phe His Arg His Lys Gln Leu Ile
65                  70                  75                  80

Arg Phe Leu Lys Arg Leu Asp Arg Asn Leu Trp Gly Leu Ala Gly Leu
                85                  90                  95

Asn Ser Cys Pro Val Lys Glu Ala Asn Gln Ser Thr Leu Glu Asn Phe
            100                 105                 110
```

Leu Glu Arg Leu Lys Thr Ile Met Arg Glu Lys Tyr Ser Lys Cys Ser
            115                 120                 125
Ser

<210> SEQ ID NO 6
<211> LENGTH: 209
<212> TYPE: PRT
<213> ORGANISM: Homo sapiens

<400> SEQUENCE: 6

Gly Asn Met Lys Val Leu Gln Glu Pro Thr Cys Val Ser Asp Tyr Met
1               5                   10                  15

Ser Ile Ser Thr Cys Glu Trp Lys Met Asn Gly Pro Thr Asn Cys Ser
            20                  25                  30

Thr Glu Leu Arg Leu Leu Tyr Gln Leu Val Phe Leu Leu Ser Glu Ala
        35                  40                  45

His Thr Cys Ile Pro Glu Asn Asn Gly Gly Ala Gly Cys Val Cys His
    50                  55                  60

Leu Leu Met Asp Asp Val Val Ser Ala Asp Asn Tyr Thr Leu Asp Leu
65                  70                  75                  80

Trp Ala Gly Gln Gln Leu Leu Trp Lys Gly Ser Phe Lys Pro Ser Glu
                85                  90                  95

His Val Lys Pro Arg Ala Pro Gly Asn Leu Thr Val His Thr Asn Val
            100                 105                 110

Ser Asp Thr Leu Leu Leu Thr Trp Ser Asn Pro Tyr Pro Pro Asp Asn
        115                 120                 125

Tyr Leu Tyr Asn His Leu Thr Tyr Ala Val Asn Ile Trp Ser Glu Asn
    130                 135                 140

Asp Pro Ala Asp Phe Arg Ile Tyr Asn Val Thr Tyr Leu Glu Pro Ser
145                 150                 155                 160

Leu Arg Ile Ala Ala Ser Thr Leu Lys Ser Gly Ile Ser Tyr Arg Ala
                165                 170                 175

Arg Val Arg Ala Trp Ala Gln Cys Tyr Asn Thr Thr Trp Ser Glu Trp
            180                 185                 190

Ser Pro Ser Thr Lys Trp His Asn Ser Tyr Arg Glu Pro Phe Glu Gln
        195                 200                 205

His

<210> SEQ ID NO 7
<211> LENGTH: 240
<212> TYPE: PRT
<213> ORGANISM: Homo sapiens

<400> SEQUENCE: 7

Leu Asn Thr Thr Ile Leu Thr Pro Asn Gly Asn Glu Asp Thr Thr Ala
1               5                   10                  15

Asp Phe Phe Leu Thr Thr Met Pro Thr Asp Ser Leu Ser Val Ser Thr
            20                  25                  30

Leu Pro Leu Pro Glu Val Gln Cys Phe Val Phe Asn Val Glu Tyr Met
        35                  40                  45

Asn Cys Thr Trp Asn Ser Ser Ser Glu Pro Gln Pro Thr Asn Leu Thr
    50                  55                  60

Leu His Tyr Trp Tyr Lys Asn Ser Asp Asn Asp Lys Val Gln Lys Cys
65                  70                  75                  80

Ser His Tyr Leu Phe Ser Glu Glu Ile Thr Ser Gly Cys Gln Leu Gln

```
                85                  90                  95
Lys Lys Glu Ile His Leu Tyr Gln Thr Phe Val Val Gln Leu Gln Asp
            100                 105                 110

Pro Arg Glu Pro Arg Gln Ala Thr Gln Met Leu Lys Leu Gln Asn
            115                 120                 125

Leu Val Ile Pro Trp Ala Pro Glu Asn Leu Thr Leu His Lys Leu Ser
    130                 135                 140

Glu Ser Gln Leu Glu Leu Asn Trp Asn Asn Arg Phe Leu Asn His Cys
145                 150                 155                 160

Leu Glu His Leu Val Gln Tyr Arg Thr Asp Trp Asp His Ser Trp Thr
                165                 170                 175

Glu Gln Ser Val Asp Tyr Arg His Lys Phe Ser Leu Pro Ser Val Asp
            180                 185                 190

Gly Gln Lys Arg Tyr Thr Phe Arg Val Arg Ser Arg Phe Asn Pro Leu
            195                 200                 205

Cys Gly Ser Ala Gln His Trp Ser Glu Trp Ser His Pro Ile His Trp
    210                 215                 220

Gly Ser Asn Thr Ser Lys Glu Asn Pro Phe Leu Phe Ala Leu Glu Ala
225                 230                 235                 240

<210> SEQ ID NO 8
<211> LENGTH: 322
<212> TYPE: PRT
<213> ORGANISM: Homo sapiens

<400> SEQUENCE: 8

Gly Gly Gly Gly Ala Ala Pro Thr Glu Thr Gln Pro Pro Val Thr Asn
1               5                   10                  15

Leu Ser Val Ser Val Glu Asn Leu Cys Thr Val Ile Trp Thr Trp Asn
                20                  25                  30

Pro Pro Glu Gly Ala Ser Ser Asn Cys Ser Leu Trp Tyr Phe Ser His
            35                  40                  45

Phe Gly Asp Lys Gln Asp Lys Lys Ile Ala Pro Glu Thr Arg Arg Ser
    50                  55                  60

Ile Glu Val Pro Leu Asn Glu Arg Ile Cys Leu Gln Val Gly Ser Gln
65                  70                  75                  80

Cys Ser Thr Asn Glu Ser Glu Lys Pro Ser Ile Leu Val Glu Lys Cys
                85                  90                  95

Ile Ser Pro Pro Glu Gly Asp Pro Glu Ser Ala Val Thr Glu Leu Gln
            100                 105                 110

Cys Ile Trp His Asn Leu Ser Tyr Met Lys Cys Ser Trp Leu Pro Gly
            115                 120                 125

Arg Asn Thr Ser Pro Asp Thr Asn Tyr Thr Leu Tyr Tyr Trp His Arg
    130                 135                 140

Ser Leu Glu Lys Ile His Gln Cys Glu Asn Ile Phe Arg Glu Gly Gln
145                 150                 155                 160

Tyr Phe Gly Cys Ser Phe Asp Leu Thr Lys Val Lys Asp Ser Ser Phe
                165                 170                 175

Glu Gln His Ser Val Gln Ile Met Val Lys Asp Asn Ala Gly Lys Ile
            180                 185                 190

Lys Pro Ser Phe Asn Ile Val Pro Leu Thr Ser Arg Val Lys Pro Asp
            195                 200                 205

Pro Pro His Ile Lys Asn Leu Ser Phe His Asn Asp Asp Leu Tyr Val
    210                 215                 220
```

```
Gln Trp Glu Asn Pro Gln Asn Phe Ile Ser Arg Cys Leu Phe Tyr Glu
225                 230                 235                 240

Val Glu Val Asn Asn Ser Gln Thr Glu Thr His Asn Val Phe Tyr Val
            245                 250                 255

Gln Glu Ala Lys Cys Glu Asn Pro Glu Phe Glu Arg Asn Val Glu Asn
            260                 265                 270

Thr Ser Cys Phe Met Val Pro Gly Val Leu Pro Asp Thr Leu Asn Thr
        275                 280                 285

Val Arg Ile Arg Val Lys Thr Asn Lys Leu Cys Tyr Glu Asp Asp Lys
        290                 295                 300

Leu Trp Ser Asn Trp Ser Gln Glu Met Ser Ile Gly Lys Lys Arg Asn
305                 310                 315                 320

Ser Thr

<210> SEQ ID NO 9
<211> LENGTH: 157
<212> TYPE: PRT
<213> ORGANISM: Artificial Sequence
<220> FEATURE:
<223> OTHER INFORMATION: Synthetic ankyrin repeat sequence

<400> SEQUENCE: 9

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Val Ser Asp
                20                  25                  30

Arg Ile Gly Asn Thr Pro Leu His Leu Ala Ala Val Tyr Val His Leu
            35                  40                  45

Glu Ile Val Glu Val Leu Leu Lys Asn Gly Ala Asp Val Asn Ala Leu
        50                  55                  60

Asp Asp Asp Gly Leu Thr Pro Leu His Leu Ala Ala Asp Gly His
65                  70                  75                  80

Leu Glu Ile Val Glu Val Leu Leu Lys His Gly Ala Asp Val Asn Ala
                85                  90                  95

Thr Asp Ser His Val Trp Thr Pro Leu His Leu Ala Ala Phe Phe Gly
            100                 105                 110

His Leu Glu Ile Val Glu Val Leu Leu Lys Tyr Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln Lys Leu Asn
145                 150                 155

<210> SEQ ID NO 10
<211> LENGTH: 157
<212> TYPE: PRT
<213> ORGANISM: Artificial Sequence
<220> FEATURE:
<223> OTHER INFORMATION: Synthetic ankyrin repeat sequence

<400> SEQUENCE: 10

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Ile Asp
                20                  25                  30

Glu Trp Gly Asp Thr Pro Leu His Leu Ala Ala Ile Glu Gly His Leu
            35                  40                  45
```

```
Glu Ile Val Glu Val Leu Leu Lys Tyr Gly Ala Asp Val Asn Ala Ser
 50                  55                  60

Asp Ala Met Gly Met Thr Pro Leu His Leu Ala Val Tyr Gly Tyr
 65                  70                  75                  80

Leu Glu Ile Val Glu Val Leu Leu Lys Asn Gly Ala Asp Val Asn Ala
                 85                  90                  95

Met Asp Phe Ser Gly Phe Thr Pro Leu His Leu Ala Ala Phe Ser Gly
                100                 105                 110

His Leu Glu Ile Val Glu Val Leu Leu Lys Tyr Gly Ala Asp Val Asn
                115                 120                 125

Ala Gln Asp Lys Phe Gly Lys Thr Ala Phe Asp Ile Ser Ile Asp Asn
130                 135                 140

Gly Asn Glu Asp Leu Ala Glu Ile Leu Gln Lys Leu Asn
145                 150                 155

<210> SEQ ID NO 11
<211> LENGTH: 157
<212> TYPE: PRT
<213> ORGANISM: Artificial Sequence
<220> FEATURE:
<223> OTHER INFORMATION: Synthetic ankyrin repeat sequence

<400> SEQUENCE: 11

Asp Leu Gly Lys Lys Leu Leu Glu Ala Ala Arg Ala Gly Gln Asp Asp
 1               5                  10                  15

Glu Val Arg Ile Leu Met Ala Asn Gly Ala Asp Val Asn Ala Thr Asp
                 20                  25                  30

Asp Trp Gly Asp Thr Leu Leu His Leu Ala Ala Thr Asp Gly His Leu
                 35                  40                  45

Glu Ile Val Glu Val Leu Leu Lys Asn Gly Ala Asp Val Asn Ala Ile
 50                  55                  60

Asp Ala Met Gly Met Thr Pro Leu His Leu Ala Ala Val Tyr Gly Tyr
 65                  70                  75                  80

Leu Glu Ile Val Glu Val Leu Leu Lys Asn Gly Ala Asp Val Asn Ala
                 85                  90                  95

Met Asp Phe Ser Gly Phe Thr Pro Leu His Leu Ala Ala Phe Ser Gly
                100                 105                 110

His Leu Glu Ile Val Glu Val Leu Leu Lys Tyr Gly Ala Asp Val Asn
                115                 120                 125

Ala Gln Asp Lys Phe Gly Lys Thr Ala Phe Asp Ile Ser Ile Asp Asn
130                 135                 140

Gly Asn Glu Asp Leu Ala Glu Ile Leu Gln Lys Leu Asn
145                 150                 155

<210> SEQ ID NO 12
<211> LENGTH: 157
<212> TYPE: PRT
<213> ORGANISM: Artificial Sequence
<220> FEATURE:
<223> OTHER INFORMATION: Synthetic ankyrin repeat sequence

<400> SEQUENCE: 12

Asp Leu Gly Lys Lys Leu Leu Glu Ala Ala Arg Ala Gly Gln Asp Asp
 1               5                  10                  15

Glu Val Arg Ile Leu Met Ala Asn Gly Ala Asp Val Asn Ala Thr Asp
                 20                  25                  30

Asp Trp Gly Asp Thr Leu Leu His Leu Ala Ala Thr Asp Gly His Leu
                 35                  40                  45
```

-continued

Glu Ile Val Glu Val Leu Leu Lys Asn Gly Ala Asp Val Asn Ala Ser
50                  55                  60

Asp Ser Gln Gly Leu Thr Pro Leu His Leu Ala Ala Tyr Tyr Gly His
65                  70                  75                  80

Leu Glu Ile Val Glu Val Leu Leu Lys Tyr Gly Ala Asp Val Asn Ala
                85                  90                  95

Asn Asp His His Gly Ile Thr Pro Leu His Leu Ala Ala Phe Ala Gly
                100                 105                 110

His Leu Glu Ile Val Glu Val Leu Leu Lys Tyr Gly Ala Asp Val Asn
            115                 120                 125

Ala Gln Asp Lys Phe Gly Lys Thr Ala Phe Asp Ile Ser Ile Asp Asn
        130                 135                 140

Gly Asn Glu Asp Leu Ala Glu Ile Leu Gln Lys Leu Asn
145                 150                 155

<210> SEQ ID NO 13
<211> LENGTH: 157
<212> TYPE: PRT
<213> ORGANISM: Artificial Sequence
<220> FEATURE:
<223> OTHER INFORMATION: Synthetic ankyrin repeat sequence

<400> SEQUENCE: 13

Asp Leu Gly Lys Lys Leu Leu Glu Ala Ala Ser Ala Gly Gln Asp Asp
1               5                   10                  15

Glu Val His Ile Leu Met Ala Asn Gly Ala Asp Val Asn Ala Val Asp
                20                  25                  30

His Asp Gly Phe Thr Pro Leu His Leu Ala Ala Ala Asp Gly His Leu
            35                  40                  45

Glu Ile Val Glu Val Leu Leu Lys His Gly Ala Asp Val Asn Ala Asp
        50                  55                  60

Asp Asn Phe Gly Trp Thr Pro Leu His Leu Ala Ala Phe Phe Gly His
65                  70                  75                  80

Leu Glu Ile Val Glu Val Leu Leu Lys His Gly Ala Asp Val Asn Ala
                85                  90                  95

Lys Asp Gln Thr Gly Leu Thr Pro Leu His Leu Ala Ala Val Asp Gly
                100                 105                 110

His Leu Glu Ile Val Glu Val Leu Leu Lys His Gly Ala Asp Val Asn
            115                 120                 125

Ala Gln Asp Lys Phe Gly Lys Thr Ala Phe Asp Ile Ser Ile Asp Asn
        130                 135                 140

Gly Asn Glu Asp Leu Ala Glu Ile Leu Gln Lys Leu Asn
145                 150                 155

<210> SEQ ID NO 14
<211> LENGTH: 190
<212> TYPE: PRT
<213> ORGANISM: Artificial Sequence
<220> FEATURE:
<223> OTHER INFORMATION: Synthetic ankyrin repeat sequence

<400> SEQUENCE: 14

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Tyr Asp
                20                  25                  30

Ser Ser Gly Asp Thr Pro Leu His Val Ala Ala Ile Asp Gly His Leu 35                  40                  45

Glu Ile Val Glu Val Leu Leu Lys His Gly Ala Asp Val Asn Ala Ser
 50                  55                  60

Asp Ala Ser Gly Asp Thr Pro Leu His Leu Ala Ala Asp Phe Gly His
 65                  70                  75                  80

Leu Lys Ile Val Glu Val Leu Leu Lys His Gly Ala Asp Val Asn Ala
                 85                  90                  95

Glu Asp Met Ile Gly Ile Thr Pro Leu His Leu Ala Ala Tyr Asn Gly
                100                 105                 110

His Leu Glu Ile Val Glu Val Leu Leu Lys Asn Gly Ala Asp Val Asn
                115                 120                 125

Ala Ser Asp Val His Gly Phe Thr Pro Leu His Leu Ala Ala Phe Ile
130                 135                 140

Gly His Leu Gly Ile Val Glu Val Leu Leu Lys Tyr Asp Ala Asp Val
145                 150                 155                 160

Asn Ala Gln Asp Lys Phe Gly Lys Thr Ala Phe Asp Ile Ser Ile Asp
                165                 170                 175

Asn Arg Asn Glu Asp Leu Ala Glu Ile Leu Gln Lys Leu Asn
                180                 185                 190

<210> SEQ ID NO 15
<211> LENGTH: 157
<212> TYPE: PRT
<213> ORGANISM: Artificial Sequence
<220> FEATURE:
<223> OTHER INFORMATION: Synthetic ankyrin repeat sequence

<400> SEQUENCE: 15

Asp Leu Gly Lys Glu Leu Leu Glu Ala Ala Ser Ala Gly Gln Asp Asp
 1               5                  10                  15

Glu Val His Ile Leu Met Ala Asn Gly Ala Asp Val Asn Ala Val Asp
                 20                  25                  30

His Asp Gly Phe Thr Pro Leu His Leu Ala Ala Ala Asp Gly His Leu
                 35                  40                  45

Glu Ile Val Glu Val Leu Leu Lys His Gly Ala Asp Val Asn Ala Asp
 50                  55                  60

Asp Asn Phe Gly Trp Thr Pro Leu His Leu Ala Ala Phe Phe Gly His
 65                  70                  75                  80

Leu Glu Ile Val Glu Val Leu Leu Lys His Gly Ala Asp Val Asn Ala
                 85                  90                  95

Lys Asp Gln Thr Gly Leu Thr Pro Leu His Leu Ala Ala Val Asp Gly
                100                 105                 110

His Leu Glu Ile Val Glu Val Leu Leu Lys Asn Gly Ala Asp Val Asn
                115                 120                 125

Ala Gln Asp Lys Phe Gly Lys Thr Ala Phe Asp Ile Ser Ile Asp Asn
130                 135                 140

Gly Asn Glu Asp Leu Ala Glu Ile Leu Gln Lys Leu Asn
145                 150                 155

<210> SEQ ID NO 16
<211> LENGTH: 157
<212> TYPE: PRT
<213> ORGANISM: Artificial Sequence
<220> FEATURE:
<223> OTHER INFORMATION: Synthetic ankyrin repeat sequence

<400> SEQUENCE: 16

```
Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Ala Asp
            20                  25                  30

Asp Ser Gly Ile Thr Pro Leu His Leu Ala Ala Glu Asp Gly His Leu
        35                  40                  45

Glu Ile Val Glu Val Leu Leu Lys Tyr Gly Ala Asp Val Asn Ala Gln
    50                  55                  60

Asp Asn Leu Gly Asp Thr Pro Leu His Leu Ala Ala Trp Thr Gly His
65                  70                  75                  80

Leu Glu Ile Val Glu Val Leu Leu Lys Asn Gly Ala Asp Val Asn Ala
                85                  90                  95

Tyr Asp Ile Ser Gly Ile Thr Pro Leu His Leu Ala Ala Phe Tyr Gly
            100                 105                 110

His Leu Glu Ile Val Glu Val Leu Leu Lys His Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln Lys Leu Asn
145                 150                 155

<210> SEQ ID NO 17
<211> LENGTH: 157
<212> TYPE: PRT
<213> ORGANISM: Artificial Sequence
<220> FEATURE:
<223> OTHER INFORMATION: Synthetic ankyrin repeat sequence

<400> SEQUENCE: 17

Asp Leu Gly Lys Lys Leu Leu Glu Ala Ala Ser Val Gly Gln Asp Asp
1               5                   10                  15

Glu Val His Ile Leu Met Ala Asn Gly Ala Asp Val Asn Ala Thr Asp
            20                  25                  30

Ala Trp Gly Leu Thr Pro Leu His Leu Ala Ala Leu Leu Gly His Leu
        35                  40                  45

Glu Ile Val Glu Val Leu Leu Lys His Gly Ala Asp Val Asn Ala His
    50                  55                  60

Asp Glu Thr Gly Phe Thr Pro Leu His Leu Ala Ala Val Glu Gly His
65                  70                  75                  80

Leu Glu Ile Val Glu Val Leu Leu Lys Tyr Gly Ala Asp Val Asn Ala
                85                  90                  95

Ser Asp Ile Leu Gly Arg Thr Pro Leu His Leu Ala Ala Asn Phe Gly
            100                 105                 110

His Leu Glu Ile Val Glu Val Leu Leu Lys His Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln Lys Leu Asn
145                 150                 155

<210> SEQ ID NO 18
<211> LENGTH: 157
<212> TYPE: PRT
<213> ORGANISM: Artificial Sequence
<220> FEATURE:
<223> OTHER INFORMATION: Synthetic ankyrin repeat sequence

<400> SEQUENCE: 18
```

Asp Leu Gly Lys Lys Leu Leu Glu Ala Ala Ser Ala Gly Gln Asp Asp
1               5                   10                  15

Glu Val Arg Ile Leu Met Ala Asn Gly Ala Asp Val Asn Ala Val Asp
            20                  25                  30

His Asp Gly Phe Thr Pro Leu His Leu Ala Ala Ala Asp Gly His Leu
        35                  40                  45

Glu Ile Val Glu Val Leu Leu Lys His Gly Ala Asp Val Asn Ala Asp
    50                  55                  60

Asp Asn Phe Gly Trp Thr Pro Leu His Leu Ala Ala Phe Phe Gly His
65                  70                  75                  80

Leu Glu Ile Val Glu Val Leu Leu Lys His Gly Ala Asp Val Asn Ala
                85                  90                  95

Lys Asp Gln Thr Gly Leu Thr Pro Leu His Leu Ala Ala Val Asp Gly
                100                 105                 110

His Leu Glu Ile Val Glu Val Leu Leu Lys His Gly Ala Asp Val Asn
            115                 120                 125

Ala Gln Asp Lys Phe Gly Lys Thr Ala Phe Asp Ile Ser Ile Asp Asn
        130                 135                 140

Gly Asn Glu Asp Leu Ala Glu Ile Leu Gln Lys Leu Asn
145                 150                 155

<210> SEQ ID NO 19
<211> LENGTH: 191
<212> TYPE: PRT
<213> ORGANISM: Artificial Sequence
<220> FEATURE:
<223> OTHER INFORMATION: Synthetic ankyrin repeat sequence

<400> SEQUENCE: 19

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Lys Asp
            20                  25                  30

Val Thr Gly Glu Thr Pro Leu His Leu Ala Ser Trp Glu Gly His Leu
        35                  40                  45

Glu Ile Val Glu Val Leu Leu Lys His Gly Ala Asp Val Asn Ala Gln
    50                  55                  60

Asp Leu Phe Gly Ile Thr Pro Leu His Leu Ala Ala Thr Asp Gly
65                  70                  75                  80

His Leu Glu Ile Val Glu Val Leu Leu Lys Asn Gly Ala Asp Val Asn
                85                  90                  95

Ala Thr Asp Ser Asn Gly Phe Thr Pro Leu His Leu Ala Ala Ser Tyr
                100                 105                 110

Gly His Leu Glu Ile Val Asp Val Leu Leu Lys Asn Gly Ala Asp Val
            115                 120                 125

Asn Ala His Asp Phe Asp Gly Phe Thr Pro Leu His Leu Ala Ala Ser
        130                 135                 140

Trp Gly His Leu Glu Ile Val Glu Val Leu Leu Lys Tyr Gly Ala Asp
145                 150                 155                 160

Val Asn Ala Gln Asp Lys Phe Gly Lys Thr Ala Phe Asp Ile Ser Ile
                165                 170                 175

Asp Asn Gly Asn Glu Asp Leu Ala Glu Ile Leu Gln Lys Leu Asn
            180                 185                 190

<210> SEQ ID NO 20

```
<211> LENGTH: 157
<212> TYPE: PRT
<213> ORGANISM: Artificial Sequence
<220> FEATURE:
<223> OTHER INFORMATION: Synthetic ankyrin repeat sequence

<400> SEQUENCE: 20

Asp Leu Gly Lys Lys Leu Leu Glu Ala Ala Ser Ala Gly Gln Asp Asp
1               5                   10                  15

Glu Val His Ile Leu Met Ala Asn Gly Ala Asp Val Asn Ala Leu Asp
                20                  25                  30

Asp Ser Gly Tyr Thr Pro Leu His Leu Ala Ala Glu Asp Gly His Leu
            35                  40                  45

Glu Ile Val Glu Val Leu Leu Lys His Gly Ala Asp Val Asn Ala Ala
        50                  55                  60

Asp Arg Met Gly Asp Thr Pro Leu His Leu Ala Ala Phe Val Gly His
65                  70                  75                  80

Leu Glu Ile Val Glu Val Leu Leu Lys Tyr Gly Ala Asp Val Asn Ala
                85                  90                  95

Val Asp Leu Ala Gly Val Thr Pro Leu His Val Ala Ala Phe Tyr Gly
            100                 105                 110

His Leu Glu Ile Val Glu Val Leu Leu Lys Tyr Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln Lys Leu Asn
145                 150                 155

<210> SEQ ID NO 21
<211> LENGTH: 157
<212> TYPE: PRT
<213> ORGANISM: Artificial Sequence
<220> FEATURE:
<223> OTHER INFORMATION: Synthetic ankyrin repeat sequence

<400> SEQUENCE: 21

Asp Leu Gly Lys Glu Leu Leu Glu Ala Ala Arg Ala Gly Gln Asp Asp
1               5                   10                  15

Glu Val His Ile Leu Met Ala Asn Gly Ala Asp Val Asn Ala Leu Asp
                20                  25                  30

Asp Ser Gly Tyr Thr Pro Leu His Leu Ala Ala Glu Asp Gly His Leu
            35                  40                  45

Glu Ile Val Glu Val Leu Leu Lys His Gly Ala Asp Val Asn Ala Met
        50                  55                  60

Asp Asn Ile Gly Asn Thr Ser Leu His Leu Ala Ala Phe Asp Gly His
65                  70                  75                  80

Leu Glu Ile Val Glu Val Leu Leu Lys Tyr Gly Ala Asp Val Asn Ala
                85                  90                  95

Val Asp Leu Ala Gly Val Thr Pro Leu His Val Ala Ala Phe Tyr Gly
            100                 105                 110

His Leu Glu Ile Val Glu Val Leu Leu Lys His Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln Lys Leu Asn
145                 150                 155
```

```
<210> SEQ ID NO 22
<211> LENGTH: 157
<212> TYPE: PRT
<213> ORGANISM: Artificial Sequence
<220> FEATURE:
<223> OTHER INFORMATION: Synthetic ankyrin repeat sequence

<400> SEQUENCE: 22

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Phe Asp
                20                  25                  30

Asp Ser Gly Leu Thr Pro Leu His Leu Ala Ala Asp Gly His Leu
        35                  40                  45

Glu Ile Val Glu Val Leu Leu Lys His Gly Ala Asp Val Asn Ala Ala
    50                  55                  60

Asp Arg Met Gly Asp Thr Pro Leu His Leu Ala Ala Phe Val Gly His
65                  70                  75                  80

Leu Glu Ile Val Glu Val Leu Leu Lys Tyr Gly Ala Asp Val Asn Ala
                85                  90                  95

Val Asp Leu Ala Gly Val Thr Pro Leu His Val Ala Ala Phe Tyr Gly
                100                 105                 110

His Leu Glu Ile Val Glu Val Leu Leu Lys Tyr Gly Ala Asp Val Asn
                115                 120                 125

Ala Gln Asp Lys Phe Gly Lys Thr Ala Phe Asp Ile Ser Ile Asp Asn
        130                 135                 140

Gly Asn Glu Asp Leu Ala Glu Ile Leu Gln Lys Leu Asn
145                 150                 155

<210> SEQ ID NO 23
<211> LENGTH: 157
<212> TYPE: PRT
<213> ORGANISM: Artificial Sequence
<220> FEATURE:
<223> OTHER INFORMATION: Synthetic ankyrin repeat sequence

<400> SEQUENCE: 23

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Ala Asn Ala Thr Asp
                20                  25                  30

Asp Trp Gly Asp Thr Leu Leu His Leu Ala Ala Thr Asp Gly His Leu
        35                  40                  45

Glu Ile Val Glu Val Leu Leu Lys Asn Gly Ala Asp Val Asn Ala Ile
    50                  55                  60

Asp Ala Met Gly Met Thr Pro Leu His Leu Ala Ala Val Tyr Gly Tyr
65                  70                  75                  80

Leu Glu Ile Val Glu Val Leu Leu Lys Asn Gly Ala Asp Val Asn Ala
                85                  90                  95

Met Asp Phe Ser Gly Phe Thr Pro Leu His Leu Ala Ala Phe Ser Gly
                100                 105                 110

His Leu Glu Ile Val Glu Val Leu Leu Lys Tyr Gly Ala Asp Val Asn
                115                 120                 125

Ala Gln Asp Lys Phe Gly Lys Thr Ala Phe Asp Ile Ser Ile Asp Asn
        130                 135                 140

Gly Asn Glu Asp Leu Ala Glu Ile Leu Gln Lys Leu Asn
145                 150                 155
```

```
<210> SEQ ID NO 24
<211> LENGTH: 157
<212> TYPE: PRT
<213> ORGANISM: Artificial Sequence
<220> FEATURE:
<223> OTHER INFORMATION: Synthetic ankyrin repeat sequence

<400> SEQUENCE: 24

Asp Leu Gly Lys Glu Leu Leu Glu Ala Ala Ser Ala Gly Gln Asp Asp
1               5                   10                  15

Glu Val His Ile Leu Met Ala Asn Gly Ala Asp Val Asn Ala Ser Asp
            20                  25                  30

Lys Asp Gly Ser Thr Pro Leu His Leu Ala Ala Val Tyr Gly His Leu
        35                  40                  45

Glu Ile Val Glu Val Leu Leu Lys Tyr Gly Ala Asp Val Asn Ala Glu
    50                  55                  60

Asp Met Asn Gly Tyr Thr Pro Leu His Leu Ala Ala Asp Gly His
65                  70                  75                  80

Leu Glu Ile Val Glu Val Leu Leu Lys Tyr Gly Ala Asp Val Asp Ala
                85                  90                  95

Lys Asp Arg Thr Gly Trp Thr Pro Leu His Leu Ala Gly Glu Phe Gly
            100                 105                 110

His Leu Glu Ile Val Glu Val Leu Leu Lys Tyr Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln Lys Leu Asn
145                 150                 155

<210> SEQ ID NO 25
<211> LENGTH: 157
<212> TYPE: PRT
<213> ORGANISM: Artificial Sequence
<220> FEATURE:
<223> OTHER INFORMATION: Synthetic ankyrin repeat sequence

<400> SEQUENCE: 25

Asn Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Thr Asp
            20                  25                  30

Asp Trp Gly Asp Thr Leu Leu His Leu Ala Ala Thr Asp Gly His Leu
        35                  40                  45

Glu Ile Val Glu Val Leu Leu Lys Tyr Gly Ala Asp Val Asn Ala Asn
    50                  55                  60

Asp Ala Ile Gly Asp Thr Pro Leu His Leu Ala Leu Tyr Gly His
65                  70                  75                  80

Leu Glu Ile Val Glu Val Leu Leu Lys Tyr Gly Ala Asp Val Asn Ala
                85                  90                  95

Thr Asp Leu His Gly Phe Thr Pro Leu His Leu Ala Ala Phe Trp Gly
            100                 105                 110

His Leu Glu Ile Val Glu Val Leu Leu Lys His Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln Lys Leu Asn
145                 150                 155
```

```
<210> SEQ ID NO 26
<211> LENGTH: 157
<212> TYPE: PRT
<213> ORGANISM: Artificial Sequence
<220> FEATURE:
<223> OTHER INFORMATION: Synthetic ankyrin repeat sequence

<400> SEQUENCE: 26

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Thr Asp
            20                  25                  30

Asp Trp Gly Asp Thr Leu Leu His Leu Ala Ala Thr Asp Gly His Leu
        35                  40                  45

Glu Ile Val Glu Val Leu Leu Lys Asn Gly Ala Asp Val Asn Ala Ile
    50                  55                  60

Asp Ala Met Gly Met Thr Pro Leu His Leu Ala Val Tyr Gly Tyr
65                  70                  75                  80

Leu Glu Ile Val Glu Val Leu Leu Lys Asn Gly Ala Asp Val Asn Ala
                85                  90                  95

Met Asp Phe Ser Gly Phe Thr Pro Leu His Leu Thr Ala Phe Ser Gly
            100                 105                 110

His Leu Glu Ile Val Glu Val Leu Leu Lys Tyr Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln Lys Leu Asn
145                 150                 155

<210> SEQ ID NO 27
<211> LENGTH: 190
<212> TYPE: PRT
<213> ORGANISM: Artificial Sequence
<220> FEATURE:
<223> OTHER INFORMATION: Synthetic ankyrin repeat sequence

<400> SEQUENCE: 27

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Ile Asp
            20                  25                  30

Ser Asp Gly Thr Thr Pro Leu His Leu Ala Ala Met Asp Gly His Leu
        35                  40                  45

Glu Ile Val Glu Val Leu Leu Lys Tyr Gly Ala Asp Val Asn Ala Val
    50                  55                  60

Asp Trp Asn Gly Asp Thr Pro Leu His Leu Ala Ala Val Asp Gly His
65                  70                  75                  80

Leu Glu Ile Val Glu Val Leu Leu Lys Tyr Gly Ala Asp Val Asn Ala
                85                  90                  95

Gln Asp Asn Leu Gly Asp Thr Pro Leu His Leu Ala Ala Tyr Tyr Gly
            100                 105                 110

His Leu Glu Ile Val Glu Val Leu Leu Lys His Gly Ala Asp Val Asn
        115                 120                 125

Ala Ser Asp Phe His Gly Ile Thr Pro Leu His Leu Ala Ala Phe Ser
    130                 135                 140

Gly His Leu Glu Ile Val Glu Val Leu Leu Lys Tyr Gly Ala Asp Val
```

```
                145                 150                 155                 160
Asn Ala Gln Asp Lys Phe Gly Lys Thr Ala Phe Asp Ile Ser Ile Asp
                    165                 170                 175

Asn Gly Asn Glu Asp Leu Ala Glu Ile Leu Gln Lys Leu Asn
                    180                 185                 190

<210> SEQ ID NO 28
<211> LENGTH: 157
<212> TYPE: PRT
<213> ORGANISM: Artificial Sequence
<220> FEATURE:
<223> OTHER INFORMATION: Synthetic ankyrin repeat sequence

<400> SEQUENCE: 28

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala His Asp
                20                  25                  30

Asn Ser Gly Phe Thr Pro Leu His Leu Ala Ala Glu Ile Gly His Leu
            35                  40                  45

Glu Ile Val Glu Val Leu Leu Lys Tyr Gly Ala Asp Val Asn Ala Ala
        50                  55                  60

Asp Arg Met Gly Asp Thr Pro Leu His Leu Ala Ala Phe Val Gly His
65                  70                  75                  80

Leu Glu Ile Val Glu Val Leu Leu Lys Tyr Gly Ala Asp Val Asn Ala
                85                  90                  95

Val Asp Leu Ala Gly Val Thr Pro Leu His Val Ala Ala Phe Tyr Gly
            100                 105                 110

His Leu Glu Ile Val Glu Val Leu Leu Lys Asn Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln Lys Leu Asn
145                 150                 155

<210> SEQ ID NO 29
<211> LENGTH: 157
<212> TYPE: PRT
<213> ORGANISM: Artificial Sequence
<220> FEATURE:
<223> OTHER INFORMATION: Synthetic ankyrin repeat sequence

<400> SEQUENCE: 29

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Glu Asp
                20                  25                  30

Asp Trp Gly Leu Thr Pro Leu His Leu Ala Ala Met Leu Gly His Leu
            35                  40                  45

Glu Ile Val Glu Val Leu Leu Lys Tyr Gly Ala Asp Val Asn Ala Lys
        50                  55                  60

Asp Asp Thr Gly Phe Thr Pro Leu His Leu Ala Ala Val Glu Gly His
65                  70                  75                  80

Leu Glu Ile Val Glu Val Leu Leu Lys Tyr Gly Ala Asp Val Asn Ala
                85                  90                  95

Ser Asp Ile Leu Gly Arg Thr Pro Leu His Leu Ala Ala Asn Phe Gly
            100                 105                 110
```

His Leu Glu Ile Val Glu Val Leu Lys Tyr Gly Ala Asp Val Asn
            115                 120                 125

Ala Gln Asp Lys Phe Gly Lys Thr Ala Phe Asp Ile Ser Ile Asp Asn
        130                 135                 140

Gly Asn Glu Asp Leu Ala Glu Ile Leu Gln Lys Leu Asn
145                 150                 155

<210> SEQ ID NO 30
<211> LENGTH: 157
<212> TYPE: PRT
<213> ORGANISM: Artificial Sequence
<220> FEATURE:
<223> OTHER INFORMATION: Synthetic ankyrin repeat sequence

<400> SEQUENCE: 30

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Thr Asp
            20                  25                  30

Ala Trp Gly Leu Thr Pro Leu His Leu Ala Ala Leu Leu Gly His Leu
        35                  40                  45

Glu Ile Val Glu Val Leu Leu Lys His Gly Ala Asp Val Asn Ala His
    50                  55                  60

Asp Glu Thr Gly Phe Thr Pro Leu His Leu Ala Ala Val Glu Gly His
65                  70                  75                  80

Leu Glu Ile Val Glu Val Leu Leu Lys Tyr Gly Ala Asp Val Asn Ala
                85                  90                  95

Ser Asp Ile Leu Gly Arg Thr Pro Leu His Leu Ala Ala Asn Phe Gly
            100                 105                 110

His Leu Glu Ile Val Glu Val Leu Leu Lys Tyr Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln Lys Leu Asn
145                 150                 155

<210> SEQ ID NO 31
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 31

Ser Asp Arg Ile Gly Asn Thr Pro Leu His Leu Ala Ala Val Tyr Val
1               5                   10                  15

His Leu Glu Ile Val Glu Val Leu Leu Lys Asn Gly Ala Asp Val Asn
            20                  25                  30

Ala

<210> SEQ ID NO 32
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 32

Ile Asp Glu Trp Gly Asp Thr Pro Leu His Leu Ala Ala Ile Glu Gly
1               5                   10                  15

```
<210> SEQ ID NO 33
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 33
```

Thr Asp Asp Trp Gly Asp Thr Leu Leu His Leu Ala Ala Thr Asp Gly
1               5                   10                  15

His Leu Glu Ile Val Glu Val Leu Leu Lys Asn Gly Ala Asp Val Asn
            20                  25                  30

Ala

```
<210> SEQ ID NO 34
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 34
```

Val Asp His Asp Gly Phe Thr Pro Leu His Leu Ala Ala Ala Asp Gly
1               5                   10                  15

His Leu Glu Ile Val Glu Val Leu Leu Lys His Gly Ala Asp Val Asn
            20                  25                  30

Ala

```
<210> SEQ ID NO 35
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 35
```

Tyr Asp Ser Ser Gly Asp Thr Pro Leu His Val Ala Ala Ile Asp Gly
1               5                   10                  15

His Leu Glu Ile Val Glu Val Leu Leu Lys His Gly Ala Asp Val Asn
            20                  25                  30

Ala

```
<210> SEQ ID NO 36
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 36
```

Ala Asp Asp Ser Gly Ile Thr Pro Leu His Leu Ala Ala Glu Asp Gly
1               5                   10                  15

His Leu Glu Ile Val Glu Val Leu Leu Lys Tyr Gly Ala Asp Val Asn
            20                  25                  30

Ala

```
<210> SEQ ID NO 37
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 37

Thr Asp Ala Trp Gly Leu Thr Pro Leu His Leu Ala Ala Leu Leu Gly
1               5                   10                  15

His Leu Glu Ile Val Glu Val Leu Leu Lys His Gly Ala Asp Val Asn
            20                  25                  30

Ala

<210> SEQ ID NO 38
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 38

Lys Asp Val Thr Gly Glu Thr Pro Leu His Leu Ala Ser Trp Glu Gly
1               5                   10                  15

His Leu Glu Ile Val Glu Val Leu Leu Lys His Gly Ala Asp Val Asn
            20                  25                  30

Ala

<210> SEQ ID NO 39
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 39

Leu Asp Asp Ser Gly Tyr Thr Pro Leu His Leu Ala Ala Glu Asp Gly
1               5                   10                  15

His Leu Glu Ile Val Glu Val Leu Leu Lys His Gly Ala Asp Val Asn
            20                  25                  30

Ala

<210> SEQ ID NO 40
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 40

Phe Asp Asp Ser Gly Leu Thr Pro Leu His Leu Ala Ala Asp Asp Gly
1               5                   10                  15

His Leu Glu Ile Val Glu Val Leu Leu Lys His Gly Ala Asp Val Asn
            20                  25                  30

Ala

<210> SEQ ID NO 41
<211> LENGTH: 336
<212> TYPE: PRT
<213> ORGANISM: Artificial Sequence
<220> FEATURE:
<223> OTHER INFORMATION: Synthetic ankyrin repeat sequence
```

<400> SEQUENCE: 41

Asp Leu Gly Lys Lys Leu Leu Glu Ala Ala Ser Ala Gly Gln Asp Asp
1               5                   10                  15

Glu Val Arg Ile Leu Met Ala Asn Gly Ala Asp Val Asn Ala Leu Asp
            20                  25                  30

Asp Ser Gly Tyr Thr Pro Leu His Leu Ala Ala Glu Asp Gly His Leu
        35                  40                  45

Glu Ile Val Glu Val Leu Leu Lys His Gly Ala Asp Val Asn Ala Ala
    50                  55                  60

Asp Arg Leu Gly Asp Thr Pro Leu His Leu Ala Ala Phe Val Gly His
65                  70                  75                  80

Leu Glu Ile Val Glu Val Leu Leu Lys Ala Gly Ala Asp Val Asn Ala
                85                  90                  95

Val Asp Leu Ala Gly Val Thr Pro Leu His Val Ala Ala Phe Tyr Gly
            100                 105                 110

His Leu Glu Ile Val Glu Val Leu Leu Lys Ala Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln Lys Ala Ala Gly Gly Gly
145                 150                 155                 160

Gly Ser Gly Gly Gly Ser Gly Gly Gly Ser Gly Gly Gly Gly
                165                 170                 175

Ser Gly Ser Asp Leu Asp Lys Lys Leu Leu Glu Ala Ala Arg Ala Gly
            180                 185                 190

Gln Asp Asp Glu Val Arg Ile Leu Met Ala Asn Gly Ala Asp Val Asn
    195                 200                 205

Ala Arg Asp Ser Tyr Gly Ser Thr Pro Leu His Leu Ala Ala Arg Glu
210                 215                 220

Gly His Leu Glu Ile Val Glu Val Leu Leu Lys Tyr Gly Ala Asp Val
225                 230                 235                 240

Asn Ala Ala Asp Phe Ile Gly Asp Thr Pro Leu His Leu Ala Ala Tyr
                245                 250                 255

Arg Gly His Leu Glu Ile Val Glu Val Leu Leu Lys Tyr Gly Ala Asp
            260                 265                 270

Val Asn Ala Ser Asp Ile Thr Gly Glu Thr Pro Leu His Leu Ala Ala
        275                 280                 285

Gln Ile Gly His Leu Glu Ile Val Glu Val Leu Leu Lys His Gly Ala
    290                 295                 300

Asp Val Asn Ala Gln Asp Lys Phe Gly Lys Thr Ala Phe Asp Ile Ser
305                 310                 315                 320

Ile Asp Asn Gly Asn Glu Asp Leu Ala Glu Ile Leu Gln Lys Ala Ala
                325                 330                 335

<210> SEQ ID NO 42
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 42

Ser Asp Lys Asp Gly Ser Thr Pro Leu His Leu Ala Ala Val Tyr Gly
1               5                   10                  15

His Leu Glu Ile Val Glu Val Leu Leu Lys Tyr Gly Ala Asp Val Asn

```
            20                  25                  30
Ala

<210> SEQ ID NO 43
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 43

Thr Asp Asp Trp Gly Asp Thr Leu Leu His Leu Ala Ala Thr Asp Gly
1               5                   10                  15

His Leu Glu Ile Val Glu Val Leu Leu Lys Tyr Gly Ala Asp Val Asn
            20                  25                  30

Ala

<210> SEQ ID NO 44
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 44

Ile Asp Ser Asp Gly Thr Thr Pro Leu His Leu Ala Ala Met Asp Gly
1               5                   10                  15

His Leu Glu Ile Val Glu Val Leu Leu Lys Tyr Gly Ala Asp Val Asn
            20                  25                  30

Ala

<210> SEQ ID NO 45
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 45

His Asp Asn Ser Gly Phe Thr Pro Leu His Leu Ala Ala Glu Ile Gly
1               5                   10                  15

His Leu Glu Ile Val Glu Val Leu Leu Lys Tyr Gly Ala Asp Val Asn
            20                  25                  30

Ala

<210> SEQ ID NO 46
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 46

Glu Asp Asp Trp Gly Leu Thr Pro Leu His Leu Ala Ala Met Leu Gly
1               5                   10                  15

His Leu Glu Ile Val Glu Val Leu Leu Lys Tyr Gly Ala Asp Val Asn
            20                  25                  30

Ala

<210> SEQ ID NO 47
<211> LENGTH: 33
```

```
<212> TYPE: PRT
<213> ORGANISM: Artificial Sequence
<220> FEATURE:
<223> OTHER INFORMATION: Synthetic ankyrin repeat sequence

<400> SEQUENCE: 47

Leu Asp Asp Asp Gly Leu Thr Pro Leu His Leu Ala Ala Ala Asp Gly
1               5                   10                  15

His Leu Glu Ile Val Glu Val Leu Leu Lys His Gly Ala Asp Val Asn
            20                  25                  30

Ala

<210> SEQ ID NO 48
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 48

Ser Asp Ala Met Gly Met Thr Pro Leu His Leu Ala Ala Val Tyr Gly
1               5                   10                  15

Tyr Leu Glu Ile Val Glu Val Leu Leu Lys Asn Gly Ala Asp Val Asn
            20                  25                  30

Ala

<210> SEQ ID NO 49
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 49

Ile Asp Ala Met Gly Met Thr Pro Leu His Leu Ala Ala Val Tyr Gly
1               5                   10                  15

Tyr Leu Glu Ile Val Glu Val Leu Leu Lys Asn Gly Ala Asp Val Asn
            20                  25                  30

Ala

<210> SEQ ID NO 50
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 50

Ser Asp Ser Gln Gly Leu Thr Pro Leu His Leu Ala Ala Tyr Tyr Gly
1               5                   10                  15

His Leu Glu Ile Val Glu Val Leu Leu Lys Tyr Gly Ala Asp Val Asn
            20                  25                  30

Ala

<210> SEQ ID NO 51
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 51
```

Asp Asp Asn Phe Gly Trp Thr Pro Leu His Leu Ala Ala Phe Phe Gly
1               5                   10                  15

His Leu Glu Ile Val Glu Val Leu Leu Lys His Gly Ala Asp Val Asn
            20                  25                  30

Ala

<210> SEQ ID NO 52
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 52

Ser Asp Ala Ser Gly Asp Thr Pro Leu His Leu Ala Ala Asp Phe Gly
1               5                   10                  15

His Leu Lys Ile Val Glu Val Leu Leu Lys His Gly Ala Asp Val Asn
            20                  25                  30

Ala

<210> SEQ ID NO 53
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 53

Gln Asp Asn Leu Gly Asp Thr Pro Leu His Leu Ala Ala Trp Thr Gly
1               5                   10                  15

His Leu Glu Ile Val Glu Val Leu Leu Lys Asn Gly Ala Asp Val Asn
            20                  25                  30

Ala

<210> SEQ ID NO 54
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 54

His Asp Glu Thr Gly Phe Thr Pro Leu His Leu Ala Ala Val Glu Gly
1               5                   10                  15

His Leu Glu Ile Val Glu Val Leu Leu Lys Tyr Gly Ala Asp Val Asn
            20                  25                  30

Ala

<210> SEQ ID NO 55
<211> LENGTH: 34
<212> TYPE: PRT
<213> ORGANISM: Artificial Sequence
<220> FEATURE:
<223> OTHER INFORMATION: Synthetic ankyrin repeat sequence

<400> SEQUENCE: 55

Gln Asp Leu Phe Gly Ile Thr Pro Leu His Leu Ala Ala Ala Thr Asp
1               5                   10                  15

Gly His Leu Glu Ile Val Glu Val Leu Leu Lys Asn Gly Ala Asp Val
            20                  25                  30

Asn Ala

<210> SEQ ID NO 56
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 56

```
Ala Asp Arg Met Gly Asp Thr Pro Leu His Leu Ala Ala Phe Val Gly
1               5                   10                  15

His Leu Glu Ile Val Glu Val Leu Leu Lys Tyr Gly Ala Asp Val Asn
            20                  25                  30

Ala
```

<210> SEQ ID NO 57
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 57

```
Met Asp Asn Ile Gly Asn Thr Ser Leu His Leu Ala Ala Phe Asp Gly
1               5                   10                  15

His Leu Glu Ile Val Glu Val Leu Leu Lys Tyr Gly Ala Asp Val Asn
            20                  25                  30

Ala
```

<210> SEQ ID NO 58
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 58

```
Glu Asp Met Asn Gly Tyr Thr Pro Leu His Leu Ala Ala Ala Asp Gly
1               5                   10                  15

His Leu Glu Ile Val Glu Val Leu Leu Lys Tyr Gly Ala Asp Val Asp
            20                  25                  30

Ala
```

<210> SEQ ID NO 59
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 59

```
Asn Asp Ala Ile Gly Asp Thr Pro Leu His Leu Ala Ala Leu Tyr Gly
1               5                   10                  15

His Leu Glu Ile Val Glu Val Leu Leu Lys Tyr Gly Ala Asp Val Asn
            20                  25                  30

Ala
```

<210> SEQ ID NO 60
<211> LENGTH: 33
<212> TYPE: PRT
<213> ORGANISM: Artificial Sequence
<220> FEATURE:

```
<223> OTHER INFORMATION: Synthetic ankyrin repeat sequence

<400> SEQUENCE: 60

Val Asp Trp Asn Gly Asp Thr Pro Leu His Leu Ala Ala Val Asp Gly
1               5                   10                  15

His Leu Glu Ile Val Glu Val Leu Leu Lys Tyr Gly Ala Asp Val Asn
            20                  25                  30

Ala

<210> SEQ ID NO 61
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 61

Lys Asp Asp Thr Gly Phe Thr Pro Leu His Leu Ala Ala Val Glu Gly
1               5                   10                  15

His Leu Glu Ile Val Glu Val Leu Leu Lys Tyr Gly Ala Asp Val Asn
            20                  25                  30

Ala

<210> SEQ ID NO 62
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 62

Thr Asp Ser His Val Trp Thr Pro Leu His Leu Ala Ala Phe Phe Gly
1               5                   10                  15

His Leu Glu Ile Val Glu Val Leu Leu Lys Tyr Gly Ala Asp Val Asn
            20                  25                  30

Ala

<210> SEQ ID NO 63
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 63

Met Asp Phe Ser Gly Phe Thr Pro Leu His Leu Ala Ala Phe Ser Gly
1               5                   10                  15

His Leu Glu Ile Val Glu Val Leu Leu Lys Tyr Gly Ala Asp Val Asn
            20                  25                  30

Ala

<210> SEQ ID NO 64
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 64

Asn Asp His His Gly Ile Thr Pro Leu His Leu Ala Ala Phe Ala Gly
1               5                   10                  15
```

His Leu Glu Ile Val Glu Val Leu Leu Lys Tyr Gly Ala Asp Val Asn
            20                  25                  30

Ala

<210> SEQ ID NO 65
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 65

Lys Asp Gln Thr Gly Leu Thr Pro Leu His Leu Ala Ala Val Asp Gly
1               5                   10                  15

His Leu Glu Ile Val Glu Val Leu Leu Lys His Gly Ala Asp Val Asn
            20                  25                  30

Ala

<210> SEQ ID NO 66
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 66

Glu Asp Met Ile Gly Ile Thr Pro Leu His Leu Ala Ala Tyr Asn Gly
1               5                   10                  15

His Leu Glu Ile Val Glu Val Leu Leu Lys Asn Gly Ala Asp Val Asn
            20                  25                  30

Ala

<210> SEQ ID NO 67
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 67

Lys Asp Gln Thr Gly Leu Thr Pro Leu His Leu Ala Ala Val Asp Gly
1               5                   10                  15

His Leu Glu Ile Val Glu Val Leu Leu Lys Asn Gly Ala Asp Val Asn
            20                  25                  30

Ala

<210> SEQ ID NO 68
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 68

Tyr Asp Ile Ser Gly Ile Thr Pro Leu His Leu Ala Ala Phe Tyr Gly
1               5                   10                  15

His Leu Glu Ile Val Glu Val Leu Leu Lys His Gly Ala Asp Val Asn
            20                  25                  30

Ala

<210> SEQ ID NO 69

<210> SEQ ID NO 69
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 69

Ser Asp Ile Leu Gly Arg Thr Pro Leu His Leu Ala Ala Asn Phe Gly
1               5                   10                  15

His Leu Glu Ile Val Glu Val Leu Leu Lys His Gly Ala Asp Val Asn
            20                  25                  30

Ala

<210> SEQ ID NO 70
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 70

Thr Asp Ser Asn Gly Phe Thr Pro Leu His Leu Ala Ala Ser Tyr Gly
1               5                   10                  15

His Leu Glu Ile Val Asp Val Leu Leu Lys Asn Gly Ala Asp Val Asn
            20                  25                  30

Ala

<210> SEQ ID NO 71
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 71

Val Asp Leu Ala Gly Val Thr Pro Leu His Val Ala Ala Phe Tyr Gly
1               5                   10                  15

His Leu Glu Ile Val Glu Val Leu Leu Lys Tyr Gly Ala Asp Val Asn
            20                  25                  30

Ala

<210> SEQ ID NO 72
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 72

Val Asp Leu Ala Gly Val Thr Pro Leu His Val Ala Ala Phe Tyr Gly
1               5                   10                  15

His Leu Glu Ile Val Glu Val Leu Leu Lys His Gly Ala Asp Val Asn
            20                  25                  30

Ala

<210> SEQ ID NO 73
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 73

Lys Asp Arg Thr Gly Trp Thr Pro Leu His Leu Ala Gly Glu Phe Gly
1               5                   10                  15

His Leu Glu Ile Val Glu Val Leu Leu Lys Tyr Gly Ala Asp Val Asn
            20                  25                  30

Ala

<210> SEQ ID NO 74
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 74

Thr Asp Leu His Gly Phe Thr Pro Leu His Leu Ala Ala Phe Trp Gly
1               5                   10                  15

His Leu Glu Ile Val Glu Val Leu Leu Lys His Gly Ala Asp Val Asn
            20                  25                  30

Ala

<210> SEQ ID NO 75
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 75

Met Asp Phe Ser Gly Phe Thr Pro Leu His Leu Thr Ala Phe Ser Gly
1               5                   10                  15

His Leu Glu Ile Val Glu Val Leu Leu Lys Tyr Gly Ala Asp Val Asn
            20                  25                  30

Ala

<210> SEQ ID NO 76
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 76

Gln Asp Asn Leu Gly Asp Thr Pro Leu His Leu Ala Ala Tyr Tyr Gly
1               5                   10                  15

His Leu Glu Ile Val Glu Val Leu Leu Lys His Gly Ala Asp Val Asn
            20                  25                  30

Ala

<210> SEQ ID NO 77
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 77

Val Asp Leu Ala Gly Val Thr Pro Leu His Val Ala Ala Phe Tyr Gly
1               5                   10                  15

His Leu Glu Ile Val Glu Val Leu Leu Lys Asn Gly Ala Asp Val Asn
            20                  25                  30

```
<210> SEQ ID NO 78
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 78

Ser Asp Ile Leu Gly Arg Thr Pro Leu His Leu Ala Ala Asn Phe Gly
1               5                   10                  15

His Leu Glu Ile Val Glu Val Leu Leu Lys Tyr Gly Ala Asp Val Asn
            20                  25                  30

Ala

<210> SEQ ID NO 79
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 79

Ser Asp Phe His Gly Ile Thr Pro Leu His Leu Ala Ala Phe Ser Gly
1               5                   10                  15

His Leu Glu Ile Val Glu Val Leu Leu Lys Tyr Gly Ala Asp Val Asn
            20                  25                  30

Ala

<210> SEQ ID NO 80
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 80

Ser Asp Val His Gly Phe Thr Pro Leu His Leu Ala Ala Phe Ile Gly
1               5                   10                  15

His Leu Gly Ile Val Glu Val Leu Leu Lys Tyr Asp Ala Asp Val Asn
            20                  25                  30

Ala

<210> SEQ ID NO 81
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 81

His Asp Phe Asp Gly Phe Thr Pro Leu His Leu Ala Ala Ser Trp Gly
1               5                   10                  15

His Leu Glu Ile Val Glu Val Leu Leu Lys Tyr Gly Ala Asp Val Asn
            20                  25                  30

Ala

<210> SEQ ID NO 82
<211> LENGTH: 33
<212> TYPE: PRT
<213> ORGANISM: Artificial Sequence
```

```
<220> FEATURE:
<223> OTHER INFORMATION: Synthetic conseneus ankyrin repeat sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid

<400> SEQUENCE: 82

Xaa Asp Asp Trp Gly Xaa Thr Pro Leu His Leu Ala Ala Thr Asp Gly
 1               5                  10                  15

His Leu Glu Ile Val Glu Val Leu Leu Lys Xaa Gly Ala Asp Val Asn
                20                  25                  30

Ala

<210> SEQ ID NO 83
<211> LENGTH: 33
<212> TYPE: PRT
<213> ORGANISM: Artificial Sequence
<220> FEATURE:
<223> OTHER INFORMATION: Synthetic conseneus ankyrin repeat sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid

<400> SEQUENCE: 83

Xaa Asp Xaa Xaa Gly Xaa Thr Pro Leu His Leu Ala Ala Xaa Xaa Gly
 1               5                  10                  15

His Leu Glu Ile Val Glu Val Leu Leu Lys Xaa Gly Ala Asp Val Asn
                20                  25                  30

Ala

<210> SEQ ID NO 84
<211> LENGTH: 33
<212> TYPE: PRT
<213> ORGANISM: Artificial Sequence
<220> FEATURE:
<223> OTHER INFORMATION: Synthetic conseneus ankyrin repeat sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid
<220> FEATURE:
```

```
<221> NAME/KEY: misc_feature
<222> LOCATION: (14)..(15)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid

<400> SEQUENCE: 84

Xaa Asp Xaa Xaa Gly Phe Thr Pro Leu His Leu Ala Ala Xaa Xaa Gly
1               5                   10                  15

His Leu Glu Ile Val Glu Val Leu Leu Lys Xaa Gly Ala Asp Val Asn
            20                  25                  30

Ala

<210> SEQ ID NO 85
<211> LENGTH: 33
<212> TYPE: PRT
<213> ORGANISM: Artificial Sequence
<220> FEATURE:
<223> OTHER INFORMATION: Synthetic conseneus ankyrin repeat sequence
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid

<400> SEQUENCE: 85

Thr Asp Asp Trp Gly Xaa Thr Pro Leu His Leu Ala Ala Thr Asp Gly
1               5                   10                  15

His Leu Glu Ile Val Glu Val Leu Leu Lys Xaa Gly Ala Asp Val Asn
            20                  25                  30

Ala

<210> SEQ ID NO 86
<211> LENGTH: 33
<212> TYPE: PRT
<213> ORGANISM: Artificial Sequence
<220> FEATURE:
<223> OTHER INFORMATION: Synthetic conseneus ankyrin repeat sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid

<400> SEQUENCE: 86

Xaa Asp Ala Met Gly Xaa Thr Pro Leu His Leu Ala Ala Val Tyr Gly
1               5                   10                  15

His Leu Glu Ile Val Glu Val Leu Leu Lys Xaa Gly Ala Asp Val Asn
            20                  25                  30

Ala

<210> SEQ ID NO 87
<211> LENGTH: 64
<212> TYPE: PRT
<213> ORGANISM: Homo sapiens
```

```
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(9)
<223> OTHER INFORMATION: Xaa can be any naturally occurring amino acid
<220> FEATURE:
<221> NAME/KEY: misc_feature
<222> LOCATION: (32)..(58)
<223> OTHER INFORMATION: Xaa can be any naturally occurring amino acid

<400> SEQUENCE: 87

Xaa Asp Xaa Xaa Xaa Xaa Xaa Xaa Xaa Gly Phe Thr Pro Leu His Leu
1               5                   10                  15

Ala Ala Phe Tyr Gly His Leu Glu Ile Val Glu Val Leu Leu Lys Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Gly Ala Asp Val Asn Ala
    50                  55                  60

<210> SEQ ID NO 88
<211> LENGTH: 33
<212> TYPE: PRT
<213> ORGANISM: Artificial Sequence
<220> FEATURE:
<223> OTHER INFORMATION: Synthetic conseneus ankyrin repeat sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid

<400> SEQUENCE: 88

Xaa Asp Asp Xaa Gly Xaa Thr Pro Leu His Leu Ala Ala Xaa Asp Gly
1               5                   10                  15

His Leu Glu Ile Val Glu Val Leu Leu Lys Xaa Gly Ala Asp Val Asn
            20                  25                  30

Ala

<210> SEQ ID NO 89
<211> LENGTH: 91
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(9)
<223> OTHER INFORMATION: Xaa can be any naturally occurring amino acid
<220> FEATURE:
```

```
<221> NAME/KEY: misc_feature
<222> LOCATION: (19)..(47)
<223> OTHER INFORMATION: Xaa can be any naturally occurring amino acid
<220> FEATURE:
<221> NAME/KEY: misc_feature
<222> LOCATION: (59)..(85)
<223> OTHER INFORMATION: Xaa can be any naturally occurring amino acid

<400> SEQUENCE: 89

Xaa Asp Xaa Xaa Xaa Xaa Xaa Xaa Gly Asp Thr Pro Leu His Leu
1               5                   10                  15

Ala Ala Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Gly
        35                  40                  45

His Leu Glu Ile Val Glu Val Leu Leu Lys Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Gly Ala Asp Val Asn Ala
                85                  90

<210> SEQ ID NO 90
<211> LENGTH: 33
<212> TYPE: PRT
<213> ORGANISM: Artificial Sequence
<220> FEATURE:
<223> OTHER INFORMATION: Synthetic conseneus ankyrin repeat sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid

<400> SEQUENCE: 90

Xaa Asp Xaa Xaa Gly Xaa Thr Pro Leu His Leu Ala Ala Phe Xaa Gly
1               5                   10                  15

His Leu Glu Ile Val Glu Val Leu Leu Lys Xaa Gly Ala Asp Val Asn
            20                  25                  30

Ala

<210> SEQ ID NO 91
<211> LENGTH: 157
<212> TYPE: PRT
<213> ORGANISM: Artificial Sequence
<220> FEATURE:
<223> OTHER INFORMATION: Synthetic ankyrin repeat sequence

<400> SEQUENCE: 91

Asp Leu Gly Lys Lys Leu Leu Glu Ala Ala Ser Ala Gly Gln Asp Asp
1               5                   10                  15
```

```
Glu Val His Ile Leu Met Ala Asn Gly Ala Asp Val Asn Ala Leu Asp
                20                  25                  30

Asp Ser Gly Tyr Thr Pro Leu His Leu Ala Ala Glu Asp Gly His Leu
            35                  40                  45

Glu Ile Val Glu Val Leu Leu Lys His Gly Ala Asp Val Asn Ala Ala
 50                  55                  60

Asp Arg Leu Gly Asp Thr Pro Leu His Leu Ala Ala Phe Val Gly His
 65                  70                  75                  80

Leu Glu Ile Val Glu Val Leu Leu Lys Ala Gly Ala Asp Val Asn Ala
                85                  90                  95

Val Asp Leu Ala Gly Val Thr Pro Leu His Val Ala Ala Phe Tyr Gly
                100                 105                 110

His Leu Glu Ile Val Glu Val Leu Leu Lys Ala Gly Ala Asp Val Asn
            115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln Lys Leu Asn
145                 150                 155

<210> SEQ ID NO 92
<211> LENGTH: 157
<212> TYPE: PRT
<213> ORGANISM: Artificial Sequence
<220> FEATURE:
<223> OTHER INFORMATION: Synthetic ankyrin repeat sequence

<400> SEQUENCE: 92

Asp Leu Gly Lys Lys Leu Leu Glu Ala Ala Arg Ala Gly Gln Asp Asp
 1               5                  10                  15

Glu Val Arg Ile Leu Met Ala Asn Gly Ala Asp Val Asn Ala Ala Asp
                20                  25                  30

Asp Ser Gly Ile Thr Pro Leu His Leu Ala Ala Glu Asp Gly His Leu
            35                  40                  45

Glu Ile Val Glu Val Leu Leu Lys Ala Gly Ala Asp Val Asn Ala Gln
 50                  55                  60

Asp Asn Leu Gly Asp Thr Pro Leu His Leu Ala Ala Trp Thr Gly His
 65                  70                  75                  80

Leu Glu Ile Val Glu Val Leu Leu Lys Ala Gly Ala Asp Val Asn Ala
                85                  90                  95

Tyr Asp Ile Ser Gly Ile Thr Pro Leu His Leu Ala Ala Phe Tyr Gly
                100                 105                 110

His Leu Glu Ile Val Glu Val Leu Leu Lys His Gly Ala Asp Val Asn
            115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln Lys Leu Asn
145                 150                 155

<210> SEQ ID NO 93
<211> LENGTH: 157
<212> TYPE: PRT
<213> ORGANISM: Artificial Sequence
<220> FEATURE:
<223> OTHER INFORMATION: Synthetic ankyrin repeat sequence

<400> SEQUENCE: 93

Asp Leu Gly Lys Lys Leu Leu Glu Ala Ala Arg Ala Gly Gln Asp Asp
 1               5                  10                  15
```

-continued

```
Glu Val Arg Ile Leu Met Ala Asn Gly Ala Asp Val Asn Ala Thr Asp
             20                  25                  30

Asp Trp Gly Asp Thr Leu Leu His Leu Ala Ala Thr Asp Gly His Leu
         35                  40                  45

Glu Ile Val Glu Val Leu Leu Lys Ala Gly Ala Asp Val Asn Ala Asn
 50                  55                  60

Asp Ala Ile Gly Asp Thr Pro Leu His Leu Ala Leu Tyr Gly His
 65                  70                  75                  80

Leu Glu Ile Val Glu Val Leu Leu Lys Tyr Gly Ala Asp Val Asn Ala
             85                  90                  95

Thr Asp Leu His Gly Phe Thr Pro Leu His Leu Ala Ala Phe Trp Gly
             100                 105                 110

His Leu Glu Ile Val Glu Val Leu Leu Lys His Gly Ala Asp Val Asn
             115                 120                 125

Ala Gln Asp Lys Phe Gly Lys Thr Ala Phe Asp Ile Ser Ile Asp Asn
             130                 135                 140

Gly Asn Glu Asp Leu Ala Glu Ile Leu Gln Lys Leu Asn
145                 150                 155
```

<210> SEQ ID NO 94
<211> LENGTH: 157
<212> TYPE: PRT
<213> ORGANISM: Artificial Sequence
<220> FEATURE:
<223> OTHER INFORMATION: Synthetic ankyrin repeat sequence

<400> SEQUENCE: 94

```
Asp Leu Asp Lys Lys Leu Leu Glu Ala Ala Arg Ala Gly Gln Asp Asp
 1               5                   10                  15

Glu Val Arg Ile Leu Met Ala Asn Gly Ala Asp Val Asn Ala Arg Asp
             20                  25                  30

Ser Tyr Gly Ser Thr Pro Leu His Leu Ala Ala Arg Glu Gly His Leu
         35                  40                  45

Glu Ile Val Glu Val Leu Leu Lys Tyr Gly Ala Asp Val Asn Ala Ala
 50                  55                  60

Asp Phe Ile Gly Asp Thr Pro Leu His Leu Ala Ala Tyr Arg Gly His
 65                  70                  75                  80

Leu Glu Ile Val Glu Val Leu Leu Lys Tyr Gly Ala Asp Val Asn Ala
             85                  90                  95

Ser Asp Ile Thr Gly Glu Thr Pro Leu His Leu Ala Ala Gln Ile Gly
             100                 105                 110

His Leu Glu Ile Val Glu Val Leu Leu Lys His Gly Ala Asp Val Asn
             115                 120                 125

Ala Gln Asp Lys Phe Gly Lys Thr Ala Phe Asp Ile Ser Ile Asp Asn
             130                 135                 140

Gly Asn Glu Asp Leu Ala Glu Ile Leu Gln Lys Leu Asn
145                 150                 155
```

<210> SEQ ID NO 95
<211> LENGTH: 335
<212> TYPE: PRT
<213> ORGANISM: Artificial Sequence
<220> FEATURE:
<223> OTHER INFORMATION: Synthetic ankyrin repeat sequence

<400> SEQUENCE: 95

```
Asp Leu Asp Lys Lys Leu Leu Glu Ala Ala Arg Ala Gly Gln Asp Asp
```

```
                1               5              10              15
            Glu Val Arg Ile Leu Met Ala Asn Gly Ala Asp Val Asn Ala Arg Asp
                           20                  25                  30

Ser Tyr Gly Ser Thr Pro Leu His Leu Ala Ala Arg Glu Gly His Leu
                           35                  40                  45

Glu Ile Val Glu Val Leu Leu Lys Tyr Gly Ala Asp Val Asn Ala Ala
                           50                  55                  60

Asp Phe Ile Gly Asp Thr Pro Leu His Leu Ala Ala Tyr Arg Gly His
             65                  70                  75                  80

Leu Glu Ile Val Glu Val Leu Leu Lys Tyr Gly Ala Asp Val Asn Ala
                                85                  90                  95

Ser Asp Ile Thr Gly Glu Thr Pro Leu His Leu Ala Ala Gln Ile Gly
                           100                 105                 110

His Leu Glu Ile Val Glu Val Leu Leu Lys His Gly Ala Asp Val Asn
                           115                 120                 125

Ala Gln Asp Lys Phe Gly Lys Thr Ala Phe Asp Ile Ser Ile Asp Asn
                           130                 135                 140

Gly Asn Glu Asp Leu Ala Glu Ile Leu Gln Lys Leu Gly Gly Gly Gly
            145                 150                 155                 160

Ser Gly Gly Gly Gly Ser Gly Gly Gly Gly Ser Gly Gly Gly Gly Ser
                           165                 170                 175

Arg Ser Asp Leu Gly Lys Lys Leu Leu Glu Ala Ala Arg Ala Gly Gln
                           180                 185                 190

Asp Asp Glu Val Arg Ile Leu Met Ala Asn Gly Ala Asp Val Asn Ala
                           195                 200                 205

Ala Asp Asp Ser Gly Ile Thr Pro Leu His Leu Ala Ala Glu Asp Gly
                           210                 215                 220

His Leu Glu Ile Val Glu Val Leu Leu Lys Ala Gly Ala Asp Val Asn
            225                 230                 235                 240

Ala Gln Asp Asn Leu Gly Asp Thr Pro Leu His Leu Ala Ala Trp Thr
                           245                 250                 255

Gly His Leu Glu Ile Val Glu Val Leu Leu Lys Ala Gly Ala Asp Val
                           260                 265                 270

Asn Ala Tyr Asp Ile Ser Gly Ile Thr Pro Leu His Leu Ala Ala Phe
                           275                 280                 285

Tyr Gly His Leu Glu Ile Val Glu Val Leu Leu Lys His Gly Ala Asp
                           290                 295                 300

Val Asn Ala Gln Asp Lys Phe Gly Lys Thr Ala Phe Asp Ile Ser Ile
            305                 310                 315                 320

Asp Asn Gly Asn Glu Asp Leu Ala Glu Ile Leu Gln Lys Leu Asn
                           325                 330                 335

<210> SEQ ID NO 96
<211> LENGTH: 334
<212> TYPE: PRT
<213> ORGANISM: Artificial Sequence
<220> FEATURE:
<223> OTHER INFORMATION: Synthetic ankyrin repeat sequence

<400> SEQUENCE: 96

Asp Leu Gly Lys Lys Leu Leu Glu Ala Ala Arg Ala Gly Gln Asp Asp
             1               5                  10                  15

Glu Val Arg Ile Leu Met Ala Asn Gly Ala Asp Val Asn Ala Ala Asp
                            20                  25                  30

Asp Ser Gly Ile Thr Pro Leu His Leu Ala Ala Glu Asp Gly His Leu
```

```
                35                  40                  45
Glu Ile Val Glu Val Leu Leu Lys Ala Gly Ala Asp Val Asn Ala Gln
 50                  55                  60

Asp Asn Leu Gly Asp Thr Pro Leu His Leu Ala Ala Trp Thr Gly His
 65                  70                  75                  80

Leu Glu Ile Val Glu Val Leu Leu Lys Ala Gly Ala Asp Val Asn Ala
                 85                  90                  95

Tyr Asp Ile Ser Gly Ile Thr Pro Leu His Leu Ala Ala Phe Tyr Gly
                100                 105                 110

His Leu Glu Ile Val Glu Val Leu Leu Lys His Gly Ala Asp Val Asn
                115                 120                 125

Ala Gln Asp Lys Phe Gly Lys Thr Ala Phe Asp Ile Ser Ile Asp Asn
130                 135                 140

Gly Asn Glu Asp Leu Ala Glu Ile Leu Gln Lys Leu Asn Gly Gly Gly
145                 150                 155                 160

Gly Ser Gly Gly Gly Gly Ser Gly Gly Gly Gly Ser Gly Gly Gly Gly
                165                 170                 175

Ser Asp Leu Asp Lys Lys Leu Leu Glu Ala Ala Arg Ala Gly Gln Asp
                180                 185                 190

Asp Glu Val Arg Ile Leu Met Ala Asn Gly Ala Asp Val Asn Ala Arg
                195                 200                 205

Asp Ser Tyr Gly Ser Thr Pro Leu His Leu Ala Ala Arg Glu Gly His
210                 215                 220

Leu Glu Ile Val Glu Val Leu Leu Lys Tyr Gly Ala Asp Val Asn Ala
225                 230                 235                 240

Ala Asp Phe Ile Gly Asp Thr Pro Leu His Leu Ala Ala Tyr Arg Gly
                245                 250                 255

His Leu Glu Ile Val Glu Val Leu Leu Lys Tyr Gly Ala Asp Val Asn
                260                 265                 270

Ala Ser Asp Ile Thr Gly Glu Thr Pro Leu His Leu Ala Ala Gln Ile
                275                 280                 285

Gly His Leu Glu Ile Val Glu Val Leu Leu Lys His Gly Ala Asp Val
                290                 295                 300

Asn Ala Gln Asp Lys Phe Gly Lys Thr Ala Phe Asp Ile Ser Ile Asp
305                 310                 315                 320

Asn Gly Asn Glu Asp Leu Ala Glu Ile Leu Gln Lys Leu Asn
                325                 330

<210> SEQ ID NO 97
<211> LENGTH: 334
<212> TYPE: PRT
<213> ORGANISM: Artificial Sequence
<220> FEATURE:
<223> OTHER INFORMATION: Synthetic ankyrin repeat sequence

<400> SEQUENCE: 97

Asp Leu Asp Lys Lys Leu Leu Glu Ala Ala Arg Ala Gly Gln Asp Asp
 1               5                  10                  15

Glu Val Arg Ile Leu Met Ala Asn Gly Ala Asp Val Asn Ala Arg Asp
                 20                  25                  30

Ser Tyr Gly Ser Thr Pro Leu His Leu Ala Ala Arg Glu Gly His Leu
             35                  40                  45

Glu Ile Val Glu Val Leu Leu Lys Tyr Gly Ala Asp Val Asn Ala Ala
 50                  55                  60

Asp Phe Ile Gly Asp Thr Pro Leu His Leu Ala Ala Tyr Arg Gly His
```

```
                65                  70                  75                  80
Leu Glu Ile Val Glu Val Leu Lys Tyr Gly Ala Asp Val Asn Ala
                    85                  90                  95
Ser Asp Ile Thr Gly Glu Thr Pro Leu His Leu Ala Ala Gln Ile Gly
                100                 105                 110
His Leu Glu Ile Val Glu Val Leu Lys His Gly Ala Asp Val Asn
                115                 120                 125
Ala Gln Asp Lys Phe Gly Lys Thr Ala Phe Asp Ile Ser Ile Asp Asn
    130                 135                 140
Gly Asn Glu Asp Leu Ala Glu Ile Leu Gln Lys Leu Asn Gly Gly
145                 150                 155                 160
Gly Ser Gly Gly Gly Gly Ser Gly Gly Gly Gly Ser Gly Gly Gly Gly
                165                 170                 175
Ser Asp Leu Gly Lys Lys Leu Leu Glu Ala Ala Ser Ala Gly Gln Asp
                180                 185                 190
Asp Glu Val His Ile Leu Met Ala Asn Gly Ala Asp Val Asn Ala Leu
                195                 200                 205
Asp Asp Ser Gly Tyr Thr Pro Leu His Leu Ala Ala Glu Asp Gly His
    210                 215                 220
Leu Glu Ile Val Glu Val Leu Leu Lys His Gly Ala Asp Val Asn Ala
225                 230                 235                 240
Ala Asp Arg Leu Gly Asp Thr Pro Leu His Leu Ala Ala Phe Val Gly
                245                 250                 255
His Leu Glu Ile Val Glu Val Leu Leu Lys Ala Gly Ala Asp Val Asn
                260                 265                 270
Ala Val Asp Leu Ala Gly Val Thr Pro Leu His Val Ala Ala Phe Tyr
    275                 280                 285
Gly His Leu Glu Ile Val Glu Val Leu Leu Lys Ala Gly Ala Asp Val
                290                 295                 300
Asn Ala Gln Asp Lys Phe Gly Lys Thr Ala Phe Asp Ile Ser Ile Asp
305                 310                 315                 320
Asn Gly Asn Glu Asp Leu Ala Glu Ile Leu Gln Lys Leu Asn
                325                 330

<210> SEQ ID NO 98
<211> LENGTH: 334
<212> TYPE: PRT
<213> ORGANISM: Artificial Sequence
<220> FEATURE:
<223> OTHER INFORMATION: Synthetic ankyrin repeat sequence

<400> SEQUENCE: 98

Asp Leu Gly Lys Lys Leu Leu Glu Ala Ala Ser Ala Gly Gln Asp Asp
1               5                   10                  15
Glu Val His Ile Leu Met Ala Asn Gly Ala Asp Val Asn Ala Leu Asp
                20                  25                  30
Asp Ser Gly Tyr Thr Pro Leu His Leu Ala Ala Glu Asp Gly His Leu
            35                  40                  45
Glu Ile Val Glu Val Leu Leu Lys His Gly Ala Asp Val Asn Ala Ala
        50                  55                  60
Asp Arg Leu Gly Asp Thr Pro Leu His Leu Ala Ala Phe Val Gly His
65                  70                  75                  80
Leu Glu Ile Val Glu Val Leu Leu Lys Ala Gly Ala Asp Val Asn Ala
                85                  90                  95
Val Asp Leu Ala Gly Val Thr Pro Leu His Val Ala Ala Phe Tyr Gly
```

His Leu Glu Ile Val Glu Val Leu Lys Ala Gly Ala Asp Val Asn
              115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln Lys Leu Asn Gly Gly Gly
145                 150                 155                 160

Gly Ser Gly Gly Gly Gly Ser Gly Gly Gly Gly Ser Gly Gly Gly Gly
                165                 170                 175

Ser Asp Leu Asp Lys Lys Leu Leu Glu Ala Ala Arg Ala Gly Gln Asp
                180                 185                 190

Asp Glu Val Arg Ile Leu Met Ala Asn Gly Ala Asp Val Asn Ala Arg
            195                 200                 205

Asp Ser Tyr Gly Ser Thr Pro Leu His Leu Ala Ala Arg Glu Gly His
    210                 215                 220

Leu Glu Ile Val Glu Val Leu Leu Lys Tyr Gly Ala Asp Val Asn Ala
225                 230                 235                 240

Ala Asp Phe Ile Gly Asp Thr Pro Leu His Leu Ala Ala Tyr Arg Gly
                245                 250                 255

His Leu Glu Ile Val Glu Val Leu Leu Lys Tyr Gly Ala Asp Val Asn
                260                 265                 270

Ala Ser Asp Ile Thr Gly Glu Thr Pro Leu His Leu Ala Ala Gln Ile
            275                 280                 285

Gly His Leu Glu Ile Val Glu Val Leu Leu Lys His Gly Ala Asp Val
    290                 295                 300

Asn Ala Gln Asp Lys Phe Gly Lys Thr Ala Phe Asp Ile Ser Ile Asp
305                 310                 315                 320

Asn Gly Asn Glu Asp Leu Ala Glu Ile Leu Gln Lys Leu Asn
                325                 330

<210> SEQ ID NO 99
<211> LENGTH: 334
<212> TYPE: PRT
<213> ORGANISM: Artificial Sequence
<220> FEATURE:
<223> OTHER INFORMATION: Synthetic ankyrin repeat sequence

<400> SEQUENCE: 99

Asp Leu Asp Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Arg Asp
            20                  25                  30

Ser Tyr Gly Ser Thr Pro Leu His Leu Ala Ala Arg Glu Gly His Leu
        35                  40                  45

Glu Ile Val Glu Val Leu Leu Lys Tyr Gly Ala Asp Val Asn Ala Ala
    50                  55                  60

Asp Phe Ile Gly Asp Thr Pro Leu His Leu Ala Ala Tyr Arg Gly His
65                  70                  75                  80

Leu Glu Ile Val Glu Val Leu Leu Lys Tyr Gly Ala Asp Val Asn Ala
                85                  90                  95

Ser Asp Ile Thr Gly Glu Thr Pro Leu His Leu Ala Ala Gln Ile Gly
            100                 105                 110

His Leu Glu Ile Val Glu Val Leu Leu Lys His Gly Ala Asp Val Asn
        115                 120                 125

Ala Gln Asp Lys Phe Gly Lys Thr Ala Phe Asp Ile Ser Ile Asp Asn

```
                130                 135                 140
Gly Asn Glu Asp Leu Ala Glu Ile Leu Gln Lys Leu Asn Gly Gly
145                 150                 155                 160

Gly Ser Gly Gly Gly Ser Gly Gly Gly Ser Gly Gly Gly
                165                 170                 175

Ser Asp Leu Gly Lys Lys Leu Leu Glu Ala Ala Arg Ala Gly Gln Asp
            180                 185                 190

Asp Glu Val Arg Ile Leu Met Ala Asn Gly Ala Asp Val Asn Ala Thr
            195                 200                 205

Asp Asp Trp Gly Asp Thr Leu Leu His Leu Ala Thr Asp Gly His
            210                 215                 220

Leu Glu Ile Val Glu Val Leu Leu Lys Ala Gly Ala Asp Val Asn Ala
225                 230                 235                 240

Asn Asp Ala Ile Gly Asp Thr Pro Leu His Leu Ala Ala Leu Tyr Gly
                245                 250                 255

His Leu Glu Ile Val Glu Val Leu Leu Lys Tyr Gly Ala Asp Val Asn
                260                 265                 270

Ala Thr Asp Leu His Gly Phe Thr Pro Leu His Leu Ala Ala Phe Trp
            275                 280                 285

Gly His Leu Glu Ile Val Glu Val Leu Leu Lys His Gly Ala Asp Val
            290                 295                 300

Asn Ala Gln Asp Lys Phe Gly Lys Thr Ala Phe Asp Ile Ser Ile Asp
305                 310                 315                 320

Asn Gly Asn Glu Asp Leu Ala Glu Ile Leu Gln Lys Leu Asn
                325                 330

<210> SEQ ID NO 100
<211> LENGTH: 334
<212> TYPE: PRT
<213> ORGANISM: Artificial Sequence
<220> FEATURE:
<223> OTHER INFORMATION: Synthetic ankyrin repeat sequence

<400> SEQUENCE: 100

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Thr Asp
            20                  25                  30

Asp Trp Gly Asp Thr Leu Leu His Leu Ala Ala Thr Asp Gly His Leu
        35                  40                  45

Glu Ile Val Glu Val Leu Leu Lys Ala Gly Ala Asp Val Asn Ala Asn
    50                  55                  60

Asp Ala Ile Gly Asp Thr Pro Leu His Leu Ala Ala Leu Tyr Gly His
65                  70                  75                  80

Leu Glu Ile Val Glu Val Leu Leu Lys Tyr Gly Ala Asp Val Asn Ala
                85                  90                  95

Thr Asp Leu His Gly Phe Thr Pro Leu His Leu Ala Ala Phe Trp Gly
            100                 105                 110

His Leu Glu Ile Val Glu Val Leu Leu Lys His Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln Lys Leu Asn Gly Gly Gly
145                 150                 155                 160

Gly Ser Gly Gly Gly Gly Ser Gly Gly Gly Ser Gly Gly Gly Gly
```

```
                     165                 170                 175
Ser Asp Leu Asp Lys Lys Leu Leu Glu Ala Ala Arg Ala Gly Gln Asp
            180                 185                 190

Asp Glu Val Arg Ile Leu Met Ala Asn Gly Ala Asp Val Asn Ala Arg
        195                 200                 205

Asp Ser Tyr Gly Ser Thr Pro Leu His Leu Ala Ala Arg Glu Gly His
    210                 215                 220

Leu Glu Ile Val Glu Val Leu Leu Lys Tyr Gly Ala Asp Val Asn Ala
225                 230                 235                 240

Ala Asp Phe Ile Gly Asp Thr Pro Leu His Leu Ala Ala Tyr Arg Gly
                245                 250                 255

His Leu Glu Ile Val Glu Val Leu Leu Lys Tyr Gly Ala Asp Val Asn
            260                 265                 270

Ala Ser Asp Ile Thr Gly Glu Thr Pro Leu His Leu Ala Ala Gln Ile
        275                 280                 285

Gly His Leu Glu Ile Val Glu Val Leu Leu Lys His Gly Ala Asp Val
    290                 295                 300

Asn Ala Gln Asp Lys Phe Gly Lys Thr Ala Phe Asp Ile Ser Ile Asp
305                 310                 315                 320

Asn Gly Asn Glu Asp Leu Ala Glu Ile Leu Gln Lys Leu Asn
                325                 330

<210> SEQ ID NO 101
<211> LENGTH: 112
<212> TYPE: PRT
<213> ORGANISM: Homo sapiens
<220> FEATURE:
<221> NAME/KEY: misc_feature
<222> LOCATION: (110)..(110)
<223> OTHER INFORMATION: Xaa can be any naturally occurring amino acid

<400> SEQUENCE: 101

Gly Pro Val Pro Pro Ser Thr Ala Leu Arg Glu Leu Ile Glu Glu Leu
1               5                   10                  15

Val Asn Ile Thr Gln Asn Gln Lys Ala Pro Leu Cys Asn Gly Ser Met
            20                  25                  30

Val Trp Ser Ile Asn Leu Thr Ala Gly Met Tyr Cys Ala Ala Leu Glu
        35                  40                  45

Ser Leu Ile Asn Val Ser Gly Cys Ser Ala Ile Glu Lys Thr Gln Arg
    50                  55                  60

Met Leu Ser Gly Phe Cys Pro His Lys Val Ser Ala Gly Gln Phe Ser
65                  70                  75                  80

Ser Leu His Val Arg Asp Thr Lys Ile Glu Val Ala Gln Phe Val Lys
                85                  90                  95

Asp Leu Leu Leu His Leu Lys Lys Leu Phe Arg Glu Gly Xaa Phe Asn
            100                 105                 110

<210> SEQ ID NO 102
<211> LENGTH: 354
<212> TYPE: PRT
<213> ORGANISM: Homo sapiens

<400> SEQUENCE: 102

Asp Thr Glu Ile Lys Val Asn Pro Pro Gln Asp Phe Glu Ile Val Asp
1               5                   10                  15

Pro Gly Tyr Leu Gly Tyr Leu Tyr Leu Gln Trp Gln Pro Pro Leu Ser
            20                  25                  30
```

-continued

```
Leu Asp His Phe Lys Glu Cys Thr Val Glu Tyr Glu Leu Lys Tyr Arg
             35                  40                  45

Asn Ile Gly Ser Glu Thr Trp Lys Thr Ile Ile Thr Lys Asn Leu His
 50                  55                  60

Tyr Lys Asp Gly Phe Asp Leu Asn Lys Gly Ile Glu Ala Lys Ile His
 65                  70                  75                  80

Thr Leu Leu Pro Trp Gln Cys Thr Asn Gly Ser Glu Val Gln Ser Ser
                 85                  90                  95

Trp Ala Glu Thr Thr Tyr Trp Ile Ser Pro Gln Gly Ile Pro Glu Thr
                100                 105                 110

Lys Val Gln Asp Met Asp Cys Val Tyr Asn Trp Gln Tyr Leu Leu
            115                 120                 125

Cys Ser Trp Lys Pro Gly Ile Gly Val Leu Leu Asp Thr Asn Tyr Asn
130                 135                 140

Leu Phe Tyr Trp Tyr Glu Gly Leu Asp His Ala Leu Gln Cys Val Asp
145                 150                 155                 160

Tyr Ile Lys Ala Asp Gly Gln Asn Ile Gly Cys Arg Phe Pro Tyr Leu
                165                 170                 175

Glu Ala Ser Asp Tyr Lys Asp Phe Tyr Ile Cys Val Asn Gly Ser Ser
            180                 185                 190

Glu Asn Lys Pro Ile Arg Ser Ser Tyr Phe Thr Phe Gln Leu Gln Asn
        195                 200                 205

Ile Val Lys Pro Leu Pro Pro Val Tyr Leu Thr Phe Thr Arg Glu Ser
    210                 215                 220

Ser Cys Glu Ile Lys Leu Lys Trp Ser Ile Pro Leu Gly Pro Ile Pro
225                 230                 235                 240

Ala Arg Cys Phe Asp Tyr Glu Ile Glu Ile Arg Glu Asp Thr Thr
                245                 250                 255

Leu Val Thr Ala Thr Val Glu Asn Glu Thr Tyr Thr Leu Lys Thr Thr
            260                 265                 270

Asn Glu Thr Arg Gln Leu Cys Phe Val Val Arg Ser Lys Val Asn Ile
        275                 280                 285

Tyr Cys Ser Asp Asp Gly Ile Trp Ser Glu Trp Ser Asp Lys Gln Cys
290                 295                 300

Trp Glu Gly Glu Asp Leu Ser Lys Lys Thr Leu Leu Arg Phe Trp Leu
305                 310                 315                 320

Pro Phe Gly Phe Ile Leu Ile Leu Val Ile Phe Val Thr Gly Leu Leu
                325                 330                 335

Leu Arg Lys Pro Asn Thr Tyr Pro Lys Met Ile Pro Glu Phe Phe Cys
            340                 345                 350

Asp Thr

<210> SEQ ID NO 103
<211> LENGTH: 28
<212> TYPE: PRT
<213> ORGANISM: Artificial Sequence
<220> FEATURE:
<223> OTHER INFORMATION: Synthetic ankyrin repeat cap

<400> SEQUENCE: 103

Gln Asp Lys Phe Gly Lys Thr Pro Ala Asp Ile Ala Ala Asp Asn Gly
 1               5                  10                  15

His Glu Asp Ile Ala Glu Val Leu Gln Lys Ala Ala
            20                  25
```

<210> SEQ ID NO 104
<211> LENGTH: 336
<212> TYPE: PRT
<213> ORGANISM: Artificial Sequence
<220> FEATURE:
<223> OTHER INFORMATION: Synthetic ankyrin repeat sequence

<400> SEQUENCE: 104

```
Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Leu Asp
            20                  25                  30

Asp Ser Gly Tyr Thr Pro Leu His Leu Ala Ala Glu Asp Gly His Leu
        35                  40                  45

Glu Ile Val Glu Val Leu Leu Lys His Gly Ala Asp Val Asn Ala Ala
    50                  55                  60

Asp Arg Leu Gly Asp Thr Pro Leu His Leu Ala Ala Phe Val Gly His
65                  70                  75                  80

Leu Glu Ile Val Glu Val Leu Leu Lys Ala Gly Ala Asp Val Asn Ala
                85                  90                  95

Val Asp Leu Ala Gly Val Thr Pro Leu His Val Ala Ala Phe Tyr Gly
            100                 105                 110

His Leu Glu Ile Val Glu Val Leu Leu Lys Ala Gly Ala Asp Val Asn
        115                 120                 125

Ala Gln Asp Lys Phe Gly Lys Thr Pro Ala Asp Ile Ala Ala Asp Asn
    130                 135                 140

Gly His Glu Asp Ile Ala Glu Val Leu Gln Lys Ala Ala Gly Gly Gly
145                 150                 155                 160

Gly Ser Gly Gly Gly Ser Gly Gly Gly Ser Gly Gly Gly
                165                 170                 175

Ser Gly Ser Asp Leu Asp Lys Lys Leu Leu Glu Ala Ala Arg Ala Gly
            180                 185                 190

Gln Asp Asp Glu Val Arg Ile Leu Met Ala Asn Gly Ala Asp Val Asn
        195                 200                 205

Ala Arg Asp Ser Tyr Gly Ser Thr Pro Leu His Leu Ala Ala Arg Glu
    210                 215                 220

Gly His Leu Glu Ile Val Glu Val Leu Leu Lys Tyr Gly Ala Asp Val
225                 230                 235                 240

Asn Ala Ala Asp Phe Ile Gly Asp Thr Pro Leu His Leu Ala Ala Tyr
                245                 250                 255

Arg Gly His Leu Glu Ile Val Glu Val Leu Leu Lys Tyr Gly Ala Asp
            260                 265                 270

Val Asn Ala Ser Asp Ile Thr Gly Glu Thr Pro Leu His Leu Ala Ala
        275                 280                 285

Gln Ile Gly His Leu Glu Ile Val Glu Val Leu Leu Lys His Gly Ala
    290                 295                 300

Asp Val Asn Ala Gln Asp Lys Phe Gly Lys Thr Pro Ala Asp Ile Ala
305                 310                 315                 320

Ala Asp Asn Gly His Glu Asp Ile Ala Glu Val Leu Gln Lys Ala Ala
                325                 330                 335
```

<210> SEQ ID NO 105
<211> LENGTH: 157
<212> TYPE: PRT
<213> ORGANISM: Artificial Sequence
<220> FEATURE:
<223> OTHER INFORMATION: Synthetic ankyrin repeat sequence

<400> SEQUENCE: 105

```
Asp Leu Gly Glu Lys Leu Leu Glu Ala Ala Arg Ala Gly Gln Asp Asp
1               5                   10                  15

Glu Val Arg Ile Leu Met Ala Asn Gly Ala Asp Val Asn Ala Tyr Asp
            20                  25                  30

Asp Asp Gly Met Thr Pro Leu His Leu Ala Ala Lys Ser Gly His Leu
        35                  40                  45

Glu Ile Val Glu Val Leu Leu Lys His Gly Ala Asp Val Asn Ala Met
    50                  55                  60

Asp Ile Thr Gly Ser Ala Pro Leu His Leu Ala Ala Asp Leu Gly His
65                  70                  75                  80

Leu Glu Ile Val Glu Val Leu Leu Lys His Gly Ala Asp Val Asn Ala
                85                  90                  95

Ile Asp Tyr Leu Gly Ala Thr Pro Leu His Leu Ala Ala Thr Tyr Gly
                100                 105                 110

His Pro Glu Ile Val Glu Val Leu Leu Lys Tyr Gly Ala Asp Val Asn
            115                 120                 125

Ala Gln Asp Lys Phe Gly Lys Thr Ala Phe Asp Ile Ser Ile Asp Asn
        130                 135                 140

Gly Asn Glu Asp Leu Ala Glu Ile Leu Gln Lys Leu Asn
145                 150                 155
```

<210> SEQ ID NO 106
<211> LENGTH: 157
<212> TYPE: PRT
<213> ORGANISM: Artificial Sequence
<220> FEATURE:
<223> OTHER INFORMATION: Synthetic ankyrin repeat sequence

<400> SEQUENCE: 106

```
Asp Leu Gly Glu Lys Leu Leu Glu Ala Ala Arg Ala Gly Gln Asp Asp
1               5                   10                  15

Glu Val Arg Ile Leu Met Ala Asn Gly Ala Asp Val Asn Ala Tyr Asp
            20                  25                  30

Asp Asp Gly Met Thr Pro Leu His Leu Ala Ala Lys Ser Gly His Leu
        35                  40                  45

Glu Ile Val Glu Val Leu Leu Lys His Gly Ala Asp Val Asn Ala Met
    50                  55                  60

Asp Ile Thr Gly Ser Ala Pro Leu His Leu Ala Ala Asp Leu Gly His
65                  70                  75                  80

Leu Glu Ile Val Glu Val Leu Leu Lys His Gly Ala Asp Val Asn Ala
                85                  90                  95

Ile Asp Tyr Leu Gly Ala Thr Pro Leu His Leu Ala Ala Thr Tyr Gly
                100                 105                 110

His Pro Glu Ile Val Glu Val Leu Leu Lys Tyr Gly Ala Asp Val Asn
            115                 120                 125

Ala Gln Asp Lys Phe Gly Lys Thr Ala Phe Asp Ile Ser Ile Asp Asn
        130                 135                 140

Gly Asn Glu Asp Leu Ala Glu Ile Leu Gln Lys Leu Asn
145                 150                 155
```

<210> SEQ ID NO 107
<211> LENGTH: 314
<212> TYPE: PRT
<213> ORGANISM: Artificial Sequence
<220> FEATURE:

<223> OTHER INFORMATION: Synthetic ankyrin repeat sequence

<400> SEQUENCE: 107

```
Met Arg Gly Ser His His His His His His Gly Ser Asp Leu Gly Lys
1               5                   10                  15

Lys Leu Met Glu Ala Ala Arg Ala Gly Gln Asp Asp Glu Val Arg Ile
            20                  25                  30

Leu Met Ala Asn Gly Ala Asp Val Asn Ala Lys Asp Leu Phe Gly Ile
        35                  40                  45

Thr Pro Leu His Leu Ala Ala Val Tyr Gly His Leu Glu Ile Val Glu
    50                  55                  60

Val Leu Leu Lys His Gly Ala Asp Val Asn Ala Thr Asp Asn Trp Gly
65                  70                  75                  80

Ser Thr Pro Leu His Leu Ala Ala Gln Phe Gly His Leu Glu Ile Val
                85                  90                  95

Glu Val Leu Leu Lys Tyr Gly Ala Asp Val Asn Ala Gln Asp Lys Phe
            100                 105                 110

Gly Lys Thr Ala Phe Asp Ile Ser Ile Asp Asn Gly Asn Glu Asp Leu
        115                 120                 125

Ala Glu Ile Leu Gln Lys Leu Gly Gly Gly Ser Gly Gly Gly
130                 135                 140

Ser Gly Gly Gly Ser Gly Gly Gly Ser Arg Ser Asp Leu Gly
145                 150                 155                 160

Glu Lys Leu Leu Glu Ala Ala Arg Ala Gly Gln Asp Asp Glu Val Arg
            165                 170                 175

Ile Leu Met Ala Asn Gly Ala Asp Val Asn Ala Tyr Asp Asp Gly
        180                 185                 190

Met Thr Pro Leu His Leu Ala Ala Lys Ser Gly His Leu Glu Ile Val
        195                 200                 205

Glu Val Leu Leu Lys His Gly Ala Asp Val Asn Ala Met Asp Ile Thr
        210                 215                 220

Gly Ser Ala Pro Leu His Leu Ala Ala Asp Leu Gly His Leu Glu Ile
225                 230                 235                 240

Val Glu Val Leu Leu Lys His Gly Ala Asp Val Asn Ala Ile Asp Tyr
                245                 250                 255

Leu Gly Ala Thr Pro Leu His Leu Ala Ala Thr Tyr Gly His Pro Glu
            260                 265                 270

Ile Val Glu Val Leu Leu Lys Tyr Gly Ala Asp Val Asn Ala Gln Asp
        275                 280                 285

Lys Phe Gly Lys Thr Ala Phe Asp Ile Ser Ile Asp Asn Gly Asn Glu
        290                 295                 300

Asp Leu Ala Glu Ile Leu Gln Lys Leu Asn
305                 310
```

<210> SEQ ID NO 108
<211> LENGTH: 33
<212> TYPE: PRT
<213> ORGANISM: Artificial Sequence
<220> FEATURE:
<223> OTHER INFORMATION: Synthetic conseneus ankyrin repeat sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid

```
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid

<400> SEQUENCE: 108

Xaa Asp Xaa Xaa Gly Xaa Thr Pro Leu His Leu Ala Ala Xaa Xaa Gly
1               5                   10                  15

His Leu Glu Ile Val Glu Val Leu Leu Lys Xaa Gly Ala Asp Val Asn
            20                  25                  30

Ala

<210> SEQ ID NO 109
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 109

Arg Asp Ser Tyr Gly Ser Thr Pro Leu His Leu Ala Ala Arg Glu Gly
1               5                   10                  15

His Leu Glu Ile Val Glu Val Leu Leu Lys Tyr Gly Ala Asp Val Asn
            20                  25                  30

Ala

<210> SEQ ID NO 110
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 110

Thr Asp Glu Phe Asp Ser Thr Pro Leu His Leu Ala Ala Arg His Gly
1               5                   10                  15

His Leu Glu Ile Val Glu Val Leu Leu Lys Tyr Gly Ala Asp Val Asn
            20                  25                  30

Ala

<210> SEQ ID NO 111
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 111

Ser Asp Ile Phe Gly Ser Thr Pro Leu His Leu Ala Ala Arg His Gly
1               5                   10                  15

His Leu Glu Ile Val Glu Val Leu Leu Lys Tyr Gly Ala Asp Val Asn
            20                  25                  30

Ala

<210> SEQ ID NO 112
```

<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 112

Ile Asp His Phe Asp Ser Thr Pro Leu His Leu Ala Ala Arg His Gly
1               5                   10                  15
His Leu Glu Ile Val Glu Val Leu Leu Lys Asn Gly Ala Asp Val Asn
            20                  25                  30
Ala

<210> SEQ ID NO 113
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 113

Thr Asp Val Phe Gly Ser Thr Pro Leu His Leu Ala Ala Arg His Gly
1               5                   10                  15
His Leu Glu Ile Val Glu Val Leu Leu Lys His Gly Ala Asp Val Asn
            20                  25                  30
Ala

<210> SEQ ID NO 114
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 114

Phe Asp Asp Phe Gly Ser Thr Pro Leu His Leu Ala Ala Arg Ser Gly
1               5                   10                  15
His Leu Glu Ile Val Glu Val Leu Leu Lys His Gly Ala Asp Val Asn
            20                  25                  30
Ala

<210> SEQ ID NO 115
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 115

Glu Asp Ile Leu Gly Ile Thr Pro Leu His Leu Ala Ala His His Gly
1               5                   10                  15
His Leu Glu Ile Val Glu Val Leu Leu Lys His Gly Ala Asp Val Asn
            20                  25                  30
Ala

<210> SEQ ID NO 116
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 116

Thr Asp Thr Tyr Gly Ser Thr Pro Leu His Leu Ala Ala Arg His Cys
1               5                   10                  15

His Gln Glu Ile Val Glu Val Leu Leu Lys His Gly Ala Asp Val Asn
            20                  25                  30

Ala

<210> SEQ ID NO 117
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 117

Val Asp Asp Tyr Gly Ser Thr Pro Leu His Leu Ala Ala Arg Gln Gly
1               5                   10                  15

His Leu Glu Ile Val Glu Val Leu Leu Lys Asn Gly Ala Asp Val Asn
            20                  25                  30

Ala

<210> SEQ ID NO 118
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 118

Lys Asp Leu Phe Gly Ser Thr Pro Leu His Leu Ala Ala Arg His Gly
1               5                   10                  15

His Leu Glu Ile Val Glu Val Leu Leu Lys Asn Gly Ala Asp Val Asn
            20                  25                  30

Ala

<210> SEQ ID NO 119
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 119

Thr Asp Met Tyr Gly Ser Thr Pro Leu His Leu Ala Ala Arg His Gly
1               5                   10                  15

His Leu Glu Ile Val Glu Val Leu Leu Lys Tyr Gly Ala Asp Val Asn
            20                  25                  30

Ala

<210> SEQ ID NO 120
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 120

Trp Asp Ser Tyr Gly Ser Thr Pro Leu His Leu Ala Ala Arg Glu Gly
1               5                   10                  15

His Leu Glu Ile Val Glu Val Leu Leu Lys Tyr Gly Ala Asp Val Asn
            20                  25                  30

Ala

<210> SEQ ID NO 121
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 121

Ala Asp Met Tyr Gly Thr Thr Pro Gln His Leu Ala Ala Arg Thr Gly
1               5                   10                  15

His Leu Glu Ile Val Glu Val Leu Leu Lys Tyr Gly Ala Asp Val Asn
            20                  25                  30

Ala

<210> SEQ ID NO 122
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 122

Ser Asp Ile Tyr Gly Ser Thr Pro Leu His Leu Ala Ala Arg His Gly
1               5                   10                  15

His Leu Glu Ile Val Glu Val Leu Leu Lys Asn Gly Ala Asp Val Asn
            20                  25                  30

Ala

<210> SEQ ID NO 123
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 123

Ala Asp Asp Tyr Gly Ser Thr Pro Leu His Leu Ala Ala Arg Ser Gly
1               5                   10                  15

His Leu Glu Ile Val Glu Val Leu Leu Lys His Gly Ala Asp Val Asn
            20                  25                  30

Ala

<210> SEQ ID NO 124
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 124

Met Asp Lys Tyr Gly Ser Thr Pro Leu His Leu Ala Ala Arg Ser Gly
1               5                   10                  15

His Leu Glu Ile Val Glu Val Leu Leu Lys His Gly Ala Asp Val Asn
            20                  25                  30

Ala

<210> SEQ ID NO 125
<211> LENGTH: 33
<212> TYPE: PRT
<213> ORGANISM: Artificial Sequence

```
<220> FEATURE:
<223> OTHER INFORMATION: Synthetic ankyrin repeat sequence

<400> SEQUENCE: 125

Phe Asp Asp Phe Gly Asp Thr Pro Leu His Leu Ala Ala Arg Glu Gly
1               5                   10                  15

His Leu Glu Ile Val Glu Val Leu Leu Lys Lys Gly Ala Asp Val Asn
            20                  25                  30

Ala

<210> SEQ ID NO 126
<211> LENGTH: 33
<212> TYPE: PRT
<213> ORGANISM: Artificial Sequence
<220> FEATURE:
<223> OTHER INFORMATION: Synthetic consensus ankyrin repeat sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid

<400> SEQUENCE: 126

Xaa Asp Xaa Xaa Gly Xaa Thr Pro Leu His Leu Ala Ala Xaa Xaa Gly
1               5                   10                  15

His Leu Glu Ile Val Glu Val Leu Leu Lys Xaa Gly Ala Xaa Val Asn
            20                  25                  30

Ala

<210> SEQ ID NO 127
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 127

Lys Asp Met Ile Gly Asp Thr Pro Leu His Leu Ala Ala Tyr Arg Gly
1               5                   10                  15

His Leu Glu Ile Val Glu Val Leu Leu Lys Asn Gly Ala Asp Val Asn
            20                  25                  30

Ala

<210> SEQ ID NO 128
<211> LENGTH: 33
<212> TYPE: PRT
<213> ORGANISM: Artificial Sequence
<220> FEATURE:
```

<223> OTHER INFORMATION: Synthetic ankyrin repeat sequence

<400> SEQUENCE: 128

Ala Asp Phe Ile Gly Asp Thr Pro Leu His Leu Ala Ala Tyr Arg Gly
1               5                   10                  15

His Leu Glu Ile Val Glu Val Leu Leu Lys Cys Gly Val Asp Val Asn
            20                  25                  30

Ala

<210> SEQ ID NO 129
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 129

Met Asp Phe Ile Gly Asp Thr Pro Leu His Leu Ala Ala Tyr Arg Gly
1               5                   10                  15

His Leu Glu Ile Val Glu Val Leu Leu Lys Tyr Gly Val Asp Val Asn
            20                  25                  30

Ala

<210> SEQ ID NO 130
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 130

Asp Asp Phe Leu Gly Asp Thr Pro Leu His Leu Ala Ala Tyr His Gly
1               5                   10                  15

His Leu Asp Ile Val Glu Val Leu Leu Lys His Gly Ala Asp Val Asn
            20                  25                  30

Ala

<210> SEQ ID NO 131
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 131

Thr Asp Phe Ile Gly Asp Thr Pro Leu His Leu Ala Ala Tyr His Gly
1               5                   10                  15

His Leu Glu Ile Val Glu Val Leu Leu Lys His Gly Ala Asp Val Asn
            20                  25                  30

Ala

<210> SEQ ID NO 132
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 132

His Asp Met Ile Gly Asp Thr Pro Leu His Leu Ala Tyr His Glu Gly
1               5                   10                  15

His Leu Glu Ile Val Glu Val Leu Leu Lys Tyr Gly Ala Asp Val Asn
            20                  25                  30

Ala

<210> SEQ ID NO 133
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 133

Asn Asp Phe Ala Gly Tyr Thr Pro Leu His Leu Ala Ala Val Tyr Gly
1               5                   10                  15

His Leu Glu Ile Val Glu Val Leu Leu Lys Tyr Gly Ala Asp Val Asn
            20                  25                  30

Ala

<210> SEQ ID NO 134
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 134

Asn Asp Phe Ile Gly Asp Thr Pro Leu His Leu Ala Ala Trp His Gly
1               5                   10                  15

His Leu Glu Ile Val Glu Val Leu Leu Lys Asn Gly Ala Asp Val Asn
            20                  25                  30

Ala

<210> SEQ ID NO 135
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 135

Asn Asp Phe Ile Gly Asp Thr Pro Leu His Leu Ala Ala Trp His Gly
1               5                   10                  15

His Leu Glu Ile Val Glu Val Leu Leu Lys Asn Gly Ala Asp Val Asn
            20                  25                  30

Ala

<210> SEQ ID NO 136
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 136

Glu Asp Phe Ile Gly Asp Thr Pro Leu His Leu Ala Ala Tyr Arg Gly
1               5                   10                  15

His Leu Glu Ile Val Glu Val Leu Leu Lys Tyr Gly Val Asp Val Asn
            20                  25                  30

Ala

<210> SEQ ID NO 137

```
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 137

Phe Asp Phe Ile Gly Asp Thr Pro Leu His Leu Ala Ala Tyr Arg Gly
1               5                   10                  15

His Leu Glu Ile Val Glu Val Leu Leu Lys Tyr Gly Val Asp Val Asn
            20                  25                  30

Ala

<210> SEQ ID NO 138
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 138

Lys Asp Met Ile Gly Asp Thr Pro Leu His Leu Ala Ala Tyr Arg Gly
1               5                   10                  15

His Leu Glu Ile Val Glu Val Leu Leu Lys Tyr Gly Val Asp Val Asn
            20                  25                  30

Ala

<210> SEQ ID NO 139
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 139

Ala Asp Phe Leu Gly Asp Thr Pro Leu His Leu Ala Ala Tyr His Gly
1               5                   10                  15

His Leu Glu Ile Val Glu Val Leu Leu Lys His Gly Ala Asp Val Asn
            20                  25                  30

Ala

<210> SEQ ID NO 140
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 140

Asn Asp Met Ile Gly Asp Thr Pro Leu His Leu Ala Ala Tyr His Gly
1               5                   10                  15

His Leu Glu Ile Val Glu Val Leu Leu Lys His Gly Ala Asp Val Asn
            20                  25                  30

Ala

<210> SEQ ID NO 141
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 141
```

```
Asn Asp Phe Ile Gly Asp Thr Pro Leu His Leu Ala Ala Tyr Asn Gly
1               5                   10                  15

His Leu Glu Ile Val Glu Val Leu Leu Lys Asn Gly Ala Asp Val Asn
            20                  25                  30

Ala

<210> SEQ ID NO 142
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 142

Thr Asp Phe Ile Gly Asp Thr Pro Leu His Leu Ala Ala Tyr His Gly
1               5                   10                  15

His Leu Glu Ile Val Glu Val Leu Leu Lys His Gly Ala Asp Val Asn
            20                  25                  30

Ala

<210> SEQ ID NO 143
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 143

Thr Asp Ile Ile Gly Asn Thr Pro Leu His Leu Ala Ala Phe Arg Gly
1               5                   10                  15

His Leu Glu Ile Val Glu Val Leu Leu Lys His Gly Ala Asp Val Asn
            20                  25                  30

Ala

<210> SEQ ID NO 144
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 144

Ser Asp Ile Thr Gly Glu Thr Pro Leu His Leu Ala Ala Gln Ile Gly
1               5                   10                  15

His Leu Glu Ile Val Glu Val Leu Leu Lys Tyr Gly Ala Asp Val Asn
            20                  25                  30

Ala

<210> SEQ ID NO 145
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 145

Asp Asp His Tyr Gly Asp Thr Pro Leu His Leu Ala Ala Ser Met Gly
1               5                   10                  15

His Leu Glu Ile Val Glu Val Leu Leu Lys Asn Gly Ala Asp Val Asn
            20                  25                  30
```

<210> SEQ ID NO 146
<211> LENGTH: 31
<212> TYPE: PRT
<213> ORGANISM: Artificial Sequence
<220> FEATURE:
<223> OTHER INFORMATION: Synthetic ankyrin repeat sequence

<400> SEQUENCE: 146

Lys Asn Gly Glu Thr Pro Leu His Leu Ala Ala Tyr His Gly His Pro
1               5                   10                  15

Asp Ile Val Glu Val Leu Leu Lys His Gly Ala Asp Val Asn Ala
            20                  25                  30

<210> SEQ ID NO 147
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 147

Lys Asp Thr Ser Gly Thr Thr Pro Leu His Leu Ala Ala Asp Ser Gly
1               5                   10                  15

His Leu Glu Ile Val Glu Val Leu Leu Lys His Gly Ala Asp Val Asn
            20                  25                  30

Ala

<210> SEQ ID NO 148
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 148

Thr Asp Ala Trp Gly Glu Thr Pro Leu His Leu Ala Ala Tyr Thr Gly
1               5                   10                  15

His Leu Glu Ile Val Glu Val Leu Leu Lys His Asp Ala Asp Val Asn
            20                  25                  30

Ala

<210> SEQ ID NO 149
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 149

Met Asp Val Thr Gly Glu Thr Pro Leu His Leu Ala Ala Tyr His Gly
1               5                   10                  15

His Leu Asp Ile Val Glu Val Leu Leu Lys Asn Gly Ala Asp Val Asn
            20                  25                  30

Ala

<210> SEQ ID NO 150
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 150

Ser Asp Ile Thr Gly Glu Thr Pro Leu His Leu Ala Ala Thr Ala Gly
1               5                   10                  15

His Leu Glu Ile Val Glu Val Leu Leu Lys His Gly Ala Asp Val Asn
            20                  25                  30

Ala

<210> SEQ ID NO 151
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 151

Ser Asp Ile Thr Gly Glu Thr Pro Leu His Leu Ala Ala His Leu Gly
1               5                   10                  15

His Leu Glu Ile Val Glu Val Leu Leu Lys Tyr Gly Ala Asp Val Asn
            20                  25                  30

Ala

<210> SEQ ID NO 152
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 152

Ser Asp Ile Thr Gly Glu Thr Pro Leu His Leu Ala Ala His Asn Gly
1               5                   10                  15

His Leu Glu Ile Val Glu Val Leu Leu Lys Tyr Gly Ala Asp Val Asn
            20                  25                  30

Ala

<210> SEQ ID NO 153
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 153

Thr Asp Ile Thr Gly Glu Thr Pro Leu His Leu Ala Ala Glu Arg Gly
1               5                   10                  15

His Leu Glu Ile Val Glu Val Leu Leu Lys Asn Gly Ala Asp Val Asn
            20                  25                  30

Thr

<210> SEQ ID NO 154
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 154

Glu Asp Ile Thr Gly Glu Thr Pro Leu His Leu Ala Ala Glu Ser Gly
1               5                   10                  15

His Leu Glu Ile Val Glu Val Leu Leu Lys His Gly Ala Asp Val Asn

```
                20                  25                  30
Ala

<210> SEQ ID NO 155
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 155

Ser Asp Ile Thr Gly Glu Thr Pro Leu His Leu Ala Ala His Leu Gly
1               5                   10                  15

His Leu Glu Ile Val Glu Val Leu Leu Lys Tyr Gly Ala Asp Val Asn
                20                  25                  30

Ala

<210> SEQ ID NO 156
<211> LENGTH: 33
<212> TYPE: PRT
<213> ORGANISM: Artificial Sequence
<220> FEATURE:
<223> OTHER INFORMATION: Synthetic conseneus ankyrin repeat sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid

<400> SEQUENCE: 156

Xaa Asp Xaa Xaa Gly Ser Thr Pro Leu His Leu Ala Ala Arg His Gly
1               5                   10                  15

His Leu Glu Ile Val Glu Val Leu Leu Lys Xaa Gly Ala Asp Val Asn
                20                  25                  30

Ala

<210> SEQ ID NO 157
<211> LENGTH: 32
<212> TYPE: PRT
<213> ORGANISM: Artificial Sequence
<220> FEATURE:
<223> OTHER INFORMATION: Synthetic conseneus ankyrin repeat sequence
<220> FEATURE:
<221> NAME/KEY: misc_feature
<222> LOCATION: (26)..(26)
<223> OTHER INFORMATION: Xaa can be any naturally occurring amino acid

<400> SEQUENCE: 157

Thr Asp Tyr Gly Ser Thr Pro Leu His Leu Ala Ala Arg His Gly His
1               5                   10                  15

Leu Glu Ile Val Glu Val Leu Leu Lys Xaa Gly Ala Asp Val Asn Ala
                20                  25                  30

<210> SEQ ID NO 158
<211> LENGTH: 33
<212> TYPE: PRT
<213> ORGANISM: Artificial Sequence
<220> FEATURE:
<223> OTHER INFORMATION: Synthetic conseneus ankyrin repeat sequence
```

```
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid

<400> SEQUENCE: 158

Xaa Asp Phe Ile Gly Asp Thr Pro Leu His Leu Ala Ala Tyr Xaa Gly
1               5                   10                  15

His Leu Glu Ile Val Glu Val Leu Leu Lys Xaa Gly Ala Asp Val Asn
            20                  25                  30

Ala

<210> SEQ ID NO 159
<211> LENGTH: 33
<212> TYPE: PRT
<213> ORGANISM: Artificial Sequence
<220> FEATURE:
<223> OTHER INFORMATION: Synthetic conseneus ankyrin repeat sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid

<400> SEQUENCE: 159

Xaa Asp Phe Ile Gly Asp Thr Pro Leu His Leu Ala Ala Tyr Xaa Gly
1               5                   10                  15

His Leu Glu Ile Val Glu Val Leu Leu Lys Xaa Gly Ala Asp Val Asn
            20                  25                  30

Ala

<210> SEQ ID NO 160
<211> LENGTH: 33
<212> TYPE: PRT
<213> ORGANISM: Artificial Sequence
<220> FEATURE:
<223> OTHER INFORMATION: Synthetic conseneus ankyrin repeat sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid

<400> SEQUENCE: 160
```

```
Xaa Asp Xaa Thr Gly Glu Thr Pro Leu His Leu Ala Ala Xaa Xaa Gly
1               5                   10                  15

His Leu Glu Ile Val Glu Val Leu Leu Lys Xaa Gly Ala Asp Val Asn
            20                  25                  30

Ala

<210> SEQ ID NO 161
<211> LENGTH: 33
<212> TYPE: PRT
<213> ORGANISM: Artificial Sequence
<220> FEATURE:
<223> OTHER INFORMATION: Synthetic conseneus ankyrin repeat sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid

<400> SEQUENCE: 161

Xaa Asp Ile Thr Gly Glu Thr Pro Leu His Leu Ala Ala Ser Met Gly
1               5                   10                  15

His Leu Glu Ile Val Glu Val Leu Leu Lys Xaa Gly Ala Asp Val Asn
            20                  25                  30

Ala

<210> SEQ ID NO 162
<211> LENGTH: 157
<212> TYPE: PRT
<213> ORGANISM: Artificial Sequence
<220> FEATURE:
<223> OTHER INFORMATION: Synthetic ankyrin repeat sequence

<400> SEQUENCE: 162

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Arg Asp
            20                  25                  30

Ser Tyr Gly Ser Thr Pro Leu His Leu Ala Ala Arg Glu Gly His Leu
        35                  40                  45

Glu Ile Val Glu Val Leu Leu Lys Tyr Gly Ala Asp Val Asn Ala Lys
    50                  55                  60

Asp Met Ile Gly Asp Thr Pro Leu His Leu Ala Ala Tyr Arg Gly His
65                  70                  75                  80

Leu Glu Ile Val Glu Val Leu Leu Lys Asn Gly Ala Asp Val Asn Ala
                85                  90                  95

Ser Asp Ile Thr Gly Glu Thr Pro Leu His Leu Ala Ala Gln Ile Gly
            100                 105                 110

His Leu Glu Ile Val Glu Val Leu Leu Lys Tyr Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln Lys Leu Asn
145                 150                 155

<210> SEQ ID NO 163
<211> LENGTH: 157
<212> TYPE: PRT
<213> ORGANISM: Artificial Sequence
```

<220> FEATURE:
<223> OTHER INFORMATION: Synthetic ankyrin repeat sequence

<400> SEQUENCE: 163

Ala Leu Asp Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Arg Asp
                20                  25                  30

Ser Tyr Gly Ser Thr Pro Leu His Leu Ala Ala Arg Glu Gly His Leu
            35                  40                  45

Glu Ile Val Glu Val Leu Leu Lys Tyr Gly Ala Asp Val Asn Ala Ala
        50                  55                  60

Asp Phe Ile Gly Asp Thr Pro Leu His Leu Ala Ala Tyr Arg Gly His
65                  70                  75                  80

Leu Glu Ile Val Glu Val Leu Leu Lys Tyr Gly Ala Asp Val Asn Ala
                85                  90                  95

Ser Asp Ile Thr Gly Glu Thr Pro Leu His Leu Ala Ala Gln Ile Gly
            100                 105                 110

His Leu Glu Ile Val Glu Val Leu Leu Lys His Gly Ala Asp Val Asn
        115                 120                 125

Ala Gln Asp Lys Phe Gly Lys Thr Ala Phe Asp Ile Ser Ile Asp Asn
130                 135                 140

Gly Asn Glu Asp Leu Ala Glu Ile Leu Gln Lys Ala Ala
145                 150                 155

<210> SEQ ID NO 164
<211> LENGTH: 156
<212> TYPE: PRT
<213> ORGANISM: Artificial Sequence
<220> FEATURE:
<223> OTHER INFORMATION: Synthetic ankyrin repeat sequence

<400> SEQUENCE: 164

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Ser Asp
                20                  25                  30

Ile Phe Gly Ser Thr Pro Leu His Leu Ala Ala Arg His Gly His Leu
            35                  40                  45

Glu Ile Val Glu Val Leu Leu Lys Tyr Gly Ala Asp Val Asn Ala Met
        50                  55                  60

Asp Phe Ile Gly Asp Thr Pro Leu His Leu Ala Ala Tyr Arg Gly His
65                  70                  75                  80

Leu Glu Ile Val Glu Val Leu Leu Lys Tyr Gly Val Asp Val Asn Ala
                85                  90                  95

Asp Asp His Gly Asp Thr Pro Leu His Leu Ala Ala Ser Met Gly His
            100                 105                 110

Leu Glu Ile Val Glu Val Leu Leu Lys Asn Gly Ala Asp Val Asn Ala
        115                 120                 125

Gln Asp Lys Phe Gly Lys Thr Ala Phe Asp Ile Ser Ile Asp Asn Gly
130                 135                 140

Asn Glu Asp Leu Ala Glu Ile Leu Gln Lys Leu Asn
145                 150                 155

<210> SEQ ID NO 165
<211> LENGTH: 156
<212> TYPE: PRT

-continued

```
<213> ORGANISM: Artificial Sequence
<220> FEATURE:
<223> OTHER INFORMATION: Synthetic ankyrin repeat signature

<400> SEQUENCE: 165

Gly Leu Asp Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Ser Asp
            20                  25                  30

Ile Phe Gly Ser Thr Pro Leu His Leu Ala Ala Arg His Gly His Leu
        35                  40                  45

Glu Ile Val Glu Val Leu Leu Lys Tyr Gly Ala Asp Val Asn Ala Phe
    50                  55                  60

Asp Phe Ile Gly Asp Thr Pro Leu His Leu Ala Ala Tyr Arg Gly His
65                  70                  75                  80

Leu Glu Ile Val Glu Val Leu Leu Lys Tyr Gly Val Asp Val Asn Ala
                85                  90                  95

Asp Asp His Gly Asp Thr Pro Leu His Leu Ala Ala Gln Ile Gly His
            100                 105                 110

Leu Glu Ile Val Glu Val Leu Leu Lys His Gly Ala Asp Val Asn Ala
        115                 120                 125

Gln Asp Lys Phe Gly Lys Thr Ala Phe Asp Ile Ser Ile Asp Asn Gly
    130                 135                 140

Asn Glu Asp Leu Ala Glu Ile Leu Gln Lys Ala Ala
145                 150                 155

<210> SEQ ID NO 166
<211> LENGTH: 156
<212> TYPE: PRT
<213> ORGANISM: Artificial Sequence
<220> FEATURE:
<223> OTHER INFORMATION: Synthetic ankyrin repeat sequence

<400> SEQUENCE: 166

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Thr Asp
            20                  25                  30

Glu Phe Asp Ser Thr Pro Leu His Leu Ala Ala Arg His Gly His Leu
        35                  40                  45

Glu Ile Val Glu Val Leu Leu Lys Tyr Gly Ala Asp Val Asn Ala Ala
    50                  55                  60

Asp Phe Ile Gly Asp Thr Pro Leu His Leu Ala Ala Tyr Arg Gly His
65                  70                  75                  80

Leu Glu Ile Val Glu Val Leu Leu Lys Cys Gly Val Asp Val Asn Ala
                85                  90                  95

Asp Asp His Gly Asp Thr Pro Leu His Leu Ala Ala Ser Met Gly His
            100                 105                 110

Leu Glu Ile Val Glu Val Leu Leu Lys Asn Gly Ala Asp Val Asn Ala
        115                 120                 125

Gln Asp Lys Phe Gly Lys Thr Ala Phe Asp Ile Ser Ile Asp Asn Gly
    130                 135                 140

Asn Glu Asp Leu Ala Glu Ile Leu Gln Lys Leu Asn
145                 150                 155

<210> SEQ ID NO 167
<211> LENGTH: 156
```

<212> TYPE: PRT
<213> ORGANISM: Artificial Sequence
<220> FEATURE:
<223> OTHER INFORMATION: Synthetic ankyrin repeat sequence

<400> SEQUENCE: 167

Gly Leu Asp Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Thr Asp
            20                  25                  30

Glu Phe Asp Ser Thr Pro Leu His Leu Ala Ala Arg His Gly His Leu
        35                  40                  45

Glu Ile Val Glu Val Leu Leu Lys Tyr Gly Ala Asp Val Asn Ala Ala
    50                  55                  60

Asp Phe Ile Gly Asp Thr Pro Leu His Leu Ala Ala Tyr Arg Gly His
65                  70                  75                  80

Leu Glu Ile Val Glu Val Leu Leu Lys Tyr Gly Val Asp Val Asn Ala
                85                  90                  95

Asp Asp His Gly Asp Thr Pro Leu His Leu Ala Ala Ser Thr Gly His
                100                 105                 110

Leu Glu Ile Val Glu Val Leu Leu Lys His Gly Ala Asp Val Asn Ala
            115                 120                 125

Gln Asp Lys Phe Gly Lys Thr Ala Phe Asp Ile Ser Ile Asp Asn Gly
130                 135                 140

Asn Glu Asp Leu Ala Glu Ile Leu Gln Lys Ala Ala
145                 150                 155

<210> SEQ ID NO 168
<211> LENGTH: 32
<212> TYPE: PRT
<213> ORGANISM: Artificial Sequence
<220> FEATURE:
<223> OTHER INFORMATION: Synthetic conseneus ankyrin repeat sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 168

Xaa Asp Xaa Xaa Ser Thr Pro Leu His Leu Ala Ala Arg Xaa Gly His
1               5                   10                  15

Leu Glu Ile Val Glu Val Leu Leu Lys Tyr Gly Ala Asp Val Asn Ala
            20                  25                  30

<210> SEQ ID NO 169
<211> LENGTH: 33
<212> TYPE: PRT
<213> ORGANISM: Artificial Sequence
<220> FEATURE:
<223> OTHER INFORMATION: Synthetic ankyrin repeat cap
<220> FEATURE:
<221> NAME/KEY: misc_feature
<222> LOCATION: (1)..(1)
<223> OTHER INFORMATION: Xaa can be any naturally occurring amino acid

<400> SEQUENCE: 169

Xaa Asp Phe Ile Gly Asp Thr Pro Leu His Leu Ala Ala Tyr Arg Gly
1               5                   10                  15

His Leu Glu Ile Val Glu Val Leu Leu Lys Tyr Gly Ala Asp Val Asn
            20                  25                  30

Ala

<210> SEQ ID NO 170
<211> LENGTH: 33
<212> TYPE: PRT
<213> ORGANISM: Artificial Sequence
<220> FEATURE:
<223> OTHER INFORMATION: Synthetic conseneus ankyrin repeat sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid

<400> SEQUENCE: 170

Xaa Asp Xaa Xaa Gly Xaa Thr Pro Leu His Leu Ala Ala Xaa Xaa Gly
1               5                   10                  15

His Leu Glu Ile Val Glu Val Leu Leu Lys His Gly Ala Asp Val Asn
            20                  25                  30

Ala

<210> SEQ ID NO 171
<211> LENGTH: 30
<212> TYPE: PRT
<213> ORGANISM: Artificial Sequence
<220> FEATURE:
<223> OTHER INFORMATION: Synthetic ankyrin consensus cap
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid

<400> SEQUENCE: 171

Xaa Leu Xaa Lys Lys Leu Leu Glu Ala Ala Arg Ala Gly Gln Asp Asp
1               5                   10                  15

Glu Val Arg Ile Leu Met Ala Asn Gly Ala Asp Val Asn Ala
            20                  25                  30

<210> SEQ ID NO 172
<211> LENGTH: 28
<212> TYPE: PRT
<213> ORGANISM: Artificial Sequence
<220> FEATURE:
<223> OTHER INFORMATION: Synthetic ankyrin repeat cap

<400> SEQUENCE: 172

Gln Asp Lys Phe Gly Lys Thr Pro Ala Asp Ile Ala Ala Asp Asn Gly
1               5                   10                  15

His Glu Asp Ile Ala Glu Val Leu Gln Lys Ala Ala
         20                  25

<210> SEQ ID NO 173
<211> LENGTH: 126
<212> TYPE: PRT
<213> ORGANISM: Artificial Sequence
<220> FEATURE:
<223> OTHER INFORMATION: Synthetic ankyrin repeat sequence

<400> SEQUENCE: 173

Gly Ser Asp Leu Gly Lys Lys Leu Met Glu Ala Ala Arg Ala Gly Gln
1               5                   10                  15

Asp Asp Glu Val Arg Ile Leu Met Ala Asn Gly Ala Asp Val Asn Ala
            20                  25                  30

Lys Asp Leu Phe Gly Ile Thr Pro Leu His Leu Ala Ala Val Tyr Gly
        35                  40                  45

His Leu Glu Ile Val Glu Val Leu Leu Lys His Gly Ala Asp Val Asn
    50                  55                  60

Ala Thr Asp Asn Trp Gly Ser Thr Pro Leu His Leu Ala Ala Gln Phe
65                  70                  75                  80

Gly His Leu Glu Ile Val Glu Val Leu Leu Lys Tyr Gly Ala Asp Val
                85                  90                  95

Asn Ala Gln Asp Lys Phe Gly Lys Thr Ala Phe Asp Ile Ser Ile Asp
            100                 105                 110

Asn Gly Asn Glu Asp Leu Ala Glu Ile Leu Gln Lys Leu Asn
        115                 120                 125

<210> SEQ ID NO 174
<211> LENGTH: 28
<212> TYPE: PRT
<213> ORGANISM: Artificial Sequence
<220> FEATURE:
<223> OTHER INFORMATION: Synthetic ankyrin repeat cap
<220> FEATURE:
<221> NAME/KEY: misc_feature
<222> LOCATION: (1)..(1)
<223> OTHER INFORMATION: Xaa can be any naturally occurring amino acid

<400> SEQUENCE: 174

Xaa Lys Lys Leu Leu Glu Ala Ala Arg Ala Gly Gln Asp Asp Glu Val
1               5                   10                  15

Arg Ile Leu Met Ala Asn Gly Ala Asp Val Asn Ala
            20                  25

<210> SEQ ID NO 175
<211> LENGTH: 28
<212> TYPE: PRT
<213> ORGANISM: Artificial Sequence
<220> FEATURE:
<223> OTHER INFORMATION: Synthetic ankyrin repeat cap
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (20)..(20)

-continued

```
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (27)..(28)
<223> OTHER INFORMATION: Xaa can be any naturally occurring amino acid

<400> SEQUENCE: 175

Gln Asp Lys Phe Gly Lys Thr Xaa Xaa Asp Ile Xaa Xaa Asp Asn Gly
 1               5                  10                  15

Xaa Glu Asp Xaa Ala Glu Xaa Leu Gln Lys Xaa Xaa
             20                  25

<210> SEQ ID NO 176
<211> LENGTH: 1017
<212> TYPE: DNA
<213> ORGANISM: Homo sapiens

<400> SEQUENCE: 176
atgggatccg acctgggtaa gaaactgctg gaagctgctc gtgctggtca ggacgacgaa      60
gttcgtatcc tgatggctaa cggtgctgac gttaacgctc tggatgatag cggttataca     120
ccgctgcatc tggcagcgga agatggtcat ctggaaattg ttgaagttct gctgaaacac     180
ggtgccgatg tgaatgccgc agatcgtctg ggtgatactc cgctgcatct ggctgccttt     240
gttggccatc tggaaatcgt agaggtgctg ctgaaagcag cgcagatgt aaacgcagtt     300
gatctggcag gcgttacccc tctgcacgtt gcagcatttt atggacactt agaaattgtg     360
gaggtactgc tgaaggcagg tgcagacgtt aacgcacagg ataaatttgg taaaaccccg     420
gcggatattg cggcggataa tggccatgag gatattgcag aagtgctgca aaaggcggcg     480
ggcggcggtg gctctggcgg tggtggctct ggcggtggcg ttctggcgg tggtggctct     540
ggatccgacc tggataagaa actgctggaa gcagcacgtg caggtcagga tgatgaagtt     600
cgtattctga tggcaaatgg cgccgatgtt aatgcacgtg atagctatgg tagcacaccg     660
ctgcatctgg ctgcacgtga gggtcatctg gaaattgtgg aagtgctgct gaaatacggt     720
gccgatgtga atgccgcaga ttttattggt gataccccgt acatctggc tgcgtatcgt     780
ggccatttag aaatcgtgga ggttctgtta aaatacggcg cagacgttaa tgcaagcgat     840
attaccggtg aaaccccctct gcatttagca gcgcagattg ccacctggga atcgtcgaa     900
gttttactga acatggcgc agatgttaac gcacaggata aatttggtaa accccggcg     960
gatattgcgg cggataatgg ccatgaggat attgcagaag tgctgcagaa ggcggcg      1017

<210> SEQ ID NO 177
<211> LENGTH: 338
<212> TYPE: PRT
<213> ORGANISM: Artificial Sequence
<220> FEATURE:
<223> OTHER INFORMATION: Synthetic ankyrin repeat sequence

<400> SEQUENCE: 177

Gly Ser Asp Leu Gly Lys Lys Leu Leu Glu Ala Ala Arg Ala Gly Gln
 1               5                  10                  15

Asp Asp Glu Val Arg Ile Leu Met Ala Asn Gly Ala Asp Val Asn Ala
             20                  25                  30

Leu Asp Asp Ser Gly Tyr Thr Pro Leu His Leu Ala Ala Glu Asp Gly
         35                  40                  45
```

His Leu Glu Ile Val Glu Val Leu Leu Lys His Gly Ala Asp Val Asn
 50                  55                  60

Ala Ala Asp Arg Leu Gly Asp Thr Pro Leu His Leu Ala Ala Phe Val
 65                  70                  75                  80

Gly His Leu Glu Ile Val Glu Val Leu Leu Lys Ala Gly Ala Asp Val
                 85                  90                  95

Asn Ala Val Asp Leu Ala Gly Val Thr Pro Leu His Val Ala Ala Phe
             100                 105                 110

Tyr Gly His Leu Glu Ile Val Glu Val Leu Leu Lys Ala Gly Ala Asp
             115                 120                 125

Val Asn Ala Gln Asp Lys Phe Gly Lys Thr Pro Ala Asp Ile Ala Ala
130                 135                 140

Asp Asn Gly His Glu Asp Ile Ala Glu Val Leu Gln Lys Ala Ala Gly
145                 150                 155                 160

Gly Gly Gly Ser Gly Gly Gly Ser Gly Gly Gly Ser Gly Gly
                165                 170                 175

Gly Gly Ser Gly Ser Asp Leu Asp Lys Lys Leu Leu Glu Ala Ala Arg
            180                 185                 190

Ala Gly Gln Asp Asp Glu Val Arg Ile Leu Met Ala Asn Gly Ala Asp
            195                 200                 205

Val Asn Ala Arg Asp Ser Tyr Gly Ser Thr Pro Leu His Leu Ala Ala
210                 215                 220

Arg Glu Gly His Leu Glu Ile Val Glu Val Leu Leu Lys Tyr Gly Ala
225                 230                 235                 240

Asp Val Asn Ala Ala Asp Phe Ile Gly Asp Thr Pro Leu His Leu Ala
            245                 250                 255

Ala Tyr Arg Gly His Leu Glu Ile Val Glu Val Leu Leu Lys Tyr Gly
            260                 265                 270

Ala Asp Val Asn Ala Ser Asp Ile Thr Gly Glu Thr Pro Leu His Leu
            275                 280                 285

Ala Ala Gln Ile Gly His Leu Glu Ile Val Glu Val Leu Leu Lys His
            290                 295                 300

Gly Ala Asp Val Asn Ala Gln Asp Lys Phe Gly Lys Thr Pro Ala Asp
305                 310                 315                 320

Ile Ala Ala Asp Asn Gly His Glu Asp Ile Ala Glu Val Leu Gln Lys
            325                 330                 335

Ala Ala

<210> SEQ ID NO 178
<211> LENGTH: 338
<212> TYPE: PRT
<213> ORGANISM: Artificial Sequence
<220> FEATURE:
<223> OTHER INFORMATION: Synthetic ankyrin repeat sequence

<400> SEQUENCE: 178

Gly Ser Asp Leu Gly Lys Lys Leu Leu Glu Ala Ala Ser Ala Gly Gln
 1               5                  10                  15

Asp Asp Glu Val Arg Ile Leu Met Ala Asn Gly Ala Asp Val Asn Ala
                 20                  25                  30

Leu Asp Asp Ser Gly Tyr Thr Pro Leu His Leu Ala Ala Glu Asp Gly
             35                  40                  45

His Leu Glu Ile Val Glu Val Leu Leu Lys His Gly Ala Asp Val Asn
 50                  55                  60

Ala Ala Asp Arg Leu Gly Asp Thr Pro Leu His Leu Ala Ala Phe Val

```
                65                  70                  75                  80
        Gly His Leu Glu Ile Val Glu Val Leu Leu Lys Ala Gly Ala Asp Val
                        85                  90                  95
        Asn Ala Val Asp Leu Ala Gly Val Thr Pro Leu His Val Ala Ala Phe
                       100                 105                 110
        Tyr Gly His Leu Glu Ile Val Glu Val Leu Leu Lys Ala Gly Ala Asp
                       115                 120                 125
        Val Asn Ala Gln Asp Lys Phe Gly Lys Thr Ala Phe Asp Ile Ser Ile
            130                 135                 140
        Asp Asn Gly Asn Glu Asp Leu Ala Glu Ile Leu Gln Lys Ala Ala Gly
        145                 150                 155                 160
        Gly Gly Gly Ser Gly Gly Gly Ser Gly Gly Gly Ser Gly Gly Gly Gly
                        165                 170                 175
        Gly Gly Ser Gly Ser Asp Leu Asp Lys Lys Leu Leu Glu Ala Ala Arg
                       180                 185                 190
        Ala Gly Gln Asp Asp Glu Val Arg Ile Leu Met Ala Asn Gly Ala Asp
                       195                 200                 205
        Val Asn Ala Arg Asp Ser Tyr Gly Ser Thr Pro Leu His Leu Ala Ala
            210                 215                 220
        Arg Glu Gly His Leu Glu Ile Val Glu Val Leu Leu Lys Tyr Gly Ala
        225                 230                 235                 240
        Asp Val Asn Ala Ala Asp Phe Ile Gly Asp Thr Pro Leu His Leu Ala
                        245                 250                 255
        Ala Tyr Arg Gly His Leu Glu Ile Val Glu Val Leu Leu Lys Tyr Gly
                       260                 265                 270
        Ala Asp Val Asn Ala Ser Asp Ile Thr Gly Glu Thr Pro Leu His Leu
                       275                 280                 285
        Ala Ala Gln Ile Gly His Leu Glu Ile Val Glu Val Leu Leu Lys His
            290                 295                 300
        Gly Ala Asp Val Asn Ala Gln Asp Lys Phe Gly Lys Thr Ala Phe Asp
        305                 310                 315                 320
        Ile Ser Ile Asp Asn Gly Asn Glu Asp Leu Ala Glu Ile Leu Gln Lys
                        325                 330                 335
        Ala Ala

<210> SEQ ID NO 179
<211> LENGTH: 33
<212> TYPE: PRT
<213> ORGANISM: Artificial Sequence
<220> FEATURE:
<223> OTHER INFORMATION: Synthetic consensus ankyrin repeat sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid

<400> SEQUENCE: 179

Xaa Asp Xaa Thr Gly Glu Thr Pro Leu His Leu Ala Ala Xaa Xaa Gly
```

```
1               5                   10                  15
His Leu Glu Ile Val Glu Val Leu Leu Lys Xaa Gly Ala Asp Val Asn
            20                  25                  30

Ala
```

<210> SEQ ID NO 180
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 180

```
Ala Asp Arg Leu Gly Asp Thr Pro Leu His Leu Ala Ala Phe Val Gly
1               5                   10                  15
His Leu Glu Ile Val Glu Val Leu Leu Lys Ala Gly Ala Asp Val Asn
            20                  25                  30

Ala
```

<210> SEQ ID NO 181
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 181

```
Val Asp Leu Ala Gly Val Thr Pro Leu His Val Ala Ala Phe Tyr Gly
1               5                   10                  15
His Leu Glu Ile Val Glu Val Leu Leu Lys Ala Gly Ala Asp Val Asn
            20                  25                  30

Ala
```

<210> SEQ ID NO 182
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 182

```
Ala Asp Phe Ile Gly Asp Thr Pro Leu His Leu Ala Ala Tyr Arg Gly
1               5                   10                  15
His Leu Glu Ile Val Glu Val Leu Leu Lys Tyr Gly Ala Asp Val Asn
            20                  25                  30

Ala
```

<210> SEQ ID NO 183
<211> LENGTH: 33
<212> TYPE: PRT
<213> ORGANISM: Artificial Sequence
<220> FEATURE:
<223> OTHER INFORMATION: Synthetic ankyrin repeat sequence

<400> SEQUENCE: 183

```
Ser Asp Ile Thr Gly Glu Thr Pro Leu His Leu Ala Ala Gln Ile Gly
1               5                   10                  15
His Leu Glu Ile Val Glu Val Leu Leu Lys His Gly Ala Asp Val Asn
            20                  25                  30

Ala
```

```
<210> SEQ ID NO 184
<211> LENGTH: 157
<212> TYPE: PRT
<213> ORGANISM: Artificial Sequence
<220> FEATURE:
<223> OTHER INFORMATION: Synthetic ankyrin repeat sequence

<400> SEQUENCE: 184

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Leu Asp
                20                  25                  30

Asp Ser Gly Tyr Thr Pro Leu His Leu Ala Ala Glu Asp Gly His Leu
            35                  40                  45

Glu Ile Val Glu Val Leu Leu Lys His Gly Ala Asp Val Asn Ala Ala
        50                  55                  60

Asp Arg Leu Gly Asp Thr Pro Leu His Leu Ala Ala Phe Val Gly His
65                  70                  75                  80

Leu Glu Ile Val Glu Val Leu Leu Lys Ala Gly Ala Asp Val Asn Ala
                85                  90                  95

Val Asp Leu Ala Gly Val Thr Pro Leu His Val Ala Ala Phe Tyr Gly
                100                 105                 110

His Leu Glu Ile Val Glu Val Leu Leu Lys Ala Gly Ala Asp Val Asn
            115                 120                 125

Ala Gln Asp Lys Phe Gly Lys Thr Pro Ala Asp Ile Ala Ala Asp Asn
        130                 135                 140

Gly His Glu Asp Ile Ala Glu Val Leu Gln Lys Ala Ala
145                 150                 155

<210> SEQ ID NO 185
<211> LENGTH: 157
<212> TYPE: PRT
<213> ORGANISM: Artificial Sequence
<220> FEATURE:
<223> OTHER INFORMATION: Synthetic ankyrin repeat sequence

<400> SEQUENCE: 185

Asp Leu Asp Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Arg Asp
                20                  25                  30

Ser Tyr Gly Ser Thr Pro Leu His Leu Ala Ala Arg Glu Gly His Leu
            35                  40                  45

Glu Ile Val Glu Val Leu Leu Lys Tyr Gly Ala Asp Val Asn Ala Ala
        50                  55                  60

Asp Phe Ile Gly Asp Thr Pro Leu His Leu Ala Ala Tyr Arg Gly His
65                  70                  75                  80

Leu Glu Ile Val Glu Val Leu Leu Lys Tyr Gly Ala Asp Val Asn Ala
                85                  90                  95

Ser Asp Ile Thr Gly Glu Thr Pro Leu His Leu Ala Ala Gln Ile Gly
                100                 105                 110

His Leu Glu Ile Val Glu Val Leu Leu Lys His Gly Ala Asp Val Asn
            115                 120                 125

Ala Gln Asp Lys Phe Gly Lys Thr Pro Ala Asp Ile Ala Ala Asp Asn
        130                 135                 140

Gly His Glu Asp Ile Ala Glu Val Leu Gln Lys Ala Ala
145                 150                 155
```